US011560435B2

(12) United States Patent
Bamdad et al.

(10) Patent No.: US 11,560,435 B2
(45) Date of Patent: *Jan. 24, 2023

(54) MUC1* ANTIBODIES

(71) Applicant: Minerva Biotechnologies Corporation, Waltham, MA (US)

(72) Inventors: Cynthia Bamdad, Waltham, MA (US); Sanjeev Mahanta, Boston, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 442 days.

This patent is subject to a terminal disclaimer.

(21) Appl. No.: 16/539,247

(22) Filed: Aug. 13, 2019

(65) Prior Publication Data

US 2020/0239594 A1 Jul. 30, 2020

Related U.S. Application Data

(63) Continuation of application No. 15/501,768, filed as application No. PCT/US2009/059754 on Oct. 6, 2009, now Pat. No. 10,421,819.

(60) Provisional application No. 61/103,204, filed on Oct. 6, 2008.

(51) Int. Cl.

| | |
|---|---|
| ***A61K 39/00*** | (2006.01) |
| ***C07K 16/30*** | (2006.01) |
| ***C12N 5/09*** | (2010.01) |
| ***A61P 35/00*** | (2006.01) |

(52) U.S. Cl.

CPC .......... *C07K 16/3092* (2013.01); *A61P 35/00* (2018.01); *C12N 5/0693* (2013.01); *A61K 39/001117* (2018.08); *A61K 2039/505* (2013.01); *C07K 2317/21* (2013.01); *C07K 2317/24* (2013.01); *C07K 2317/31* (2013.01); *C07K 2317/35* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/73* (2013.01); *C12N 2501/998* (2013.01)

(58) Field of Classification Search

CPC ..... C07K 16/3092; C07K 16/30; A61P 35/00; C12N 5/0693; A61K 2039/505

See application file for complete search history.

(56) References Cited

U.S. PATENT DOCUMENTS

| | | | |
|---|---|---|---|
| 4,816,567 | A | 3/1989 | Cabilly et al. |
| 9,932,407 | B2 | 4/2018 | Bamdad |
| 10,421,819 | B2 | 9/2019 | Bamdad et al. |
| 2002/0018750 | A1 | 2/2002 | Hansen et al. |
| 2002/0042089 | A1 | 4/2002 | Bodmer et al. |
| 2002/0052311 | A1 | 5/2002 | Solomon et al. |
| 2002/0064528 | A1 | 5/2002 | Zhu et al. |
| 2002/0136725 | A1 | 9/2002 | Blackburn et al. |
| 2003/0119018 | A1 | 6/2003 | Omura et al. |
| 2003/0170237 | A1 | 9/2003 | Ni et al. |
| 2003/0235868 | A1 | 12/2003 | Hogenboom et al. |
| 2004/0131612 | A1 | 7/2004 | Watkins et al. |
| 2005/0287145 | A1 | 12/2005 | Stewart et al. |
| 2006/0122377 | A1 | 6/2006 | Dennis |
| 2006/0147451 | A1 | 7/2006 | Kirchhofer et al. |
| 2006/0173171 | A1 | 8/2006 | Bamdad |
| 2006/0222637 | A1 | 10/2006 | Bamdad |
| 2007/0212350 | A1 | 9/2007 | Govindan et al. |
| 2017/0204191 | A1 | 7/2017 | Bamdad et al. |

FOREIGN PATENT DOCUMENTS

| | | | |
|---|---|---|---|
| JP | 2005-508839 | A | 4/2005 |
| WO | WO-9308829 | A1 | 5/1993 |
| WO | 2000/029029 | A1 | 5/2000 |
| WO | WO 2000/029029 | A1 | 5/2000 |
| WO | 2002/000255 | A1 | 1/2002 |
| WO | 2002/022685 | A2 | 3/2002 |
| WO | WO 2002/022685 | A2 | 3/2002 |
| WO | 02/056022 | A2 | 7/2002 |
| WO | 2002/056022 | A2 | 7/2002 |
| WO | WO 2002/056022 | A2 | 7/2002 |
| WO | 2002/078598 | A2 | 10/2002 |
| WO | WO 2002/078598 | A2 | 10/2002 |
| WO | 2003/020279 | A2 | 3/2003 |
| WO | WO 2003/020279 | A2 | 3/2003 |
| WO | 2003/089451 | A2 | 10/2003 |
| WO | WO 2003/089451 | A2 | 10/2003 |
| WO | 2005/019269 | A2 | 3/2005 |
| WO | WO 2005/019269 | A2 | 3/2005 |
| WO | 2006/105448 | A2 | 10/2006 |
| WO | 2008/070171 | A2 | 6/2008 |
| WO | 2008/073817 | A2 | 6/2008 |
| WO | WO 2008/070171 | A2 | 6/2008 |
| WO | WO 2008073817 | A2 | 6/2008 |
| WO | 2010/042562 | A2 | 4/2010 |
| WO | WO 2010/042562 | A2 | 4/2010 |

OTHER PUBLICATIONS

Brown et al J. Immunol. May 1996; 156(9):3285-3291 (Year: 1996).*

Vajdos et al (J. Mol. Biol. 2002, Jul. 5;320(2); 415-428) (Year: 2002).*

Xiong, Cheng-Yi et al., "Development of tumor targeting anti-MUC-1 multimer: effects of di-scFv unpaired cysteine location on PEGylation and tumor binding," Protein Engineering, Design & Selection, vol. 19, No. 8, pp. 359-367, Jun. 7, 2006.

Brand, Francois-Xavier et al., "Prospect for Anti-HER2 Receptor Therapy in Breast Cancer," Anticancer Research, vol. 26, pp. 463-470, 2006.

(Continued)

*Primary Examiner* — Sheela J. Huff

(74) *Attorney, Agent, or Firm* — Wilson Sonsini Goodrich & Rosati

(57) ABSTRACT

The present describes monoclonal antibody to MUC1*.

17 Claims, 24 Drawing Sheets

Specification includes a Sequence Listing.

(56) References Cited

OTHER PUBLICATIONS

Strome, Scott E. et al., "A Mechanistic Perspective of Monoclonal Antibodies in Cancer Therapy Beyond Target-Related Effects," The Oncologist, vol. 12, pp. 1084-1095, 2007.
Aboud-Pirak et al., "Inhibition of human tumor growth in nude mice by a conjugate of doxorubicin with monoclonal antibodies to epidermal growth factor receptor," Proceedings of the National Academy of Sciences, vol. 86, pp. 3778-3781, May 1989.
Baeuerle et al., "Bispecific T Cell Engaging Antibodies for Cancer Therapy," Cancer Research, vol. 69, No. 12, pp. 4941-4944, Jun. 15, 2009.
Bortoletto et al., "Optimizing anti-CD3 affinity for effective T cell targeting against tumor cells," European Journal of Immunology, vol. 32, pp. 3102-3107, 2002.
Bruenke, J. et al., "Effective lysis of lymphoma cells with a stabilized bispecific single-chain Fv antibody against CD19 and FcgammaRIII (CD16)," British Journal of Haematology, vol. 130, No. 2, pp. 218-228, 2005.
Cao et al., "Construction and characterization of an enhanced GFP-tagged anti-BAFF scFv antibody," Applied Microbiology and Biotechnology, vol. 79, No. 3, pp. 423-431, 2008.
Chames and Baty, "Bispecific Antibodies for Cancer Therapy," Current Opinion Drug Discovery & Development, vol. 12, No. 2, pp. 276-283, 2009.
Finlay et al., "Affinity maturation of a humanized rat antibody for anti-RAGE therapy: comprehensive mutagenesis reveals a high level of mutational plasticity both inside and outside the complementarity-determining regions," Journal of Molecular Biology, vol. 388, No. 3, pp. 541-558, 2009.
Holliger, Phillip et al., "'Diabodies': Small bivalent and bispecific antibody fragments," Proceedings of the National Academy of Science, vol. 90, No. 14, pp. 6444-6448, Jul. 1993.
Hurwitz et al., "The covalent binding of daunomycin and adriamycin to antibodies, with retention of both drug and antibody activities," Cancer Research, vol. 35, No. 5, pp. 1175-1181, May 1975.
Jakobovits et al., "From XenoMouse technoloby to panitumumab, the first fully human antibody product from transgenic mice," Nature Biotechnology, vol. 25, No. 10, pp. 1134-1143, Oct. 2007.
Johansson et al., "Efficient expression of recombinant human monoclonal antibodies in Drosophila S2 cells," Journal of Immunological Methods, vol. 318, pp. 37-46, 2007.
Juárez-González et al., "Directed Evolution, Phage Display and Combination of Evolved Mutants: A Strategy to Recover the Neutralization Properties of the scFv Version of BCF2 a Neutralizing Monoclonal Antibody Specific to Scorpion Toxin Cn2," Journal of Molecular Biology, vol. 346, pp. 1287-1297, 2005.
Kettleborough et al., "Optimization of primers for cloning libraries of mouse immunoglobulin genes using the polymerase chain reaction," European Journal of Immunology, vol. 23, pp. 206-211, 1993.
Lonberg, Nils, "Human antibodies from transgenic animals," Nature Biotechnology, vol. 23, No. 9, pp. 1117-1125, Sep. 2005.
Lu et al., "Simultaneous Blockade of Both the Epidermal Growth Factor Receptor and the Insulin-like Growth Factor Receptor Signaling Pathways in Cancer Cells with a Fully Human Recombinant Bispecific Antibody," Journal of Biological Chemistry, vol. 279, No. 4, pp. 2856-2865, Jan. 23, 2004.
Majors et al., "MCI-1 overexpression leads to higher viabilities and increased production of humanized monoclonal antibody in Chinese hamster ovary cells," Biotechnology Progress, vol. 25, No. 4, pp. 1161-1168, 2009.
McCall et al., "Isolation and characterization of an anti-CD16 single-chain Fv fragment and construction of an anti-HER2/neu/anti-CD16 bispecific scFv that triggers CD16-dependent tumor cytolysis," Molecular Immunology, vol. 36, No. 7, pp. 433-446, 1999.
McCarron et al., "Antibody Conjugates and Therapeutic Strategies," Molecular Interventions, vol. 5, No. 6, pp. 368-380, Dec. 2005.
Morrison, S.L., "Cloning, expression, and modification of antibody V regions," Current Protocols in Immunology, 2.12.1-2.12.17, 2002.
Muzard et al., "Design and humanization of a murine scFv that blocks human platelet glycoprotein VI in vitro," FEBS Journal, vol. 276, pp. 4207-4222, 2009.
Nahary and Benhar, "Chapter 3: Design of a human synthetic combinatorial library of single-chain antibodies," Therapeutic Antibodies: Methods and Protocols, vol. 525, pp. 61-80, 2009.
Razai et al., "Molecular evolution of antibody affinity for sensitive detection of botulinum neurotoxin type A," Journal of Molecular Biology , vol. 351, No. 1, pp. 158-169, 2005.
Robinson et al., "Targeting ErbB2 and ErbB3 with a bispecific single-chain Fv enhances targeting specificity and induces a therapeutic effect in vitro," British Journal of Cancer, vol. 99, No. 9, pp. 1415-1425, 2008.
Wang et al., "Universal PCR amplification of mouse immunoglobulin gene variable regions: The design of degenerate primers and an assessment of the effect of DNA polymerase 3' to 5' exonuclease activity," Journal of Immunological Methods, vol. 233, pp. 167-177, 2000.
Notification of Transmittal of the Internal Search Report and the Written Opinion for corresponding PCT Application No. PCT/US2009/059754 dated Jul. 6, 2010, 17 pages.
Partial European Search Report for corresponding EP Application No. 16190400.8 dated Dec. 23, 2016, 10 pages.
Extended European Search Report for corresponding EP Application No. 16190400.8 dated May 29, 2017, 18 pages.
Berezov et al. Disabling erbB receptors with rationally designed exocyclic mimetics of antibodies: structure-function analysis. J Med Chem 44:2565 (2001).
Carter et al. Humanization of an anti-p185HER2 antibody for human cancer therapy. PNAS USA 89(10):4285-4289 (1992).
Finlay et al. Affinity maturation of a humanized rat antibody for anti-RAGE therapy: comprehensive mutagenesis reveals a high level of mutational plasticity both inside and outside the complementarity-determining regions. J Mol Biol. 388(3):541-58 (2009).
Hoogenboom, et al. By-passing immunisation. Human antibodies from synthetic repertoires of germline VH gene segments rearranged in vitro. J Mol Biol. Sep. 20, 1992;227(2):381-8.
Jones et al. Replacing the complementarity-determining regions in a human antibody with those from a mouse. Nature 321:522-525 (1986).
Kortt et al. Recombinant anti-sialidase single-chain variable fragment antibody. Characterization, formation of dimer and higher-molecular-mass multimers and the solution of the crystal structure of the single-chain variable fragment/sialidase complex. Eur J Biochem 221:151 (1994).
Marks et al. By-passing immunization: Human antibodies from v-gene libraries displayed on phage. J. Mol. Biol. 222:581-597 (1991).
Milstein et al. Hybrid hybridomas and their use in immunohistochemistry. Nature 305:537 (1983).
Riechmann et al. Reshaping human antibodies for therapy. Nature 332:323-327 (1988).
Schoonooghe et al. Efficient production of human bivalent and trivalent anti-MUC1 Fab-scFv antibodies in Pichia pastoris. MBC Biotechnol 9:70 (2009).
Suresh et al. Bispecific monoclonal antibodies from hybrid hybridomas. Methods Enzymol. 121:210-228 (1986).
Traunecker et al. Bispecific single chain molecules (Janusins) target cytotoxic lymphocytes on HIV infected cells. EMBO J. 10(12):3655-9 (1991).
U.S. Appl. No. 15/501,768 Office Action dated Apr. 22, 2019.
U.S. Appl. No. 15/501,768 Office Action dated Mar. 22, 2019.
Verhoeyen et al. Reshaping human antibodies: Grafting an antilysozyme activity. Science 239:1534-1536 (1988).
Xiong, Cheng-Yi et al., "Development of tumor targeting anti-MUC-1 multimer: effects of di-scFv unpaired cysteine location on PEGylation and tumor binding." *Protein Engineering, Design & Selection*, vol. 19, No. 8, pp. 350-367, Jun. 7, 2006.
Strome, Scott E. et al., "A Mechanistic Perspective of Monoclonal Antibodies in Cancer Therapy Beyond Target-Related Effects," *The Oncologist*, vol. 12, pp. 1084-1005, 2007.

(56) References Cited

OTHER PUBLICATIONS

Baeuerle et al., "Bispecific T Cell Engaging Antibodies for Cancer Therapy," *Cancer Research*, vol. 60, No. 12, pp. 4941-4944, Jun. 15, 2009.
Bortoletto et al., "Optimizing anti-CD3 affinity for effeetive T cell targeting against tumor cells," *European Journal of Immunology*, vol. 32, pp. 3102-3107, 2002.
Holliger, Phillip et al., "'Diabodies': Small bivalent and bispecific antibody fragments." *Proceedings of the National Academy of Science*, vol. 90, No. 14, pp. 6444-6448, Jul. 1993.
Jakobovits et al., "From XenoMouse technology to panitumumab, the first fully human antibody product from transgenic mice," *Nature Biotechnology*, vol. 25, No. 10, pp. 1134-1143, Oct. 2007.
Lu et al., "Simultaneous Blockade of Both the Epidermal Growth Factor Receptor and the Insulin-like Growth Factor Receptor Signaling Pathways in Cancel Cells with a Fully Human Recombinant Bispecific Antibody," *Journal of Biological Chemistry*, vol. 279, No. 4, pp. 2856-2865, Jan. 23, 2004.
Robinson et al., "Targeting ErbB2 and ErbB3 with a bispecific single-chain Fv enhances targeting specificity and induces a therapeutic effect in vitro," *British Journal of Cancer*, vol. 99, No. 9, pp. 1415-1425, 2008.
Communication pursuant to Article 94(3) EPC dated Apr. 30, 2020, issued in European Application No. 16190400.8, 3 pages.

* cited by examiner

MIN-C2 mAb versus
MIN-C2 Fab

MIN-E6 mAb versus
MIN-E6 Fab

FIG. 10A

Anti-MUC1* scFv single chain fragment variable region

FIG. 10B

Anti-MUC1* scFab single chain antibody fragment

FIG. 10C 2-part Anti-MUC1* Fab fragment variable region

FIG. 10D

Anti-MUC1*/Anti-HER2 bscAb bi-specific single chain antibody fragment

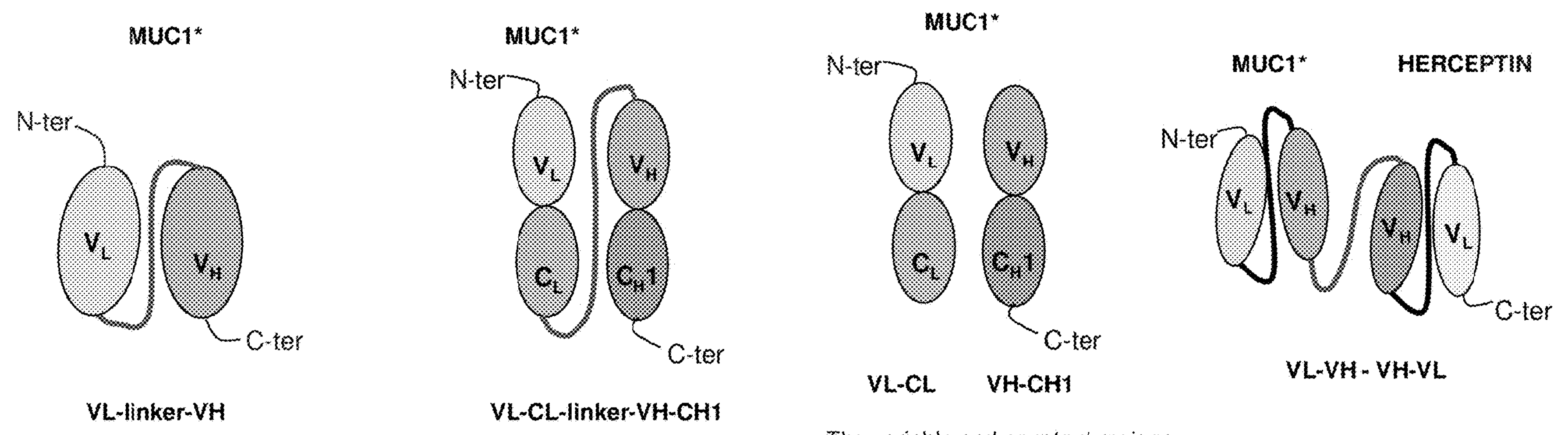

Binds to MUC1*-positive cancer cells; competes with full mab in peptide ELISA assay +/- pegylation. Affinity just short of what's required for a drug.

Higher affinity & stability than scFv. Easier to produce in recombinant form in large scale (Hust et al 2007). Campath is an example of a scFab drug.

The variable and constant regions of light and heavy chains were also separately cloned into vectors and expressed separately in the same cell. The chains spontaneously associated to form a stable anti-MUC1* antibody variant.

Diabody increases specificity for cancer cells and knocks out 2 growth factor receptors operative in breast cancers. Cooperative binding increases avidity.

FIG. 11

Anti MUC1* IgG monoclonal antibody light chain variable region sequences

| | FWR1 | CDR1 | FWR2 | CDR2 |
|---|---|---|---|---|
| MIN-C2 | DIVITQSTASLGVSLGQRATISC | RASKSVSTSGYSYMH | WYQQRPGQPPKLLIY | LASNLES |
| MIN-E6 | DIVITQTTAIMSASPGEEVTLTC | SATSSV-----SYIH | WFQQRPGTSPKLWIY | STSNLAS |
| MIN-A2-1 | DIVLTQSTEIMSASPGEKVTITC | SASSSI-----SYIH | WFQQKPGTSPKLWIF | GTSNLAS |
| MIN-A2-2 | DIVMTQSPAIMSASPGEKVTMTC | SASSSV-----SYMH | WFQQKPGTSPKLWIY | STSNLAS |
| MIN-C9-1 | DIVLTQTTAIMSASPGEKVTITC | SASSSV-----SYMY | WFQQKPGTSPKLWIY | STSNLAS |
| MIN-C9-2 | DIVITQSTAIMSASPGEKVTITC | SASSSV-----SYTY | WFQQKPGTSPKLWIY | STSNLAS |
| MIN-D7-1 | DIVITQTPAIMSASPGEKVTMTC | SASSSV-----SYMH | WFQQKPGTSPKLWIY | STSNLAS |
| MIN-D7-2 | DIVLTQSTAIMSASPGEKVTMTC | SASSSV-----SYMH | WFQQKPGTSPKLWIY | STSNLAS |
| MIN-F2-1 | DIVMTQSPEIMSASPGEKVTITC | SASSSI-----SYIH | WFQQKPGTSPKLWIF | GTSNLAS |
| MIN-F2-2 | DIVITQSTEIMSASPGEKVTITC | SASSSI-----SYIH | WFQQKPGTSPKLWIF | GTSNLAS |

| | FWR3 | CDR3 | | |
|---|---|---|---|---|
| MIN-C2 | GVPARFSGSGSGTDFTLNIHPVEEEDAATYYC | QHSRELPFT | FGGGTKLEIKRADAAPTVS | (SEQ ID NO:13) |
| MIN-E6 | GVPVRFSGSGYGTSYSLTISRMEAEDAATYYC | QQRSSSPFT | FGSGTKLEIKRADAAPTVS | (SEQ ID NO:24) |
| MIN-A2-1 | GVPARFSGSGSGTSYSLTVSRMEAEDTATYYC | QQRSNYPFT | FGSGTKLQIKRADAAPTVS | (SEQ ID NO:51) |
| MIN-A2-2 | GAPARFSGSGSGTSYSLTVSRMESEDAATYYC | QQRSSYPST | FGGGTKLEIKRADAAPTVS | (SEQ ID NO:52) |
| MIN-C9-1 | GVPARFSGSGSGTSYSLTISRMEAEDAATYYC | QQRSSYPST | FGGGTKLEIKRADAAPTVS | (SEQ ID NO:53) |
| MIN-C9-2 | GVPARFSGSGSGTSYSLTISRMEAEDAATYYC | QQRSSYPST | FGGGTKLEIKRADAAPTVS | (SEQ ID NO:54) |
| MIN-D7-1 | GVPARFSGSGSGTSYSLTVSRMESEDAATYYC | QQRSSYPST | FGGGTKLEIKRADAAPTVS | (SEQ ID NO:55) |
| MIN-D7-2 | GVPARFSGSGSGTSYSLTVSRMESEDAATYYC | QQRSSYPST | FGGGTKLEIKRADAAPTVS | (SEQ ID NO:56) |
| MIN-F2-1 | GVPARFSGSGSGTSYSLTVSRMEAEDTATYYC | QQRSNYPFT | FGSGTKLQIKRADAAPTVS | (SEQ ID NO:57) |
| MIN-F2-2 | GVPARFSGSGSGTSYSLTVSRMEAEDTATYYC | QQRSNYPFT | FGSGTKLQIKRADAAPTVS | (SEQ ID NO:58) |

FIG. 12

Anti MUC1* IgG monoclonal antibody heavy chain variable region sequences

| | FWR1 | CDR1 | FWR2 | CDR2 |
|---|---|---|---|---|
| MIN-C2 | EVQLEESGGGLVKPGGSLKLSCAASGFTFS | GYAMS | WVRQTPEKRLEWVA | TISSGGTYIYY |
| MIN-E6-7 | EVKLEESGGDLVKPGGSLKLSCAASGFTFS | RYGMS | WVRQTPDKRLEWVA | TISSGGTYIYY |
| MIN-E6-8 | EVKLEESGGDLVKPGGSLKLSCVVSGFTFS | RYGMS | WVRQTPGKRLEWVA | TISGGGTYIYY |
| MIN-A2-1 | EVKLQESGPELKKPGETVEISCKASGYTFT | NYGMN | WVKQAPGKGLKWMG | WINTYTGEPTY |
| MIN-A2-2 | EVQLQQSGPELKKPGETVKISCKASGYTFT | NYGMN | WVKQAPGKGLKWMG | WINTYTGEPTY |
| MIN-C9-1 | QVQLQESGPELKQPGETVKISCKASGYTFT | NNGMN | WVKQAPGKGLKWMG | WINTYTGEPTY |
| MIN-C9-2 | QVQLQQSGPELKQPGETVKISCKASGYTFT | NNGMN | WVKQAPGKGLKWMG | WINTYTGEPTY |
| MIN-D7-1 | EVQLEQSGPELKKPGETVKISCKASGYTFI | NYGMN | WVKQAPGKGLKWMG | WINTYTGEPTY |
| MIN-D7-2 | EVQLQQSGPELKKPGETVKISCKASGYTFT | NYGMN | WVKQAPGKGLKWMG | WINTYTGEPTY |
| MIN-F2-1 | EVKLEESGPELKKPGETVKISCKASGYTFI | NYGMN | WVKQAPGKGLKWMG | WINTYTGEPTY |
| MIN-F2-2 | EVQLEQSGAELVRPGASVKLSCKALGYTFT | DYEMH | WVKQTPVHGLEWIG | AIHPGSGGTAY |
| MIN-F2-3 | RCRLQQSGPELKKPGETVKISCKASGYTFI | NYGMN | WVKQAPGKGLKWMG | WINTYTGEPTY |
| MIN-F2-4 | EVQLEQSGPELKKPGETVKISCKASGYTFI | NYGMN | WVKQAPGKGLKWMG | WINTYTGEPTY |

| | | FWR3 | CDR3 | | |
|---|---|---|---|---|---|
| MIN-C2 | PDSVKG | RFTISRDNAKNTLYLQMSSLRSEDTAMYYCAR | LGGDNYY-EY | FDVWGAGTTVTVSSAKTTPPSVY | (SEQ ID NO:11) |
| MIN-E6-7 | PDSVKG | RFTISRDNAKNTLYLQMSSLKSEDTAMYYCAR | DNYGSSYDYA | MDYWGQGTSVTVSSAKTTAPSVY | (SEQ ID NO:20) |
| MIN-E6-8 | PDSVKG | RFTISRDNAKNTLYLQMSSLKSEDTAMYHCTR | DNYGRNYDYG | MDYWGQGTSVTVSSAKTTAPSVY | (SEQ ID NO:22) |
| MIN-A2-1 | AGDFKG | RFAFSLETSASTAYLQINTLKNEDTATYFCAR | SGDGYWY-YA | MDYWGQGTSVTVSSAKTTPPSVY | (SEQ ID NO:59) |
| MIN-A2-2 | AGDFKG | RFAFSLETSASTAYLQINTLKNEDTATYFCAR | SGDGYWY-YA | MDYWGQGTSVTVSSAKTTPPSVY | (SEQ ID NO:60) |
| MIN-C9-1 | ADDFKG | RFAFSLDTSASTAYLQINNLKNEDMATYFCAR | TGTARAF-YA | MDYWGQGTSVTVSSTKTTAPSVY | (SEQ ID NO:61) |
| MIN-C9-2 | ADDFKG | RFAFSLGTSASTAYLQINNLKNEDMATYFCAR | TGTARAF-YA | MDYWGQGTSVTVSSTKTTAPSVY | (SEQ ID NO:62) |
| MIN-D7-1 | VDDFKG | RFAFSLETSARTAYLQINNLKNEDMATYFCAR | TGTTAIL-NG | MDYWGQGTSVTVSSAKTTPPSVY | (SEQ ID NO:63) |
| MIN-D7-2 | AGDFKG | RFAFSLETSASTAYLQINTLKNEDTATYFCAR | SGDGYWY-YA | MDYWGQGTSVTVSSAKTTPPSVY | (SEQ ID NO:64) |
| MIN-F2-1 | VDDFKG | RFAFSLETSARTAYLQINNLKNEDMATYFCAR | TGTTAIL-NG | MDYWGQGTSVTVSSAKTTPPSVY | (SEQ ID NO:65) |
| MIN-F2-2 | NQKFKG | KATLTADKSSSTAYMELSSLTSEDSAVYYCTN | YGSFA------ | --YWGQGTLVTVSAAKTTPPSVY | (SEQ ID NO:66) |
| MIN-F2-3 | VDDFKG | RFAFSLETSARTAYLQINNLKNEDMATYFCAR | TGTTAIL-NG | MDYWGQGTSVTVSSAKTTPPSCL | (SEQ ID NO:67) |
| MIN-F2-4 | VDDFKG | RFAFSLETSARTAYLQINNLKNEDMATYFCAR | TGTTAIL-NG | MDYWGQGTSVTVSSAKTTPPSVY | (SEQ ID NO:68) |

FIG. 13

Anti MUC1* IgM monoclonal antibody light chain variable region sequences

| | FWR1 | CDR1 |
|---|---|---|
| MIN-14 | DIQMTQSPSSLSASLGERVSLTC | RASQDIGSS----LN |
| MIN-17-1 | DIVLTQSPASLAVSLGQRATISY | RASKSVSTSGYSYMH |
| MIN-17-2 | DIQMTQSPASQSASLGESVTITC | LASQTIGTW----LA |
| MIN-29 | DIVLTQSPASLAVSLGQRATISY | RASKSVSTSGYSYMH |
| MIN-34 | DIVLTQSPASLAVSLGQRATISY | RASKSVSTSGYSYMH |
| MIN-42 | DIVMTQSQKFMSTSVGDRVSVTC | KASQNVGTN----VG |
| MIN-45 | DIQMTQPPASLSASVGETVTITC | RASGNIHNF----LA |

| | FWR2 | CDR2 | FWR3 | |
|---|---|---|---|---|
| MIN-14 | WLQQEPDGTIKRLIY | ATSSLDS | GVPKRFSGSRSGSDYSLTISSLESEDFVDYYC | LQYASSPH |
| MIN-17-1 | WNQQKPGQPPRLLIY | LVSNLES | GVPARFSGSGSGTDFTLNIHPVEEEDAATYYC | QHIR---- |
| MIN-17-2 | WYQQKPGKSPQLLIY | AATSLAD | GVPSRFSGSGSGTKFSFKISSLQAEDFVSYYC | QQLYSTPW |
| MIN-29 | WNQQKPGQPPRLLIY | LVSNLES | GVPARFSGSGSGTDFTLNIHPVEEEDAATYYC | QHIR---- |
| MIN-34 | WNQQKPGQPPRLLIY | LVSNLES | GVPARFSGSGSGTDFTLNIHPVEEEDAATYYC | QHIR---- |
| MIN-42 | WYQQKPGQSPKALIY | SASYRYS | GVPDRFTGSGSGTDFTLTISNVQSEDLAEYFC | QQYNNYPY |
| MIN-45 | WYQQKQGKSPQLLVY | NAKTLAD | GVPSRFSGSGSGTQYSLKINSLQPEDFGSYYC | QHFWSTPW |

| | | |
|---|---|---|
| MIN-14 | VRCWDQAGAETGCCTNC-- | (SEQ ID NO:69) |
| MIN-17-1 | ---------ELTRSEGGPSW | (SEQ ID NO:70) |
| MIN-17-2 | TFGGGTKLEIKRADAAPTV | (SEQ ID NO:71) |
| MIN-29 | ---------ELTRSEGGPSW | (SEQ ID NO:72) |
| MIN-34 | ---------ELTRSEGGPSW | (SEQ ID NO:73) |
| MIN-42 | TFGGGTKLEIKRADAAPTV | (SEQ ID NO:74) |
| MIN-45 | TFGGGTKLEIKRADAAPTV | (SEQ ID NO:75) |

FIG. 14

Anti MUC1* IgM monoclonal antibody heavy chain variable region sequences

| | FWR1 |
|---|---|
| MIN-14 | QVQLQQPGAELVK---------------------------PGASVK- |
| MIN-17-1 | QVQLQQPGAELVK---------------------------PGASVK- |
| MIN-17-2 | QITLKESGPGIVQ---------------------------PSQPFR- |
| MIN-29 | DVKLVESGGDLXKLTEGEDIWEGLTLCRDSDQSPLAPVSKPGRVVRPQ |
| MIN-34 | QVQLKQSGPGLVQ---------------------------PSQSLS- |
| MIN-42 | EVQLVESGGDLVK---------------------------PGRSLK- |
| MIN-45 | EVQLQQSGPELVK---------------------------PGASVK-- |

| | | CDR1 | FWR2 | CDR2 | |
|---|---|---|---|---|---|
| MIN-14 | LSCKA-SGYTF-T | SYWMH | WVKQRPGQGLEWIG | EINPSNGRTNYNEK-FKS | KATLTVDKS |
| MIN-17-1 | LSCKA-SGYTF-T | SYWMH | WVKQRPGQGLEWIG | EINPSNGRTNYNEK-FKS | KATLTVDKS |
| MIN-17-2 | LTCTF-SGFSLSTS | GIGVT | WIRQPSGKGLEWLA | TIW-WDDDNRYNPS-LKS | RLTVSKDTS |
| MIN-29 | RSCTVIQGCVL--- | ----- | -RLQTAHLQVQGVL | GIVSGDGESALHSVWIVG | ATTITINGC |
| MIN-34 | ITCTV-SGFSL-T | SYGVH | WVRQSPGKGLEWLG | VIW-GGGSTDYNAA-FIS | RLSISKDNS |
| MIN-42 | LSCAA-SGFTF-S | SFGMS | WVRQTPDKRLEWVA | TISSGGTYTYYPDS-VKG | RFTISRDNA |
| MIN-45 | ISCKA-SGYSF-T | GYFMS | WVMQSHGKSLEWIG | RINPYNGDTFYNQK-FKG | KATLTVDKS |

| | FWR3 | | |
|---|---|---|---|
| MIN-14 | SSTAYMQLSSLTSEDSAVYYCAT | YGNYWYF | (SEQ ID NO:76) |
| MIN-17-1 | SSTAYMQLSSLTSEDSAVYYCAT | YGNYWYF | (SEQ ID NO:78) |
| MIN-17-2 | NNQAFLNIITVETADTAIYYCAQ | STMVTAG | (SEQ ID NO:77) |
| MIN-29 | DQLQPL-LWSL-ANPRHVIATES | ESRGCTG | (SEQ ID NO:79) |
| MIN-34 | KSQVFFKMNSLQANDTAIYYCAR | NDYPAWF | (SEQ ID NO:80) |
| MIN-42 | KNTLYLQMSSLKSEDTAMYYCSR | RFYYDYD | (SEQ ID NO:81) |
| MIN-45 | STTAHIELRSLASEDSAVYYCAR | KGL--YG | (SEQ ID NO:84) |

FIG. 15

FWR1 CDR1 FWR2 CDR2
EVQLEESGGGLVKPGGSLKLSCAASGFTFS GYAMS WVRQTPEKRLEWVA TISSGGTYIYYPDSVKG

FWR3 CDR3
RFTISRDNAKNTLYLQMSSLRSEDTAMYYCAR LGGDNYYEY FDVWGAGTTVTVSSAKTTPPSVYKL linker FWR1 CDR1 FWR2
GGGGSGGGGSGGGGS SSS DIVITQSTASLGVSLGQRATISC RASKSVSTSGYSYMH WYQQRPGQPP

CDR2 FWR3 CDR3
KLLIY LASNLES GVPARFSGSGSGTDFTLNIHPVEEEDAATYYC QHSRELPFT FGGGTKLE

IKRADAAPTVSVD (SEQ ID NO:17)

FIG. 16

FWR1 CDR1 FWR2 CDR2
EVKLEESGGDLVKPGGSLKLSCAASGFTFS RYGMS WVRQTPDKRLEWVA TISSGGTYIYYPDSVKG

FWR3 CDR3
RFTISRDNAKNTLYLQMSSLKSEDTAMYYCAR DNYGSSYDYA MDYWGQGTSVTVSSAKTTAP linker FWR1
SVYPLAPVCGDTTGSSVTLGCLVK GGGGSGGGGSGGGGS DIVITQTTAIMSASPGEEVTLTC CDR1 FWR2 CDR2 FWR3
SATSSVSYIH WFQQRPGTSPKLWIY STSNLAS GVPVRFSGSGYGTSYSLTISRMEAEDAATYYC

CDR3
QQRSSSPFT FGSGTKLEIKRADAAPTVS (SEQ ID NO:27)

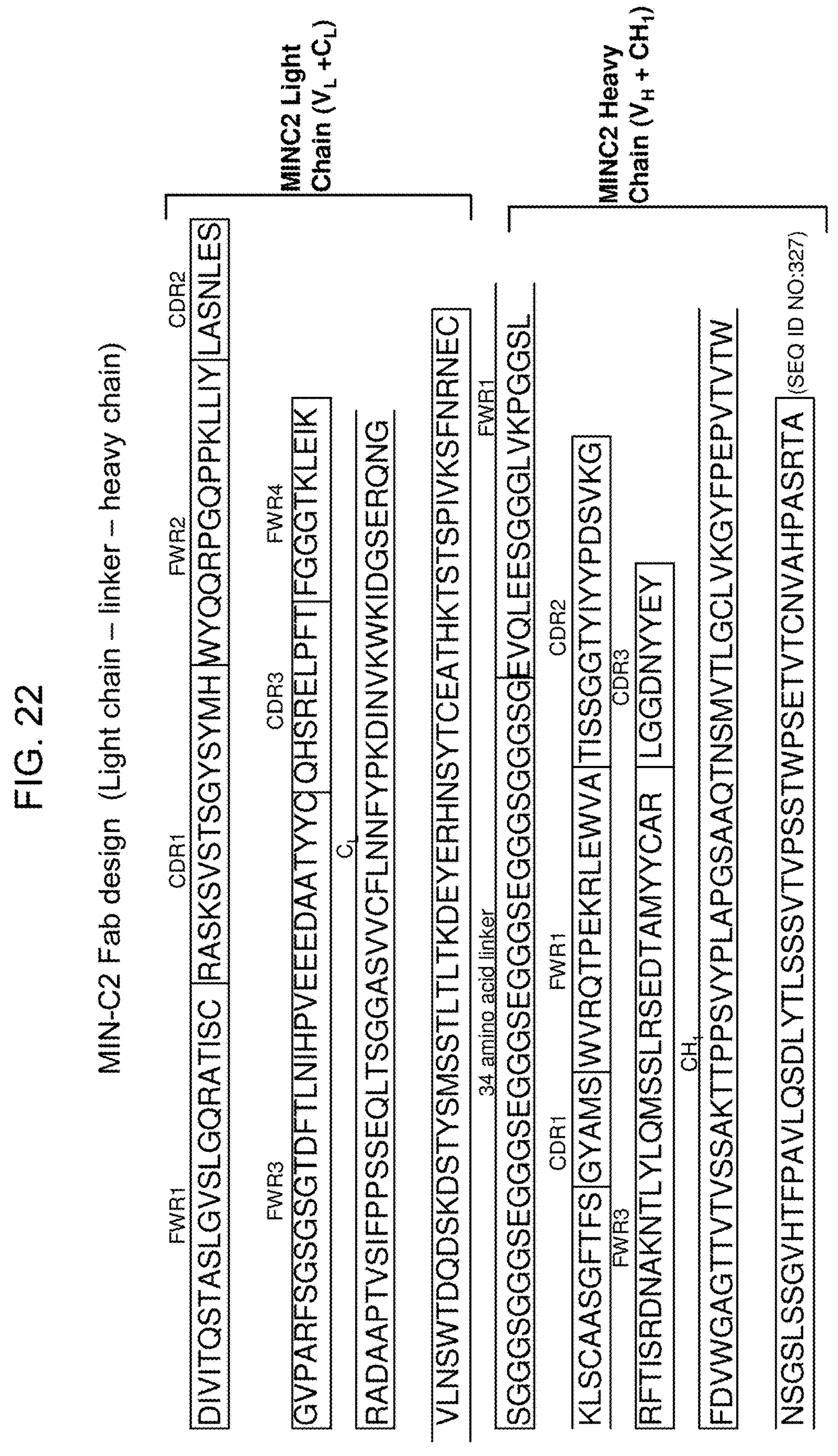
FIG. 22
MIN-C2 Fab design (Light chain – linker – heavy chain)
FWR1 CDR1 FWR2 CDR2
DIVITQSTASLGVSLGQRATISC RASKSVSTSGYSYMH WYQQRPGQPPKLLIY LASNLES
FWR3 CDR3 FWR4
GVPARFSGSGSGTDFTLNIHPVEEEDAATYYC QHSRELPFT FGGGTKLEIK
C_L
RADAAPTVSIFPPSSEQLTSGGASVVCFLNNFYPKDINVKWKIDGSERQNG
VLNSWTDQDSKDSTYSMSSTLTLTKDEYERHNSYTCEATHKTSTSPIVKSFNRNEC
MINC2 Light Chain ($V_L$ +$C_L$)
34 amino acid linker FWR1
SGGGSGGGSEGGGSEGGGSEGGGSEGGGSG EVQLEESGGGLVKPGGSL
CDR1 FWR1 CDR2
KLSCAASGFTFS GYAMS WVRQTPEKRLEWVA TISSGGTYIYYPDSVKG
FWR3 CDR3
RFTISRDNAKNTLYLQMSSLRSEDTAMYYCAR LGGDNYYEY
$CH_1$
FDVWGAGTTVTVSSAKTTPPSVYPLAPGSAAQTNSMVTLGCLVKGYFPEPVTVTW
NSGSLSSGVHTFPAVLQSDLYTLSSSVTVPSSTWPSETVTCNVAHPASRTA (SEQ ID NO:327)
MINC2 Heavy Chain ($V_H$ + $CH_1$)

FIG. 24
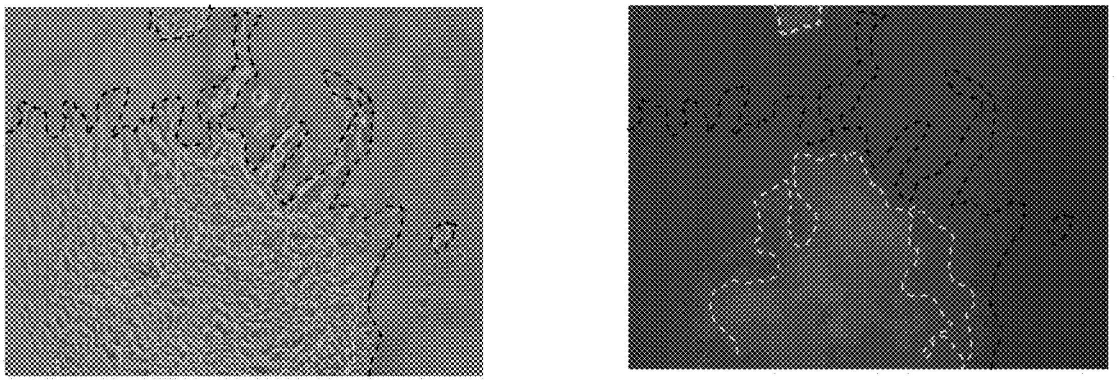
minimal media alone
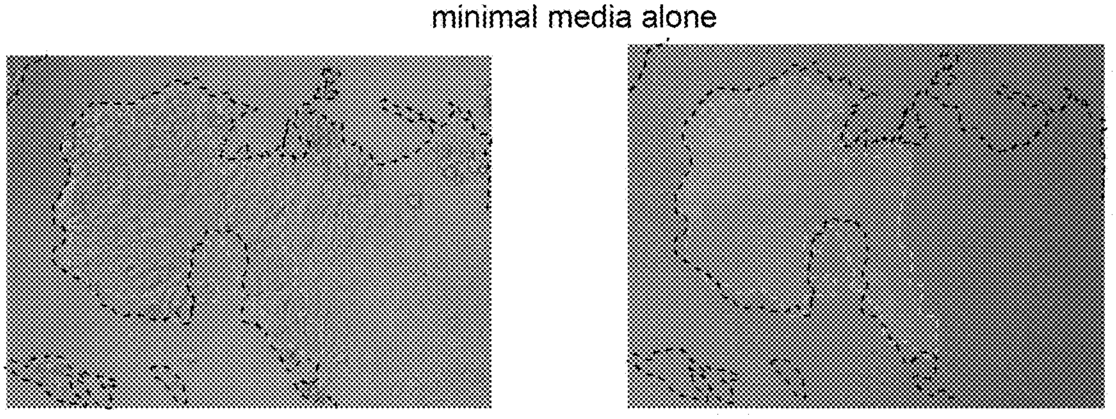
minimal media supplemented with bFGF and feeder cell conditioned media
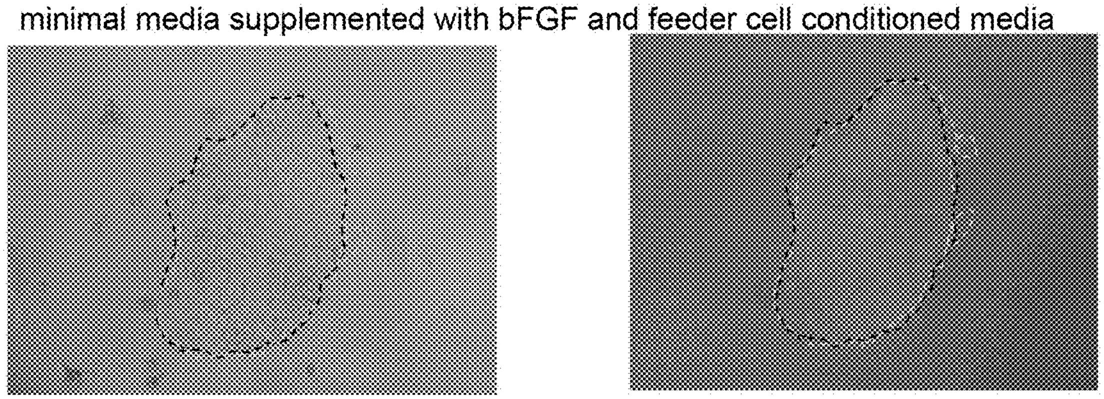
minimal media supplemented with bivalent rannit polyclonal anti-MUC1*
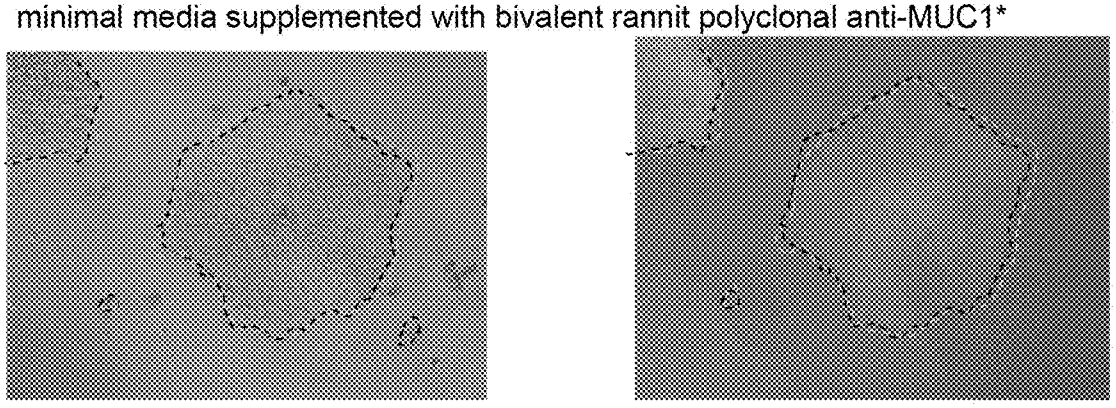
minimal media supplemented with bivalent mouse monoclonal anti-MUC1*: MIN-C2

SEQUENCE LISTING

<160> NUMBER OF SEQ ID NOS: 375

<210> SEQ ID NO 1
<211> LENGTH: 45
<212> TYPE: PRT
<213> ORGANISM: Artificial Sequence
<220> FEATURE:
<223> OTHER INFORMATION: Synthesized

<400> SEQUENCE: 1

```
Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala
        35                  40                  45
```

<210> SEQ ID NO 2
<211> LENGTH: 45
<212> TYPE: PRT
<213> ORGANISM: Artificial Sequence
<220> FEATURE:
<223> OTHER INFORMATION: Synthesized

<400> SEQUENCE: 2

```
Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser Asp Val Pro Phe Pro Phe Ser Ala Gln Ser Gly Ala
        35                  40                  45
```

<210> SEQ ID NO 3
<211> LENGTH: 36
<212> TYPE: DNA
<213> ORGANISM: Artificial Sequence
<220> FEATURE:
<223> OTHER INFORMATION: Synthesized

<400> SEQUENCE: 3

```
ggaaagctta tagacagatg ggggtgtcgt tttggc                            36
```

<210> SEQ ID NO 4
<211> LENGTH: 32
<212> TYPE: DNA
<213> ORGANISM: Artificial Sequence
<220> FEATURE:
<223> OTHER INFORMATION: Synthesized

<400> SEQUENCE: 4

```
ggaaagcttc ttgaccaggc atcctagagt ca                                32
```

<210> SEQ ID NO 5
<211> LENGTH: 33
<212> TYPE: DNA
<213> ORGANISM: Artificial Sequence
<220> FEATURE:
<223> OTHER INFORMATION: Synthesized

<400> SEQUENCE: 5

```
ggaaagctta ggggccagtg gatagactga tgg                               33
```

<210> SEQ ID NO 6
<211> LENGTH: 32

<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (18)..(18)
<223> OTHER INFORMATION: n is a, c, g, or t

<400> SEQUENCE: 6
cttccggaat tcsargtnma gctgsagsag tc 32

<210> SEQ ID NO 7
<211> LENGTH: 35
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (18)..(18)
<223> OTHER INFORMATION: n is a, c, g, or t

<400> SEQUENCE: 7
cttccggaat tcsargtnma gctgsagsag tcwgg 35

<210> SEQ ID NO 8
<211> LENGTH: 30
<212> TYPE: DNA
<213> ORGANISM: Artificial Sequence
<220> FEATURE:
<223> OTHER INFORMATION: Synthesized

<400> SEQUENCE: 8
ggtgtcgacg gatacagttg gtgcagcatc 30

<210> SEQ ID NO 9
<211> LENGTH: 32
<212> TYPE: DNA
<213> ORGANISM: Artificial Sequence
<220> FEATURE:
<223> OTHER INFORMATION: Synthesized

<400> SEQUENCE: 9
gggagctcga yattgtgmts acmcarwctm ca 32

<210> SEQ ID NO 10
<211> LENGTH: 390
<212> TYPE: DNA
<213> ORGANISM: Artificial Sequence
<220> FEATURE:
<223> OTHER INFORMATION: Synthesized

<400> SEQUENCE: 10
gaggtccagc tggaggagtc aggggaggc ttagtgaagc ctggagggtc cctgaaactc 60
tcctgtgcag cctctggatt cactttcagt ggctatgcca tgtcttgggt tcgccagact 120
ccggagaaga ggctggagtg ggtcgcaacc attagtagtg gtggtactta tatctactat 180
ccagacagtg tgaaggggcg attcaccatc tccagagaca atgccaagaa caccctgtac 240
ctgcaaatga gcagtctgag gtctgaggac acggccatgt attactgtgc aagacttggg 300
ggggataatt actacgaata cttcgatgtc tggggcgcag ggaccacggt caccgtctcc 360
tccgccaaaa cgacaccccc atctgtctat 390

<210> SEQ ID NO 11

<211> LENGTH: 130
<212> TYPE: PRT
<213> ORGANISM: Artificial Sequence
<220> FEATURE:
<223> OTHER INFORMATION: Synthesized

<400> SEQUENCE: 11

Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Thr Phe Ser Gly Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Leu Gly Gly Asp Asn Tyr Tyr Glu Tyr Phe Asp Val Trp Gly
            100                 105                 110

Ala Gly Thr Thr Val Thr Val Ser Ser Ala Lys Thr Thr Pro Pro Ser
        115                 120                 125

Val Tyr
    130

<210> SEQ ID NO 12
<211> LENGTH: 360
<212> TYPE: DNA
<213> ORGANISM: Artificial Sequence
<220> FEATURE:
<223> OTHER INFORMATION: Synthesized

<400> SEQUENCE: 12
gacattgtga tcacacagtc tacagcttcc ttaggtgtat ctctggggca gagggccacc 60
atctcatgca gggccagcaa aagtgtcagt acatctggct atagttatat gcactggtac 120
caacagagac caggacagcc acccaaactc ctcatctatc ttgcatccaa cctagaatct 180
ggggtccctg ccaggttcag tggcagtggg tctgggacag acttcaccct caacatccat 240
cctgtggagg aggaggatgc tgcaacctat tactgtcagc acagtaggga gcttccgttc 300
acgttcggag gggggaccaa gctggagata aaacgggctg atgctgcacc aactgtatcc 360

<210> SEQ ID NO 13
<211> LENGTH: 120
<212> TYPE: PRT
<213> ORGANISM: Artificial Sequence
<220> FEATURE:
<223> OTHER INFORMATION: Synthesized

<400> SEQUENCE: 13

Asp Ile Val Ile Thr Gln Ser Thr Ala Ser Leu Gly Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Arg Pro Gly Gln Pro Pro
        35                  40                  45

Lys Leu Leu Ile Tyr Leu Ala Ser Asn Leu Glu Ser Gly Val Pro Ala
    50                  55                  60

-continued

```
Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Gly Gly Thr Lys Leu Glu Ile Lys Arg
            100                 105                 110

Ala Asp Ala Ala Pro Thr Val Ser
        115                 120


<210> SEQ ID NO 14
<211> LENGTH: 45
<212> TYPE: DNA
<213> ORGANISM: Artificial Sequence
<220> FEATURE:
<223> OTHER INFORMATION: Synthesized

<400> SEQUENCE: 14

ggtggaggcg gatcaggtgg aggcggatca ggtggaggcg gatca                     45


<210> SEQ ID NO 15
<211> LENGTH: 795
<212> TYPE: DNA
<213> ORGANISM: Artificial Sequence
<220> FEATURE:
<223> OTHER INFORMATION: Synthesized

<400> SEQUENCE: 15

gaggtccagc tggaggagtc aggggggaggc ttagtgaagc ctggagggtc cctgaaactc     60

tcctgtgcag cctctggatt cactttcagt ggctatgcca tgtcttgggt tcgccagact    120

ccggagaaga ggctggagtg ggtcgcaacc attagtagtg gtggtactta tatctactat    180

ccagacagtg tgaaggggcg attcaccatc tccagagaca atgccaagaa caccctgtac    240

ctgcaaatga gcagtctgag gtctgaggac acggccatgt attactgtgc aagacttggg    300

ggggataatt actacgaata cttcgatgtc tggggcgcag ggaccacggt caccgtctcc    360

tccgccaaaa cgacaccccc atctgtctat ggtggaggcg gatcaggtgg aggcggatca    420

ggtggaggcg gatcagacat tgtgatcaca cagtctacag cttccttagg tgtatctctg    480

gggcagaggg ccaccatctc atgcagggcc agcaaaagtg tcagtacatc tggctatagt    540

tatatgcact ggtaccaaca gagaccagga cagccaccca aactcctcat ctatcttgca    600

tccaacctag aatctggggt ccctgccagg ttcagtggca gtgggtctgg gacagacttc    660

accctcaaca tccatcctgt ggaggaggag gatgctgcaa cctattactg tcagcacagt    720

agggagcttc cgttcacgtt cggagggggg accaagctgg agataaaacg ggctgatgct    780

gcaccaactg tatcc                                                      795


<210> SEQ ID NO 16
<211> LENGTH: 798
<212> TYPE: DNA
<213> ORGANISM: Artificial Sequence
<220> FEATURE:
<223> OTHER INFORMATION: Synthesized

<400> SEQUENCE: 16

gaggtccagc tggaggagtc aggggggaggc ttagtgaagc ctggagggtc cctgaaactc     60

tcctgtgcag cctctggatt cactttcagt ggctatgcca tgtcttgggt tcgccagact    120

ccggagaaga ggctggagtg ggtcgcaacc attagtagtg gtggtactta tatctactat    180

ccagacagtg tgaaggggcg attcaccatc tccagagaca atgccaagaa caccctgtac    240
```

-continued

```
ctgcaaatga gcagtctgag gtctgaggac acggccatgt attactgtgc aagacttggg    300

ggggataatt actacgaata cttcgatgtc tggggcgcag ggaccacggt caccgtctcc    360

tccgccaaaa cgacaccccc atctgtctat ggtggaggcg gatcaggtgg aggcggatca    420

ggtggaggcg gatcagacat tgtgatcaca cagtctacag cttccttagg tgtatctctg    480

gggcagaggg ccaccatctc atgcagggcc agcaaaagtg tcagtacatc tggctatagt    540

tatatgcact ggtaccaaca gagaccagga cagccaccca aactcctcat ctatcttgca    600

tccaacctag aatctggggt ccctgccagg ttcagtggca gtgggtctgg gacagacttc    660

accctcaaca tccatcctgt ggaggaggag gatgctgcaa cctattactg tcagcacagt    720

agggagcttc cgttcacgtt cggagggggg accaagctgg agataaaacg ggctgatgct    780

gcaccaactg tatcctgt                                                  798
```

<210> SEQ ID NO 17
<211> LENGTH: 267
<212> TYPE: PRT
<213> ORGANISM: Artificial Sequence
<220> FEATURE:
<223> OTHER INFORMATION: Synthesized

<400> SEQUENCE: 17

```
Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Thr Phe Ser Gly Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Leu Gly Gly Asp Asn Tyr Tyr Glu Tyr Phe Asp Val Trp Gly
            100                 105                 110

Ala Gly Thr Thr Val Thr Val Ser Ser Ala Lys Thr Thr Pro Pro Ser
        115                 120                 125

Val Tyr Gly Gly Gly Gly Ser Gly Gly Gly Gly Ser Gly Gly Gly Gly
    130                 135                 140

Ser Asp Ile Val Ile Thr Gln Ser Thr Ala Ser Leu Gly Val Ser Leu
145                 150                 155                 160

Gly Gln Arg Ala Thr Ile Ser Cys Arg Ala Ser Lys Ser Val Ser Thr
                165                 170                 175

Ser Gly Tyr Ser Tyr Met His Trp Tyr Gln Gln Arg Pro Gly Gln Pro
            180                 185                 190

Pro Lys Leu Leu Ile Tyr Leu Ala Ser Asn Leu Glu Ser Gly Val Pro
        195                 200                 205

Ala Arg Phe Ser Gly Ser Gly Ser Gly Thr Asp Phe Thr Leu Asn Ile
    210                 215                 220

His Pro Val Glu Glu Glu Asp Ala Ala Thr Tyr Tyr Cys Gln His Ser
225                 230                 235                 240

Arg Glu Leu Pro Phe Thr Phe Gly Gly Gly Thr Lys Leu Glu Ile Lys
                245                 250                 255
```

```
Arg Ala Asp Ala Ala Pro Thr Val Ser Val Asp
            260                 265


<210> SEQ ID NO 18
<211> LENGTH: 266
<212> TYPE: PRT
<213> ORGANISM: Artificial Sequence
<220> FEATURE:
<223> OTHER INFORMATION: Synthesized

<400> SEQUENCE: 18

Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Thr Phe Ser Gly Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Leu Gly Gly Asp Asn Tyr Tyr Glu Tyr Phe Asp Val Trp Gly
            100                 105                 110

Ala Gly Thr Thr Val Thr Val Ser Ser Ala Lys Thr Thr Pro Pro Ser
        115                 120                 125

Val Tyr Gly Gly Gly Gly Ser Gly Gly Gly Gly Ser Gly Gly Gly Gly
    130                 135                 140

Ser Asp Ile Val Ile Thr Gln Ser Thr Ala Ser Leu Gly Val Ser Leu
145                 150                 155                 160

Gly Gln Arg Ala Thr Ile Ser Cys Arg Ala Ser Lys Ser Val Ser Thr
                165                 170                 175

Ser Gly Tyr Ser Tyr Met His Trp Tyr Gln Gln Arg Pro Gly Gln Pro
            180                 185                 190

Pro Lys Leu Leu Ile Tyr Leu Ala Ser Asn Leu Glu Ser Gly Val Pro
        195                 200                 205

Ala Arg Phe Ser Gly Ser Gly Ser Gly Thr Asp Phe Thr Leu Asn Ile
    210                 215                 220

His Pro Val Glu Glu Glu Asp Ala Ala Thr Tyr Tyr Cys Gln His Ser
225                 230                 235                 240

Arg Glu Leu Pro Phe Thr Phe Gly Gly Gly Thr Lys Leu Glu Ile Lys
                245                 250                 255

Arg Ala Asp Ala Ala Pro Thr Val Ser Cys
            260                 265


<210> SEQ ID NO 19
<211> LENGTH: 393
<212> TYPE: DNA
<213> ORGANISM: Artificial Sequence
<220> FEATURE:
<223> OTHER INFORMATION: Synthesized

<400> SEQUENCE: 19

gaggttaagc tggaggagtc tgggggagac ttagtgaagc ctggagggtc cctgaaactc      60

tcctgtgcag cctctggatt cactttcagt agatatggca tgtcttgggt tcgccagact     120

ccagacaaga ggctggagtg ggtcgcaacc attagtagtg gtggtactta catctactat     180
```

-continued

```
ccagacagtg tgaaggggcg attcaccatc tccagagaca atgccaagaa caccctgtac    240

ctgcaaatga gcagtctgaa gtctgaggac acagccatgt attactgtgc aagggataac    300

tacggtagta gctacgacta tgctatggac tactggggtc aaggaacctc agtcaccgtc    360

tcctcagcca aaacaacagc cccatcggtc tat                                  393
```

<210> SEQ ID NO 20
<211> LENGTH: 131
<212> TYPE: PRT
<213> ORGANISM: Artificial Sequence
<220> FEATURE:
<223> OTHER INFORMATION: Synthesized

<400> SEQUENCE: 20

```
Glu Val Lys Leu Glu Glu Ser Gly Gly Asp Leu Val Lys Pro Gly Gly
1               5                   10                  15

Ser Leu Lys Leu Ser Cys Ala Ala Ser Gly Phe Thr Phe Ser Arg Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Asn Tyr Gly Ser Ser Tyr Asp Tyr Ala Met Asp Tyr Trp
            100                 105                 110

Gly Gln Gly Thr Ser Val Thr Val Ser Ser Ala Lys Thr Thr Ala Pro
        115                 120                 125

Ser Val Tyr
    130
```

<210> SEQ ID NO 21
<211> LENGTH: 456
<212> TYPE: DNA
<213> ORGANISM: Artificial Sequence
<220> FEATURE:
<223> OTHER INFORMATION: Synthesized

<400> SEQUENCE: 21

```
gaggtaaagc tggaggagtc tgggggagac ttagtgaagc ctggagggtc cctgaaactc    60

tcctgtgtag tctctggatt cactttcagt agatatggca tgtcttgggt tcgccagact   120

ccaggcaaga ggctggagtg gtcgcaacc attagtggtg gcggtactta catctactat    180

ccagacagtg tgaaggggcg attcaccatc tccagagaca atgccaagaa caccctgtac    240

ctgcaaatga gcagtctgaa gtctgaggac acagccatgt atcactgtac aagggataac    300

tacggtagga actacgacta cggtatggac tactggggtc aaggaacctc agtcaccgtc    360

tcctcagcca aaacaacagc cccatcggtc tatccactgg cccctgtgtg tggagataca    420

actggctcct cggtgactct aggatgcctg gtcaag                              456
```

<210> SEQ ID NO 22
<211> LENGTH: 152
<212> TYPE: PRT
<213> ORGANISM: Artificial Sequence
<220> FEATURE:
<223> OTHER INFORMATION: Synthesized

<400> SEQUENCE: 22

Glu Val Lys Leu Glu Glu Ser Gly Gly Asp Leu Val Lys Pro Gly Gly
1 5 10 15

Ser Leu Lys Leu Ser Cys Val Val Ser Gly Phe Thr Phe Ser Arg Tyr
20 25 30

Gly Met Ser Trp Val Arg Gln Thr Pro Gly Lys Arg Leu Glu Trp Val
35 40 45

Ala Thr Ile Ser Gly Gly Gly Thr Tyr Ile Tyr Tyr Pro Asp Ser Val
50 55 60

Lys Gly Arg Phe Thr Ile Ser Arg Asp Asn Ala Lys Asn Thr Leu Tyr
65 70 75 80

Leu Gln Met Ser Ser Leu Lys Ser Glu Asp Thr Ala Met Tyr His Cys
85 90 95

Thr Arg Asp Asn Tyr Gly Arg Asn Tyr Asp Tyr Gly Met Asp Tyr Trp
100 105 110

Gly Gln Gly Thr Ser Val Thr Val Ser Ser Ala Lys Thr Thr Ala Pro
115 120 125

Ser Val Tyr Pro Leu Ala Pro Val Cys Gly Asp Thr Thr Gly Ser Ser
130 135 140

Val Thr Leu Gly Cys Leu Val Lys
145 150

<210> SEQ ID NO 23
<211> LENGTH: 345
<212> TYPE: DNA
<213> ORGANISM: Artificial Sequence
<220> FEATURE:
<223> OTHER INFORMATION: Synthesized

<400> SEQUENCE: 23
gatattgtga tcacccagac tacagcaatc atgtctgcat ctccagggga ggaggtcacc 60
ctaacctgca gtgccacctc aagtgtaagt tacatacact ggttccagca gaggccaggc 120
acttctccca aactctggat ttatagcaca tccaacctgg cttctggagt ccctgttcgc 180
ttcagtggca gtggatatgg gacctcttac tctctcacaa tcagccgaat ggaggctgaa 240
gatgctgcca cttattactg ccagcaaagg agtagttccc cattcacgtt cggctcgggg 300
acaaagttgg aaataaaacg ggctgatgct gcaccaactg tatcc 345

<210> SEQ ID NO 24
<211> LENGTH: 115
<212> TYPE: PRT
<213> ORGANISM: Artificial Sequence
<220> FEATURE:
<223> OTHER INFORMATION: Synthesized

<400> SEQUENCE: 24

Asp Ile Val Ile Thr Gln Thr Thr Ala Ile Met Ser Ala Ser Pro Gly
1 5 10 15

Glu Glu Val Thr Leu Thr Cys Ser Ala Thr Ser Ser Val Ser Tyr Ile
20 25 30

His Trp Phe Gln Gln Arg Pro Gly Thr Ser Pro Lys Leu Trp Ile Tyr
35 40 45

Ser Thr Ser Asn Leu Ala Ser Gly Val Pro Val Arg Phe Ser Gly Ser
50 55 60

Gly Tyr Gly Thr Ser Tyr Ser Leu Thr Ile Ser Arg Met Glu Ala Glu
65 70 75 80

```
Asp Ala Ala Thr Tyr Tyr Cys Gln Gln Arg Ser Ser Ser Pro Phe Thr
                85                  90                  95

Phe Gly Ser Gly Thr Lys Leu Glu Ile Lys Arg Ala Asp Ala Ala Pro
            100                 105                 110

Thr Val Ser
        115
```

<210> SEQ ID NO 25
<211> LENGTH: 846
<212> TYPE: DNA
<213> ORGANISM: Artificial Sequence
<220> FEATURE:
<223> OTHER INFORMATION: Synthesized

<400> SEQUENCE: 25

```
gaggttaagc tggaggagtc tgggggagac ttagtgaagc ctggagggtc cctgaaactc     60

tcctgtgcag cctctggatt cactttcagt agatatggca tgtcttgggt tcgccagact    120

ccagacaaga ggctggagtg ggtcgcaacc attagtagtg gtggtactta catctactat    180

ccagacagtg tgaaggggcg attcaccatc tccagagaca atgccaagaa caccctgtac    240

ctgcaaatga gcagtctgaa gtctgaggac acagccatgt attactgtgc aagggataac    300

tacggtagta gctacgacta tgctatggac tactggggtc aaggaacctc agtcaccgtc    360

tcctcagcca aaacaacagc cccatcggtc tatccactgg cccctgtgtg tggagataca    420

actggctcct cggtgactct aggatgcctg gtcaagggtg gaggcggatc aggtggaggc    480

ggatcaggtg gaggcggatc agatattgtg atcacccaga ctacagcaat catgtctgca    540

tctccagggg aggaggtcac cctaacctgc agtgccacct caagtgtaag ttacatacac    600

tggttccagc agaggccagg cacttctccc aaactctgga tttatagcac atccaacctg    660

gcttctggag tccctgttcg cttcagtggc agtggatatg ggacctctta ctctctcaca    720

atcagccgaa tggaggctga agatgctgcc acttattact gccagcaaag gagtagttcc    780

ccattcacgt tcggctcggg gacaaagttg gaaataaaac gggctgatgc tgcaccaact    840

gtatcc                                                               846
```

<210> SEQ ID NO 26
<211> LENGTH: 849
<212> TYPE: DNA
<213> ORGANISM: Artificial Sequence
<220> FEATURE:
<223> OTHER INFORMATION: Synthesized

<400> SEQUENCE: 26

```
gaggttaagc tggaggagtc tgggggagac ttagtgaagc ctggagggtc cctgaaactc     60

tcctgtgcag cctctggatt cactttcagt agatatggca tgtcttgggt tcgccagact    120

ccagacaaga ggctggagtg ggtcgcaacc attagtagtg gtggtactta catctactat    180

ccagacagtg tgaaggggcg attcaccatc tccagagaca atgccaagaa caccctgtac    240

ctgcaaatga gcagtctgaa gtctgaggac acagccatgt attactgtgc aagggataac    300

tacggtagta gctacgacta tgctatggac tactggggtc aaggaacctc agtcaccgtc    360

tcctcagcca aaacaacagc cccatcggtc tatccactgg cccctgtgtg tggagataca    420

actggctcct cggtgactct aggatgcctg gtcaagggtg gaggcggatc aggtggaggc    480

ggatcaggtg gaggcggatc agatattgtg atcacccaga ctacagcaat catgtctgca    540

tctccagggg aggaggtcac cctaacctgc agtgccacct caagtgtaag ttacatacac    600
```

```
tggttccagc agaggccagg cacttctccc aaactctgga tttatagcac atccaacctg    660

gcttctggag tccctgttcg cttcagtggc agtggatatg ggacctctta ctctctcaca    720

atcagccgaa tggaggctga agatgctgcc acttattact gccagcaaag gagtagttcc    780

ccattcacgt tcggctcggg gacaaagttg gaaataaaac gggctgatgc tgcaccaact    840

gtatcctgt                                                            849
```

```
<210> SEQ ID NO 27
<211> LENGTH: 282
<212> TYPE: PRT
<213> ORGANISM: Artificial Sequence
<220> FEATURE:
<223> OTHER INFORMATION: Synthesized

<400> SEQUENCE: 27

Glu Val Lys Leu Glu Glu Ser Gly Gly Asp Leu Val Lys Pro Gly Gly
1               5                   10                  15

Ser Leu Lys Leu Ser Cys Ala Ala Ser Gly Phe Thr Phe Ser Arg Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Asn Tyr Gly Ser Ser Tyr Asp Tyr Ala Met Asp Tyr Trp
            100                 105                 110

Gly Gln Gly Thr Ser Val Thr Val Ser Ser Ala Lys Thr Thr Ala Pro
        115                 120                 125

Ser Val Tyr Pro Leu Ala Pro Val Cys Gly Asp Thr Thr Gly Ser Ser
    130                 135                 140

Val Thr Leu Gly Cys Leu Val Lys Gly Gly Gly Gly Ser Gly Gly Gly
145                 150                 155                 160

Gly Ser Gly Gly Gly Gly Ser Asp Ile Val Ile Thr Gln Thr Thr Ala
                165                 170                 175

Ile Met Ser Ala Ser Pro Gly Glu Glu Val Thr Leu Thr Cys Ser Ala
            180                 185                 190

Thr Ser Ser Val Ser Tyr Ile His Trp Phe Gln Gln Arg Pro Gly Thr
        195                 200                 205

Ser Pro Lys Leu Trp Ile Tyr Ser Thr Ser Asn Leu Ala Ser Gly Val
    210                 215                 220

Pro Val Arg Phe Ser Gly Ser Gly Tyr Gly Thr Ser Tyr Ser Leu Thr
225                 230                 235                 240

Ile Ser Arg Met Glu Ala Glu Asp Ala Ala Thr Tyr Tyr Cys Gln Gln
                245                 250                 255

Arg Ser Ser Ser Pro Phe Thr Phe Gly Ser Gly Thr Lys Leu Glu Ile
            260                 265                 270

Lys Arg Ala Asp Ala Ala Pro Thr Val Ser
        275                 280


<210> SEQ ID NO 28
<211> LENGTH: 283
<212> TYPE: PRT
```

<213> ORGANISM: Artificial Sequence
<220> FEATURE:
<223> OTHER INFORMATION: Synthesized

<400> SEQUENCE: 28

```
Glu Val Lys Leu Glu Glu Ser Gly Gly Asp Leu Val Lys Pro Gly Gly
1               5                   10                  15

Ser Leu Lys Leu Ser Cys Ala Ala Ser Gly Phe Thr Phe Ser Arg Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Asn Tyr Gly Ser Ser Tyr Asp Tyr Ala Met Asp Tyr Trp
            100                 105                 110

Gly Gln Gly Thr Ser Val Thr Val Ser Ser Ala Lys Thr Thr Ala Pro
        115                 120                 125

Ser Val Tyr Pro Leu Ala Pro Val Cys Gly Asp Thr Thr Gly Ser Ser
    130                 135                 140

Val Thr Leu Gly Cys Leu Val Lys Gly Gly Gly Gly Ser Gly Gly Gly
145                 150                 155                 160

Gly Ser Gly Gly Gly Gly Ser Asp Ile Val Ile Thr Gln Thr Thr Ala
                165                 170                 175

Ile Met Ser Ala Ser Pro Gly Glu Glu Val Thr Leu Thr Cys Ser Ala
            180                 185                 190

Thr Ser Ser Val Ser Tyr Ile His Trp Phe Gln Gln Arg Pro Gly Thr
        195                 200                 205

Ser Pro Lys Leu Trp Ile Tyr Ser Thr Ser Asn Leu Ala Ser Gly Val
    210                 215                 220

Pro Val Arg Phe Ser Gly Ser Gly Tyr Gly Thr Ser Tyr Ser Leu Thr
225                 230                 235                 240

Ile Ser Arg Met Glu Ala Glu Asp Ala Ala Thr Tyr Tyr Cys Gln Gln
                245                 250                 255

Arg Ser Ser Ser Pro Phe Thr Phe Gly Ser Gly Thr Lys Leu Glu Ile
            260                 265                 270

Lys Arg Ala Asp Ala Ala Pro Thr Val Ser Cys
        275                 280
```

<210> SEQ ID NO 29
<211> LENGTH: 846
<212> TYPE: DNA
<213> ORGANISM: Artificial Sequence
<220> FEATURE:
<223> OTHER INFORMATION: Synthesized

<400> SEQUENCE: 29

```
gaggtaaagc tggaggagtc tgggggagac ttagtgaagc ctggagggtc cctgaaactc      60

tcctgtgtag tctctggatt cactttcagt agatatggca tgtcttgggt tcgccagact     120

ccaggcaaga ggctggagtg ggtcgcaacc attagtggtg gcggtactta catctactat     180

ccagacagtg tgaaggggcg attcaccatc tccagagaca atgccaagaa caccctgtac     240

ctgcaaatga gcagtctgaa gtctgaggac acagccatgt atcactgtac aagggataac     300
```

```
tacggtagga actacgacta cggtatggac tactggggtc aaggaacctc agtcaccgtc    360

tcctcagcca aaacaacagc cccatcggtc tatccactgg cccctgtgtg tggagataca    420

actggctcct cggtgactct aggatgcctg gtcaagggtg gaggcggatc aggtggaggc    480

ggatcaggtg gaggcggatc agatattgtg atcacccaga ctacagcaat catgtctgca    540

tctccagggg aggaggtcac cctaacctgc agtgccacct caagtgtaag ttacatacac    600

tggttccagc agaggccagg cacttctccc aaactctgga tttatagcac atccaacctg    660

gcttctggag tccctgttcg cttcagtggc agtggatatg ggacctctta ctctctcaca    720

atcagccgaa tggaggctga agatgctgcc acttattact gccagcaaag gagtagttcc    780

ccattcacgt tcggctcggg gacaaagttg gaaataaaac gggctgatgc tgcaccaact    840

gtatcc                                                               846
```

<210> SEQ ID NO 30
<211> LENGTH: 849
<212> TYPE: DNA
<213> ORGANISM: Artificial Sequence
<220> FEATURE:
<223> OTHER INFORMATION: Synthesized

<400> SEQUENCE: 30

```
gaggtaaagc tggaggagtc tgggggagac ttagtgaagc ctggagggtc cctgaaactc     60

tcctgtgtag tctctggatt cactttcagt agatatggca tgtcttgggt tcgccagact    120

ccaggcaaga ggctggagtg ggtcgcaacc attagtggtg gcggtactta catctactat    180

ccagacagtg tgaaggggcg attcaccatc tccagagaca atgccaagaa caccctgtac    240

ctgcaaatga gcagtctgaa gtctgaggac acagccatgt atcactgtac aagggataac    300

tacggtagga actacgacta cggtatggac tactggggtc aaggaacctc agtcaccgtc    360

tcctcagcca aaacaacagc cccatcggtc tatccactgg cccctgtgtg tggagataca    420

actggctcct cggtgactct aggatgcctg gtcaagggtg gaggcggatc aggtggaggc    480

ggatcaggtg gaggcggatc agatattgtg atcacccaga ctacagcaat catgtctgca    540

tctccagggg aggaggtcac cctaacctgc agtgccacct caagtgtaag ttacatacac    600

tggttccagc agaggccagg cacttctccc aaactctgga tttatagcac atccaacctg    660

gcttctggag tccctgttcg cttcagtggc agtggatatg ggacctctta ctctctcaca    720

atcagccgaa tggaggctga agatgctgcc acttattact gccagcaaag gagtagttcc    780

ccattcacgt tcggctcggg gacaaagttg gaaataaaac gggctgatgc tgcaccaact    840

gtatcctgt                                                            849
```

<210> SEQ ID NO 31
<211> LENGTH: 282
<212> TYPE: PRT
<213> ORGANISM: Artificial Sequence
<220> FEATURE:
<223> OTHER INFORMATION: Synthesized

<400> SEQUENCE: 31

```
Glu Val Lys Leu Glu Glu Ser Gly Gly Asp Leu Val Lys Pro Gly Gly
1               5                   10                  15

Ser Leu Lys Leu Ser Cys Val Val Ser Gly Phe Thr Phe Ser Arg Tyr
            20                  25                  30

Gly Met Ser Trp Val Arg Gln Thr Pro Gly Lys Arg Leu Glu Trp Val
        35                  40                  45
```

Ala Thr Ile Ser Gly Gly Gly Thr Tyr Ile Tyr Tyr Pro Asp Ser Val
50 55 60

Lys Gly Arg Phe Thr Ile Ser Arg Asp Asn Ala Lys Asn Thr Leu Tyr
65 70 75 80

Leu Gln Met Ser Ser Leu Lys Ser Glu Asp Thr Ala Met Tyr His Cys
85 90 95

Thr Arg Asp Asn Tyr Gly Arg Asn Tyr Asp Tyr Gly Met Asp Tyr Trp
100 105 110

Gly Gln Gly Thr Ser Val Thr Val Ser Ser Ala Lys Thr Thr Ala Pro
115 120 125

Ser Val Tyr Pro Leu Ala Pro Val Cys Gly Asp Thr Thr Gly Ser Ser
130 135 140

Val Thr Leu Gly Cys Leu Val Lys Gly Gly Gly Gly Ser Gly Gly Gly
145 150 155 160

Gly Ser Gly Gly Gly Gly Ser Asp Ile Val Ile Thr Gln Thr Thr Ala
165 170 175

Ile Met Ser Ala Ser Pro Gly Glu Glu Val Thr Leu Thr Cys Ser Ala
180 185 190

Thr Ser Ser Val Ser Tyr Ile His Trp Phe Gln Gln Arg Pro Gly Thr
195 200 205

Ser Pro Lys Leu Trp Ile Tyr Ser Thr Ser Asn Leu Ala Ser Gly Val
210 215 220

Pro Val Arg Phe Ser Gly Ser Gly Tyr Gly Thr Ser Tyr Ser Leu Thr
225 230 235 240

Ile Ser Arg Met Glu Ala Glu Asp Ala Ala Thr Tyr Tyr Cys Gln Gln
245 250 255

Arg Ser Ser Ser Pro Phe Thr Phe Gly Ser Gly Thr Lys Leu Glu Ile
260 265 270

Lys Arg Ala Asp Ala Ala Pro Thr Val Ser
275 280

<210> SEQ ID NO 32
<211> LENGTH: 283
<212> TYPE: PRT
<213> ORGANISM: Artificial Sequence
<220> FEATURE:
<223> OTHER INFORMATION: Synthesized

<400> SEQUENCE: 32

Glu Val Lys Leu Glu Glu Ser Gly Gly Asp Leu Val Lys Pro Gly Gly
1 5 10 15

Ser Leu Lys Leu Ser Cys Val Val Ser Gly Phe Thr Phe Ser Arg Tyr
20 25 30

Gly Met Ser Trp Val Arg Gln Thr Pro Gly Lys Arg Leu Glu Trp Val
35 40 45

Ala Thr Ile Ser Gly Gly Gly Thr Tyr Ile Tyr Tyr Pro Asp Ser Val
50 55 60

Lys Gly Arg Phe Thr Ile Ser Arg Asp Asn Ala Lys Asn Thr Leu Tyr
65 70 75 80

Leu Gln Met Ser Ser Leu Lys Ser Glu Asp Thr Ala Met Tyr His Cys
85 90 95

Thr Arg Asp Asn Tyr Gly Arg Asn Tyr Asp Tyr Gly Met Asp Tyr Trp
100 105 110

Gly Gln Gly Thr Ser Val Thr Val Ser Ser Ala Lys Thr Thr Ala Pro
115 120 125

-continued

```
Ser Val Tyr Pro Leu Ala Pro Val Cys Gly Asp Thr Thr Gly Ser Ser
    130                 135                 140

Val Thr Leu Gly Cys Leu Val Lys Gly Gly Gly Gly Ser Gly Gly Gly
145                 150                 155                 160

Gly Ser Gly Gly Gly Gly Ser Asp Ile Val Ile Thr Gln Thr Thr Ala
                165                 170                 175

Ile Met Ser Ala Ser Pro Gly Glu Glu Val Thr Leu Thr Cys Ser Ala
            180                 185                 190

Thr Ser Ser Val Ser Tyr Ile His Trp Phe Gln Gln Arg Pro Gly Thr
        195                 200                 205

Ser Pro Lys Leu Trp Ile Tyr Ser Thr Ser Asn Leu Ala Ser Gly Val
    210                 215                 220

Pro Val Arg Phe Ser Gly Ser Gly Tyr Gly Thr Ser Tyr Ser Leu Thr
225                 230                 235                 240

Ile Ser Arg Met Glu Ala Glu Asp Ala Ala Thr Tyr Tyr Cys Gln Gln
                245                 250                 255

Arg Ser Ser Ser Pro Phe Thr Phe Gly Ser Gly Thr Lys Leu Glu Ile
            260                 265                 270

Lys Arg Ala Asp Ala Ala Pro Thr Val Ser Cys
        275                 280


<210> SEQ ID NO 33
<211> LENGTH: 38
<212> TYPE: DNA
<213> ORGANISM: Artificial Sequence
<220> FEATURE:
<223> OTHER INFORMATION: Synthesized

<400> SEQUENCE: 33

gggaattcca ccatggratg sagctgkgtm atsctctt                              38


<210> SEQ ID NO 34
<211> LENGTH: 38
<212> TYPE: DNA
<213> ORGANISM: Artificial Sequence
<220> FEATURE:
<223> OTHER INFORMATION: Synthesized

<400> SEQUENCE: 34

gggaattcca ccatgractt cgggytgagc tkggtttt                              38


<210> SEQ ID NO 35
<211> LENGTH: 37
<212> TYPE: DNA
<213> ORGANISM: Artificial Sequence
<220> FEATURE:
<223> OTHER INFORMATION: Synthesized

<400> SEQUENCE: 35

gggaattcca ccatggctgt cttggggctg ctcttct                               37


<210> SEQ ID NO 36
<211> LENGTH: 30
<212> TYPE: DNA
<213> ORGANISM: Artificial Sequence
<220> FEATURE:
<223> OTHER INFORMATION: Synthesized

<400> SEQUENCE: 36

gggaattcca ccatggrcag rcttacwtyy                                       30
```

-continued

<210> SEQ ID NO 37
<211> LENGTH: 31
<212> TYPE: DNA
<213> ORGANISM: Artificial Sequence
<220> FEATURE:
<223> OTHER INFORMATION: Synthesized

<400> SEQUENCE: 37
ctacctcgag ckyggtsytg ctggcygggt g 31

<210> SEQ ID NO 38
<211> LENGTH: 38
<212> TYPE: DNA
<213> ORGANISM: Artificial Sequence
<220> FEATURE:
<223> OTHER INFORMATION: Synthesized

<400> SEQUENCE: 38
gggaattcca ccatggattt tcaggtgcag attttcag 38

<210> SEQ ID NO 39
<211> LENGTH: 38
<212> TYPE: DNA
<213> ORGANISM: Artificial Sequence
<220> FEATURE:
<223> OTHER INFORMATION: Synthesized

<400> SEQUENCE: 39
gggaattcca ccatggattt tcaggtgcag attttcag 38

<210> SEQ ID NO 40
<211> LENGTH: 39
<212> TYPE: DNA
<213> ORGANISM: Artificial Sequence
<220> FEATURE:
<223> OTHER INFORMATION: Synthesized

<400> SEQUENCE: 40
gggaattcca ccatgragtc acakacycag gtcttyrta 39

<210> SEQ ID NO 41
<211> LENGTH: 39
<212> TYPE: DNA
<213> ORGANISM: Artificial Sequence
<220> FEATURE:
<223> OTHER INFORMATION: Synthesized

<400> SEQUENCE: 41
gggaattcca ccatgaggkc cccwgctcag ytyctkggr 39

<210> SEQ ID NO 42
<211> LENGTH: 36
<212> TYPE: DNA
<213> ORGANISM: Artificial Sequence
<220> FEATURE:
<223> OTHER INFORMATION: Synthesized

<400> SEQUENCE: 42
gggaattcca ccatgaagtt gcctgttagg ctgttg 36

<210> SEQ ID NO 43
<211> LENGTH: 34
<212> TYPE: DNA
<213> ORGANISM: Artificial Sequence
<220> FEATURE:
<223> OTHER INFORMATION: Synthesized

<400> SEQUENCE: 43
gggaattcca ccatgatgag tcctgcccag ttcc 34

<210> SEQ ID NO 44
<211> LENGTH: 33
<212> TYPE: DNA
<213> ORGANISM: Artificial Sequence
<220> FEATURE:
<223> OTHER INFORMATION: Synthesized

<400> SEQUENCE: 44
ctacctcgag ttaacactca ttcctgttga agc 33

<210> SEQ ID NO 45
<211> LENGTH: 639
<212> TYPE: DNA
<213> ORGANISM: Artificial Sequence
<220> FEATURE:
<223> OTHER INFORMATION: Synthesized

<400> SEQUENCE: 45
gaggtccagc tggaggagtc tgggggaggc ttagtgaagc ctggagggtc cctgaaactc 60
tcctgtgcag cctctggatt cactttcagt ggctatgcca tgtcttgggt tcgccagact 120
ccggagaaga ggctggagtg ggtcgcaacc attagtagtg gtggtactta tatctactat 180
ccagacagtg tgaaggggcg attcaccatc tccagagaca atgccaagaa caccctgtac 240
ctgcaaatga gcagtctgag gtctgaggac acggccatgt attactgtgc aagacttggg 300
ggggataatt actacgaata cttcgatgtc tggggcgcag ggaccacggt caccgtctcc 360
tccgccaaaa cgacaccccc atctgtctat ccactggccc ctggatctgc tgcccaaact 420
aactccatgg tgaccctggg atgcctggtc aagggctatt tccctgagcc agtgacagtg 480
acctggaact ctggatccct gtccagcggt gtgcacacct tcccagctgt cctgcagtct 540
gacctctaca ctctgagcag ctcagtgact gtcccctcca gcacctggcc cagcgagacc 600
gtcacctgca acgttgccca cccagccagc aggaccgcg 639

<210> SEQ ID NO 46
<211> LENGTH: 654
<212> TYPE: DNA
<213> ORGANISM: Artificial Sequence
<220> FEATURE:
<223> OTHER INFORMATION: Synthesized

<400> SEQUENCE: 46
gacattgtga tcacacagtc tacagcttcc ttaggtgtat ctctggggca gagggccacc 60
atctcatgca gggccagcaa aagtgtcagt acatctggct atagttatat gcactggtac 120
caacagagac caggacagcc acccaaactc ctcatctatc ttgcatccaa cctagaatct 180
ggggtccctg ccaggttcag tggcagtggg tctgggacag acttcaccct caacatccat 240
cctgtggagg aggaggatgc tgcaacctat tactgtcagc acagtaggga gcttccgttc 300
acgttcggag gggggaccaa gctggagata aaacgggctg atgctgcacc aactgtatcc 360
atcttcccac catccagtga gcagttaaca tctggaggtg cctcagtcgt gtgcttcttg 420
aacaacttct accccaaaga catcaatgtc aagtggaaga ttgatggcag tgaacgacaa 480
aatggcgtcc tgaacagttg gactgatcag gacagcaaag acagcaccta cagcatgagc 540
agcaccctca cgttgaccaa ggacgagtat gaacgacata acagctatac ctgtgaggcc 600
actcacaaga catcaacttc acccattgtc aagagcttca acaggaatga gtgt 654

<210> SEQ ID NO 47
<211> LENGTH: 213
<212> TYPE: PRT
<213> ORGANISM: Artificial Sequence
<220> FEATURE:
<223> OTHER INFORMATION: Synthesized

<400> SEQUENCE: 47

```
Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Thr Phe Ser Gly Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Leu Gly Gly Asp Asn Tyr Tyr Glu Tyr Phe Asp Val Trp Gly
            100                 105                 110

Ala Gly Thr Thr Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Arg Thr Ala
    210
```

<210> SEQ ID NO 48
<211> LENGTH: 218
<212> TYPE: PRT
<213> ORGANISM: Artificial Sequence
<220> FEATURE:
<223> OTHER INFORMATION: Synthesized

<400> SEQUENCE: 48

```
Asp Ile Val Ile Thr Gln Ser Thr Ala Ser Leu Gly Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Arg Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80
```

-continued

```
Pro Val Glu Glu Glu Asp Ala Ala Thr Tyr Tyr Cys Gln His Ser Arg
                85                  90                  95

Glu Leu Pro Phe Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

```
<210> SEQ ID NO 49
<211> LENGTH: 107
<212> TYPE: PRT
<213> ORGANISM: Artificial Sequence
<220> FEATURE:
<223> OTHER INFORMATION: Synthesized

<400> SEQUENCE: 49

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

```
<210> SEQ ID NO 50
<211> LENGTH: 106
<212> TYPE: PRT
<213> ORGANISM: Artificial Sequence
<220> FEATURE:
<223> OTHER INFORMATION: Synthesized

<400> SEQUENCE: 50

Phe Asp Val Trp Gly Ala Gly Thr Thr Val Thr Val Ser Ser Ala Lys
1               5                   10                  15

Thr Thr Pro Pro Ser Val Tyr Pro Leu Ala Pro Gly Ser Ala Ala Gln
            20                  25                  30

Thr Asn Ser Met Val Thr Leu Gly Cys Leu Val Lys Gly Tyr Phe Pro
        35                  40                  45

Glu Pro Val Thr Val Thr Trp Asn Ser Gly Ser Leu Ser Ser Gly Val
    50                  55                  60
```

His Thr Phe Pro Ala Val Leu Gln Ser Asp Leu Tyr Thr Leu Ser Ser
65 70 75 80

Ser Val Thr Val Pro Ser Ser Thr Trp Pro Ser Glu Thr Val Thr Cys
85 90 95

Asn Val Ala His Pro Ala Ser Arg Thr Ala
100 105

<210> SEQ ID NO 51
<211> LENGTH: 115
<212> TYPE: PRT
<213> ORGANISM: Artificial Sequence
<220> FEATURE:
<223> OTHER INFORMATION: Synthesized

<400> SEQUENCE: 51

Asp Ile Val Leu Thr Gln Ser Thr Glu Ile Met Ser Ala Ser Pro Gly
1 5 10 15

Glu Lys Val Thr Ile Thr Cys Ser Ala Ser Ser Ser Ile Ser Tyr Ile
20 25 30

His Trp Phe Gln Gln Lys Pro Gly Thr Ser Pro Lys Leu Trp Ile Phe
35 40 45

Gly Thr Ser Asn Leu Ala Ser Gly Val Pro Ala Arg Phe Ser Gly Ser
50 55 60

Gly Ser Gly Thr Ser Tyr Ser Leu Thr Val Ser Arg Met Glu Ala Glu
65 70 75 80

Asp Thr Ala Thr Tyr Tyr Cys Gln Gln Arg Ser Asn Tyr Pro Phe Thr
85 90 95

Phe Gly Ser Gly Thr Lys Leu Gln Ile Lys Arg Ala Asp Ala Ala Pro
100 105 110

Thr Val Ser
115

<210> SEQ ID NO 52
<211> LENGTH: 115
<212> TYPE: PRT
<213> ORGANISM: Artificial Sequence
<220> FEATURE:
<223> OTHER INFORMATION: Synthesized

<400> SEQUENCE: 52

Asp Ile Val Met Thr Gln Ser Pro Ala Ile Met Ser Ala Ser Pro Gly
1 5 10 15

Glu Lys Val Thr Met Thr Cys Ser Ala Ser Ser Ser Val Ser Tyr Met
20 25 30

His Trp Phe Gln Gln Lys Pro Gly Thr Ser Pro Lys Leu Trp Ile Tyr
35 40 45

Ser Thr Ser Asn Leu Ala Ser Gly Ala Pro Ala Arg Phe Ser Gly Ser
50 55 60

Gly Ser Gly Thr Ser Tyr Ser Leu Thr Val Ser Arg Met Glu Ser Glu
65 70 75 80

Asp Ala Ala Thr Tyr Tyr Cys Gln Gln Arg Ser Ser Tyr Pro Ser Thr
85 90 95

Phe Gly Gly Gly Thr Lys Leu Glu Ile Lys Arg Ala Asp Ala Ala Pro
100 105 110

Thr Val Ser
115

<210> SEQ ID NO 53
<211> LENGTH: 115
<212> TYPE: PRT
<213> ORGANISM: Artificial Sequence
<220> FEATURE:
<223> OTHER INFORMATION: Synthesized

<400> SEQUENCE: 53

```
Asp Ile Val Leu Thr Gln Thr Thr Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Tyr Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Ser Thr
                85                  90                  95

Phe Gly Gly Gly Thr Lys Leu Glu Ile Lys Arg Ala Asp Ala Ala Pro
            100                 105                 110

Thr Val Ser
        115
```

<210> SEQ ID NO 54
<211> LENGTH: 115
<212> TYPE: PRT
<213> ORGANISM: Artificial Sequence
<220> FEATURE:
<223> OTHER INFORMATION: Synthesized

<400> SEQUENCE: 54

```
Asp Ile Val Ile Thr Gln Ser Thr Ala Ile Met Ser Ala Ser Pro Gly
1               5                   10                  15

Glu Lys Val Thr Ile Thr Cys Ser Ala Ser Ser Ser Val Ser Tyr Thr
            20                  25                  30

Tyr Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Ser Thr
                85                  90                  95

Phe Gly Gly Gly Thr Lys Leu Glu Ile Lys Arg Ala Asp Ala Ala Pro
            100                 105                 110

Thr Val Ser
        115
```

<210> SEQ ID NO 55
<211> LENGTH: 115
<212> TYPE: PRT
<213> ORGANISM: Artificial Sequence
<220> FEATURE:
<223> OTHER INFORMATION: Synthesized

<400> SEQUENCE: 55

```
Asp Ile Val Ile Thr Gln Thr Pro Ala Ile Met Ser Ala Ser Pro Gly
1               5                   10                  15
```

Glu Lys Val Thr Met Thr Cys Ser Ala Ser Ser Ser Val Ser Tyr Met
20 25 30

His Trp Phe Gln Gln Lys Pro Gly Thr Ser Pro Lys Leu Trp Ile Tyr
35 40 45

Ser Thr Ser Asn Leu Ala Ser Gly Val Pro Ala Arg Phe Ser Gly Ser
50 55 60

Gly Ser Gly Thr Ser Tyr Ser Leu Thr Val Ser Arg Met Glu Ser Glu
65 70 75 80

Asp Ala Ala Thr Tyr Tyr Cys Gln Gln Arg Ser Ser Tyr Pro Ser Thr
85 90 95

Phe Gly Gly Gly Thr Lys Leu Glu Ile Lys Arg Ala Asp Ala Ala Pro
100 105 110

Thr Val Ser
115

<210> SEQ ID NO 56
<211> LENGTH: 115
<212> TYPE: PRT
<213> ORGANISM: Artificial Sequence
<220> FEATURE:
<223> OTHER INFORMATION: Synthesized

<400> SEQUENCE: 56

Asp Ile Val Leu Thr Gln Ser Thr Ala Ile Met Ser Ala Ser Pro Gly
1 5 10 15

Glu Lys Val Thr Met Thr Cys Ser Ala Ser Ser Ser Val Ser Tyr Met
20 25 30

His Trp Phe Gln Gln Lys Pro Gly Thr Ser Pro Lys Leu Trp Ile Tyr
35 40 45

Ser Thr Ser Asn Leu Ala Ser Gly Val Pro Ala Arg Phe Ser Gly Ser
50 55 60

Gly Ser Gly Thr Ser Tyr Ser Leu Thr Val Ser Arg Met Glu Ser Glu
65 70 75 80

Asp Ala Ala Thr Tyr Tyr Cys Gln Gln Arg Ser Ser Tyr Pro Ser Thr
85 90 95

Phe Gly Gly Gly Thr Lys Leu Glu Ile Lys Arg Ala Asp Ala Ala Pro
100 105 110

Thr Val Ser
115

<210> SEQ ID NO 57
<211> LENGTH: 115
<212> TYPE: PRT
<213> ORGANISM: Artificial Sequence
<220> FEATURE:
<223> OTHER INFORMATION: Synthesized

<400> SEQUENCE: 57

Asp Ile Val Met Thr Gln Ser Pro Glu Ile Met Ser Ala Ser Pro Gly
1 5 10 15

Glu Lys Val Thr Ile Thr Cys Ser Ala Ser Ser Ser Ile Ser Tyr Ile
20 25 30

His Trp Phe Gln Gln Lys Pro Gly Thr Ser Pro Lys Leu Trp Ile Phe
35 40 45

Gly Thr Ser Asn Leu Ala Ser Gly Val Pro Ala Arg Phe Ser Gly Ser
50 55 60

Gly Ser Gly Thr Ser Tyr Ser Leu Thr Val Ser Arg Met Glu Ala Glu

```
65                  70                  75                  80

Asp Thr Ala Thr Tyr Tyr Cys Gln Gln Arg Ser Asn Tyr Pro Phe Thr
                85                  90                  95

Phe Gly Ser Gly Thr Lys Leu Gln Ile Lys Arg Ala Asp Ala Ala Pro
            100                 105                 110

Thr Val Ser
        115
```

```
<210> SEQ ID NO 58
<211> LENGTH: 115
<212> TYPE: PRT
<213> ORGANISM: Artificial Sequence
<220> FEATURE:
<223> OTHER INFORMATION: Synthesized

<400> SEQUENCE: 58

Asp Ile Val Ile Thr Gln Ser Thr Glu Ile Met Ser Ala Ser Pro Gly
1               5                   10                  15

Glu Lys Val Thr Ile Thr Cys Ser Ala Ser Ser Ser Ile Ser Tyr Ile
            20                  25                  30

His Trp Phe Gln Gln Lys Pro Gly Thr Ser Pro Lys Leu Trp Ile Phe
        35                  40                  45

Gly Thr Ser Asn Leu Ala Ser Gly Val Pro Ala Arg Phe Ser Gly Ser
    50                  55                  60

Gly Ser Gly Thr Ser Tyr Ser Leu Thr Val Ser Arg Met Glu Ala Glu
65                  70                  75                  80

Asp Thr Ala Thr Tyr Tyr Cys Gln Gln Arg Ser Asn Tyr Pro Phe Thr
                85                  90                  95

Phe Gly Ser Gly Thr Lys Leu Gln Ile Lys Arg Ala Asp Ala Ala Pro
            100                 105                 110

Thr Val Ser
        115
```

```
<210> SEQ ID NO 59
<211> LENGTH: 130
<212> TYPE: PRT
<213> ORGANISM: Artificial Sequence
<220> FEATURE:
<223> OTHER INFORMATION: Synthesized

<400> SEQUENCE: 59

Glu Val Lys Leu Gln Glu Ser Gly Pro Glu Leu Lys Lys Pro Gly Glu
1               5                   10                  15

Thr Val Glu Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Gly Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Thr Leu Lys Asn Glu Asp Thr Ala Thr Tyr Phe Cys
                85                  90                  95

Ala Arg Ser Gly Asp Gly Tyr Trp Tyr Tyr Ala Met Asp Tyr Trp Gly
            100                 105                 110

Gln Gly Thr Ser Val Thr Val Ser Ser Ala Lys Thr Thr Pro Pro Ser
        115                 120                 125
```

Val Tyr
130

<210> SEQ ID NO 60
<211> LENGTH: 130
<212> TYPE: PRT
<213> ORGANISM: Artificial Sequence
<220> FEATURE:
<223> OTHER INFORMATION: Synthesized

<400> SEQUENCE: 60

Glu Val Gln Leu Gln Gln Ser Gly Pro Glu Leu Lys Lys Pro Gly Glu
1 5 10 15

Thr Val Lys Ile Ser Cys Lys Ala Ser Gly Tyr Thr Phe Thr Asn Tyr
20 25 30

Gly Met Asn Trp Val Lys Gln Ala Pro Gly Lys Gly Leu Lys Trp Met
35 40 45

Gly Trp Ile Asn Thr Tyr Thr Gly Glu Pro Thr Tyr Ala Gly Asp Phe
50 55 60

Lys Gly Arg Phe Ala Phe Ser Leu Glu Thr Ser Ala Ser Thr Ala Tyr
65 70 75 80

Leu Gln Ile Asn Thr Leu Lys Asn Glu Asp Thr Ala Thr Tyr Phe Cys
85 90 95

Ala Arg Ser Gly Asp Gly Tyr Trp Tyr Tyr Ala Met Asp Tyr Trp Gly
100 105 110

Gln Gly Thr Ser Val Thr Val Ser Ser Ala Lys Thr Thr Pro Pro Ser
115 120 125

Val Tyr
130

<210> SEQ ID NO 61
<211> LENGTH: 130
<212> TYPE: PRT
<213> ORGANISM: Artificial Sequence
<220> FEATURE:
<223> OTHER INFORMATION: Synthesized

<400> SEQUENCE: 61

Gln Val Gln Leu Gln Glu Ser Gly Pro Glu Leu Lys Gln Pro Gly Glu
1 5 10 15

Thr Val Lys Ile Ser Cys Lys Ala Ser Gly Tyr Thr Phe Thr Asn Asn
20 25 30

Gly Met Asn Trp Val Lys Gln Ala Pro Gly Lys Gly Leu Lys Trp Met
35 40 45

Gly Trp Ile Asn Thr Tyr Thr Gly Glu Pro Thr Tyr Ala Asp Asp Phe
50 55 60

Lys Gly Arg Phe Ala Phe Ser Leu Asp Thr Ser Ala Ser Thr Ala Tyr
65 70 75 80

Leu Gln Ile Asn Asn Leu Lys Asn Glu Asp Met Ala Thr Tyr Phe Cys
85 90 95

Ala Arg Thr Gly Thr Ala Arg Ala Phe Tyr Ala Met Asp Tyr Trp Gly
100 105 110

Gln Gly Thr Ser Val Thr Val Ser Ser Thr Lys Thr Thr Ala Pro Ser
115 120 125

Val Tyr
130

<210> SEQ ID NO 62

<211> LENGTH: 130
<212> TYPE: PRT
<213> ORGANISM: Artificial Sequence
<220> FEATURE:
<223> OTHER INFORMATION: Synthesized

<400> SEQUENCE: 62

```
Gln Val Gln Leu Gln Gln Ser Gly Pro Glu Leu Lys Gln Pro Gly Glu
1               5                   10                  15

Thr Val Lys Ile Ser Cys Lys Ala Ser Gly Tyr Thr Phe Thr Asn Asn
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Gly Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Thr Gly Thr Ala Arg Ala Phe Tyr Ala Met Asp Tyr Trp Gly
            100                 105                 110

Gln Gly Thr Ser Val Thr Val Ser Ser Thr Lys Thr Thr Ala Pro Ser
        115                 120                 125

Val Tyr
    130
```

<210> SEQ ID NO 63
<211> LENGTH: 130
<212> TYPE: PRT
<213> ORGANISM: Artificial Sequence
<220> FEATURE:
<223> OTHER INFORMATION: Synthesized

<400> SEQUENCE: 63

```
Glu Val Gln Leu Glu Gln Ser Gly Pro Glu Leu Lys Lys Pro Gly Glu
1               5                   10                  15

Thr Val Lys Ile Ser Cys Lys Ala Ser Gly Tyr Thr Phe Ile Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Val Asp Asp Phe
    50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Met Ala Thr Tyr Phe Cys
                85                  90                  95

Ala Arg Thr Gly Thr Thr Ala Ile Leu Asn Gly Met Asp Tyr Trp Gly
            100                 105                 110

Gln Gly Thr Ser Val Thr Val Ser Ser Ala Lys Thr Thr Pro Pro Ser
        115                 120                 125

Val Tyr
    130
```

<210> SEQ ID NO 64
<211> LENGTH: 130
<212> TYPE: PRT
<213> ORGANISM: Artificial Sequence
<220> FEATURE:
<223> OTHER INFORMATION: Synthesized

<400> SEQUENCE: 64

Glu Val Gln Leu Gln Gln Ser Gly Pro Glu Leu Lys Lys Pro Gly Glu
1 5 10 15

Thr Val Lys Ile Ser Cys Lys Ala Ser Gly Tyr Thr Phe Thr Asn Tyr
20 25 30

Gly Met Asn Trp Val Lys Gln Ala Pro Gly Lys Gly Leu Lys Trp Met
35 40 45

Gly Trp Ile Asn Thr Tyr Thr Gly Glu Pro Thr Tyr Ala Gly Asp Phe
50 55 60

Lys Gly Arg Phe Ala Phe Ser Leu Glu Thr Ser Ala Ser Thr Ala Tyr
65 70 75 80

Leu Gln Ile Asn Thr Leu Lys Asn Glu Asp Thr Ala Thr Tyr Phe Cys
85 90 95

Ala Arg Ser Gly Asp Gly Tyr Trp Tyr Tyr Ala Met Asp Tyr Trp Gly
100 105 110

Gln Gly Thr Ser Val Thr Val Ser Ser Ala Lys Thr Thr Pro Pro Ser
115 120 125

Val Tyr
130

<210> SEQ ID NO 65
<211> LENGTH: 130
<212> TYPE: PRT
<213> ORGANISM: Artificial Sequence
<220> FEATURE:
<223> OTHER INFORMATION: Synthesized

<400> SEQUENCE: 65

Glu Val Lys Leu Glu Glu Ser Gly Pro Glu Leu Lys Lys Pro Gly Glu
1 5 10 15

Thr Val Lys Ile Ser Cys Lys Ala Ser Gly Tyr Thr Phe Ile Asn Tyr
20 25 30

Gly Met Asn Trp Val Lys Gln Ala Pro Gly Lys Gly Leu Lys Trp Met
35 40 45

Gly Trp Ile Asn Thr Tyr Thr Gly Glu Pro Thr Tyr Val Asp Asp Phe
50 55 60

Lys Gly Arg Phe Ala Phe Ser Leu Glu Thr Ser Ala Arg Thr Ala Tyr
65 70 75 80

Leu Gln Ile Asn Asn Leu Lys Asn Glu Asp Met Ala Thr Tyr Phe Cys
85 90 95

Ala Arg Thr Gly Thr Thr Ala Ile Leu Asn Gly Met Asp Tyr Trp Gly
100 105 110

Gln Gly Thr Ser Val Thr Val Ser Ser Ala Lys Thr Thr Pro Pro Ser
115 120 125

Val Tyr
130

<210> SEQ ID NO 66
<211> LENGTH: 124
<212> TYPE: PRT
<213> ORGANISM: Artificial Sequence
<220> FEATURE:
<223> OTHER INFORMATION: Synthesized

<400> SEQUENCE: 66

Glu Val Gln Leu Glu Gln Ser Gly Ala Glu Leu Val Arg Pro Gly Ala
1 5 10 15

```
Ser Val Lys Leu Ser Cys Lys Ala Leu Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile His Pro Gly Ser Gly Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Asn Tyr Gly Ser Phe Ala Tyr Trp Gly Gln Gly Thr Leu Val Thr
            100                 105                 110

Val Ser Ala Ala Lys Thr Thr Pro Pro Ser Val Tyr
        115                 120


<210> SEQ ID NO 67
<211> LENGTH: 130
<212> TYPE: PRT
<213> ORGANISM: Artificial Sequence
<220> FEATURE:
<223> OTHER INFORMATION: Synthesized

<400> SEQUENCE: 67

Arg Cys Arg Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Ile Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Val Asp Asp Phe
    50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Met Ala Thr Tyr Phe Cys
                85                  90                  95

Ala Arg Thr Gly Thr Thr Ala Ile Leu Asn Gly Met Asp Tyr Trp Gly
            100                 105                 110

Gln Gly Thr Ser Val Thr Val Ser Ser Ala Lys Thr Thr Pro Pro Ser
        115                 120                 125

Cys Leu
    130


<210> SEQ ID NO 68
<211> LENGTH: 130
<212> TYPE: PRT
<213> ORGANISM: Artificial Sequence
<220> FEATURE:
<223> OTHER INFORMATION: Synthesized

<400> SEQUENCE: 68

Glu Val Gln Leu Glu Gln Ser Gly Pro Glu Leu Lys Lys Pro Gly Glu
1               5                   10                  15

Thr Val Lys Ile Ser Cys Lys Ala Ser Gly Tyr Thr Phe Ile Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Val Asp Asp Phe
```

50 55 60

Lys Gly Arg Phe Ala Phe Ser Leu Glu Thr Ser Ala Arg Thr Ala Tyr
65 70 75 80

Leu Gln Ile Asn Asn Leu Lys Asn Glu Asp Met Ala Thr Tyr Phe Cys
85 90 95

Ala Arg Thr Gly Thr Thr Ala Ile Leu Asn Gly Met Asp Tyr Trp Gly
100 105 110

Gln Gly Thr Ser Val Thr Val Ser Ser Ala Lys Thr Thr Pro Pro Ser
115 120 125

Val Tyr
130

<210> SEQ ID NO 69
<211> LENGTH: 113
<212> TYPE: PRT
<213> ORGANISM: Artificial Sequence
<220> FEATURE:
<223> OTHER INFORMATION: Synthesized

<400> SEQUENCE: 69

Asp Ile Gln Met Thr Gln Ser Pro Ser Ser Leu Ser Ala Ser Leu Gly
1 5 10 15

Glu Arg Val Ser Leu Thr Cys Arg Ala Ser Gln Asp Ile Gly Ser Ser
20 25 30

Leu Asn Trp Leu Gln Gln Glu Pro Asp Gly Thr Ile Lys Arg Leu Ile
35 40 45

Tyr Ala Thr Ser Ser Leu Asp Ser Gly Val Pro Lys Arg Phe Ser Gly
50 55 60

Ser Arg Ser Gly Ser Asp Tyr Ser Leu Thr Ile Ser Ser Leu Glu Ser
65 70 75 80

Glu Asp Phe Val Asp Tyr Tyr Cys Leu Gln Tyr Ala Ser Ser Pro His
85 90 95

Val Arg Cys Trp Asp Gln Ala Gly Ala Glu Thr Gly Cys Cys Thr Asn
100 105 110

Cys

<210> SEQ ID NO 70
<211> LENGTH: 107
<212> TYPE: PRT
<213> ORGANISM: Artificial Sequence
<220> FEATURE:
<223> OTHER INFORMATION: Synthesized

<400> SEQUENCE: 70

Asp Ile Val Leu Thr Gln Ser Pro Ala Ser Leu Ala Val Ser Leu Gly
1 5 10 15

Gln Arg Ala Thr Ile Ser Tyr Arg Ala Ser Lys Ser Val Ser Thr Ser
20 25 30

Gly Tyr Ser Tyr Met His Trp Asn Gln Gln Lys Pro Gly Gln Pro Pro
35 40 45

Arg Leu Leu Ile Tyr Leu Val Ser Asn Leu Glu Ser Gly Val Pro Ala
50 55 60

Arg Phe Ser Gly Ser Gly Ser Gly Thr Asp Phe Thr Leu Asn Ile His
65 70 75 80

Pro Val Glu Glu Glu Asp Ala Ala Thr Tyr Tyr Cys Gln His Ile Arg
85 90 95

Glu Leu Thr Arg Ser Glu Gly Gly Pro Ser Trp

```
            100                 105


<210> SEQ ID NO 71
<211> LENGTH: 115
<212> TYPE: PRT
<213> ORGANISM: Artificial Sequence
<220> FEATURE:
<223> OTHER INFORMATION: Synthesized

<400> SEQUENCE: 71

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Trp
                85                  90                  95

Thr Phe Gly Gly Gly Thr Lys Leu Glu Ile Lys Arg Ala Asp Ala Ala
            100                 105                 110

Pro Thr Val
        115


<210> SEQ ID NO 72
<211> LENGTH: 107
<212> TYPE: PRT
<213> ORGANISM: Artificial Sequence
<220> FEATURE:
<223> OTHER INFORMATION: Synthesized

<400> SEQUENCE: 72

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp
            100                 105


<210> SEQ ID NO 73
<211> LENGTH: 107
<212> TYPE: PRT
<213> ORGANISM: Artificial Sequence
<220> FEATURE:
<223> OTHER INFORMATION: Synthesized

<400> SEQUENCE: 73

Asp Ile Val Leu Thr Gln Ser Pro Ala Ser Leu Ala Val Ser Leu Gly
1               5                   10                  15
```

```
Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp
            100                 105


<210> SEQ ID NO 74
<211> LENGTH: 115
<212> TYPE: PRT
<213> ORGANISM: Artificial Sequence
<220> FEATURE:
<223> OTHER INFORMATION: Synthesized

<400> SEQUENCE: 74

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Gly Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Tyr
                85                  90                  95

Thr Phe Gly Gly Gly Thr Lys Leu Glu Ile Lys Arg Ala Asp Ala Ala
            100                 105                 110

Pro Thr Val
        115


<210> SEQ ID NO 75
<211> LENGTH: 115
<212> TYPE: PRT
<213> ORGANISM: Artificial Sequence
<220> FEATURE:
<223> OTHER INFORMATION: Synthesized

<400> SEQUENCE: 75

Asp Ile Gln Met Thr Gln Pro Pro Ala Ser Leu Ser Ala Ser Val Gly
1               5                   10                  15

Glu Thr Val Thr Ile Thr Cys Arg Ala Ser Gly Asn Ile His Asn Phe
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
```

```
                85                  90                  95

Thr Phe Gly Gly Gly Thr Lys Leu Glu Ile Lys Arg Ala Asp Ala Ala
            100                 105                 110

Pro Thr Val
        115


<210> SEQ ID NO 76
<211> LENGTH: 105
<212> TYPE: PRT
<213> ORGANISM: Artificial Sequence
<220> FEATURE:
<223> OTHER INFORMATION: Synthesized

<400> SEQUENCE: 76

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Thr Tyr Gly Asn Tyr Trp Tyr Phe
            100                 105


<210> SEQ ID NO 77
<211> LENGTH: 106
<212> TYPE: PRT
<213> ORGANISM: Artificial Sequence
<220> FEATURE:
<223> OTHER INFORMATION: Synthesized

<400> SEQUENCE: 77

Gln Ile Thr Leu Lys Glu Ser Gly Pro Gly Ile Val Gln Pro Ser Gln
1               5                   10                  15

Pro Phe Arg Leu Thr Cys Thr Phe Ser Gly Phe Ser Leu Ser Thr Ser
            20                  25                  30

Gly Ile Gly Val Thr Trp Ile Arg Gln Pro Ser Gly Lys Gly Leu Glu
        35                  40                  45

Trp Leu Ala Thr Ile Trp Trp Asp Asp Asp Asn Arg Tyr Asn Pro Ser
    50                  55                  60

Leu Lys Ser Arg Leu Thr Val Ser Lys Asp Thr Ser Asn Asn Gln Ala
65                  70                  75                  80

Phe Leu Asn Ile Ile Thr Val Glu Thr Ala Asp Thr Ala Ile Tyr Tyr
                85                  90                  95

Cys Ala Gln Ser Thr Met Val Thr Ala Gly
            100                 105


<210> SEQ ID NO 78
<211> LENGTH: 105
<212> TYPE: PRT
<213> ORGANISM: Artificial Sequence
<220> FEATURE:
<223> OTHER INFORMATION: Synthesized

<400> SEQUENCE: 78
```

Gln Val Gln Leu Gln Gln Pro Gly Ala Glu Leu Val Lys Pro Gly Ala
1 5 10 15

Ser Val Lys Leu Ser Cys Lys Ala Ser Gly Tyr Thr Phe Thr Ser Tyr
20 25 30

Trp Met His Trp Val Lys Gln Arg Pro Gly Gln Gly Leu Glu Trp Ile
35 40 45

Gly Glu Ile Asn Pro Ser Asn Gly Arg Thr Asn Tyr Asn Glu Lys Phe
50 55 60

Lys Ser Lys Ala Thr Leu Thr Val Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Thr Tyr Gly Asn Tyr Trp Tyr Phe
100 105

<210> SEQ ID NO 79
<211> LENGTH: 127
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (12)..(12)
<223> OTHER INFORMATION: Xaa can be any naturally occurring amino acid

<400> SEQUENCE: 79

Asp Val Lys Leu Val Glu Ser Gly Gly Asp Leu Xaa Lys Leu Thr Glu
1 5 10 15

Gly Glu Asp Ile Trp Glu Gly Leu Thr Leu Cys Arg Asp Ser Asp Gln
20 25 30

Ser Pro Leu Ala Pro Val Ser Lys Pro Gly Arg Val Val Arg Pro Gln
35 40 45

Arg Ser Cys Thr Val Ile Gln Gly Cys Val Leu Arg Leu Gln Thr Ala
50 55 60

His Leu Gln Val Gln Gly Val Leu Gly Ile Val Ser Gly Asp Gly Glu
65 70 75 80

Ser Ala Leu His Ser Val Trp Ile Val Gly Ala Thr Thr Ile Thr Ile
85 90 95

Asn Gly Cys Asp Gln Leu Gln Pro Leu Leu Trp Ser Leu Ala Asn Pro
100 105 110

Arg His Val Ile Ala Thr Glu Ser Glu Ser Arg Gly Cys Thr Gly
115 120 125

<210> SEQ ID NO 80
<211> LENGTH: 104
<212> TYPE: PRT
<213> ORGANISM: Artificial Sequence
<220> FEATURE:
<223> OTHER INFORMATION: Synthesized

<400> SEQUENCE: 80

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Ser Tyr
20 25 30

Gly Val His Trp Val Arg Gln Ser Pro Gly Lys Gly Leu Glu Trp Leu
35 40 45

Gly Val Ile Trp Gly Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Asn Asp Tyr Pro Ala Trp Phe
            100

<210> SEQ ID NO 81
<211> LENGTH: 105
<212> TYPE: PRT
<213> ORGANISM: Artificial Sequence
<220> FEATURE:
<223> OTHER INFORMATION: Synthesized

<400> SEQUENCE: 81

Glu Val Gln Leu Val Glu Ser Gly Gly Asp Leu Val Lys Pro Gly Arg
1               5                   10                  15

Ser Leu Lys Leu Ser Cys Ala Ala Ser Gly Phe Thr Phe Ser Ser Phe
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ser Arg Arg Phe Tyr Tyr Asp Tyr Asp
            100                 105

<210> SEQ ID NO 82
<211> LENGTH: 321
<212> TYPE: DNA
<213> ORGANISM: Artificial Sequence
<220> FEATURE:
<223> OTHER INFORMATION: Synthesized

<400> SEQUENCE: 82
cgggctgatg ctgcaccaac tgtatccatc ttcccaccat ccagtgagca gttaacatct 60
ggaggtgcct cagtcgtgtg cttcttgaac aacttctacc ccaaagacat caatgtcaag 120
tggaagattg atggcagtga acgacaaaat ggcgtcctga acagttggac tgatcaggac 180
agcaaagaca gcacctacag catgagcagc accctcacgt tgaccaagga cgagtatgaa 240
cgacataaca gctatacctg tgaggccact cacaagacat caacttcacc cattgtcaag 300
agcttcaaca ggaatgagtg t 321

<210> SEQ ID NO 83
<211> LENGTH: 318
<212> TYPE: DNA
<213> ORGANISM: Artificial Sequence
<220> FEATURE:
<223> OTHER INFORMATION: Synthesized

<400> SEQUENCE: 83
ttcgatgtct ggggcgcagg gaccacggtc accgtctcct ccgccaaaac gacaccccca 60
tctgtctatc cactggcccc tggatctgct gcccaaacta actccatggt gaccctggga 120

-continued

```
tgcctggtca agggctattt ccctgagcca gtgacagtga cctggaactc tggatccctg    180

tccagcggtg tgcacacctt cccagctgtc ctgcagtctg acctctacac tctgagcagc    240

tcagtgactg tcccctccag cacctggccc agcgagaccg tcacctgcaa cgttgcccac    300

ccagccagca ggaccgcg                                                  318
```

<210> SEQ ID NO 84
<211> LENGTH: 103
<212> TYPE: PRT
<213> ORGANISM: Artificial Sequence
<220> FEATURE:
<223> OTHER INFORMATION: Synthesized

<400> SEQUENCE: 84

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Ser Trp Val Met Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Thr Thr Ala His
65                  70                  75                  80

Ile Glu Leu Arg Ser Leu Ala Ser Glu Asp Ser Ala Val Tyr Tyr Cys
                85                  90                  95

Ala Arg Lys Gly Leu Tyr Gly
            100
```

<210> SEQ ID NO 85
<211> LENGTH: 324
<212> TYPE: DNA
<213> ORGANISM: Artificial Sequence
<220> FEATURE:
<223> OTHER INFORMATION: Synthesized

<400> SEQUENCE: 85

```
gacatccaga tgacccagtc tccatcctcc ttatctgcct ctctgggaga aagagtcagt     60

ctcacttgtc gagcaagtca ggacattggt agtagcttaa actggcttca gcaggaacca    120

gatggaacta ttaaacgcct gatctacgcc acatccagtt tagattctgg tgtccccaaa    180

aggttcagtg gcagtaggtc tgggtcagat tattctctca ccatcagcag ccttgagtct    240

gaagattttg tagactatta ctgtctacaa tatgctagtt ctcctcacgt tcggtgctgg    300

gaccaagctg gagctgaaac gggc                                           324
```

<210> SEQ ID NO 86
<211> LENGTH: 323
<212> TYPE: DNA
<213> ORGANISM: Artificial Sequence
<220> FEATURE:
<223> OTHER INFORMATION: Synthesized

<400> SEQUENCE: 86

```
gacattgtgc tgacacagtc tcctgcttcc ttagctgtat ctctggggca gagggccacc     60

atctcataca gggccagcaa aagtgtcagt acatctggct atagttatat gcactggaac    120

caacagaaac caggacagcc acccagactc ctcatctatc ttgtatccaa cctagaatct    180

ggggtccctg ccaggttcag tggcagtggg tctgggacag acttcaccct caacatccat    240
```

-continued

```
cctgtggagg aggaggatgc tgcaacctat tactgtcagc acattaggga gcttacacgt    300

tcggaggggg gaccaagctg gaa                                            323


<210> SEQ ID NO 87
<211> LENGTH: 345
<212> TYPE: DNA
<213> ORGANISM: Artificial Sequence
<220> FEATURE:
<223> OTHER INFORMATION: Synthesized

<400> SEQUENCE: 87

gacattcaga tgacccagtc tcctgcctcc cagtctgcat ctctgggaga aagtgtcacc     60

atcacatgcc tggcaagtca gaccattggt acatggttag catggtatca gcagaaacca    120

gggaaatctc ctcagctcct gatttatgct gcaaccagct tggcagatgg ggtcccatca    180

aggttcagtg gtagtggatc tggcacaaaa ttttctttca agatcagcag cctacaggct    240

gaagattttg taagttatta ctgtcaacaa ctttacagta ctccgtggac gttcggtgga    300

ggcaccaagc tggaaatcaa acgggctgat gctgcaccaa ctgta                    345


<210> SEQ ID NO 88
<211> LENGTH: 323
<212> TYPE: DNA
<213> ORGANISM: Artificial Sequence
<220> FEATURE:
<223> OTHER INFORMATION: Synthesized

<400> SEQUENCE: 88

gtgacattgt gctgacacag tctcctgctt ccttagctgt atctctgggg cagagggcca     60

ccatctcata cagggccagc aaaagtgtca gtacatctgg ctatagttat atgcactgga    120

accaacagaa accaggacag ccacccagac tcctcatcta tcttgtatcc aacctagaat    180

ctggggtccc tgccaggttc agtggcagtg ggtctgggac agacttcacc ctcaacatcc    240

atcctgtgga ggaggaggat gctgcaacct attactgtca gcacattagg gagcttacac    300

gttcggaggg gggaccaagc tgg                                            323


<210> SEQ ID NO 89
<211> LENGTH: 321
<212> TYPE: DNA
<213> ORGANISM: Artificial Sequence
<220> FEATURE:
<223> OTHER INFORMATION: Synthesized

<400> SEQUENCE: 89

gacattgtgc tgacacagtc tcctgcttcc ttagctgtat ctctggggca gagggccacc     60

atctcataca gggccagcaa aagtgtcagt acatctggct atagttatat gcactggaac    120

caacagaaac caggacagcc acccagactc ctcatctatc ttgtatccaa cctagaatct    180

ggggtccctg ccaggttcag tggcagtggg tctgggacag acttcaccct caacatccat    240

cctgtggagg aggaggatgc tgcaacctat tactgtcagc acattaggga gcttacacgt    300

tcggaggggg gaccaagctg g                                              321


<210> SEQ ID NO 90
<211> LENGTH: 345
<212> TYPE: DNA
<213> ORGANISM: Artificial Sequence
<220> FEATURE:
<223> OTHER INFORMATION: Synthesized

<400> SEQUENCE: 90
```

gacattgtga tgacccagtc tcaaaaattc atgtccacat cagtaggaga cagggtcagc 60
gtcacctgca aggccagtca gaatgtgggt actaatgtag gttggtatca acagaaacca 120
gggcaatctc ctaaagcact gatttactcg gcatcctacc ggtacagtgg agtccctgat 180
cgcttcacag gcagtggatc tgggacagat ttcactctca ccatcagcaa tgtgcagtct 240
gaagacttgg cagagtattt ctgtcagcaa tataacaact atccgtacac gttcggaggg 300
gggaccaagc tggaaataaa acgggctgat gctgcaccaa ctgta 345

<210> SEQ ID NO 91
<211> LENGTH: 345
<212> TYPE: DNA
<213> ORGANISM: Artificial Sequence
<220> FEATURE:
<223> OTHER INFORMATION: Synthesized

<400> SEQUENCE: 91
gacatccaga tgactcagcc tccagcctcc ctatctgcat ctgtgggaga aactgtcacc 60
atcacatgtc gagcaagtgg gaatattcac aatttttag catggtatca gcagaaacag 120
ggaaaatctc ctcagctcct ggtctataat gcaaaaacct tagcagatgg tgtgccatca 180
aggttcagtg gcagtggatc aggaacacaa tattctctca agatcaacag cctgcagcct 240
gaagattttg ggagttatta ctgtcaacat ttttggagta ctccgtggac gttcggtgga 300
ggcaccaagc tggaaatcaa acgggctgat gctgcaccaa ctgta 345

<210> SEQ ID NO 92
<211> LENGTH: 315
<212> TYPE: DNA
<213> ORGANISM: Artificial Sequence
<220> FEATURE:
<223> OTHER INFORMATION: Synthesized

<400> SEQUENCE: 92
caggtccaac tgcagcagcc tggggctgaa ctggtgaagc ctggggcttc agtgaagctg 60
tcctgcaagg cttctggcta caccttcacc agctactgga tgcactgggt gaagcagagg 120
cctggacaag gccttgagtg gattggagag attaatccta gcaacggtcg tactaactac 180
aatgagaagt tcaagagcaa ggccacactg actgtagaca aatcctccag cacagcctac 240
atgcaactca gcagcctgac atctgaggac tctgcggtct attactgtgc aacctatggt 300
aactactggt acttc 315

<210> SEQ ID NO 93
<211> LENGTH: 315
<212> TYPE: DNA
<213> ORGANISM: Artificial Sequence
<220> FEATURE:
<223> OTHER INFORMATION: Synthesized

<400> SEQUENCE: 93
caggtccaac tgcagcagcc tggggctgaa ctggtgaagc ctggggcttc agtgaagctg 60
tcctgcaagg cttctggcta caccttcacc agctactgga tgcactgggt gaagcagagg 120
cctggacaag gccttgagtg gattggagag attaatccta gcaacggtcg tactaactac 180
aatgagaagt tcaagagcaa ggccacactg actgtagaca aatcctccag cacagcctac 240
atgcaactca gcagcctgac atctgaggac tctgcggtct attactgtgc aacctatggt 300
aactactggt acttc 315

<210> SEQ ID NO 94
<211> LENGTH: 318
<212> TYPE: DNA
<213> ORGANISM: Artificial Sequence
<220> FEATURE:
<223> OTHER INFORMATION: Synthesized

<400> SEQUENCE: 94
cagattactc tgaaagagtc tggccctggg atagttcagc catcccagcc cttcagactt 60
acttgcactt tctctgggtt ttcactgagc acttctggta taggtgtaac ctggattcgt 120
cagccctcag ggaaaggtct ggagtggctg gcaacgattt ggtgggatga tgataaccgc 180
tacaacccat ctctaaagag caggctcaca gtctccaaag acacctccaa caaccaagca 240
ttcctgaata tcatcactgt ggaaactgca gatactgcca tatactactg tgctcagtct 300
actatggtta cggcggga 318

<210> SEQ ID NO 95
<211> LENGTH: 313
<212> TYPE: DNA
<213> ORGANISM: Artificial Sequence
<220> FEATURE:
<223> OTHER INFORMATION: Synthesized

<400> SEQUENCE: 95
ccaggtgcag ctgaagcagt caggacctgg cctagtgcag ccctcacaga gcctgtccat 60
cacctgcaca gtctctggtt tctcattaac tagctatggt gtacactggg ttcgccagtc 120
tccaggaaag ggtctggagt ggctgggagt gatatggggt ggtggaagca cagactataa 180
tgcagctttc atatccagac tgagcatcag caaggacaat tccaagagcc aagttttctt 240
taaaatgaac agtctgcaag ctaatgacac agccatatat tactgtgcca gaaatgacta 300
tccggcctgg ttt 313

<210> SEQ ID NO 96
<211> LENGTH: 317
<212> TYPE: DNA
<213> ORGANISM: Artificial Sequence
<220> FEATURE:
<223> OTHER INFORMATION: Synthesized

<400> SEQUENCE: 96
gtgaggtgca actggtggag tctgggggag acttagtgaa gcctggaagg tccctgaaac 60
tctcctgtgc agcctctgga ttcactttca gtagctttgg catgtcttgg gttcgccaga 120
ctccagacaa gaggctggag tgggtcgcaa ccattagtag tggtggtact tacacctact 180
atccagacag tgtgaagggg cgattcacca tctccagaga caatgccaag aacaccctgt 240
acctgcaaat gagcagtctg aagtctgagg acacagccat gtattactgt tcaagaaggt 300
tctactatga ttacgac 317

<210> SEQ ID NO 97
<211> LENGTH: 309
<212> TYPE: DNA
<213> ORGANISM: Artificial Sequence
<220> FEATURE:
<223> OTHER INFORMATION: Synthesized

<400> SEQUENCE: 97
gaggttcagc tgcagcagtc tggacctgag ctggtgaagc ctggggcttc agtgaagata 60
tcctgcaagg cttctggtta ctcatttact ggctacttta tgagctgggt gatgcagagc 120

```
catggaaaga gccttgagtg gattggacgt attaatcctt acaatggtga tactttctac    180

aaccagaagt tcaagggcaa ggccacattg actgtagaca aatcctctac cacagcccac    240

atagagctcc ggagcctggc atctgaggac tctgcagtct attattgtgc aagaaagggc    300

ctctatggg                                                            309
```

<210> SEQ ID NO 98
<211> LENGTH: 23
<212> TYPE: PRT
<213> ORGANISM: Artificial Sequence
<220> FEATURE:
<223> OTHER INFORMATION: Synthesized

<400> SEQUENCE: 98

```
Asp Ile Val Ile Thr Gln Ser Thr Ala Ser Leu Gly Val Ser Leu Gly
1               5                   10                  15

Gln Arg Ala Thr Ile Ser Cys
            20
```

<210> SEQ ID NO 99
<211> LENGTH: 23
<212> TYPE: PRT
<213> ORGANISM: Artificial Sequence
<220> FEATURE:
<223> OTHER INFORMATION: Synthesized

<400> SEQUENCE: 99

```
Asp Ile Val Ile Thr Gln Thr Thr Ala Ile Met Ser Ala Ser Pro Gly
1               5                   10                  15

Glu Glu Val Thr Leu Thr Cys
            20
```

<210> SEQ ID NO 100
<211> LENGTH: 23
<212> TYPE: PRT
<213> ORGANISM: Artificial Sequence
<220> FEATURE:
<223> OTHER INFORMATION: Synthesized

<400> SEQUENCE: 100

```
Asp Ile Val Leu Thr Gln Ser Thr Glu Ile Met Ser Ala Ser Pro Gly
1               5                   10                  15

Glu Lys Val Thr Ile Thr Cys
            20
```

<210> SEQ ID NO 101
<211> LENGTH: 23
<212> TYPE: PRT
<213> ORGANISM: Artificial Sequence
<220> FEATURE:
<223> OTHER INFORMATION: MIN-A2-2 light chain variable framework region 1 (FWR1) amino acid sequence

<400> SEQUENCE: 101

```
Asp Ile Val Met Thr Gln Ser Pro Ala Ile Met Ser Ala Ser Pro Gly
1               5                   10                  15

Glu Lys Val Thr Met Thr Cys
            20
```

<210> SEQ ID NO 102
<211> LENGTH: 23
<212> TYPE: PRT
<213> ORGANISM: Artificial Sequence -continued
<220> FEATURE:
<223> OTHER INFORMATION: Synthesized

<400> SEQUENCE: 102

Asp Ile Val Leu Thr Gln Thr Thr Ala Ile Met Ser Ala Ser Pro Gly
1 5 10 15

Glu Lys Val Thr Ile Thr Cys
20

<210> SEQ ID NO 103
<211> LENGTH: 23
<212> TYPE: PRT
<213> ORGANISM: Artificial Sequence
<220> FEATURE:
<223> OTHER INFORMATION: Synthesized

<400> SEQUENCE: 103

Asp Ile Val Ile Thr Gln Ser Thr Ala Ile Met Ser Ala Ser Pro Gly
1 5 10 15

Glu Lys Val Thr Ile Thr Cys
20

<210> SEQ ID NO 104
<211> LENGTH: 23
<212> TYPE: PRT
<213> ORGANISM: Artificial Sequence
<220> FEATURE:
<223> OTHER INFORMATION: Synthesized

<400> SEQUENCE: 104

Asp Ile Val Ile Thr Gln Thr Pro Ala Ile Met Ser Ala Ser Pro Gly
1 5 10 15

Glu Lys Val Thr Met Thr Cys
20

<210> SEQ ID NO 105
<211> LENGTH: 23
<212> TYPE: PRT
<213> ORGANISM: Artificial Sequence
<220> FEATURE:
<223> OTHER INFORMATION: Synthesized

<400> SEQUENCE: 105

Asp Ile Val Leu Thr Gln Ser Thr Ala Ile Met Ser Ala Ser Pro Gly
1 5 10 15

Glu Lys Val Thr Met Thr Cys
20

<210> SEQ ID NO 106
<211> LENGTH: 23
<212> TYPE: PRT
<213> ORGANISM: Artificial Sequence
<220> FEATURE:
<223> OTHER INFORMATION: Synthesized

<400> SEQUENCE: 106

Asp Ile Val Met Thr Gln Ser Pro Glu Ile Met Ser Ala Ser Pro Gly
1 5 10 15

Glu Lys Val Thr Ile Thr Cys
20

<210> SEQ ID NO 107
<211> LENGTH: 23
<212> TYPE: PRT

-continued

<213> ORGANISM: Artificial Sequence
<220> FEATURE:
<223> OTHER INFORMATION: Synthesized

<400> SEQUENCE: 107

Asp Ile Val Ile Thr Gln Ser Thr Glu Ile Met Ser Ala Ser Pro Gly
1 5 10 15

Glu Lys Val Thr Ile Thr Cys
20

<210> SEQ ID NO 108
<211> LENGTH: 15
<212> TYPE: PRT
<213> ORGANISM: Artificial Sequence
<220> FEATURE:
<223> OTHER INFORMATION: Synthesized

<400> SEQUENCE: 108

Arg Ala Ser Lys Ser Val Ser Thr Ser Gly Tyr Ser Tyr Met His
1 5 10 15

<210> SEQ ID NO 109
<211> LENGTH: 10
<212> TYPE: PRT
<213> ORGANISM: Artificial Sequence
<220> FEATURE:
<223> OTHER INFORMATION: Synthesized

<400> SEQUENCE: 109

Ser Ala Thr Ser Ser Val Ser Tyr Ile His
1 5 10

<210> SEQ ID NO 110
<211> LENGTH: 10
<212> TYPE: PRT
<213> ORGANISM: Artificial Sequence
<220> FEATURE:
<223> OTHER INFORMATION: Synthesized

<400> SEQUENCE: 110

Ser Ala Ser Ser Ser Ile Ser Tyr Ile His
1 5 10

<210> SEQ ID NO 111

<400> SEQUENCE: 111

000

<210> SEQ ID NO 112
<211> LENGTH: 10
<212> TYPE: PRT
<213> ORGANISM: Artificial Sequence
<220> FEATURE:
<223> OTHER INFORMATION: Synthesized

<400> SEQUENCE: 112

Ser Ala Ser Ser Ser Val Ser Tyr Met His
1 5 10

<210> SEQ ID NO 113
<211> LENGTH: 10
<212> TYPE: PRT
<213> ORGANISM: Artificial Sequence
<220> FEATURE:
<223> OTHER INFORMATION: Synthesized

<400> SEQUENCE: 113

Ser Ala Ser Ser Ser Val Ser Tyr Met Tyr
1 5 10

<210> SEQ ID NO 114
<211> LENGTH: 10
<212> TYPE: PRT
<213> ORGANISM: Artificial Sequence
<220> FEATURE:
<223> OTHER INFORMATION: Synthesized

<400> SEQUENCE: 114

Ser Ala Ser Ser Ser Val Ser Tyr Thr Tyr
1 5 10

<210> SEQ ID NO 115
<211> LENGTH: 10
<212> TYPE: PRT
<213> ORGANISM: Artificial Sequence
<220> FEATURE:
<223> OTHER INFORMATION: Synthesized

<400> SEQUENCE: 115

Ser Ala Ser Ser Ser Val Ser Tyr Met His
1 5 10

<210> SEQ ID NO 116
<211> LENGTH: 10
<212> TYPE: PRT
<213> ORGANISM: Artificial Sequence
<220> FEATURE:
<223> OTHER INFORMATION: Synthesized

<400> SEQUENCE: 116

Ser Ala Ser Ser Ser Val Ser Tyr Met His
1 5 10

<210> SEQ ID NO 117
<211> LENGTH: 10
<212> TYPE: PRT
<213> ORGANISM: Artificial Sequence
<220> FEATURE:
<223> OTHER INFORMATION: Synthesized

<400> SEQUENCE: 117

Ser Ala Ser Ser Ser Ile Ser Tyr Ile His
1 5 10

<210> SEQ ID NO 118
<211> LENGTH: 10
<212> TYPE: PRT
<213> ORGANISM: Artificial Sequence
<220> FEATURE:
<223> OTHER INFORMATION: Synthesized

<400> SEQUENCE: 118

Ser Ala Ser Ser Ser Ile Ser Tyr Ile His
1 5 10

<210> SEQ ID NO 119
<211> LENGTH: 15
<212> TYPE: PRT
<213> ORGANISM: Artificial Sequence
<220> FEATURE:
<223> OTHER INFORMATION: Synthesized

<400> SEQUENCE: 119

Trp Tyr Gln Gln Arg Pro Gly Gln Pro Pro Lys Leu Leu Ile Tyr
1 5 10 15

<210> SEQ ID NO 120
<211> LENGTH: 15
<212> TYPE: PRT
<213> ORGANISM: Artificial Sequence
<220> FEATURE:
<223> OTHER INFORMATION: Synthesized

<400> SEQUENCE: 120

Trp Phe Gln Gln Arg Pro Gly Thr Ser Pro Lys Leu Trp Ile Tyr
1 5 10 15

<210> SEQ ID NO 121
<211> LENGTH: 15
<212> TYPE: PRT
<213> ORGANISM: Artificial Sequence
<220> FEATURE:
<223> OTHER INFORMATION: Synthesized

<400> SEQUENCE: 121

Trp Phe Gln Gln Lys Pro Gly Thr Ser Pro Lys Leu Trp Ile Phe
1 5 10 15

<210> SEQ ID NO 122
<211> LENGTH: 15
<212> TYPE: PRT
<213> ORGANISM: Artificial Sequence
<220> FEATURE:
<223> OTHER INFORMATION: Synthesized

<400> SEQUENCE: 122

Trp Phe Gln Gln Lys Pro Gly Thr Ser Pro Lys Leu Trp Ile Tyr
1 5 10 15

<210> SEQ ID NO 123
<211> LENGTH: 15
<212> TYPE: PRT
<213> ORGANISM: Artificial Sequence
<220> FEATURE:
<223> OTHER INFORMATION: Synthesized

<400> SEQUENCE: 123

Trp Phe Gln Gln Lys Pro Gly Thr Ser Pro Lys Leu Trp Ile Tyr
1 5 10 15

<210> SEQ ID NO 124
<211> LENGTH: 15
<212> TYPE: PRT
<213> ORGANISM: Artificial Sequence
<220> FEATURE:
<223> OTHER INFORMATION: Synthesized

<400> SEQUENCE: 124

Trp Phe Gln Gln Lys Pro Gly Thr Ser Pro Lys Leu Trp Ile Tyr
1 5 10 15

<210> SEQ ID NO 125
<211> LENGTH: 15
<212> TYPE: PRT
<213> ORGANISM: Artificial Sequence
<220> FEATURE:
<223> OTHER INFORMATION: Synthesized

<400> SEQUENCE: 125

Trp Phe Gln Gln Lys Pro Gly Thr Ser Pro Lys Leu Trp Ile Tyr
1 5 10 15

<210> SEQ ID NO 126
<211> LENGTH: 15
<212> TYPE: PRT
<213> ORGANISM: Artificial Sequence
<220> FEATURE:
<223> OTHER INFORMATION: Synthesized

<400> SEQUENCE: 126

Trp Phe Gln Gln Lys Pro Gly Thr Ser Pro Lys Leu Trp Ile Tyr
1 5 10 15

<210> SEQ ID NO 127
<211> LENGTH: 15
<212> TYPE: PRT
<213> ORGANISM: Artificial Sequence
<220> FEATURE:
<223> OTHER INFORMATION: Synthesized

<400> SEQUENCE: 127

Trp Phe Gln Gln Lys Pro Gly Thr Ser Pro Lys Leu Trp Ile Phe
1 5 10 15

<210> SEQ ID NO 128
<211> LENGTH: 15
<212> TYPE: PRT
<213> ORGANISM: Artificial Sequence
<220> FEATURE:
<223> OTHER INFORMATION: Synthesized

<400> SEQUENCE: 128

Trp Phe Gln Gln Lys Pro Gly Thr Ser Pro Lys Leu Trp Ile Phe
1 5 10 15

<210> SEQ ID NO 129
<211> LENGTH: 7
<212> TYPE: PRT
<213> ORGANISM: Artificial Sequence
<220> FEATURE:
<223> OTHER INFORMATION: Synthesized

<400> SEQUENCE: 129

Leu Ala Ser Asn Leu Glu Ser
1 5

<210> SEQ ID NO 130
<211> LENGTH: 7
<212> TYPE: PRT
<213> ORGANISM: Artificial Sequence
<220> FEATURE:
<223> OTHER INFORMATION: Synthesized

<400> SEQUENCE: 130

Ser Thr Ser Asn Leu Ala Ser
1 5

<210> SEQ ID NO 131
<211> LENGTH: 7
<212> TYPE: PRT
<213> ORGANISM: Artificial Sequence
<220> FEATURE:
<223> OTHER INFORMATION: Synthesized

<400> SEQUENCE: 131

Gly Thr Ser Asn Leu Ala Ser

-continued 1 5

<210> SEQ ID NO 132
<211> LENGTH: 7
<212> TYPE: PRT
<213> ORGANISM: Artificial Sequence
<220> FEATURE:
<223> OTHER INFORMATION: Synthesized

<400> SEQUENCE: 132

Ser Thr Ser Asn Leu Ala Ser
1 5

<210> SEQ ID NO 133
<211> LENGTH: 7
<212> TYPE: PRT
<213> ORGANISM: Artificial Sequence
<220> FEATURE:
<223> OTHER INFORMATION: Synthesized

<400> SEQUENCE: 133

Ser Thr Ser Asn Leu Ala Ser
1 5

<210> SEQ ID NO 134
<211> LENGTH: 7
<212> TYPE: PRT
<213> ORGANISM: Artificial Sequence
<220> FEATURE:
<223> OTHER INFORMATION: Synthesized

<400> SEQUENCE: 134

Ser Thr Ser Asn Leu Ala Ser
1 5

<210> SEQ ID NO 135
<211> LENGTH: 7
<212> TYPE: PRT
<213> ORGANISM: Artificial Sequence
<220> FEATURE:
<223> OTHER INFORMATION: Synthesized

<400> SEQUENCE: 135

Ser Thr Ser Asn Leu Ala Ser
1 5

<210> SEQ ID NO 136
<211> LENGTH: 7
<212> TYPE: PRT
<213> ORGANISM: Artificial Sequence
<220> FEATURE:
<223> OTHER INFORMATION: Synthesized

<400> SEQUENCE: 136

Ser Thr Ser Asn Leu Ala Ser
1 5

<210> SEQ ID NO 137
<211> LENGTH: 7
<212> TYPE: PRT
<213> ORGANISM: Artificial Sequence
<220> FEATURE:
<223> OTHER INFORMATION: Synthesized

<400> SEQUENCE: 137

Gly Thr Ser Asn Leu Ala Ser
1 5

```
<210> SEQ ID NO 138
<211> LENGTH: 7
<212> TYPE: PRT
<213> ORGANISM: Artificial Sequence
<220> FEATURE:
<223> OTHER INFORMATION: Synthesized

<400> SEQUENCE: 138

Gly Thr Ser Asn Leu Ala Ser
1               5


<210> SEQ ID NO 139
<211> LENGTH: 32
<212> TYPE: PRT
<213> ORGANISM: Artificial Sequence
<220> FEATURE:
<223> OTHER INFORMATION: Synthesized

<400> SEQUENCE: 139

Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
            20                  25                  30


<210> SEQ ID NO 140
<211> LENGTH: 32
<212> TYPE: PRT
<213> ORGANISM: Artificial Sequence
<220> FEATURE:
<223> OTHER INFORMATION: Synthesized

<400> SEQUENCE: 140

Gly Val Pro Val Arg Phe Ser Gly Ser Gly Tyr Gly Thr Ser Tyr Ser
1               5                   10                  15

Leu Thr Ile Ser Arg Met Glu Ala Glu Asp Ala Ala Thr Tyr Tyr Cys
            20                  25                  30


<210> SEQ ID NO 141
<211> LENGTH: 32
<212> TYPE: PRT
<213> ORGANISM: Artificial Sequence
<220> FEATURE:
<223> OTHER INFORMATION: Synthesized

<400> SEQUENCE: 141

Gly Val Pro Ala Arg Phe Ser Gly Ser Gly Ser Gly Thr Ser Tyr Ser
1               5                   10                  15

Leu Thr Val Ser Arg Met Glu Ala Glu Asp Thr Ala Thr Tyr Tyr Cys
            20                  25                  30


<210> SEQ ID NO 142
<211> LENGTH: 32
<212> TYPE: PRT
<213> ORGANISM: Artificial Sequence
<220> FEATURE:
<223> OTHER INFORMATION: Synthesized

<400> SEQUENCE: 142

Gly Ala Pro Ala Arg Phe Ser Gly Ser Gly Ser Gly Thr Ser Tyr Ser
1               5                   10                  15

Leu Thr Val Ser Arg Met Glu Ser Glu Asp Ala Ala Thr Tyr Tyr Cys
            20                  25                  30
```

<210> SEQ ID NO 143
<211> LENGTH: 32
<212> TYPE: PRT
<213> ORGANISM: Artificial Sequence
<220> FEATURE:
<223> OTHER INFORMATION: Synthesized

<400> SEQUENCE: 143

```
Gly Val Pro Ala Arg Phe Ser Gly Ser Gly Ser Gly Thr Ser Tyr Ser
1               5                   10                  15

Leu Thr Ile Ser Arg Met Glu Ala Glu Asp Ala Ala Thr Tyr Tyr Cys
            20                  25                  30
```

<210> SEQ ID NO 144
<211> LENGTH: 32
<212> TYPE: PRT
<213> ORGANISM: Artificial Sequence
<220> FEATURE:
<223> OTHER INFORMATION: Synthesized

<400> SEQUENCE: 144

```
Gly Val Pro Ala Arg Phe Ser Gly Ser Gly Ser Gly Thr Ser Tyr Ser
1               5                   10                  15

Leu Thr Ile Ser Arg Met Glu Ala Glu Asp Ala Ala Thr Tyr Tyr Cys
            20                  25                  30
```

<210> SEQ ID NO 145
<211> LENGTH: 32
<212> TYPE: PRT
<213> ORGANISM: Artificial Sequence
<220> FEATURE:
<223> OTHER INFORMATION: Synthesized

<400> SEQUENCE: 145

```
Gly Val Pro Ala Arg Phe Ser Gly Ser Gly Ser Gly Thr Ser Tyr Ser
1               5                   10                  15

Leu Thr Val Ser Arg Met Glu Ser Glu Asp Ala Ala Thr Tyr Tyr Cys
            20                  25                  30
```

<210> SEQ ID NO 146
<211> LENGTH: 32
<212> TYPE: PRT
<213> ORGANISM: Artificial Sequence
<220> FEATURE:
<223> OTHER INFORMATION: Synthesized

<400> SEQUENCE: 146

```
Gly Val Pro Ala Arg Phe Ser Gly Ser Gly Ser Gly Thr Ser Tyr Ser
1               5                   10                  15

Leu Thr Val Ser Arg Met Glu Ser Glu Asp Ala Ala Thr Tyr Tyr Cys
            20                  25                  30
```

<210> SEQ ID NO 147
<211> LENGTH: 32
<212> TYPE: PRT
<213> ORGANISM: Artificial Sequence
<220> FEATURE:
<223> OTHER INFORMATION: Synthesized

<400> SEQUENCE: 147

```
Gly Val Pro Ala Arg Phe Ser Gly Ser Gly Ser Gly Thr Ser Tyr Ser
1               5                   10                  15

Leu Thr Val Ser Arg Met Glu Ala Glu Asp Thr Ala Thr Tyr Tyr Cys
            20                  25                  30
```

<210> SEQ ID NO 148
<211> LENGTH: 32
<212> TYPE: PRT
<213> ORGANISM: Artificial Sequence
<220> FEATURE:
<223> OTHER INFORMATION: Synthesized

<400> SEQUENCE: 148

Gly Val Pro Ala Arg Phe Ser Gly Ser Gly Ser Gly Thr Ser Tyr Ser
1 5 10 15

Leu Thr Val Ser Arg Met Glu Ala Glu Asp Thr Ala Thr Tyr Tyr Cys
20 25 30

<210> SEQ ID NO 149
<211> LENGTH: 9
<212> TYPE: PRT
<213> ORGANISM: Artificial Sequence
<220> FEATURE:
<223> OTHER INFORMATION: Synthesized

<400> SEQUENCE: 149

Gln His Ser Arg Glu Leu Pro Phe Thr
1 5

<210> SEQ ID NO 150
<211> LENGTH: 9
<212> TYPE: PRT
<213> ORGANISM: Artificial Sequence
<220> FEATURE:
<223> OTHER INFORMATION: Synthesized

<400> SEQUENCE: 150

Gln Gln Arg Ser Ser Ser Pro Phe Thr
1 5

<210> SEQ ID NO 151
<211> LENGTH: 9
<212> TYPE: PRT
<213> ORGANISM: Artificial Sequence
<220> FEATURE:
<223> OTHER INFORMATION: Synthesized

<400> SEQUENCE: 151

Gln Gln Arg Ser Asn Tyr Pro Phe Thr
1 5

<210> SEQ ID NO 152

<400> SEQUENCE: 152

000

<210> SEQ ID NO 153
<211> LENGTH: 9
<212> TYPE: PRT
<213> ORGANISM: Artificial Sequence
<220> FEATURE:
<223> OTHER INFORMATION: Synthesized

<400> SEQUENCE: 153

Gln Gln Arg Ser Ser Tyr Pro Ser Thr
1 5

<210> SEQ ID NO 154
<211> LENGTH: 9
<212> TYPE: PRT

<213> ORGANISM: Artificial Sequence
<220> FEATURE:
<223> OTHER INFORMATION: Synthesized

<400> SEQUENCE: 154

Gln Gln Arg Ser Ser Tyr Pro Ser Thr
1 5

<210> SEQ ID NO 155
<211> LENGTH: 9
<212> TYPE: PRT
<213> ORGANISM: Artificial Sequence
<220> FEATURE:
<223> OTHER INFORMATION: Synthesized

<400> SEQUENCE: 155

Gln Gln Arg Ser Ser Tyr Pro Ser Thr
1 5

<210> SEQ ID NO 156
<211> LENGTH: 9
<212> TYPE: PRT
<213> ORGANISM: Artificial Sequence
<220> FEATURE:
<223> OTHER INFORMATION: Synthesized

<400> SEQUENCE: 156

Gln Gln Arg Ser Ser Tyr Pro Ser Thr
1 5

<210> SEQ ID NO 157
<211> LENGTH: 9
<212> TYPE: PRT
<213> ORGANISM: Artificial Sequence
<220> FEATURE:
<223> OTHER INFORMATION: Synthesized

<400> SEQUENCE: 157

Gln Gln Arg Ser Asn Tyr Pro Phe Thr
1 5

<210> SEQ ID NO 158
<211> LENGTH: 9
<212> TYPE: PRT
<213> ORGANISM: Artificial Sequence
<220> FEATURE:
<223> OTHER INFORMATION: Synthesized

<400> SEQUENCE: 158

Gln Gln Arg Ser Asn Tyr Pro Phe Thr
1 5

<210> SEQ ID NO 159
<211> LENGTH: 30
<212> TYPE: PRT
<213> ORGANISM: Artificial Sequence
<220> FEATURE:
<223> OTHER INFORMATION: Synthesized

<400> SEQUENCE: 159

Glu Val Gln Leu Glu Glu Ser Gly Gly Gly Leu Val Lys Pro Gly Gly
1 5 10 15

Ser Leu Lys Leu Ser Cys Ala Ala Ser Gly Phe Thr Phe Ser
20 25 30

<210> SEQ ID NO 160

<211> LENGTH: 30
<212> TYPE: PRT
<213> ORGANISM: Artificial Sequence
<220> FEATURE:
<223> OTHER INFORMATION: Synthesized

<400> SEQUENCE: 160

Glu Val Lys Leu Glu Glu Ser Gly Gly Asp Leu Val Lys Pro Gly Gly
1               5                   10                  15

Ser Leu Lys Leu Ser Cys Ala Ala Ser Gly Phe Thr Phe Ser
            20                  25                  30

<210> SEQ ID NO 161
<211> LENGTH: 30
<212> TYPE: PRT
<213> ORGANISM: Artificial Sequence
<220> FEATURE:
<223> OTHER INFORMATION: Synthesized

<400> SEQUENCE: 161

Glu Val Lys Leu Glu Glu Ser Gly Gly Asp Leu Val Lys Pro Gly Gly
1               5                   10                  15

Ser Leu Lys Leu Ser Cys Val Val Ser Gly Phe Thr Phe Ser
            20                  25                  30

<210> SEQ ID NO 162
<211> LENGTH: 30
<212> TYPE: PRT
<213> ORGANISM: Artificial Sequence
<220> FEATURE:
<223> OTHER INFORMATION: Synthesized

<400> SEQUENCE: 162

Glu Val Lys Leu Gln Glu Ser Gly Pro Glu Leu Lys Lys Pro Gly Glu
1               5                   10                  15

Thr Val Glu Ile Ser Cys Lys Ala Ser Gly Tyr Thr Phe Thr
            20                  25                  30

<210> SEQ ID NO 163
<211> LENGTH: 30
<212> TYPE: PRT
<213> ORGANISM: Artificial Sequence
<220> FEATURE:
<223> OTHER INFORMATION: Synthesized

<400> SEQUENCE: 163

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr
            20                  25                  30

<210> SEQ ID NO 164
<211> LENGTH: 30
<212> TYPE: PRT
<213> ORGANISM: Artificial Sequence
<220> FEATURE:
<223> OTHER INFORMATION: Synthesized

<400> SEQUENCE: 164

Gln Val Gln Leu Gln Glu Ser Gly Pro Glu Leu Lys Gln Pro Gly Glu
1               5                   10                  15

Thr Val Lys Ile Ser Cys Lys Ala Ser Gly Tyr Thr Phe Thr
            20                  25                  30

<210> SEQ ID NO 165
<211> LENGTH: 30
<212> TYPE: PRT
<213> ORGANISM: Artificial Sequence
<220> FEATURE:
<223> OTHER INFORMATION: Synthesized

<400> SEQUENCE: 165

```
Gln Val Gln Leu Gln Gln Ser Gly Pro Glu Leu Lys Gln Pro Gly Glu
1               5                   10                  15

Thr Val Lys Ile Ser Cys Lys Ala Ser Gly Tyr Thr Phe Thr
            20                  25                  30
```

<210> SEQ ID NO 166
<211> LENGTH: 30
<212> TYPE: PRT
<213> ORGANISM: Artificial Sequence
<220> FEATURE:
<223> OTHER INFORMATION: Synthesized

<400> SEQUENCE: 166

```
Glu Val Gln Leu Glu Gln Ser Gly Pro Glu Leu Lys Lys Pro Gly Glu
1               5                   10                  15

Thr Val Lys Ile Ser Cys Lys Ala Ser Gly Tyr Thr Phe Ile
            20                  25                  30
```

<210> SEQ ID NO 167
<211> LENGTH: 30
<212> TYPE: PRT
<213> ORGANISM: Artificial Sequence
<220> FEATURE:
<223> OTHER INFORMATION: Synthesized

<400> SEQUENCE: 167

```
Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr
            20                  25                  30
```

<210> SEQ ID NO 168
<211> LENGTH: 30
<212> TYPE: PRT
<213> ORGANISM: Artificial Sequence
<220> FEATURE:
<223> OTHER INFORMATION: Synthesized

<400> SEQUENCE: 168

```
Glu Val Lys Leu Glu Glu Ser Gly Pro Glu Leu Lys Lys Pro Gly Glu
1               5                   10                  15

Thr Val Lys Ile Ser Cys Lys Ala Ser Gly Tyr Thr Phe Ile
            20                  25                  30
```

<210> SEQ ID NO 169
<211> LENGTH: 30
<212> TYPE: PRT
<213> ORGANISM: Artificial Sequence
<220> FEATURE:
<223> OTHER INFORMATION: Synthesized

<400> SEQUENCE: 169

```
Glu Val Gln Leu Glu Gln Ser Gly Ala Glu Leu Val Arg Pro Gly Ala
1               5                   10                  15

Ser Val Lys Leu Ser Cys Lys Ala Leu Gly Tyr Thr Phe Thr
            20                  25                  30
```

<210> SEQ ID NO 170
<211> LENGTH: 30
<212> TYPE: PRT
<213> ORGANISM: Artificial Sequence
<220> FEATURE:
<223> OTHER INFORMATION: Synthesized

<400> SEQUENCE: 170

```
Arg Cys Arg Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Ile
            20                  25                  30
```

<210> SEQ ID NO 171
<211> LENGTH: 30
<212> TYPE: PRT
<213> ORGANISM: Artificial Sequence
<220> FEATURE:
<223> OTHER INFORMATION: Synthesized

<400> SEQUENCE: 171

```
Glu Val Gln Leu Glu Gln Ser Gly Pro Glu Leu Lys Lys Pro Gly Glu
1               5                   10                  15

Thr Val Lys Ile Ser Cys Lys Ala Ser Gly Tyr Thr Phe Ile
            20                  25                  30
```

<210> SEQ ID NO 172
<211> LENGTH: 5
<212> TYPE: PRT
<213> ORGANISM: Artificial Sequence
<220> FEATURE:
<223> OTHER INFORMATION: Synthesized

<400> SEQUENCE: 172

```
Gly Tyr Ala Met Ser
1               5
```

<210> SEQ ID NO 173
<211> LENGTH: 5
<212> TYPE: PRT
<213> ORGANISM: Artificial Sequence
<220> FEATURE:
<223> OTHER INFORMATION: Synthesized

<400> SEQUENCE: 173

```
Arg Tyr Gly Met Ser
1               5
```

<210> SEQ ID NO 174
<211> LENGTH: 5
<212> TYPE: PRT
<213> ORGANISM: Artificial Sequence
<220> FEATURE:
<223> OTHER INFORMATION: Synthesized

<400> SEQUENCE: 174

```
Arg Tyr Gly Met Ser
1               5
```

<210> SEQ ID NO 175
<211> LENGTH: 5
<212> TYPE: PRT
<213> ORGANISM: Artificial Sequence
<220> FEATURE:
<223> OTHER INFORMATION: Synthesized

<400> SEQUENCE: 175

Asn Tyr Gly Met Asn
1 5

<210> SEQ ID NO 176
<211> LENGTH: 5
<212> TYPE: PRT
<213> ORGANISM: Artificial Sequence
<220> FEATURE:
<223> OTHER INFORMATION: Synthesized

<400> SEQUENCE: 176

Asn Tyr Gly Met Asn
1 5

<210> SEQ ID NO 177
<211> LENGTH: 5
<212> TYPE: PRT
<213> ORGANISM: Artificial Sequence
<220> FEATURE:
<223> OTHER INFORMATION: Synthesized

<400> SEQUENCE: 177

Asn Asn Gly Met Asn
1 5

<210> SEQ ID NO 178
<211> LENGTH: 5
<212> TYPE: PRT
<213> ORGANISM: Artificial Sequence
<220> FEATURE:
<223> OTHER INFORMATION: Synthesized

<400> SEQUENCE: 178

Asn Asn Gly Met Asn
1 5

<210> SEQ ID NO 179
<211> LENGTH: 5
<212> TYPE: PRT
<213> ORGANISM: Artificial Sequence
<220> FEATURE:
<223> OTHER INFORMATION: Synthesized

<400> SEQUENCE: 179

Asn Tyr Gly Met Asn
1 5

<210> SEQ ID NO 180
<211> LENGTH: 5
<212> TYPE: PRT
<213> ORGANISM: Artificial Sequence
<220> FEATURE:
<223> OTHER INFORMATION: Synthesized

<400> SEQUENCE: 180

Asn Tyr Gly Met Asn
1 5

<210> SEQ ID NO 181
<211> LENGTH: 5
<212> TYPE: PRT
<213> ORGANISM: Artificial Sequence
<220> FEATURE:
<223> OTHER INFORMATION: Synthesized

<400> SEQUENCE: 181

Asn Tyr Gly Met Asn
1 5

<210> SEQ ID NO 182
<211> LENGTH: 5
<212> TYPE: PRT
<213> ORGANISM: Artificial Sequence
<220> FEATURE:
<223> OTHER INFORMATION: Synthesized

<400> SEQUENCE: 182

Asp Tyr Glu Met His
1 5

<210> SEQ ID NO 183
<211> LENGTH: 5
<212> TYPE: PRT
<213> ORGANISM: Artificial Sequence
<220> FEATURE:
<223> OTHER INFORMATION: Synthesized

<400> SEQUENCE: 183

Asn Tyr Gly Met Asn
1 5

<210> SEQ ID NO 184
<211> LENGTH: 5
<212> TYPE: PRT
<213> ORGANISM: Artificial Sequence
<220> FEATURE:
<223> OTHER INFORMATION: Synthesized

<400> SEQUENCE: 184

Asn Tyr Gly Met Asn
1 5

<210> SEQ ID NO 185
<211> LENGTH: 14
<212> TYPE: PRT
<213> ORGANISM: Artificial Sequence
<220> FEATURE:
<223> OTHER INFORMATION: Synthesized

<400> SEQUENCE: 185

Trp Val Arg Gln Thr Pro Glu Lys Arg Leu Glu Trp Val Ala
1 5 10

<210> SEQ ID NO 186
<211> LENGTH: 14
<212> TYPE: PRT
<213> ORGANISM: Artificial Sequence
<220> FEATURE:
<223> OTHER INFORMATION: Synthesized

<400> SEQUENCE: 186

Trp Val Arg Gln Thr Pro Asp Lys Arg Leu Glu Trp Val Ala
1 5 10

<210> SEQ ID NO 187
<211> LENGTH: 14
<212> TYPE: PRT
<213> ORGANISM: Artificial Sequence
<220> FEATURE:
<223> OTHER INFORMATION: Synthesized

<400> SEQUENCE: 187

-continued

```
Trp Val Arg Gln Thr Pro Gly Lys Arg Leu Glu Trp Val Ala
1               5                   10


<210> SEQ ID NO 188
<211> LENGTH: 14
<212> TYPE: PRT
<213> ORGANISM: Artificial Sequence
<220> FEATURE:
<223> OTHER INFORMATION: Synthesized

<400> SEQUENCE: 188

Trp Val Lys Gln Ala Pro Gly Lys Gly Leu Lys Trp Met Gly
1               5                   10


<210> SEQ ID NO 189
<211> LENGTH: 14
<212> TYPE: PRT
<213> ORGANISM: Artificial Sequence
<220> FEATURE:
<223> OTHER INFORMATION: Synthesized

<400> SEQUENCE: 189

Trp Val Lys Gln Ala Pro Gly Lys Gly Leu Lys Trp Met Gly
1               5                   10


<210> SEQ ID NO 190
<211> LENGTH: 14
<212> TYPE: PRT
<213> ORGANISM: Artificial Sequence
<220> FEATURE:
<223> OTHER INFORMATION: Synthesized

<400> SEQUENCE: 190

Trp Val Lys Gln Ala Pro Gly Lys Gly Leu Lys Trp Met Gly
1               5                   10


<210> SEQ ID NO 191
<211> LENGTH: 14
<212> TYPE: PRT
<213> ORGANISM: Artificial Sequence
<220> FEATURE:
<223> OTHER INFORMATION: Synthesized

<400> SEQUENCE: 191

Trp Val Lys Gln Ala Pro Gly Lys Gly Leu Lys Trp Met Gly
1               5                   10


<210> SEQ ID NO 192
<211> LENGTH: 14
<212> TYPE: PRT
<213> ORGANISM: Artificial Sequence
<220> FEATURE:
<223> OTHER INFORMATION: Synthesized

<400> SEQUENCE: 192

Trp Val Lys Gln Ala Pro Gly Lys Gly Leu Lys Trp Met Gly
1               5                   10


<210> SEQ ID NO 193
<211> LENGTH: 14
<212> TYPE: PRT
<213> ORGANISM: Artificial Sequence
<220> FEATURE:
<223> OTHER INFORMATION: Synthesized

<400> SEQUENCE: 193

Trp Val Lys Gln Ala Pro Gly Lys Gly Leu Lys Trp Met Gly
```

-continued 1 5 10

<210> SEQ ID NO 194
<211> LENGTH: 14
<212> TYPE: PRT
<213> ORGANISM: Artificial Sequence
<220> FEATURE:
<223> OTHER INFORMATION: Synthesized

<400> SEQUENCE: 194

Trp Val Lys Gln Ala Pro Gly Lys Gly Leu Lys Trp Met Gly
1 5 10

<210> SEQ ID NO 195
<211> LENGTH: 14
<212> TYPE: PRT
<213> ORGANISM: Artificial Sequence
<220> FEATURE:
<223> OTHER INFORMATION: Synthesized

<400> SEQUENCE: 195

Trp Val Lys Gln Thr Pro Val His Gly Leu Glu Trp Ile Gly
1 5 10

<210> SEQ ID NO 196
<211> LENGTH: 14
<212> TYPE: PRT
<213> ORGANISM: Artificial Sequence
<220> FEATURE:
<223> OTHER INFORMATION: Synthesized

<400> SEQUENCE: 196

Trp Val Lys Gln Ala Pro Gly Lys Gly Leu Lys Trp Met Gly
1 5 10

<210> SEQ ID NO 197
<211> LENGTH: 14
<212> TYPE: PRT
<213> ORGANISM: Artificial Sequence
<220> FEATURE:
<223> OTHER INFORMATION: Synthesized

<400> SEQUENCE: 197

Trp Val Lys Gln Ala Pro Gly Lys Gly Leu Lys Trp Met Gly
1 5 10

<210> SEQ ID NO 198
<211> LENGTH: 17
<212> TYPE: PRT
<213> ORGANISM: Artificial Sequence
<220> FEATURE:
<223> OTHER INFORMATION: Synthesized

<400> SEQUENCE: 198

Thr Ile Ser Ser Gly Gly Thr Tyr Ile Tyr Tyr Pro Asp Ser Val Lys
1 5 10 15

Gly

<210> SEQ ID NO 199
<211> LENGTH: 17
<212> TYPE: PRT
<213> ORGANISM: Artificial Sequence
<220> FEATURE:
<223> OTHER INFORMATION: Synthesized

<400> SEQUENCE: 199

Thr Ile Ser Ser Gly Gly Thr Tyr Ile Tyr Tyr Pro Asp Ser Val Lys
1 5 10 15

Gly

<210> SEQ ID NO 200
<211> LENGTH: 17
<212> TYPE: PRT
<213> ORGANISM: Artificial Sequence
<220> FEATURE:
<223> OTHER INFORMATION: Synthesized

<400> SEQUENCE: 200

Thr Ile Ser Gly Gly Gly Thr Tyr Ile Tyr Tyr Pro Asp Ser Val Lys
1 5 10 15

Gly

<210> SEQ ID NO 201
<211> LENGTH: 17
<212> TYPE: PRT
<213> ORGANISM: Artificial Sequence
<220> FEATURE:
<223> OTHER INFORMATION: Synthesized

<400> SEQUENCE: 201

Trp Ile Asn Thr Tyr Thr Gly Glu Pro Thr Tyr Ala Gly Asp Phe Lys
1 5 10 15

Gly

<210> SEQ ID NO 202
<211> LENGTH: 17
<212> TYPE: PRT
<213> ORGANISM: Artificial Sequence
<220> FEATURE:
<223> OTHER INFORMATION: Synthesized

<400> SEQUENCE: 202

Trp Ile Asn Thr Tyr Thr Gly Glu Pro Thr Tyr Ala Gly Asp Phe Lys
1 5 10 15

Gly

<210> SEQ ID NO 203
<211> LENGTH: 17
<212> TYPE: PRT
<213> ORGANISM: Artificial Sequence
<220> FEATURE:
<223> OTHER INFORMATION: Synthesized

<400> SEQUENCE: 203

Trp Ile Asn Thr Tyr Thr Gly Glu Pro Thr Tyr Ala Asp Asp Phe Lys
1 5 10 15

Gly

<210> SEQ ID NO 204
<211> LENGTH: 17
<212> TYPE: PRT
<213> ORGANISM: Artificial Sequence
<220> FEATURE:
<223> OTHER INFORMATION: Synthesized

<400> SEQUENCE: 204

Trp Ile Asn Thr Tyr Thr Gly Glu Pro Thr Tyr Ala Asp Asp Phe Lys
1 5 10 15

Gly

<210> SEQ ID NO 205
<211> LENGTH: 17
<212> TYPE: PRT
<213> ORGANISM: Artificial Sequence
<220> FEATURE:
<223> OTHER INFORMATION: Synthesized

<400> SEQUENCE: 205

Trp Ile Asn Thr Tyr Thr Gly Glu Pro Thr Tyr Val Asp Asp Phe Lys
1 5 10 15

Gly

<210> SEQ ID NO 206
<211> LENGTH: 17
<212> TYPE: PRT
<213> ORGANISM: Artificial Sequence
<220> FEATURE:
<223> OTHER INFORMATION: Synthesized

<400> SEQUENCE: 206

Trp Ile Asn Thr Tyr Thr Gly Glu Pro Thr Tyr Ala Gly Asp Phe Lys
1 5 10 15

Gly

<210> SEQ ID NO 207
<211> LENGTH: 17
<212> TYPE: PRT
<213> ORGANISM: Artificial Sequence
<220> FEATURE:
<223> OTHER INFORMATION: Synthesized

<400> SEQUENCE: 207

Trp Ile Asn Thr Tyr Thr Gly Glu Pro Thr Tyr Val Asp Asp Phe Lys
1 5 10 15

Gly

<210> SEQ ID NO 208
<211> LENGTH: 17
<212> TYPE: PRT
<213> ORGANISM: Artificial Sequence
<220> FEATURE:
<223> OTHER INFORMATION: Synthesized

<400> SEQUENCE: 208

Ala Ile His Pro Gly Ser Gly Gly Thr Ala Tyr Asn Gln Lys Phe Lys
1 5 10 15

Gly

<210> SEQ ID NO 209
<211> LENGTH: 17
<212> TYPE: PRT
<213> ORGANISM: Artificial Sequence
<220> FEATURE:
<223> OTHER INFORMATION: Synthesized

<400> SEQUENCE: 209

Trp Ile Asn Thr Tyr Thr Gly Glu Pro Thr Tyr Val Asp Asp Phe Lys
1 5 10 15

Gly

<210> SEQ ID NO 210
<211> LENGTH: 17

<212> TYPE: PRT
<213> ORGANISM: Artificial Sequence
<220> FEATURE:
<223> OTHER INFORMATION: Synthesized

<400> SEQUENCE: 210

```
Trp Ile Asn Thr Tyr Thr Gly Glu Pro Thr Tyr Val Asp Asp Phe Lys
1               5                   10                  15

Gly
```

<210> SEQ ID NO 211
<211> LENGTH: 32
<212> TYPE: PRT
<213> ORGANISM: Artificial Sequence
<220> FEATURE:
<223> OTHER INFORMATION: Synthesized

<400> SEQUENCE: 211

```
Arg Phe Thr Ile Ser Arg Asp Asn Ala Lys Asn Thr Leu Tyr Leu Gln
1               5                   10                  15

Met Ser Ser Leu Arg Ser Glu Asp Thr Ala Met Tyr Tyr Cys Ala Arg
            20                  25                  30
```

<210> SEQ ID NO 212
<211> LENGTH: 32
<212> TYPE: PRT
<213> ORGANISM: Artificial Sequence
<220> FEATURE:
<223> OTHER INFORMATION: Synthesized

<400> SEQUENCE: 212

```
Arg Phe Thr Ile Ser Arg Asp Asn Ala Lys Asn Thr Leu Tyr Leu Gln
1               5                   10                  15

Met Ser Ser Leu Lys Ser Glu Asp Thr Ala Met Tyr Tyr Cys Ala Arg
            20                  25                  30
```

<210> SEQ ID NO 213
<211> LENGTH: 32
<212> TYPE: PRT
<213> ORGANISM: Artificial Sequence
<220> FEATURE:
<223> OTHER INFORMATION: Synthesized

<400> SEQUENCE: 213

```
Arg Phe Thr Ile Ser Arg Asp Asn Ala Lys Asn Thr Leu Tyr Leu Gln
1               5                   10                  15

Met Ser Ser Leu Lys Ser Glu Asp Thr Ala Met Tyr His Cys Thr Arg
            20                  25                  30
```

<210> SEQ ID NO 214
<211> LENGTH: 32
<212> TYPE: PRT
<213> ORGANISM: Artificial Sequence
<220> FEATURE:
<223> OTHER INFORMATION: Synthesized

<400> SEQUENCE: 214

```
Arg Phe Ala Phe Ser Leu Glu Thr Ser Ala Ser Thr Ala Tyr Leu Gln
1               5                   10                  15

Ile Asn Thr Leu Lys Asn Glu Asp Thr Ala Thr Tyr Phe Cys Ala Arg
            20                  25                  30
```

<210> SEQ ID NO 215
<211> LENGTH: 32

<212> TYPE: PRT
<213> ORGANISM: Artificial Sequence
<220> FEATURE:
<223> OTHER INFORMATION: Synthesized

<400> SEQUENCE: 215

Arg Phe Ala Phe Ser Leu Glu Thr Ser Ala Ser Thr Ala Tyr Leu Gln
1 5 10 15

Ile Asn Thr Leu Lys Asn Glu Asp Thr Ala Thr Tyr Phe Cys Ala Arg
20 25 30

<210> SEQ ID NO 216
<211> LENGTH: 32
<212> TYPE: PRT
<213> ORGANISM: Artificial Sequence
<220> FEATURE:
<223> OTHER INFORMATION: Synthesized

<400> SEQUENCE: 216

Arg Phe Ala Phe Ser Leu Asp Thr Ser Ala Ser Thr Ala Tyr Leu Gln
1 5 10 15

Ile Asn Asn Leu Lys Asn Glu Asp Met Ala Thr Tyr Phe Cys Ala Arg
20 25 30

<210> SEQ ID NO 217
<211> LENGTH: 32
<212> TYPE: PRT
<213> ORGANISM: Artificial Sequence
<220> FEATURE:
<223> OTHER INFORMATION: Synthesized

<400> SEQUENCE: 217

Arg Phe Ala Phe Ser Leu Gly Thr Ser Ala Ser Thr Ala Tyr Leu Gln
1 5 10 15

Ile Asn Asn Leu Lys Asn Glu Asp Met Ala Thr Tyr Phe Cys Ala Arg
20 25 30

<210> SEQ ID NO 218
<211> LENGTH: 32
<212> TYPE: PRT
<213> ORGANISM: Artificial Sequence
<220> FEATURE:
<223> OTHER INFORMATION: Synthesized

<400> SEQUENCE: 218

Arg Phe Ala Phe Ser Leu Glu Thr Ser Ala Arg Thr Ala Tyr Leu Gln
1 5 10 15

Ile Asn Asn Leu Lys Asn Glu Asp Met Ala Thr Tyr Phe Cys Ala Arg
20 25 30

<210> SEQ ID NO 219
<211> LENGTH: 32
<212> TYPE: PRT
<213> ORGANISM: Artificial Sequence
<220> FEATURE:
<223> OTHER INFORMATION: Synthesized

<400> SEQUENCE: 219

Arg Phe Ala Phe Ser Leu Glu Thr Ser Ala Ser Thr Ala Tyr Leu Gln
1 5 10 15

Ile Asn Thr Leu Lys Asn Glu Asp Thr Ala Thr Tyr Phe Cys Ala Arg
20 25 30

<210> SEQ ID NO 220

```
<211> LENGTH: 32
<212> TYPE: PRT
<213> ORGANISM: Artificial Sequence
<220> FEATURE:
<223> OTHER INFORMATION: Synthesized

<400> SEQUENCE: 220

Arg Phe Ala Phe Ser Leu Glu Thr Ser Ala Arg Thr Ala Tyr Leu Gln
1               5                   10                  15

Ile Asn Asn Leu Lys Asn Glu Asp Met Ala Thr Tyr Phe Cys Ala Arg
            20                  25                  30


<210> SEQ ID NO 221
<211> LENGTH: 32
<212> TYPE: PRT
<213> ORGANISM: Artificial Sequence
<220> FEATURE:
<223> OTHER INFORMATION: MIN-F2-2 heavy chain variable framework region
      3 (FWR3) amino acid sequence

<400> SEQUENCE: 221

Lys Ala Thr Leu Thr Ala Asp Lys Ser Ser Ser Thr Ala Tyr Met Glu
1               5                   10                  15

Leu Ser Ser Leu Thr Ser Glu Asp Ser Ala Val Tyr Tyr Cys Thr Asn
            20                  25                  30


<210> SEQ ID NO 222
<211> LENGTH: 32
<212> TYPE: PRT
<213> ORGANISM: Artificial Sequence
<220> FEATURE:
<223> OTHER INFORMATION: Synthesized

<400> SEQUENCE: 222

Arg Phe Ala Phe Ser Leu Glu Thr Ser Ala Arg Thr Ala Tyr Leu Gln
1               5                   10                  15

Ile Asn Asn Leu Lys Asn Glu Asp Met Ala Thr Tyr Phe Cys Ala Arg
            20                  25                  30


<210> SEQ ID NO 223
<211> LENGTH: 32
<212> TYPE: PRT
<213> ORGANISM: Artificial Sequence
<220> FEATURE:
<223> OTHER INFORMATION: Synthesized

<400> SEQUENCE: 223

Arg Phe Ala Phe Ser Leu Glu Thr Ser Ala Arg Thr Ala Tyr Leu Gln
1               5                   10                  15

Ile Asn Asn Leu Lys Asn Glu Asp Met Ala Thr Tyr Phe Cys Ala Arg
            20                  25                  30


<210> SEQ ID NO 224
<211> LENGTH: 9
<212> TYPE: PRT
<213> ORGANISM: Artificial Sequence
<220> FEATURE:
<223> OTHER INFORMATION: Synthesized

<400> SEQUENCE: 224

Leu Gly Gly Asp Asn Tyr Tyr Glu Tyr
1               5


<210> SEQ ID NO 225
<211> LENGTH: 10
```

<212> TYPE: PRT
<213> ORGANISM: Artificial Sequence
<220> FEATURE:
<223> OTHER INFORMATION: Synthesized

<400> SEQUENCE: 225

Asp Asn Tyr Gly Ser Ser Tyr Asp Tyr Ala
1 5 10

<210> SEQ ID NO 226
<211> LENGTH: 10
<212> TYPE: PRT
<213> ORGANISM: Artificial Sequence
<220> FEATURE:
<223> OTHER INFORMATION: Synthesized

<400> SEQUENCE: 226

Asp Asn Tyr Gly Arg Asn Tyr Asp Tyr Gly
1 5 10

<210> SEQ ID NO 227
<211> LENGTH: 9
<212> TYPE: PRT
<213> ORGANISM: Artificial Sequence
<220> FEATURE:
<223> OTHER INFORMATION: Synthesized

<400> SEQUENCE: 227

Ser Gly Asp Gly Tyr Trp Tyr Tyr Ala
1 5

<210> SEQ ID NO 228
<211> LENGTH: 9
<212> TYPE: PRT
<213> ORGANISM: Artificial Sequence
<220> FEATURE:
<223> OTHER INFORMATION: Synthesized

<400> SEQUENCE: 228

Ser Gly Asp Gly Tyr Trp Tyr Tyr Ala
1 5

<210> SEQ ID NO 229
<211> LENGTH: 9
<212> TYPE: PRT
<213> ORGANISM: Artificial Sequence
<220> FEATURE:
<223> OTHER INFORMATION: Synthesized

<400> SEQUENCE: 229

Thr Gly Thr Ala Arg Ala Phe Tyr Ala
1 5

<210> SEQ ID NO 230
<211> LENGTH: 9
<212> TYPE: PRT
<213> ORGANISM: Artificial Sequence
<220> FEATURE:
<223> OTHER INFORMATION: Synthesized

<400> SEQUENCE: 230

Thr Gly Thr Ala Arg Ala Phe Tyr Ala
1 5

<210> SEQ ID NO 231
<211> LENGTH: 9
<212> TYPE: PRT

<213> ORGANISM: Artificial Sequence
<220> FEATURE:
<223> OTHER INFORMATION: Synthesized

<400> SEQUENCE: 231

Thr Gly Thr Thr Ala Ile Leu Asn Gly
1               5

<210> SEQ ID NO 232
<211> LENGTH: 9
<212> TYPE: PRT
<213> ORGANISM: Artificial Sequence
<220> FEATURE:
<223> OTHER INFORMATION: Synthesized

<400> SEQUENCE: 232

Ser Gly Asp Gly Tyr Trp Tyr Tyr Ala
1               5

<210> SEQ ID NO 233
<211> LENGTH: 9
<212> TYPE: PRT
<213> ORGANISM: Artificial Sequence
<220> FEATURE:
<223> OTHER INFORMATION: Synthesized

<400> SEQUENCE: 233

Thr Gly Thr Thr Ala Ile Leu Asn Gly
1               5

<210> SEQ ID NO 234
<211> LENGTH: 5
<212> TYPE: PRT
<213> ORGANISM: Artificial Sequence
<220> FEATURE:
<223> OTHER INFORMATION: Synthesized

<400> SEQUENCE: 234

Tyr Gly Ser Phe Ala
1               5

<210> SEQ ID NO 235
<211> LENGTH: 9
<212> TYPE: PRT
<213> ORGANISM: Artificial Sequence
<220> FEATURE:
<223> OTHER INFORMATION: Synthesized

<400> SEQUENCE: 235

Thr Gly Thr Thr Ala Ile Leu Asn Gly
1               5

<210> SEQ ID NO 236
<211> LENGTH: 9
<212> TYPE: PRT
<213> ORGANISM: Artificial Sequence
<220> FEATURE:
<223> OTHER INFORMATION: Synthesized

<400> SEQUENCE: 236

Thr Gly Thr Thr Ala Ile Leu Asn Gly
1               5

<210> SEQ ID NO 237
<211> LENGTH: 23
<212> TYPE: PRT
<213> ORGANISM: Artificial Sequence
<220> FEATURE:
<223> OTHER INFORMATION: Synthesized

<400> SEQUENCE: 237

Asp Ile Gln Met Thr Gln Ser Pro Ser Ser Leu Ser Ala Ser Leu Gly
1 5 10 15

Glu Arg Val Ser Leu Thr Cys
20

<210> SEQ ID NO 238
<211> LENGTH: 23
<212> TYPE: PRT
<213> ORGANISM: Artificial Sequence
<220> FEATURE:
<223> OTHER INFORMATION: Synthesized

<400> SEQUENCE: 238

Asp Ile Val Leu Thr Gln Ser Pro Ala Ser Leu Ala Val Ser Leu Gly
1 5 10 15

Gln Arg Ala Thr Ile Ser Tyr
20

<210> SEQ ID NO 239
<211> LENGTH: 23
<212> TYPE: PRT
<213> ORGANISM: Artificial Sequence
<220> FEATURE:
<223> OTHER INFORMATION: Synthesized

<400> SEQUENCE: 239

Asp Ile Gln Met Thr Gln Ser Pro Ala Ser Gln Ser Ala Ser Leu Gly
1 5 10 15

Glu Ser Val Thr Ile Thr Cys
20

<210> SEQ ID NO 240
<211> LENGTH: 23
<212> TYPE: PRT
<213> ORGANISM: Artificial Sequence
<220> FEATURE:
<223> OTHER INFORMATION: Synthesized

<400> SEQUENCE: 240

Asp Ile Val Leu Thr Gln Ser Pro Ala Ser Leu Ala Val Ser Leu Gly
1 5 10 15

Gln Arg Ala Thr Ile Ser Tyr
20

<210> SEQ ID NO 241
<211> LENGTH: 23
<212> TYPE: PRT
<213> ORGANISM: Artificial Sequence
<220> FEATURE:
<223> OTHER INFORMATION: Synthesized

<400> SEQUENCE: 241

Asp Ile Val Leu Thr Gln Ser Pro Ala Ser Leu Ala Val Ser Leu Gly
1 5 10 15

Gln Arg Ala Thr Ile Ser Tyr
20

<210> SEQ ID NO 242
<211> LENGTH: 23
<212> TYPE: PRT

<213> ORGANISM: Artificial Sequence
<220> FEATURE:
<223> OTHER INFORMATION: Synthesized

<400> SEQUENCE: 242

Asp Ile Val Met Thr Gln Ser Gln Lys Phe Met Ser Thr Ser Val Gly
1 5 10 15

Asp Arg Val Ser Val Thr Cys
20

<210> SEQ ID NO 243
<211> LENGTH: 23
<212> TYPE: PRT
<213> ORGANISM: Artificial Sequence
<220> FEATURE:
<223> OTHER INFORMATION: Synthesized

<400> SEQUENCE: 243

Asp Ile Gln Met Thr Gln Pro Pro Ala Ser Leu Ser Ala Ser Val Gly
1 5 10 15

Glu Thr Val Thr Ile Thr Cys
20

<210> SEQ ID NO 244
<211> LENGTH: 11
<212> TYPE: PRT
<213> ORGANISM: Artificial Sequence
<220> FEATURE:
<223> OTHER INFORMATION: Synthesized

<400> SEQUENCE: 244

Arg Ala Ser Gln Asp Ile Gly Ser Ser Leu Asn
1 5 10

<210> SEQ ID NO 245
<211> LENGTH: 15
<212> TYPE: PRT
<213> ORGANISM: Artificial Sequence
<220> FEATURE:
<223> OTHER INFORMATION: Synthesized

<400> SEQUENCE: 245

Arg Ala Ser Lys Ser Val Ser Thr Ser Gly Tyr Ser Tyr Met His
1 5 10 15

<210> SEQ ID NO 246
<211> LENGTH: 11
<212> TYPE: PRT
<213> ORGANISM: Artificial Sequence
<220> FEATURE:
<223> OTHER INFORMATION: Synthesized

<400> SEQUENCE: 246

Leu Ala Ser Gln Thr Ile Gly Thr Trp Leu Ala
1 5 10

<210> SEQ ID NO 247
<211> LENGTH: 15
<212> TYPE: PRT
<213> ORGANISM: Artificial Sequence
<220> FEATURE:
<223> OTHER INFORMATION: Synthesized

<400> SEQUENCE: 247

Arg Ala Ser Lys Ser Val Ser Thr Ser Gly Tyr Ser Tyr Met His
1 5 10 15

<210> SEQ ID NO 248
<211> LENGTH: 15
<212> TYPE: PRT
<213> ORGANISM: Artificial Sequence
<220> FEATURE:
<223> OTHER INFORMATION: Synthesized

<400> SEQUENCE: 248

Arg Ala Ser Lys Ser Val Ser Thr Ser Gly Tyr Ser Tyr Met His
1 5 10 15

<210> SEQ ID NO 249
<211> LENGTH: 11
<212> TYPE: PRT
<213> ORGANISM: Artificial Sequence
<220> FEATURE:
<223> OTHER INFORMATION: Synthesized

<400> SEQUENCE: 249

Lys Ala Ser Gln Asn Val Gly Thr Asn Val Gly
1 5 10

<210> SEQ ID NO 250
<211> LENGTH: 11
<212> TYPE: PRT
<213> ORGANISM: Artificial Sequence
<220> FEATURE:
<223> OTHER INFORMATION: Synthesized

<400> SEQUENCE: 250

Arg Ala Ser Gly Asn Ile His Asn Phe Leu Ala
1 5 10

<210> SEQ ID NO 251
<211> LENGTH: 15
<212> TYPE: PRT
<213> ORGANISM: Artificial Sequence
<220> FEATURE:
<223> OTHER INFORMATION: Synthesized

<400> SEQUENCE: 251

Trp Leu Gln Gln Glu Pro Asp Gly Thr Ile Lys Arg Leu Ile Tyr
1 5 10 15

<210> SEQ ID NO 252
<211> LENGTH: 15
<212> TYPE: PRT
<213> ORGANISM: Artificial Sequence
<220> FEATURE:
<223> OTHER INFORMATION: Synthesized

<400> SEQUENCE: 252

Trp Asn Gln Gln Lys Pro Gly Gln Pro Pro Arg Leu Leu Ile Tyr
1 5 10 15

<210> SEQ ID NO 253
<211> LENGTH: 15
<212> TYPE: PRT
<213> ORGANISM: Artificial Sequence
<220> FEATURE:
<223> OTHER INFORMATION: Synthesized

<400> SEQUENCE: 253

Trp Tyr Gln Gln Lys Pro Gly Lys Ser Pro Gln Leu Leu Ile Tyr
1 5 10 15

<210> SEQ ID NO 254
<211> LENGTH: 15
<212> TYPE: PRT
<213> ORGANISM: Artificial Sequence
<220> FEATURE:
<223> OTHER INFORMATION: Synthesized

<400> SEQUENCE: 254

Trp Asn Gln Gln Lys Pro Gly Gln Pro Pro Arg Leu Leu Ile Tyr
1 5 10 15

<210> SEQ ID NO 255
<211> LENGTH: 15
<212> TYPE: PRT
<213> ORGANISM: Artificial Sequence
<220> FEATURE:
<223> OTHER INFORMATION: Synthesized

<400> SEQUENCE: 255

Trp Asn Gln Gln Lys Pro Gly Gln Pro Pro Arg Leu Leu Ile Tyr
1 5 10 15

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267
<211> LENGTH: 15
<212> TYPE: PRT
<213> ORGANISM: Artificial Sequence
<220> FEATURE:
<223> OTHER INFORMATION: Synthesized

<400> SEQUENCE: 267

Trp Tyr Gln Gln Lys Gln Gly Lys Ser Pro Gln Leu Leu Val Tyr
1               5                   10                  15

<210> SEQ ID NO 268
<211> LENGTH: 7
<212> TYPE: PRT
<213> ORGANISM: Artificial Sequence
<220> FEATURE:
<223> OTHER INFORMATION: Synthesized

<400> SEQUENCE: 268

Ala Thr Ser Ser Leu Asp Ser
1               5

<210> SEQ ID NO 269
<211> LENGTH: 7
<212> TYPE: PRT
<213> ORGANISM: Artificial Sequence
<220> FEATURE:
<223> OTHER INFORMATION: Synthesized

<400> SEQUENCE: 269

Leu Val Ser Asn Leu Glu Ser
1               5

<210> SEQ ID NO 270
<211> LENGTH: 7
<212> TYPE: PRT
<213> ORGANISM: Artificial Sequence
<220> FEATURE:
<223> OTHER INFORMATION: Synthesized

<400> SEQUENCE: 270

Ala Ala Thr Ser Leu Ala Asp
1               5

<210> SEQ ID NO 271
<211> LENGTH: 7

<212> TYPE: PRT
<213> ORGANISM: Artificial Sequence
<220> FEATURE:
<223> OTHER INFORMATION: Synthesized

<400> SEQUENCE: 271

Leu Val Ser Asn Leu Glu Ser
1 5

<210> SEQ ID NO 272
<211> LENGTH: 7
<212> TYPE: PRT
<213> ORGANISM: Artificial Sequence
<220> FEATURE:
<223> OTHER INFORMATION: Synthesized

<400> SEQUENCE: 272

Leu Val Ser Asn Leu Glu Ser
1 5

<210> SEQ ID NO 273
<211> LENGTH: 7
<212> TYPE: PRT
<213> ORGANISM: Artificial Sequence
<220> FEATURE:
<223> OTHER INFORMATION: Synthesized

<400> SEQUENCE: 273

Ser Ala Ser Tyr Arg Tyr Ser
1 5

<210> SEQ ID NO 274
<211> LENGTH: 7
<212> TYPE: PRT
<213> ORGANISM: Artificial Sequence
<220> FEATURE:
<223> OTHER INFORMATION: Synthesized

<400> SEQUENCE: 274

Asn Ala Lys Thr Leu Ala Asp
1 5

<210> SEQ ID NO 275
<211> LENGTH: 32
<212> TYPE: PRT
<213> ORGANISM: Artificial Sequence
<220> FEATURE:
<223> OTHER INFORMATION: Synthesized

<400> SEQUENCE: 275

Gly Val Pro Lys Arg Phe Ser Gly Ser Arg Ser Gly Ser Asp Tyr Ser
1 5 10 15

Leu Thr Ile Ser Ser Leu Glu Ser Glu Asp Phe Val Asp Tyr Tyr Cys
20 25 30

<210> SEQ ID NO 276
<211> LENGTH: 32
<212> TYPE: PRT
<213> ORGANISM: Artificial Sequence
<220> FEATURE:
<223> OTHER INFORMATION: Synthesized

<400> SEQUENCE: 276

Gly Val Pro Ala Arg Phe Ser Gly Ser Gly Ser Gly Thr Asp Phe Thr
1 5 10 15

Leu Asn Ile His Pro Val Glu Glu Glu Asp Ala Ala Thr Tyr Tyr Cys 20 25 30

<210> SEQ ID NO 277
<211> LENGTH: 32
<212> TYPE: PRT
<213> ORGANISM: Artificial Sequence
<220> FEATURE:
<223> OTHER INFORMATION: Synthesized

<400> SEQUENCE: 277

Gly Val Pro Ser Arg Phe Ser Gly Ser Gly Ser Gly Thr Lys Phe Ser
1 5 10 15

Phe Lys Ile Ser Ser Leu Gln Ala Glu Asp Phe Val Ser Tyr Tyr Cys
20 25 30

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

-continued

000

<210> SEQ ID NO 287

<400> SEQUENCE: 287

000

<210> SEQ ID NO 288
<211> LENGTH: 32
<212> TYPE: PRT
<213> ORGANISM: Artificial Sequence
<220> FEATURE:
<223> OTHER INFORMATION: Synthesized

<400> SEQUENCE: 288

```
Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
            20                  25                  30
```

<210> SEQ ID NO 289
<211> LENGTH: 32
<212> TYPE: PRT
<213> ORGANISM: Artificial Sequence
<220> FEATURE:
<223> OTHER INFORMATION: Synthesized

<400> SEQUENCE: 289

```
Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
            20                  25                  30
```

<210> SEQ ID NO 290
<211> LENGTH: 32
<212> TYPE: PRT
<213> ORGANISM: Artificial Sequence
<220> FEATURE:
<223> OTHER INFORMATION: Synthesized

<400> SEQUENCE: 290

```
Gly Val Pro Asp Arg Phe Thr Gly Ser Gly Ser Gly Thr Asp Phe Thr
1               5                   10                  15

Leu Thr Ile Ser Asn Val Gln Ser Glu Asp Leu Ala Glu Tyr Phe Cys
            20                  25                  30
```

<210> SEQ ID NO 291
<211> LENGTH: 32
<212> TYPE: PRT
<213> ORGANISM: Artificial Sequence
<220> FEATURE:
<223> OTHER INFORMATION: Synthesized

<400> SEQUENCE: 291

```
Gly Val Pro Ser Arg Phe Ser Gly Ser Gly Ser Gly Thr Gln Tyr Ser
1               5                   10                  15

Leu Lys Ile Asn Ser Leu Gln Pro Glu Asp Phe Gly Ser Tyr Tyr Cys
            20                  25                  30
```

<210> SEQ ID NO 292
<211> LENGTH: 30
<212> TYPE: PRT
<213> ORGANISM: Artificial Sequence
<220> FEATURE:

<223> OTHER INFORMATION: Synthesized

<400> SEQUENCE: 292

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr
            20                  25                  30

<210> SEQ ID NO 293
<211> LENGTH: 30
<212> TYPE: PRT
<213> ORGANISM: Artificial Sequence
<220> FEATURE:
<223> OTHER INFORMATION: Synthesized

<400> SEQUENCE: 293

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr
            20                  25                  30

<210> SEQ ID NO 294
<211> LENGTH: 32
<212> TYPE: PRT
<213> ORGANISM: Artificial Sequence
<220> FEATURE:
<223> OTHER INFORMATION: Synthesized

<400> SEQUENCE: 294

Gln Ile Thr Leu Lys Glu Ser Gly Pro Gly Ile Val Gln Pro Ser Gln
1               5                   10                  15

Pro Phe Arg Leu Thr Cys Thr Phe Ser Gly Phe Ser Leu Ser Thr Ser
            20                  25                  30

<210> SEQ ID NO 295
<211> LENGTH: 59
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (12)..(12)
<223> OTHER INFORMATION: Xaa can be any naturally occurring amino acid

<400> SEQUENCE: 295

Asp Val Lys Leu Val Glu Ser Gly Gly Asp Leu Xaa Lys Leu Thr Glu
1               5                   10                  15

Gly Glu Asp Ile Trp Glu Gly Leu Thr Leu Cys Arg Asp Ser Asp Gln
            20                  25                  30

Ser Pro Leu Ala Pro Val Ser Lys Pro Gly Arg Val Val Arg Pro Gln
        35                  40                  45

Arg Ser Cys Thr Val Ile Gln Gly Cys Val Leu
    50                  55

<210> SEQ ID NO 296
<211> LENGTH: 30
<212> TYPE: PRT
<213> ORGANISM: Artificial Sequence
<220> FEATURE:
<223> OTHER INFORMATION: Synthesized

<400> SEQUENCE: 296

Gln Val Gln Leu Lys Gln Ser Gly Pro Gly Leu Val Gln Pro Ser Gln 1 5 10 15

Ser Leu Ser Ile Thr Cys Thr Val Ser Gly Phe Ser Leu Thr
20 25 30

<210> SEQ ID NO 297

<400> SEQUENCE: 297

000

<210> SEQ ID NO 298
<211> LENGTH: 30
<212> TYPE: PRT
<213> ORGANISM: Artificial Sequence
<220> FEATURE:
<223> OTHER INFORMATION: Synthesized

<400> SEQUENCE: 298

Glu Val Gln Leu Val Glu Ser Gly Gly Asp Leu Val Lys Pro Gly Arg
1 5 10 15

Ser Leu Lys Leu Ser Cys Ala Ala Ser Gly Phe Thr Phe Ser
20 25 30

<210> SEQ ID NO 299
<211> LENGTH: 30
<212> TYPE: PRT
<213> ORGANISM: Artificial Sequence
<220> FEATURE:
<223> OTHER INFORMATION: Synthesized

<400> SEQUENCE: 299

Glu Val Gln Leu Gln Gln Ser Gly Pro Glu Leu Val Lys Pro Gly Ala
1 5 10 15

Ser Val Lys Ile Ser Cys Lys Ala Ser Gly Tyr Ser Phe Thr
20 25 30

<210> SEQ ID NO 300
<211> LENGTH: 5
<212> TYPE: PRT
<213> ORGANISM: Artificial Sequence
<220> FEATURE:
<223> OTHER INFORMATION: Synthesized

<400> SEQUENCE: 300

Ser Tyr Trp Met His
1 5

<210> SEQ ID NO 301
<211> LENGTH: 5
<212> TYPE: PRT
<213> ORGANISM: Artificial Sequence
<220> FEATURE:
<223> OTHER INFORMATION: Synthesized

<400> SEQUENCE: 301

Ser Tyr Trp Met His
1 5

<210> SEQ ID NO 302
<211> LENGTH: 5
<212> TYPE: PRT
<213> ORGANISM: Artificial Sequence
<220> FEATURE:
<223> OTHER INFORMATION: Synthesized

<400> SEQUENCE: 302

Gly Ile Gly Val Thr
1 5

<210> SEQ ID NO 303
<211> LENGTH: 5
<212> TYPE: PRT
<213> ORGANISM: Artificial Sequence
<220> FEATURE:
<223> OTHER INFORMATION: Synthesized

<400> SEQUENCE: 303

Ser Tyr Gly Val His
1 5

<210> SEQ ID NO 304
<211> LENGTH: 5
<212> TYPE: PRT
<213> ORGANISM: Artificial Sequence
<220> FEATURE:
<223> OTHER INFORMATION: Synthesized

<400> SEQUENCE: 304

Ser Phe Gly Met Ser
1 5

<210> SEQ ID NO 305
<211> LENGTH: 5
<212> TYPE: PRT
<213> ORGANISM: Artificial Sequence
<220> FEATURE:
<223> OTHER INFORMATION: Synthesized

<400> SEQUENCE: 305

Gly Tyr Phe Met Ser
1 5

<210> SEQ ID NO 306
<211> LENGTH: 14
<212> TYPE: PRT
<213> ORGANISM: Artificial Sequence
<220> FEATURE:
<223> OTHER INFORMATION: Synthesized

<400> SEQUENCE: 306

Trp Val Lys Gln Arg Pro Gly Gln Gly Leu Glu Trp Ile Gly
1 5 10

<210> SEQ ID NO 307
<211> LENGTH: 14
<212> TYPE: PRT
<213> ORGANISM: Artificial Sequence
<220> FEATURE:
<223> OTHER INFORMATION: Synthesized

<400> SEQUENCE: 307

Trp Val Lys Gln Arg Pro Gly Gln Gly Leu Glu Trp Ile Gly
1 5 10

<210> SEQ ID NO 308
<211> LENGTH: 14
<212> TYPE: PRT
<213> ORGANISM: Artificial Sequence
<220> FEATURE:
<223> OTHER INFORMATION: Synthesized

<400> SEQUENCE: 308

-continued

Trp Ile Arg Gln Pro Ser Gly Lys Gly Leu Glu Trp Leu Ala
1 5 10

<210> SEQ ID NO 309
<211> LENGTH: 13
<212> TYPE: PRT
<213> ORGANISM: Artificial Sequence
<220> FEATURE:
<223> OTHER INFORMATION: Synthesized

<400> SEQUENCE: 309

Arg Leu Gln Thr Ala His Leu Gln Val Gln Gly Val Leu
1 5 10

<210> SEQ ID NO 310
<211> LENGTH: 14
<212> TYPE: PRT
<213> ORGANISM: Artificial Sequence
<220> FEATURE:
<223> OTHER INFORMATION: Synthesized

<400> SEQUENCE: 310

Trp Val Arg Gln Ser Pro Gly Lys Gly Leu Glu Trp Leu Gly
1 5 10

<210> SEQ ID NO 311
<211> LENGTH: 14
<212> TYPE: PRT
<213> ORGANISM: Artificial Sequence
<220> FEATURE:
<223> OTHER INFORMATION: Synthesized

<400> SEQUENCE: 311

Trp Val Arg Gln Thr Pro Asp Lys Arg Leu Glu Trp Val Ala
1 5 10

<210> SEQ ID NO 312
<211> LENGTH: 14
<212> TYPE: PRT
<213> ORGANISM: Artificial Sequence
<220> FEATURE:
<223> OTHER INFORMATION: Synthesized

<400> SEQUENCE: 312

Trp Val Met Gln Ser His Gly Lys Ser Leu Glu Trp Ile Gly
1 5 10

<210> SEQ ID NO 313
<211> LENGTH: 17
<212> TYPE: PRT
<213> ORGANISM: Artificial Sequence
<220> FEATURE:
<223> OTHER INFORMATION: Synthesized

<400> SEQUENCE: 313

Glu Ile Asn Pro Ser Asn Gly Arg Thr Asn Tyr Asn Glu Lys Phe Lys
1 5 10 15

Ser

<210> SEQ ID NO 314
<211> LENGTH: 17
<212> TYPE: PRT
<213> ORGANISM: Artificial Sequence
<220> FEATURE:
<223> OTHER INFORMATION: Synthesized

<400> SEQUENCE: 314

Glu Ile Asn Pro Ser Asn Gly Arg Thr Asn Tyr Asn Glu Lys Phe Lys
1 5 10 15

Ser

<210> SEQ ID NO 315
<211> LENGTH: 16
<212> TYPE: PRT
<213> ORGANISM: Artificial Sequence
<220> FEATURE:
<223> OTHER INFORMATION: Synthesized

<400> SEQUENCE: 315

Thr Ile Trp Trp Asp Asp Asp Asn Arg Tyr Asn Pro Ser Leu Lys Ser
1 5 10 15

<210> SEQ ID NO 316
<211> LENGTH: 18
<212> TYPE: PRT
<213> ORGANISM: Artificial Sequence
<220> FEATURE:
<223> OTHER INFORMATION: Synthesized

<400> SEQUENCE: 316

Gly Ile Val Ser Gly Asp Gly Glu Ser Ala Leu His Ser Val Trp Ile
1 5 10 15

Val Gly

<210> SEQ ID NO 317
<211> LENGTH: 16
<212> TYPE: PRT
<213> ORGANISM: Artificial Sequence
<220> FEATURE:
<223> OTHER INFORMATION: Synthesized

<400> SEQUENCE: 317

Val Ile Trp Gly Gly Gly Ser Thr Asp Tyr Asn Ala Ala Phe Ile Ser
1 5 10 15

<210> SEQ ID NO 318
<211> LENGTH: 17
<212> TYPE: PRT
<213> ORGANISM: Artificial Sequence
<220> FEATURE:
<223> OTHER INFORMATION: Synthesized

<400> SEQUENCE: 318

Thr Ile Ser Ser Gly Gly Thr Tyr Thr Tyr Tyr Pro Asp Ser Val Lys
1 5 10 15

Gly

<210> SEQ ID NO 319
<211> LENGTH: 17
<212> TYPE: PRT
<213> ORGANISM: Artificial Sequence
<220> FEATURE:
<223> OTHER INFORMATION: Synthesized

<400> SEQUENCE: 319

Arg Ile Asn Pro Tyr Asn Gly Asp Thr Phe Tyr Asn Gln Lys Phe Lys
1 5 10 15

Gly

<210> SEQ ID NO 320

<211> LENGTH: 32
<212> TYPE: PRT
<213> ORGANISM: Artificial Sequence
<220> FEATURE:
<223> OTHER INFORMATION: Synthesized

<400> SEQUENCE: 320

Lys Ala Thr Leu Thr Val Asp Lys Ser Ser Ser Thr Ala Tyr Met Gln
1 5 10 15

Leu Ser Ser Leu Thr Ser Glu Asp Ser Ala Val Tyr Tyr Cys Ala Thr
20 25 30

<210> SEQ ID NO 321
<211> LENGTH: 32
<212> TYPE: PRT
<213> ORGANISM: Artificial Sequence
<220> FEATURE:
<223> OTHER INFORMATION: Synthesized

<400> SEQUENCE: 321

Lys Ala Thr Leu Thr Val Asp Lys Ser Ser Ser Thr Ala Tyr Met Gln
1 5 10 15

Leu Ser Ser Leu Thr Ser Glu Asp Ser Ala Val Tyr Tyr Cys Ala Thr
20 25 30

<210> SEQ ID NO 322
<211> LENGTH: 32
<212> TYPE: PRT
<213> ORGANISM: Artificial Sequence
<220> FEATURE:
<223> OTHER INFORMATION: Synthesized

<400> SEQUENCE: 322

Arg Leu Thr Val Ser Lys Asp Thr Ser Asn Asn Gln Ala Phe Leu Asn
1 5 10 15

Ile Ile Thr Val Glu Thr Ala Asp Thr Ala Ile Tyr Tyr Cys Ala Gln
20 25 30

<210> SEQ ID NO 323
<211> LENGTH: 30
<212> TYPE: PRT
<213> ORGANISM: Artificial Sequence
<220> FEATURE:
<223> OTHER INFORMATION: Synthesized

<400> SEQUENCE: 323

Ala Thr Thr Ile Thr Ile Asn Gly Cys Asp Gln Leu Gln Pro Leu Leu
1 5 10 15

Trp Ser Leu Ala Asn Pro Arg His Val Ile Ala Thr Glu Ser
20 25 30

<210> SEQ ID NO 324
<211> LENGTH: 32
<212> TYPE: PRT
<213> ORGANISM: Artificial Sequence
<220> FEATURE:
<223> OTHER INFORMATION: Synthesized

<400> SEQUENCE: 324

Arg Leu Ser Ile Ser Lys Asp Asn Ser Lys Ser Gln Val Phe Phe Lys
1 5 10 15

Met Asn Ser Leu Gln Ala Asn Asp Thr Ala Ile Tyr Tyr Cys Ala Arg
20 25 30

-continued

<210> SEQ ID NO 325
<211> LENGTH: 32
<212> TYPE: PRT
<213> ORGANISM: Artificial Sequence
<220> FEATURE:
<223> OTHER INFORMATION: Synthesized

<400> SEQUENCE: 325

```
Arg Phe Thr Ile Ser Arg Asp Asn Ala Lys Asn Thr Leu Tyr Leu Gln
1               5                   10                  15

Met Ser Ser Leu Lys Ser Glu Asp Thr Ala Met Tyr Tyr Cys Ser Arg
            20                  25                  30
```

<210> SEQ ID NO 326
<211> LENGTH: 32
<212> TYPE: PRT
<213> ORGANISM: Artificial Sequence
<220> FEATURE:
<223> OTHER INFORMATION: Synthesized

<400> SEQUENCE: 326

```
Lys Ala Thr Leu Thr Val Asp Lys Ser Ser Thr Thr Ala His Ile Glu
1               5                   10                  15

Leu Arg Ser Leu Ala Ser Glu Asp Ser Ala Val Tyr Tyr Cys Ala Arg
            20                  25                  30
```

<210> SEQ ID NO 327
<211> LENGTH: 465
<212> TYPE: PRT
<213> ORGANISM: Artificial Sequence
<220> FEATURE:
<223> OTHER INFORMATION: Synthesized

<400> SEQUENCE: 327

```
Asp Ile Val Ile Thr Gln Ser Thr Ala Ser Leu Gly Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Arg Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205
```

Ile Val Lys Ser Phe Asn Arg Asn Glu Cys Ser Gly Gly Gly Ser Gly
    210                 215                 220

Gly Gly Ser Glu Gly Gly Gly Ser Glu Gly Gly Gly Ser Glu Gly Gly
225                 230                 235                 240

Gly Ser Glu Gly Gly Gly Ser Gly Gly Gly Ser Gly Glu Val Gln Leu
                245                 250                 255

Glu Glu Ser Gly Gly Gly Leu Val Lys Pro Gly Gly Ser Leu Lys Leu
            260                 265                 270

Ser Cys Ala Ala Ser Gly Phe Thr Phe Ser Gly Tyr Ala Met Ser Trp
        275                 280                 285

Val Arg Gln Thr Pro Glu Lys Arg Leu Glu Trp Val Ala Thr Ile Ser
    290                 295                 300

Ser Gly Gly Thr Tyr Ile Tyr Tyr Pro Asp Ser Val Lys Gly Arg Phe
305                 310                 315                 320

Thr Ile Ser Arg Asp Asn Ala Lys Asn Thr Leu Tyr Leu Gln Met Ser
                325                 330                 335

Ser Leu Arg Ser Glu Asp Thr Ala Met Tyr Tyr Cys Ala Arg Leu Gly
            340                 345                 350

Gly Asp Asn Tyr Tyr Glu Tyr Phe Asp Val Trp Gly Ala Gly Thr Thr
        355                 360                 365

Val Thr Val Ser Ser Ala Lys Thr Thr Pro Pro Ser Val Tyr Pro Leu
    370                 375                 380

Ala Pro Gly Ser Ala Ala Gln Thr Asn Ser Met Val Thr Leu Gly Cys
385                 390                 395                 400

Leu Val Lys Gly Tyr Phe Pro Glu Pro Val Thr Val Thr Trp Asn Ser
                405                 410                 415

Gly Ser Leu Ser Ser Gly Val His Thr Phe Pro Ala Val Leu Gln Ser
            420                 425                 430

Asp Leu Tyr Thr Leu Ser Ser Ser Val Thr Val Pro Ser Ser Thr Trp
        435                 440                 445

Pro Ser Glu Thr Val Thr Cys Asn Val Ala His Pro Ala Ser Arg Thr
    450                 455                 460

Ala
465

<210> SEQ ID NO 328
<211> LENGTH: 21
<212> TYPE: PRT
<213> ORGANISM: Artificial Sequence
<220> FEATURE:
<223> OTHER INFORMATION: Synthesized

<400> SEQUENCE: 328

Met Glu Thr Asp Thr Leu Leu Leu Trp Val Leu Leu Leu Trp Val Pro
1               5                   10                  15

Gly Ser Thr Gly Asp
            20

<210> SEQ ID NO 329
<211> LENGTH: 10
<212> TYPE: PRT
<213> ORGANISM: Artificial Sequence
<220> FEATURE:
<223> OTHER INFORMATION: Synthesized

<400> SEQUENCE: 329

Glu Gln Lys Leu Ile Ser Glu Glu Asp Leu

-continued 1 5 10

<210> SEQ ID NO 330
<211> LENGTH: 5
<212> TYPE: PRT
<213> ORGANISM: Artificial Sequence
<220> FEATURE:
<223> OTHER INFORMATION: Synthesized

<400> SEQUENCE: 330

Asn Tyr Gly Met Asn
1 5

<210> SEQ ID NO 331
<211> LENGTH: 5
<212> TYPE: PRT
<213> ORGANISM: Artificial Sequence
<220> FEATURE:
<223> OTHER INFORMATION: Synthesized

<400> SEQUENCE: 331

Gly Tyr Ala Met Ser
1 5

<210> SEQ ID NO 332
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 332

Xaa Tyr Xaa Met Ser
1 5

<210> SEQ ID NO 333
<211> LENGTH: 17
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (12)..(13)
<223> OTHER INFORMATION: Xaa can be any naturally occurring amino acid

<400> SEQUENCE: 333

Trp Ile Asn Thr Tyr Thr Gly Glu Pro Thr Tyr Xaa Xaa Asp Phe Lys
1 5 10 15

Gly

<210> SEQ ID NO 334
<211> LENGTH: 17
<212> TYPE: PRT
<213> ORGANISM: Artificial Sequence
<220> FEATURE:
<223> OTHER INFORMATION: Synthesized

<400> SEQUENCE: 334

Thr Ile Ser Ser Gly Gly Thr Tyr Ile Tyr Tyr Pro Asp Ser Val Lys

-continued 1 5 10 15

Gly

<210> SEQ ID NO 335
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(7)
<223> OTHER INFORMATION: Xaa can be any naturally occurring amino acid

<400> SEQUENCE: 335

Xaa Gly Xaa Xaa Xaa Xaa Xaa Tyr Ala
1 5

<210> SEQ ID NO 336
<211> LENGTH: 9
<212> TYPE: PRT
<213> ORGANISM: Artificial Sequence
<220> FEATURE:
<223> OTHER INFORMATION: Synthesized

<400> SEQUENCE: 336

Thr Gly Thr Thr Ala Ile Leu Asn Gly
1 5

<210> SEQ ID NO 337
<211> LENGTH: 9
<212> TYPE: PRT
<213> ORGANISM: Artificial Sequence
<220> FEATURE:
<223> OTHER INFORMATION: Synthesized

<400> SEQUENCE: 337

Ser Gly Asp Gly Tyr Trp Tyr Tyr Ala
1 5

<210> SEQ ID NO 338
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 338

Asp Asn Tyr Gly Xaa Xaa Tyr Asp Tyr Xaa
1 5 10

<210> SEQ ID NO 339
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 339

Ser Ala Ser Ser Ser Xaa Ser Tyr Xaa Xaa
1 5 10

<210> SEQ ID NO 340
<211> LENGTH: 15
<212> TYPE: PRT
<213> ORGANISM: Artificial Sequence
<220> FEATURE:
<223> OTHER INFORMATION: Synthesized

<400> SEQUENCE: 340

Arg Ala Ser Lys Ser Val Ser Thr Ser Gly Tyr Ser Tyr Met His
1 5 10 15

<210> SEQ ID NO 341
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: Xaa can be any naturally occurring amino acid

<400> SEQUENCE: 341

Xaa Thr Ser Asn Leu Ala Ser
1 5

<210> SEQ ID NO 342
<211> LENGTH: 7
<212> TYPE: PRT
<213> ORGANISM: Artificial Sequence
<220> FEATURE:
<223> OTHER INFORMATION: Synthesized

<400> SEQUENCE: 342

Leu Ala Ser Asn Leu Glu Ser
1 5

<210> SEQ ID NO 343
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 343

Gln Gln Arg Ser Xaa Tyr Pro Xaa Thr
1 5

<210> SEQ ID NO 344
<211> LENGTH: 9
<212> TYPE: PRT
<213> ORGANISM: Artificial Sequence
<220> FEATURE:
<223> OTHER INFORMATION: Synthesized

<400> SEQUENCE: 344

Gln His Ser Arg Glu Leu Pro Phe Thr
1               5

<210> SEQ ID NO 345
<211> LENGTH: 23
<212> TYPE: PRT
<213> ORGANISM: Artificial Sequence
<220> FEATURE:
<223> OTHER INFORMATION: Synthesized

<400> SEQUENCE: 345

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 346
<211> LENGTH: 75
<212> TYPE: DNA
<213> ORGANISM: Artificial Sequence
<220> FEATURE:
<223> OTHER INFORMATION: Synthesized

<400> SEQUENCE: 346
gatatccaga tgacccagtc cccgagctcc ctgtccgcct ctgtgggcga tagggtcacc     60
atcacctgcc gtgcc                                                      75

<210> SEQ ID NO 347
<211> LENGTH: 15
<212> TYPE: PRT
<213> ORGANISM: Artificial Sequence
<220> FEATURE:
<223> OTHER INFORMATION: Synthesized

<400> SEQUENCE: 347

Trp Tyr Gln Gln Lys Pro Gly Lys Ala Pro Lys Leu Leu Ile Tyr
1               5                   10                  15

<210> SEQ ID NO 348
<211> LENGTH: 45
<212> TYPE: DNA
<213> ORGANISM: Artificial Sequence
<220> FEATURE:
<223> OTHER INFORMATION: Synthesized

<400> SEQUENCE: 348
tggtatcaac agaaaccagg aaaagctccg aaactactga tttac                     45

<210> SEQ ID NO 349
<211> LENGTH: 32
<212> TYPE: PRT
<213> ORGANISM: Artificial Sequence
<220> FEATURE:
<223> OTHER INFORMATION: Synthesized

<400> SEQUENCE: 349

Gly Val Pro Ser Arg Phe Ser Gly Ser Arg Ser Gly Thr Asp Phe Thr
1               5                   10                  15

Leu Thr Ile Ser Ser Leu Gln Pro Glu Asp Phe Ala Thr Tyr Tyr Cys
20 25 30

<210> SEQ ID NO 350
<211> LENGTH: 93
<212> TYPE: DNA
<213> ORGANISM: Artificial Sequence
<220> FEATURE:
<223> OTHER INFORMATION: Synthesized

<400> SEQUENCE: 350
ggagtccctt ctcgcttctc tggatccaga tctgggacgg atttcactct gaccatcagc 60
agtctgcagc cggaagactt cgcaatctat tac 93

<210> SEQ ID NO 351
<211> LENGTH: 10
<212> TYPE: PRT
<213> ORGANISM: Artificial Sequence
<220> FEATURE:
<223> OTHER INFORMATION: Synthesized

<400> SEQUENCE: 351

Phe Gly Gln Gly Thr Lys Val Glu Ile Lys
1 5 10

<210> SEQ ID NO 352
<211> LENGTH: 30
<212> TYPE: DNA
<213> ORGANISM: Artificial Sequence
<220> FEATURE:
<223> OTHER INFORMATION: Synthesized

<400> SEQUENCE: 352
ttcggacagg gtaccaaggt ggagatcaaa 30

<210> SEQ ID NO 353
<211> LENGTH: 25
<212> TYPE: PRT
<213> ORGANISM: Artificial Sequence
<220> FEATURE:
<223> OTHER INFORMATION: Synthesized

<400> SEQUENCE: 353

Glu Val Gln Leu Val Glu Ser Gly Gly Gly Leu Val Gln Pro Gly Gly
1 5 10 15

Ser Leu Arg Leu Ser Cys Ala Ala Ser
20 25

<210> SEQ ID NO 354
<211> LENGTH: 75
<212> TYPE: DNA
<213> ORGANISM: Artificial Sequence
<220> FEATURE:
<223> OTHER INFORMATION: Synthesized

<400> SEQUENCE: 354
gaggttcagc tggtggagtc tggcggtggc ctggtgcagc cagggggctc actccgtttg 60
tcctgtgcag cttct 75

<210> SEQ ID NO 355
<211> LENGTH: 14
<212> TYPE: PRT
<213> ORGANISM: Artificial Sequence
<220> FEATURE:

<223> OTHER INFORMATION: Synthesized

<400> SEQUENCE: 355

Trp Val Arg Gln Ala Pro Gly Lys Gly Leu Glu Trp Val Ala
1 5 10

<210> SEQ ID NO 356
<211> LENGTH: 42
<212> TYPE: DNA
<213> ORGANISM: Artificial Sequence
<220> FEATURE:
<223> OTHER INFORMATION: Synthesized

<400> SEQUENCE: 356
tgggtgcgtc aggccccggg taagggcctg gaatgggttg ca 42

<210> SEQ ID NO 357
<211> LENGTH: 32
<212> TYPE: PRT
<213> ORGANISM: Artificial Sequence
<220> FEATURE:
<223> OTHER INFORMATION: Synthesized

<400> SEQUENCE: 357

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ser Arg
20 25 30

<210> SEQ ID NO 358
<211> LENGTH: 96
<212> TYPE: DNA
<213> ORGANISM: Artificial Sequence
<220> FEATURE:
<223> OTHER INFORMATION: Synthesized

<400> SEQUENCE: 358
cgtttcacta taagcgcaga cacatccaaa aacacagcct acctgcagat gaacagcctg 60
cgtgctgagg acactgccgt ctattattgt tctaga 96

<210> SEQ ID NO 359
<211> LENGTH: 11
<212> TYPE: PRT
<213> ORGANISM: Artificial Sequence
<220> FEATURE:
<223> OTHER INFORMATION: Synthesized

<400> SEQUENCE: 359

Trp Gly Gln Gly Thr Leu Val Thr Val Ser Ser
1 5 10

<210> SEQ ID NO 360
<211> LENGTH: 33
<212> TYPE: DNA
<213> ORGANISM: Artificial Sequence
<220> FEATURE:
<223> OTHER INFORMATION: Synthesized

<400> SEQUENCE: 360
tggggtcaag gaaccctggt caccgtctcc tcg 33

<210> SEQ ID NO 361
<211> LENGTH: 34
<212> TYPE: PRT
<213> ORGANISM: Artificial Sequence
<220> FEATURE:
<223> OTHER INFORMATION: Synthesized

<400> SEQUENCE: 361

Ser Gly Gly Gly Ser Gly Gly Gly Ser Glu Gly Gly Gly Ser Glu Gly
1               5                   10                  15

Gly Gly Ser Glu Gly Gly Gly Ser Glu Gly Gly Gly Ser Gly Gly Gly
            20                  25                  30

Ser Gly

<210> SEQ ID NO 362
<211> LENGTH: 30
<212> TYPE: PRT
<213> ORGANISM: Artificial Sequence
<220> FEATURE:
<223> OTHER INFORMATION: Synthesized

<400> SEQUENCE: 362

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 363
<211> LENGTH: 14
<212> TYPE: PRT
<213> ORGANISM: Artificial Sequence
<220> FEATURE:
<223> OTHER INFORMATION: Synthesized

<400> SEQUENCE: 363

Trp Val Arg Gln Ala Pro Gly Lys Gly Leu Glu Trp Val Ser
1               5                   10

<210> SEQ ID NO 364
<211> LENGTH: 27
<212> TYPE: PRT
<213> ORGANISM: Artificial Sequence
<220> FEATURE:
<223> OTHER INFORMATION: Synthesized

<400> SEQUENCE: 364

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val
            20                  25

<210> SEQ ID NO 365
<211> LENGTH: 23
<212> TYPE: PRT
<213> ORGANISM: Artificial Sequence
<220> FEATURE:
<223> OTHER INFORMATION: Synthesized

<400> SEQUENCE: 365

Asp Ile Val Leu Thr Gln Ser Pro Ala Ser Leu Ala Val Ser Pro Gly
1               5                   10                  15

Gln Arg Ala Thr Ile Thr Cys
            20

<210> SEQ ID NO 366
<211> LENGTH: 15
<212> TYPE: PRT
<213> ORGANISM: Artificial Sequence
<220> FEATURE:
<223> OTHER INFORMATION: Synthesized

<400> SEQUENCE: 366

Trp Tyr Gln Gln Lys Pro Gly Gln Pro Pro Lys Leu Leu Ile Tyr
1 5 10 15

<210> SEQ ID NO 367
<211> LENGTH: 31
<212> TYPE: PRT
<213> ORGANISM: Artificial Sequence
<220> FEATURE:
<223> OTHER INFORMATION: Synthesized

<400> SEQUENCE: 367

Gly Val Pro Ala Arg Phe Ser Gly Ser Gly Ser Gly Thr Asp Phe Thr
1 5 10 15

Leu Thr Ile Asn Pro Val Glu Ala Asn Asp Thr Ala Asn Tyr Tyr
20 25 30

<210> SEQ ID NO 368
<211> LENGTH: 30
<212> TYPE: PRT
<213> ORGANISM: Artificial Sequence
<220> FEATURE:
<223> OTHER INFORMATION: Synthesized

<400> SEQUENCE: 368

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser
20 25 30

<210> SEQ ID NO 369
<211> LENGTH: 14
<212> TYPE: PRT
<213> ORGANISM: Artificial Sequence
<220> FEATURE:
<223> OTHER INFORMATION: Synthesized

<400> SEQUENCE: 369

Trp Val Arg Gln Ala Pro Gly Lys Gly Leu Glu Trp Val Ser
1 5 10

<210> SEQ ID NO 370
<211> LENGTH: 32
<212> TYPE: PRT
<213> ORGANISM: Artificial Sequence
<220> FEATURE:
<223> OTHER INFORMATION: Synthesized

<400> SEQUENCE: 370

Arg Phe Thr Ile Ser Arg Asp Asn Ala Lys Asn Ser Leu Tyr Leu Gln
1 5 10 15

Met Asn Ser Leu Arg Ala Glu Asp Thr Ala Val Tyr Tyr Cys Ala Arg
20 25 30

<210> SEQ ID NO 371
<211> LENGTH: 23
<212> TYPE: PRT
<213> ORGANISM: Artificial Sequence
<220> FEATURE:
<223> OTHER INFORMATION: Synthesized

<400> SEQUENCE: 371

-continued

```
Glu Ile Val Met Thr Gln Ser Pro Ala Thr Leu Ser Val Ser Pro Gly
1               5                   10                  15

Glu Arg Ala Thr Leu Ser Cys
            20


<210> SEQ ID NO 372
<211> LENGTH: 15
<212> TYPE: PRT
<213> ORGANISM: Artificial Sequence
<220> FEATURE:
<223> OTHER INFORMATION: Synthesized

<400> SEQUENCE: 372

Trp Phe Gln Gln Arg Pro Gly Thr Ser Pro Lys Leu Leu Ile Tyr
1               5                   10                  15


<210> SEQ ID NO 373
<211> LENGTH: 32
<212> TYPE: PRT
<213> ORGANISM: Artificial Sequence
<220> FEATURE:
<223> OTHER INFORMATION: Synthesized

<400> SEQUENCE: 373

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30


<210> SEQ ID NO 374
<211> LENGTH: 9
<212> TYPE: PRT
<213> ORGANISM: Artificial Sequence
<220> FEATURE:
<223> OTHER INFORMATION: Synthesized

<400> SEQUENCE: 374

Leu Gly Gly Asp Asn Tyr Tyr Glu Tyr
1               5


<210> SEQ ID NO 375
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 375

His His His His His His
1               5
```

MUC1* ANTIBODIES

CROSS-REFERENCE TO RELATED APPLICATIONS

The present application is a continuation of U.S. patent application Ser. No. 15/501,768, filed Sep. 18, 2017, now U.S. Pat. No. 10,421,819, which is a national stage entry of International Patent Application No. PCT/US2009/059754, filed Oct. 6, 2009, which claims the benefit of U.S. Provisional Patent Application No. 61/103,204, filed Oct. 6, 2008, the contents of each of which are incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: 56699-718.301_ST25.txt; date created: Aug. 22, 2022; file size: 160,727 bytes.

BACKGROUND OF THE INVENTION

1. Field of the Invention

The present invention relates to monoclonal antibodies to MUC1* and uses of thereof.

2. General Background and State of the Art

The MUC1 receptor is a Type I transmembrane glycoprotein from the mucin family that has been implicated in many human cancers. It is estimated that approximately 75% of all solid tumors aberrantly express the MUC1 receptor. The group of MUC1* cancers includes more than 90% of breast carcinomas, 47% of prostate tumors and a high percentage of ovarian, colorectal, lung, and pancreatic cancers. There is some evidence that among the normal functions of the MUC1 receptor are roles in cell adhesion, fertility and immune response. The role of the MUC1 receptor in cancers has not yet been established in the literature. However, major differences in cell surface expression and receptor patterning in cancers have been well documented. The most striking difference between MUC1 expression on a healthy cell and expression in a cancer cell is that on a healthy cell, the receptor is clustered at the apical border, while on cancer cells the receptor is uniformly distributed over the entire surface of the cell. Additionally, there is some evidence that the receptor is overexpressed on tumor cells in addition to the aberrant patterning.

The normal function of MUC1 as well as its link to cancer has not yet been definitively determined. What is known is that a portion of the extracellular domain of MUC1 is shed or cleaved and can be detected in the serum of breast cancer patients. In breast cancer patients, levels of shed MUC1 in the serum are sometimes measured to monitor the patient's response to treatment. The cytoplasmic tail of MUC1 is rich in motifs for a variety of signal transduction proteins. It has been reported in the literature that Grb2 and SOS, which are common signaling proteins, associate with MUC1's cytoplasmic tail. It is noted in the scientific literature that in cancer cells, the extracellular domain is under-glycosylated.

A membrane-bound MUC1 cleavage product, MUC1*, is the predominant form of the protein on cultured cancer cells and on cancerous tissues. MUC1* consists of the cytoplasmic tail, transmembrane domain, and about 45 amino acids of the extracellular domain (ECD). Although the exact site(s) of cleavage remain somewhat uncertain.

MUC1* stimulates cell growth when it is activated by ligand-induced dimerization. There are several instances when it is desirable to enhance the growth of certain cells and to this end, a convenient method for doing so is via the addition of a bivalent anti-MUC1* antibody, which simulates a dimeric ligand. In other cases, it is desirable to inhibit the growth of MUC1*-positive cells. For example, many cancer cells express MUC1*. The growth of MUC1-positive cancer cells is inhibited when a monovalent agent binds to MUC1* and prevents dimerization. A convenient monovalent agent for blocking MUC1*-mediated cell growth is a monovalent antibody. Monovalent antibodies can be antibody fragments that are enzymatic digestion products, or they can be engineered to have only one antigen binding site. Antibodies that bind MUC1* monovalently also include bispecific antibodies since they, too, inhibit dimerization of the extracellular domain of MUC1*. The stimulation (bivalent) and inhibition (monovalent) of MUC1*-mediated cell growth using polyclonal antibodies that recognize the primary sequence of MUC1 growth factor receptor (PSMGFR) sequence (SEQ ID NO:1) and variants thereof. Here, we disclose the generation of monoclonal antibodies that recognize the PSMGFR sequence and variants.

There are many reasons for identifying monoclonal antibodies. For example, a hybridoma that produces a single antibody species provides a reproducible supply of a single antibody, the monoclonal, rather than a collection of antibodies which have a variety of affinities, specificities and the generation of which is not totally reproducible. Each batch of antibodies comes from a different animal and a different immunization. By contrast, once a hybridoma is identified that produces an antibody with the desired characteristics, then by maintaining the hybridoma, one has an unlimited supply of a reproducible, single species antibody. Additionally, once a monoclonal or single species of antibody has been identified, one can determine the sequence of the antibody or its variable regions. This enables many forms of protein engineering and recombinant DNA technology which can be used for example to make antibody derivatives, including but not limited to single chain, bispecific, diabodies, and antibody-chemical fusions or antibody-protein fusions. For example, knowing the sequence of an antibody enables generating a monovalent, single chain antibody consisting of variable light and heavy chain regions connected by a linker sequence. Depending upon the target, it may also be desirable to generate a bispecific antibody wherein each variable region (heavy and light chain) recognizes a different target.

SUMMARY OF THE INVENTION

The present invention includes using MUC1* antibodies and antibody derivatives. The invention further includes using genes encoding the MUC1* antibody, which may be used in combination with genes for other MUC1* stimulating species such as MMP-14 or TACE or other MUC1 cleavage enzymes such as NM23, which is the natural ligand for MUC1*, and the like. These genes are used to stimulate MUC1* growth factor receptor activity in cells or in a host animal or human.

In one embodiment, nucleic acids encoding a MUC1* antibody are inserted downstream of a tissue specific promoter and injected into a pronucleus or similar just prior to the complete fusion of egg and sperm to generate a transgenic animal. This will generate a mouse or other transgenic animal that would spontaneously form tumors or would be more prone to forming tumors. Similarly, genes encoding an anti-MUC1* antibody are simultaneously injected or inserted into a plasmid that also encodes another tumor-promoting gene to enhance tumor formation.

Methods for increasing stimulation of stem-like cell growth by introducing genes for MUC1, MUC1* or MUC1* stimulating agents are used in recipient animals or humans as well as in vitro in cell cultures. In one embodiment, a plasmid encoding a MUC1* antibody is added exogenously or transfected into an antibody-producing hybridoma in order to increase antibody production by increasing cell growth rate and rendering the cells resistant to cell death through the stimulation of MUC1*. In this aspect of the invention, the growth of antibody-producing cells is enhanced without contaminating the product which is the desired antibody. Antibody-producing cells are typically grown in media that contains reduced serum because the serum component contain many antibodies itself. Reducing the amount of serum in the cell culture media minimizes the carry over contamination but also reduces cell growth and overall yield of the desired antibody. The addition of exogenous anti-MUC1* or the transfection of the plasmid that codes for the anti-MUC1* increases cell growth and survival, while the single, known antibody can be selectively purified away from the product which is the desired antibody. The addition of a MUC1* dimerizing ligand such as NM23 may alternatively be used.

In one embodiment, the MUC1* stimulating antibody is administered to a patient for the treatment of sepsis. Many cell types increase expression of MUC1* in response to stress. Patients rapidly succumb to sepsis because of massive cell death. Administering to the patient a MUC1* dimerizing agent such as its natural ligand NM23 or its cognate antibody would increase cell survival while patient is treated with agents to kill the infectious agent and thus increase patient survival.

In another embodiment, the MUC1* stimulating antibody is administered to a patient suffering from an infection wherein it is desirable to reduce an amount of cell death. For example, certain pathogens act locally and rapidly destroy tissues. A MUC1* stimulating antibody is administered either systemically or locally to reduce or prevent pathogen-induced cell death.

In another embodiment, the gene encoding a MUC1* stimulating antibody can be inserted into a newly fertilized egg to make a primitive cell, such as a stem cell, wherein the resultant cells produce their own MUC1* stimulating ligand, which enhances or induces pluripotency and other stem cell-like features.

In one aspect of the invention, the invention is directed to an isolated monoclonal antibody to MUC1*. The antibody may be bivalent or mono-valent for MUC1*. The antibody may specifically bind to the amino acid sequence of SEQ ID NO:1. The monoclonal antibody may have an amino acid sequence in the heavy chain variable region in the CDR1 region that is at least 90% identical to NYGMN (SEQ ID NO:330), GYAMS (SEQ ID NO:331) or R/GYA/GMS (SEQ ID NO:332) or at least 90% identical to a sequence selected from among SEQ ID NOS:172-184; in the CDR2 region that is at least 90% identical to WINTYTGEPTYA/VG/DDFKG (SEQ ID NO:333) or TISSGGTYIYYPDSVKG (SEQ ID NO:334) or at least 90% identical to a sequence selected from among SEQ ID NOS: 198-210; in the CDR3 region that is at least 90% identical to S/TGT/DT/AXXY/FYA (SEQ ID NO:335), TGTTAILNG (SEQ ID NO:336), SGDGYWYYA (SEQ ID NO:337) or DNYGXXYDYG/A (SEQ ID NO:338) or at least 90% identical to a sequence selected from among SEQ ID NOS:224-236.

In another aspect, the invention is directed to a monoclonal antibody having an amino acid sequence in the heavy chain variable region comprised of the following: (i) in the CDR1 region, a sequence that is at least 90% identical to NYGMN (SEQ ID NO:330), GYAMS (SEQ ID NO:331) or R/GYA/GMS (SEQ ID NO:332); and (ii) in the CDR2 region, a sequence that is at least 90% identical to WINTYTGEPTYA/VG/DDFKG (SEQ ID NO:333) or TISSGGTYIYYPDSVKG (SEQ ID NO:334). The monoclonal antibody may have an amino acid sequence in the heavy chain variable region comprised of the following: (i) in the CDR1 region, a sequence that is at least 90% identical to NYGMN (SEQ ID NO:330), GYAMS (SEQ ID NO:331) or R/GYA/GMS (SEQ ID NO:332); and (ii) in the CDR3 region, a sequence that is at least 90% identical to S/TGT/DT/AXXY/FYA (SEQ ID NO:335), TGTTAILNG (SEQ ID NO:336), SGDGYWYYA (SEQ ID NO:337) or DNYGXXYDYG/A (SEQ ID NO:338). The monoclonal antibody may have an amino acid sequence in the heavy chain variable region comprised of the following: (i) in the CDR2 region, a sequence that is at least 90% identical to WINTYTGEPTYA/VG/DDFKG (SEQ ID NO:333) or TISSGGTYIYYPDSVKG (SEQ ID NO:334); and (ii) in the CDR3 region, a sequence that is at least 90% identical to S/TGT/DT/AXXY/FYA (SEQ ID NO:335), TGTTAILNG (SEQ ID NO:336), SGDGYWYYA (SEQ ID NO:337) or DNYGXXYDYG/A (SEQ ID NO:338). The monoclonal antibody may have an amino acid sequence in the heavy chain variable region comprised of the following: (i) in the CDR1 region, a sequence that is at least 90% identical to NYGMN (SEQ ID NO:330), GYAMS (SEQ ID NO:331) or R/GYA/GMS (SEQ ID NO:332); (ii) in the CDR2 region, a sequence that is at least 90% identical to WINTYTGEPTYA/VG/DDFKG (SEQ ID NO:333) or TISSGGTYIYYPDSVKG (SEQ ID NO:334); and (iii) in the CDR3 region, a sequence that is at least 90% identical to S/TGT/DT/AXXY/FYA (SEQ ID NO:335), TGTTAILNG (SEQ ID NO:336), SGDGYWYYA (SEQ ID NO:337) or DNYGXXYDYG/A (SEQ ID NO:338).

In another aspect, the invention is directed to a monoclonal antibody having an amino acid sequence in the kappa chain variable region in the CDR1 region that is at least 90% identical to SASSSV/ISYM/IWY (SEQ ID NO:339) or RASKSVSTSGYSYMH (SEQ ID NO:340). The monoclonal antibody may have an amino acid sequence in the kappa chain variable region in the CDR1 region selected from among SEQ ID NOS:108-110 and SEQ ID NOS:112-118. The monoclonal antibody may have an amino acid sequence in the kappa chain variable region in the CDR2 region that is at least 90% identical to S/GTSNLAS (SEQ ID NO:341) or LASNLES (SEQ ID NO:342) or at least 90% identical to region selected from among SEQ ID NOS:129-138; in the CDR3 region that is at least 90% identical to QQRSS/NYPS/FT (SEQ ID NO:343) or QHSRELPFT (SEQ ID NO:344) or at least 90% identical to a sequence selected from among SEQ ID NOS:149-158.

In another aspect, the invention is directed to a monoclonal antibody having an amino acid sequence in the kappa chain variable region comprised of the following: (i) in the CDR1 region, a sequence that is at least 90% identical to SASSSV/ISYM/IH/Y (SEQ ID NO:339) or RASKSVSTSGYSYMH (SEQ ID NO:340); and (ii) in the CDR2 region, a sequence that is at least 90% identical to S/GTSNLAS (SEQ ID NO:341) or LASNLES (SEQ ID NO:342). The monoclonal antibody may have an amino acid sequence in the kappa chain variable region comprised of the following: (i) in the CDR1 region, a sequence that is at least 90% identical to SASSSV/ISYM/IH/Y (SEQ ID NO:339) or RASKSVSTSGYSYMH (SEQ ID NO:340); and (ii) in the CDR3 region, a sequence that is at least 90% identical to QQRSS/NYPS/FT (SEQ ID NO:343) or QHSRELPFT (SEQ ID NO:344). The monoclonal antibody may have an amino acid sequence in the kappa chain variable region comprised of the following: (i) in the CDR2 region, a sequence that is at least 90% identical to S/GTSNLAS (SEQ ID NO:341) or LASNLES (SEQ ID NO:342); and (ii) in the CDR3 region, a sequence that is at least 90% identical to QQRSS/NYPS/FT (SEQ ID NO:343) or QHSRELPFT (SEQ ID NO:344). The monoclonal antibody according to claim 1 may have an amino acid sequence in the kappa chain variable region comprised of the following: (i) in the CDR1 region, a sequence that is at least 90% identical to SASSSV/ISYM/IH/Y (SEQ ID NO:339) or RASKSVSTSGYSYMH (SEQ ID NO:340); (ii) in the CDR2 region, in the CDR2 region, a sequence that is at least 90% identical to S/GTSNLAS (SEQ ID NO:341) or LASNLES (SEQ ID NO:342); and (iii) in the CDR3 region, a sequence that is at least 90% identical to QQRSS/NYPS/FT (SEQ ID NO:343) or QHSRELPFT (SEQ ID NO:344).

In another aspect, the invention is directed to a monoclonal antibody that has an amino acid sequence in the heavy chain variable region comprised of the following: (i) in the CDR1 region, a sequence that is at least 90% identical to NYGMN (SEQ ID NO:330), GYAMS (SEQ ID NO:331) or R/GYA/GMS (SEQ ID NO:332); (ii) in the CDR2 region, a sequence that is at least 90% identical to WINTYTGEPTYA/VG/DDFKG (SEQ ID NO:333) or TISSGGTYIYYPDSVKG (SEQ ID NO:334); and (iii) in the CDR3 region, a sequence that is at least 90% identical to S/TGT/DT/AXXY/FYA (SEQ ID NO:335), TGTTAILNG (SEQ ID NO:336), SGDGYWYYA (SEQ ID NO:337) or DNYGXXYDYG/A (SEQ ID NO:338); and an amino acid sequence in the kappa chain variable region comprised of the following: (i) in the CDR1 region, a sequence that is at least 90% identical to SASSSV/ISYM/IH/Y (SEQ ID NO:339) or RASKSVSTSGYSYMH (SEQ ID NO:340); (ii) in the CDR2 region, in the CDR2 region, a sequence that is at least 90% identical to S/GTSNLAS (SEQ ID NO:341) or LASNLES (SEQ ID NO:342); and (iii) in the CDR3 region, a sequence that is at least 90% identical to QQRSS/NYPS/FT (SEQ ID NO:343) or QHSRELPFT (SEQ ID NO:344).

In yet another aspect, the invention is directed to a monoclonal antibody having an amino acid sequence in the heavy chain variable region in CDR1 region that is at least 90% identical to SEQ ID NO:331, in CDR2 region that is at least 90% identical to SEQ ID NO:334, and in CDR3 region that is at least 90% identical to SEQ ID NO:374, and an amino acid sequence in the light chain variable region in CDR1 region that is at least 90% identical to SEQ ID NO:340, in CDR2 region that is at least 90% identical to SEQ ID NO:342, and in CDR3 region that is at least 90% identical to SEQ ID NO:344.

In another aspect, the monoclonal antibody may have an amino acid sequence in the heavy chain variable region in CDR1 region that is at least 90% identical to SEQ ID NO:332, in CDR2 region that is at least 90% identical to SEQ ID NO:334, and in CDR3 region that is at least 90% identical to SEQ ID NO:338, and an amino acid sequence in the light chain variable region in CDR1 region that is at least 90% identical to SEQ ID NO:339, in CDR2 region that is at least 90% identical to SEQ ID NO:341, and in CDR3 region that is at least 90% identical to SEQ ID NO:343.

In yet another aspect, the invention is directed to a monoclonal antibody comprising human FWR sequences comprising: in human heavy chain, FWR1 sequence that is at least 90% identical to SEQ ID NO:353, FWR2 sequence that is at least 90% identical to SEQ ID NO:355, FWR3 sequence that is at least 90% identical to SEQ ID NO:357, or FWR4 sequence that is 90% identical to SEQ ID NO:359, and in human light chain, FWR1 sequence that is at least 90% identical to SEQ ID NO:345, FWR2 sequence that is at least 90% identical to SEQ ID NO:347, FWR3 sequence that is at least 90% identical to SEQ ID NO:349, or FWR4 sequence that is at least 90% identical to SEQ ID NO:351.

In yet another aspect, the invention is directed to a monoclonal antibody comprising human FWR sequences comprising: in human heavy chain, FWR1 sequence that is at least 90% identical to SEQ ID NO:362, FWR2 sequence that is at least 90% identical to SEQ ID NO:363, or FWR3 sequence that is at least 90% identical to SEQ ID NO:364, and in human light chain, FWR1 sequence that is at least 90% identical to SEQ ID NO:365, FWR2 sequence that is at least 90% identical to SEQ ID NO:366, or FWR3 sequence that is at least 90% identical to SEQ ID NO:367.

In another aspect, the invention is directed to an antibody further comprising human FWR sequences comprising: in human heavy chain, FWR1 sequence that is at least 90% identical to SEQ ID NO:353, FWR2 sequence that is at least 90% identical to SEQ ID NO:355, FWR3 sequence that is at least 90% identical to SEQ ID NO:357, or FWR4 sequence that is 90% identical to SEQ ID NO:359, and in human light chain, FWR1 sequence that is at least 90% identical to SEQ ID NO:345, FWR2 sequence that is at least 90% identical to SEQ ID NO:347, FWR3 sequence that is at least 90% identical to SEQ ID NO:349, or FWR4 sequence that is at least 90% identical to SEQ ID NO:351.

In another aspect, the invention is directed to an antibody comprising human FWR sequences comprising: in human heavy chain, FWR1 sequence that is at least 90% identical to SEQ ID NO:368, FWR2 sequence that is at least 90% identical to SEQ ID NO:369, or FWR3 sequence that is at least 90% identical to SEQ ID NO:370, and in human light chain, FWR1 sequence that is at least 90% identical to SEQ ID NO:371, FWR2 sequence that is at least 90% identical to SEQ ID NO:372, or FWR3 sequence that is at least 90% identical to SEQ ID NO:373.

In another aspect, the invention is directed to a humanized monoclonal antibody, wherein preferably the framework region is known human framework sequence.

In another aspect, the invention is directed to an isolated nucleic acid encoding the monoclonal antibody described above.

The invention is further directed to an isolated hybridoma expressing the monoclonal antibody described above. The antibody may be an Fab, or single chain monovalent antibody. The antibody may be bispecific, wherein one recognition aspect binds to the peptide of SEQ ID NO:1 and the other recognizes another epitope. The other epitope may be HER2 or DLL4.

The invention is also directed to a scFv fusion protein specific for MUC1* in which an immunoglobulin-like VH domain is linked to an immunoglobulin-like VL domain, wherein said VH chain and said VL chain are linked via a peptide linker.

In another aspect, the invention is directed to a method of inhibiting cell proliferation, comprising contacting cells expressing MUC1* with the monovalent monoclonal antibody described above. The cells may be cancer cells.

In yet another aspect, the invention is directed to a method of increasing cell proliferation, comprising contacting cells expressing MUC1* with the bivalent monoclonal antibody described above. The cells may be pluripotent or progenitor cells.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIGS. 10A-10D show cartoons of recombinant antibody variants. A) shows a single chain variable region (scFv) antibody fragment that is comprised of the variable regions of heavy and light chains, connected by a linker; B) shows a single chain Fab (scFab), which contains at least a portion of the heavy and light chain constant regions, in addition to the variable domains. Heavy and light chains are connected by a linker; C) shows a single chain Fab (scFab) wherein the heavy and light chains are not connected by a linker. Heavy and light chains are separately expressed, usually in the same cell. Heavy and light chains spontaneously associate or cysteines can be introduced to facilitate association; D) shows a bispecific single chain antibody variant (bscFv) comprised of the variable domains. The bscFv shown recognizes MUC1* and the HER2 receptor.

FIG. 11 shows anti-MUC1* IgG monoclonal antibody light chain variable region sequences.

FIG. 12 shows anti-MUC1* IgG monoclonal antibody heavy chain variable region sequences.

FIG. 13 shows anti-MUC1* IgM monoclonal antibody light chain variable region sequences.

FIG. 14 shows anti-MUC1* IgM monoclonal antibody heavy chain variable region sequences.

FIG. 15 shows the amino acid sequence of a MIN-C2 (single chain fragment variable) design (heavy chain variable-linker-light chain variable). The scFv construct was expressed in bacteria and purified using C-terminal poly-histidine (HHHHHH; SEQ ID NO: 375) tag.

FIG. 16 shows the amino acid sequence of a MIN-E6 scFv (single chain fragment variable) design heavy chain variable (MIN-E6 VH7)-linker-light chain variable). The scFv construct was expressed in bacteria and purified using C-terminal poly-histidine (HHHHHH; SEQ ID NO: 375) tag.

FIG. 22 shows the N-terminus of the above MIN-C2 Fab polypeptide was fused with an Ig kappa-chain leader sequence (METDTLLLWVLLLWVPGSTGD (SEQ ID NO: 328)) for efficient secretion. The C-terminus was fused with a myc tag (EQKLISEEDL (SEQ ID NO: 329)) and polyhistidine (HHHHHH; SEQ ID NO: 375) tags to facilitate purification. The MIN-C2 Fab thus assembled was expressed in mammalian cells using a vector that allows high-copy episomal replication, pCEP4 (Invitrogen, Carlsbad, Calif.).

FIG. 24 shows comparison of anti-MUC1* rabbit polyclonal antibody to mouse monoclonal MIN-C2 for stimulating pluripotent growth of human embryonic stem cells; fluorescence indicates pluripotency of cells. Experiment shows that the monoclonal MIN-C2 functions similarly to the polyclonal antibody in that both stimulate pluripotent stem cell growth.

DETAILED DESCRIPTION OF THE PREFERRED EMBODIMENTS

Figure 1:
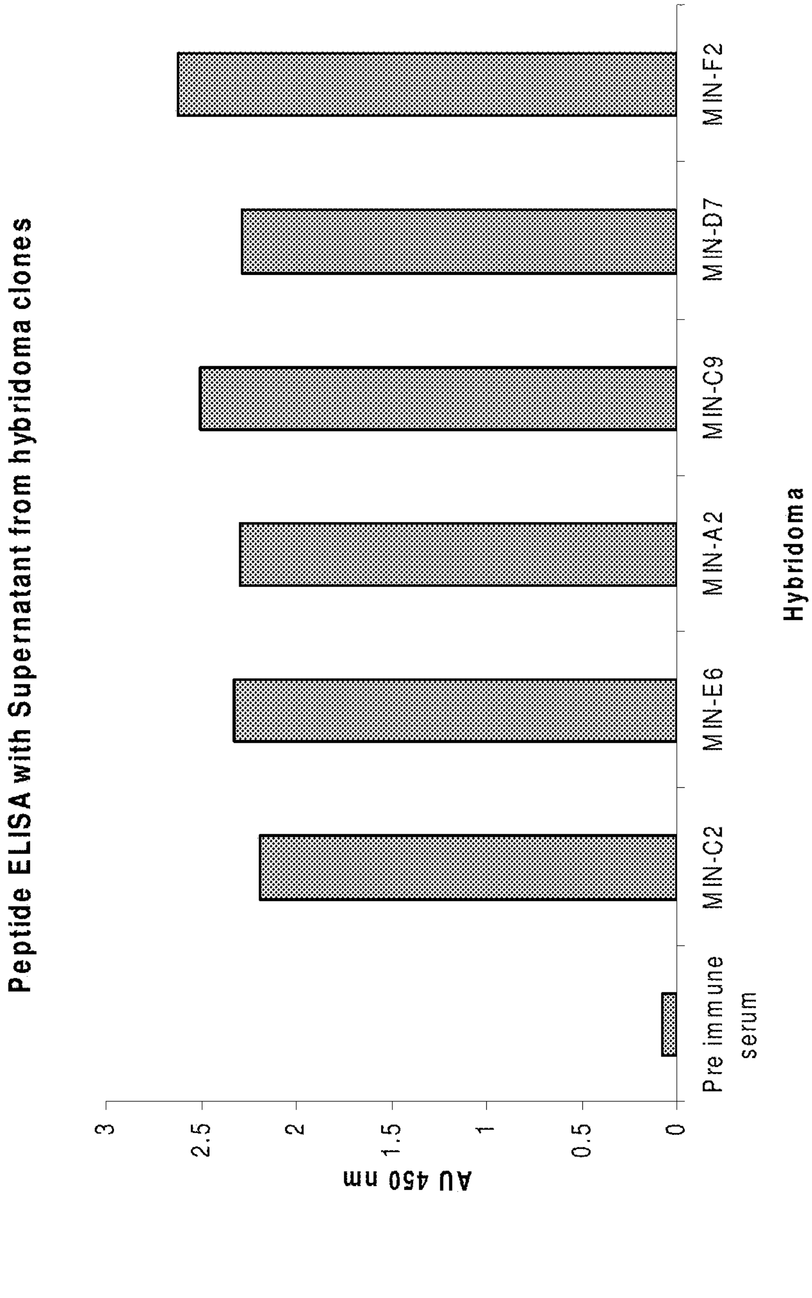
FIG. 1 shows that supernatants of selected hybridoma clones specifically bind to the immunizing peptide (GTINVHDVETQFNQYKTEAASRYNLTISDVSVSDVPFPFSAQSGA (SEQ ID NO:1) by standard ELISA.

In the present application, "a" and "an" are used to refer to both single and a plurality of objects.

As used herein, "MUC1 Growth Factor Receptor" (MGFR) is a functional definition meaning that portion of the MUC1 receptor that interacts with an activating ligand, such as a growth factor or a modifying enzyme such as a cleavage enzyme. The MGFR region of MUC1 is that extracellular portion that is closest to the cell surface and is defined by most or all of the PSMGFR, as defined below. The MGFR is inclusive of both unmodified peptides and peptides that have undergone enzyme modifications, such as, for example, phosphorylation, glycosylation and so forth.

As used herein, "Primary Sequence of the MUC1 Growth Factor Receptor" (PSMGFR) refers to peptide sequence that defines most or all of the MGFR in some cases, and functional variants and fragments of the peptide sequence. The PSMGFR is defined as SEQ ID NO:1, and all functional variants and fragments thereof having any integer value of amino acid substitutions up to 20 (i.e. 1, 2, 3, 4, 5, 6, 7, 8, 9, 10, 11, 12, 13, 14, 15, 16, 17, 18, 19, or 20) and/or any integer value of amino acid additions or deletions up to 20 at its N-terminus and/or C-terminus. A "functional variant or fragment" in the above context refers to such variant or fragment having the ability to specifically bind to, or other ways specifically interact with, ligands that specifically bind to, or otherwise specifically interact with, the peptide of SEQ ID NO:1, while not binding strongly to identical regions of other peptide molecules identical to themselves, such that the peptide molecules would have the ability to aggregate (i.e. self-aggregate) with other identical peptide molecules. One example of a PSMGFR that is a functional variant of the PSMGFR peptide of SEQ NO:1 is SEQ ID NO:2, which differs from SEQ ID NO:1 by including an -SPY- sequence instead of the -SRY-.

As used herein, "MUC1*" refers to the MUC1 protein with the N-terminus truncated such that the extracellular domain is essentially comprised of the PSMGFR (SEQ ID NO: 1).

Sequence Listing Free Text

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

GTINVHDVETQFNQYKTEAAS-RYNLTISDVSVSDVPFPFSAQSGA (SEQ ID NO:1) describes the membrane proximal extracellular region of MUC1 from amino acid 1110 to 1155.

GTINVHDVETQFNQYK-TEAASPYNLTISDVSVSDVPFPFSAQSGA (SEQ ID NO:2) describes a variant of the membrane proximal extracellular region of MUC1 from amino acid 1110 to 1155.

5'-ggaaagcttatagacagatgggggtgtcgttttggc-3' (SEQ ID NO:3) describes HindIII restriction site containing PCR primer, IgG1 constant region reverse primer.

5'-ggaaagcttcttgaccaggcatcctagagtca-3' (SEQ ID NO:4) describes HindIII restriction site containing PCR primer, IgG2A constant region reverse primer.

5'-ggaaagcttaggggccagtggatagactgatgg-3' (SEQ ID NO:5) describes HindIII restriction site containing PCR primer, IgG2B constant region reverse primer.

5'-cttccggaattcsargtnmagctgsagsagtc-3' (SEQ ID NO:6) describes EcoRI restriction site containing PCR primer, heavy chain FR1 region forward primer 1.

5'-cttccggaattcsargtnmagctgsagsagtcwgg-3' (SEQ ID NO:7) describes EcoRI restriction site containing PCR primer, heavy chain FR1 region forward primer 2.

5'-ggtgtcgacggatacagttggtgcagcatc-3' (SEQ ID NO:8) describes SalI restriction site containing PCR primer, kappa chain constant region reverse primer.

5'-gggagctcgayattgtgmtsacmcarwctmca-3' (SEQ ID NO:9) describes SacI restriction site containing PCR primer, kappa chain FR1 region universal degenerate forward primer.

gaggtccagctggaggagtcagggggaggcttagtgaagcctg-gagggtccctgaaactctcctgtgcagcctctggattcactttcagt ggctatgc-catgtcttgggttcgccagactccggagaagaggctggagtgggtcgcaaccatt-agtagtggtggtacttatatctactatccagacagt gtgaaggggcgattcaccatctccagagacaatgc-caagaacaccctgtacctgcaaatgagcagtctgaggtctgaggacacggc-catgtattact gtgcaagacttggggggggataattactacgaatacttc-gatgtctggggcgcagggaccacggtcaccgtctcctccgccaaaacgacacccc-cat ctgtctat (SEQ ID NO:10) describes MIN-C2 Heavy chain variable region.

EVQLEESGGGLVKPGGSLKLSCAASGFTFSGYAM-SWVRQTPEKRLEWVATISSGGTYI YYPDSVKGRFTIS-RDNAKNTLYLQMSSLRSEDTAMYYCARLGGDNYY-EYFDVWGAGTTVTV SSAKTTPPSVY (SEQ ID NO:11) describes MIN-C2 Heavy chain variable region.

gacattgtgatcacacagtctacagcttcct-taggtgtatctctggggcagagggccaccatct-catgcagggccagcaaaagtgtcagta catctggctatagttatatgcactggtac-caacagagaccaggacagcccacccaaactcctcatctatcttgcatccaacctaga atctggggtccctg ccaggttcagtggcagtgggtctgggacagacttcaccct-caacatccatcctgtggaggaggaggatgctgcaacctat-tactgtcagcacagtag ggagcttccgttcacgttcggaggggggaccaagctg-gagataaaacgggctgatgctgcaccaactgtatcc (SEQ ID NO:12) describes MIN-C2 Kappa chain variable region.

DIVITQSTASLGVSLGQRATISCRASKSVST-SGYSYMHWYQQRPGQPPKLLIYLASNLES GVPARFSGSGSGTDFTLNIHPVEEEDAATYYCQHS-RELPFTFGGGTKLEIKRADAAPTVS (SEQ ID NO:13) describes MIN-C2 Kappa chain variable region.

ggtggaggcggatcaggtggaggcggatcaggtggaggcggatca (SEQ ID NO:14) describes Linker.

(SEQ ID NO: 15)

```
gaggtccagctggaggagtcagggggaggcttagtgaagcctggagggt
ccctgaaactctcctgtgcagcctctggattcactttcagtggctatgc
catgtcttgggttcgccagactccggagaagaggctggagtgggtcgca
accattagtagtggtggtacttatatctactatccagacagtgtgaagg
ggcgattcaccatctccagagacaatgccaagaacaccctgtacctgca
aatgagcagtctgaggtctgaggacacggccatgtattactgtgcaaga
cttggggggggataattactacgaatacttcgatgtctggggcgcaggga
ccacggtcaccgtctcctccgccaaaacgacaccccccatctgtctatgg
tggaggcggatcaggtggaggcggatcaggtggaggcggatcagacatt
gtgatcacacagtctacagcttccttaggtgtatctctggggcagaggg
ccaccatctcatgcagggccagcaaaagtgtcagtacatctggctatag
ttatatgcactggtaccaacagagaccaggacagcccacccaaactcctc
atctatcttgcatccaacctagaatctggggtccctgccaggttcagtg
gcagtgggtctgggacagacttcaccctcaacatccatcctgtggagga
```

-continued

```
ggaggatgctgcaacctattactgtcagcacagtagggagcttccgttc
acgttcggaggggggaccaagctggagataaaacgggctgatgctgcac
caactgtatcc
```

describes MIN-C2 Heavy chain-linker-light chain.

(SEQ ID NO: 16)

```
gaggtccagctggaggagtcagggggaggcttagtgaagcctggagggt
ccctgaaactctcctgtgcagcctctggattcactttcagtggctatgc
catgtcttgggttcgccagactccggagaagaggctggagtgggtcgca
accattagtagtggtggtacttatatctactatccagacagtgtgaagg
ggcgattcaccatctccagagacaatgccaagaacaccctgtacctgca
aatgagcagtctgaggtctgaggacacggccatgtattactgtgcaaga
cttggggggggataattactacgaatacttcgatgtctggggcgcaggga
ccacggtcaccgtctcctccgccaaaacgacaccccccatctgtctatgg
tggaggcggatcaggtggaggcggatcaggtggaggcggatcagacatt
gtgatcacacagtctacagcttccttaggtgtatctctggggcagaggg
ccaccatctcatgcagggccagcaaaagtgtcagtacatctggctatag
ttatatgcactggtaccaacagagaccaggacagcccacccaaactcctc
atctatcttgcatccaacctagaatctggggtccctgccaggttcagtg
gcagtgggtctgggacagacttcaccctcaacatccatcctgtggagga
ggaggatgctgcaacctattactgtcagcacagtagggagcttccgttc
acgttcggaggggggaccaagctggagataaaacgggctgatgctgcac
caactgtatcctgt
```

describes MIN-C2 Heavy chain-linker-light chain-Cys.

EVQLEESGGGLVKPGGSLKLSCAASGFTFSGYAM-SWVRQTPEKRLEWVATISSGGTYI YYPDSVKGRFTIS-RDNAKNTLYLQMSSLRSEDTAMYYCARLGGDNYY-EYFDVWGAGTTVTV SSAKTTPPSVYGGGGSGGGGSGGGGSDIVITQS-TASLGVSLGQRATISCRASKSVSTSGYSYMH WYQQRPGQPPKLLIYLASN-LESGVPARFSGSGSGTDFTLNIHPVEEEDAATYYCQ HSRELPFTF GGGTKLEIKRADAAPTVSVD (SEQ ID NO:17) describes MIN-C2 Heavy chain-linker-light chain.

EVQLEESGGGLVKPGGSLKLSCAASGFTFSGYAM-SWVRQTPEKRLEWVATISSGGTYI YYPDSVKGRFTIS-RDNAKNTLYLQMSSLRSEDTAMYYCARLGGDNYY-EYFDVWGAGTTVTV SSAKTTPPSVYGGGGSGGGGSGGGGSDIVITQS-TASLGVSLGQRATISCRASKSVSTSGYSYMH WYQQRPGQPPKLLIYLASN-LESGVPARFSGSGSGTDFTLNIHPVEEEDAATYYCQ HSRELPFTF GGGTKLEIKRADAAPTVSC (SEQ ID NO:18) describes MIN-C2 Heavy chain-linker-light chain-Cys.

gaggttaagctggaggagtctgggggagacttagtgaagcctg-gagggtccctgaaactctcctgtgcagcctctggattcactttcagta gatatgg-catgtcttgggttcgccagactccagacaagaggctggagtgggtcgcaaccatt-agtagtggtggtacttacatctactatccagacagt gtgaaggggcgattcaccatctccagagacaatgc-caagaacaccctgtacctgcaaatgagcagtctgaagtctgaggacacagc-catgtattact gtgcaagggataactacggtagtagctacgactatgctatggactactggggtcaaggaacctcagtcaccgtctcctcagccaaaacaacagcccc atcggtctat (SEQ ID NO:19) describes MIN-E6 Heavy chain-7 variable region.

EVKLEESGGDLVKPGGSLKLSCAASGFTFSRY GMSWVRQTPDKRLEWVATISSGGTYI YYPDSVKGRFTISRDNAKNTLYLQMSSLKSEDTAMYYCARDNYGSSYDYAMDYWGQGTSV TVSSAKTTAPSVY (SEQ ID NO:20) describes MIN-E6 Heavy chain-7 variable region.

gaggtaaagctggaggagtctggggggagacttagtgaagcctggagggtccctgaaactctcctgtgtagtctctggattcactttcagta gatatggcatgtcttgggttcgccagactccaggcaagaggctggagtgggtcgcaaccattagtggtggcggtacttacatctactatccagacagt gtgaaggggcgattcaccatctccagagacaatgccaagaacaccctgtacctgcaaatgagcagtctgaagtctgaggacacagccatgtatcact gtacaagggataactacggtaggaactacgactacggtatggactactggggtcaaggaacctcagtcaccgtctcctcagccaaaacaacagccc catcggtctatccactggcccctgtgtgtggagatacaactggctcctcggtgactctaggatgcctggtcaag (SEQ ID NO:21) describes MIN-E6 Heavy chain-8 variable region.

EVKLEESGGDLVKPGGSLKLSCVVSGFTFSRYGMS WVRQTPGKRLEWVATISGGGTYI YYPDSVKGRFTISRDNAKNTLYLQMSSLKSEDTAMYHCTRDNYGRNYDYGMDYWGQGTSV TVSSAKTTAPSVYPLAPVCGDTTGSSVTLGCLVK (SEQ ID NO:22) describes MIN-E6 Heavy chain-8 variable region.

gatattgtgatcacccagactacagcaatcatgtctgcatctccaggggaggaggtcaccctaacctgcagtgccacctcaagtgtaagtt acatacactggttccagcagaggccaggcacttctcccaaactctggatttatagcacatccaacctggcttctggagtccctgttcgcttcagtggca gtggatatgggacctcttactctctcacaatcagccgaatggaggctgaagatgctgccacttattactgccagcaaaggagtagttccccattcacgtt cggctcggggacaaagttggaaataaaacgggctgatgctgcaccaactgtatcc (SEQ ID NO:23) describes MIN-E6 Kappa chain variable region.

DIVITQTTAIMSASPGEEVTLTCSATSSVSYIHWFQQRPGTSPKLWIYSTSNLASGVPVR FSGSGYGTSYSLTISRMEAEDAATYYCQQRSSSPFTFGSGTKLEIKRADAAPTVS (SEQ ID NO:24) describes MIN-E6 Kappa chain variable region.

(SEQ ID NO: 25)

gaggttaagctggaggagtctggggggagacttagtgaagcctggagggt ccctgaaactctcctgtgcagcctctggattcactttcagtagatatgg catgtcttgggttcgccagactccagacaagaggctggagtgggtcgca accattagtagtggtggtacttacatctactatccagacagtgtgaagg ggcgattcaccatctccagagacaatgccaagaacaccctgtacctgca aatgagcagtctgaagtctgaggacacagccatgtattactgtgcaagg gataactacggtagtagctacgactatgctatggactactggggtcaag gaacctcagtcaccgtctcctcagccaaaacaacagccccatcggtcta tccactggcccctgtgtgtggagatacaactggctcctcggtgactcta ggatgcctggtcaagggtggaggcggatcaggtggaggcggatcaggtg gaggcggatcagatattgtgatcacccagactacagcaatcatgtctgc atctccaggggaggaggtcaccctaacctgcagtgccacctcaagtgta agttacatacactggttccagcagaggccaggcacttctcccaaactct ggatttatagcacatccaacctggcttctggagtccctgttcgcttcag -continued tggcagtggatatgggacctcttactctctcacaatcagccgaatggag gctgaagatgctgccacttattactgccagcaaaggagtagttccccat tcacgttcggctcggggacaaagttggaaataaaacgggctgatgctgc accaactgtatcc describes MIN-E6 scFv: Heavy chain 7-linker-light chain (VH+linker+VL).

(SEQ ID NO: 26)

gaggttaagctggaggagtctggggggagacttagtgaagcctggagggt ccctgaaactctcctgtgcagcctctggattcactttcagtagatatgg catgtcttgggttcgccagactccagacaagaggctggagtgggtcgca accattagtagtggtggtacttacatctactatccagacagtgtgaagg ggcgattcaccatctccagagacaatgccaagaacaccctgtacctgca aatgagcagtctgaagtctgaggacacagccatgtattactgtgcaagg gataactacggtagtagctacgactatgctatggactactggggtcaag gaacctcagtcaccgtctcctcagccaaaacaacagccccatcggtcta tccactggcccctgtgtgtggagatacaactggctcctcggtgactcta ggatgcctggtcaagggtggaggcggatcaggtggaggcggatcaggtg gaggcggatcagatattgtgatcacccagactacagcaatcatgtctgc atctccaggggaggaggtcaccctaacctgcagtgccacctcaagtgta agttacatacactggttccagcagaggccaggcacttctcccaaactct ggatttatagcacatccaacctggcttctggagtccctgttcgcttcag tggcagtggatatgggacctcttactctctcacaatcagccgaatggag gctgaagatgctgccacttattactgccagcaaaggagtagttccccat tcacgttcggctcggggacaaagttggaaataaaacgggctgatgctgc accaactgtatcctgt describes MIN-E6 scFv-Cys: Heavy chain 7-linker-light chain-Cys (VH+linker+VL+Cys).

EVKLEESGGDLVKPGGSLKLSCAASGFTFSRY GMSWVRQTPDKRLEWVATISSGGTYI YYPDSVKGRFTISRDNAKNTLYLQMSSLKSEDTAMYYCARDNYGSSYDYAMDYWGQGTSV TVSSAKTTAPSVYPLAPVCGDTTGSSVTLGCLVKGGGGSGGGGSGGGG SDIVITQTTAIMSAS PGEEVTLTCSATSSVSYIHWFQQRPGTSPKLWIYSTSNLASGVPVRFSGSGYGTSYSLTISRME AEDAATYYCQQRSSSPFTFGSGTKLEIKRADAAPTVS (SEQ ID NO:27) describes MIN-E6 scFv Heavy chain 7-linker-light chain (VH+linker+VL).

EVKLEESGGDLVKPGGSLKLSCAASGFTFSRY GMSWVRQTPDKRLEWVATISSGGTYI YYPDSVKGRFTISRDNAKNTLYLQMSSLKSEDTAMYYCARDNYGSSYDYAMDYWGQGTSV TVSSAKTTAPSVYPLAPVCGDTTGSSVTLGCLVKGGGGSGGGGSGGGG SDIVITQTTAIMSAS PGEEVTLTCSATSSVSYIHWFQQRPGTSPKLWIYSTSNLASGVPVRFSGSGYGTSYSLTISRME AEDAATYYCQQRSSSPFTFGSGTKLEIKRADAAPTVS C (SEQ ID NO:28) describes MIN-E6 scFv-Cys Heavy chain 7-linker-light chain-Cys (VH+linker+VL+Cys).

(SEQ ID NO: 29)

```
gaggtaaagctggaggagtctgggggagacttagtgaagcctggagggt
ccctgaaactctcctgtgtagtctctggattcactttcagtagatatgg
catgtcttgggttcgccagactccaggcaagaggctggagtgggtcgca
accattagtggtggcggtacttacatctactatccagacagtgtgaagg
ggcgattcaccatctccagagacaatgccaagaacaccctgtacctgca
aatgagcagtctgaagtctgaggacacagccatgtatcactgtacaagg
gataactacggtaggaactacgactacggtatggactactggggtcaag
gaacctcagtcaccgtctcctcagccaaaacaacagccccatcggtcta
tccactggcccctgtgtgtggagatacaactggctcctcggtgactcta
ggatgcctggtcaagggtggaggcggatcaggtggaggcggatcaggtg
gaggcggatcagatattgtgatcacccagactacagcaatcatgtctgc
atctccaggggaggaggtcaccctaacctgcagtgccacctcaagtgta
agttacatacactggttccagcagaggccaggcacttctcccaaactct
ggatttatagcacatccaacctggcttctggagtccctgttcgcttcag
tggcagtggatatgggacctcttactctctcacaatcagccgaatggag
gctgaagatgctgccacttattactgccagcaaaggagtagttccccat
tcacgttcggctcggggacaaagttggaaataaaacgggctgatgctgc
accaactgtatcc
```

describes MIN-E6 Heavy chain 8-linker-light chain.

(SEQ ID NO: 30)

```
gaggtaaagctggaggagtctgggggagacttagtgaagcctggagggt
ccctgaaactctcctgtgtagtctctggattcactttcagtagatatgg
catgtcttgggttcgccagactccaggcaagaggctggagtgggtcgca
accattagtggtggcggtacttacatctactatccagacagtgtgaagg
ggcgattcaccatctccagagacaatgccaagaacaccctgtacctgca
aatgagcagtctgaagtctgaggacacagccatgtatcactgtacaagg
gataactacggtaggaactacgactacggtatggactactggggtcaag
gaacctcagtcaccgtctcctcagccaaaacaacagccccatcggtcta
tccactggcccctgtgtgtggagatacaactggctcctcggtgactcta
ggatgcctggtcaagggtggaggcggatcaggtggaggcggatcaggtg
gaggcggatcagatattgtgatcacccagactacagcaatcatgtctgc
atctccaggggaggaggtcaccctaacctgcagtgccacctcaagtgta
agttacatacactggttccagcagaggccaggcacttctcccaaactct
ggatttatagcacatccaacctggcttctggagtccctgttcgcttcag
tggcagtggatatgggacctcttactctctcacaatcagccgaatggag
gctgaagatgctgccacttattactgccagcaaaggagtagttccccat
tcacgttcggctcggggacaaagttggaaataaaacgggctgatgctgc
accaactgtatcctgt
```

describes MIN-E6 Heavy chain 8-linker-light chain-Cys.

EVKLEESGGDLVKPGGSLKLSCVVSGFTFSRYGMS WVRQTPGKRLEWVATISGGGTYI YYPDSVKGRFTISRDNAKNTLYLQMSSLKSEDTAMYHCTRDNYGRNYDYGMDYWGQGTSV TVSSAKTTAPSVYPLAPVCGDTTGSSVTLGCLVKGGGGSGGGGSGGGG SDIVITQTTAIMSAS PGEEVTLTCSATSSVSYIHWFQQRPGTSPKLWIYSTSNLASGVPVRFSGSGYGTSYSLTISRME AEDAATYYCQQRSSSPFTFGSGTKLEIKRADAAPTVS (SEQ ID NO:31) describes MIN-E6 Heavy chain 8-linker-light chain.

EVKLEESGGDLVKPGGSLKLSCVVSGFTFSRYGMS WVRQTPGKRLEWVATISGGGTYI YYPDSVKGRFTISRDNAKNTLYLQMSSLKSEDTAMYHCTRDNYGRNYDYGMDYWGQGTSV TVSSAKTTAPSVYPLAPVCGDTTGSSVTLGCLVKGGGGSGGGGSGGGG SDIVITQTTAIMSAS PGEEVTLTCSATSSVSYIHWFQQRPGTSPKLWIYSTSNLASGVPVRFSGSGYGTSYSLTISRME AEDAATYYCQQRSSSPFTFGSGTKLEIKRADAAPTVS C (SEQ ID NO:32) describes MIN-E6 Heavy chain 8-linker-light chain-Cys.

5'-gggaattccaccatggratgsagctgkgtmatsctctt-3' (SEQ ID NO:33) describes EcoRI restriction site containing PCR primer, Gamma forward-1.

5'-gggaattccaccatgracttcgggytgagctkggtttt-3'(SEQ ID NO:34) describes EcoRI restriction site containing PCR primer, Gamma forward-2.

5'-gggaattccaccatggctgtcttggggctgctcttct-3' (SEQ ID NO:35) describes EcoRI restriction site containing PCR primer, Gamma forward-3.

5'-gggaattccaccatggrcagrcttacwtyy-3' (SEQ ID NO:36) describes EcoRI restriction site containing PCR primer, Gamma forward-4.

5'-ctacctcgagckyggtsytgctggcygggtg-3' (SEQ ID NO:37) describes XhoI restriction site containing PCR primer, Gamma reverse.

5'-gggaattccaccatggagacagacacactcctgctat-3' (SEQ ID NO:38) describes EcoRI restriction site containing PCR primer, Kappa forward-1.

5'-gggaattccaccatggattttcaggtgcagattttcag-3' (SEQ ID NO:39) describes EcoRI restriction site containing PCR primer, Kappa forward-2.

5'-gggaattccaccatgragtcacakacycaggtcttyrta-3' (SEQ ID NO:40) describes EcoRI restriction site containing PCR primer, Kappa forward-3.

5'-gggaattccaccatgaggkccccwgctcagytyctkggr-3' (SEQ ID NO:41) describes EcoRI restriction site containing PCR primer, Kappa forward-4.

5'-gggaattccaccatgaagttgcctgttaggctgttg-3' (SEQ ID NO:42) describes EcoRI restriction site containing PCR primer, Kappa forward-5.

5'-gggaattccaccatgatgagtcctgcccagttcc-3' (SEQ ID NO:43) describes EcoRI restriction site containing PCR primer, Kappa forward-6.

5'-ctacctcgagttaacactcattcctgttgaagc-3' (SEQ ID NO:44) describes XhoI restriction site containing PCR primer, Kappa reverse.

gaggtccagctggaggagtctgggggaggcttagtgaagcctggagggtccctgaaactctcctgtgcagcctctggattca etttcagtggetatgccatgtettgggttegccagactceggagaagaggetggagtgggtcgcaaccattagtagtggtggtacttatatetactatcc agacagtgtgaaggggcgattcaccatctccagagacaatgccaagaacaccctgtacctgcaaatgagcagtctgaggtctgaggacacggcca tgtattactgtgcaagacttgggggggataattactacgaatacttcgatgtctggggcgcagggaccacggtcaccgtctcctccgccaaaacgaca cccccatctgtctatccactggcccctggatctgctgcccaaactaactccatggtgaccctgggatgcctggtcaagggctatttccctgagccagtg acagtgacctggaactctggatccctgtccagcggtgtgcacaccttcccagctgtcctgcagtctgacctctacactctgagcagctcagtgactgtc ccctccagcacctggcccagcgagaccgtcacctgcaacgttgcccacccagccagcaggaccgcg (SEQ ID NO:45) describes MIN-C2 Fab Heavy chain.

gacattgtgatcacacagtctacagcttccttaggtgtatctctggggcagagggccaccatctcatgcagggccagcaaaagt gtcagtacatctggctatagttatatgcactggtaccaacagagaccaggacagccacccaaactcctcatctatcttgcatccaacctagaatctggg gtccctgccaggttcagtggcagtgggtctgggacagacttcaccctcaacatccatcctgtggaggaggaggatgctgcaacctattactgtcagc acagtagggagcttccgttcacgttcggaggggggaccaagctggagataaaacgggctgatgctgcaccaactgtatccatcttcccaccatcca gtgagcagttaacatctggaggtgcctcagtcgtgtgcttcttgaacaacttctaccccaaagacatcaatgtcaagtggaagattgatggcagtgaac gacaaaatggcgtcctgaacagttggactgatcaggacagcaaagacagcacctacagcatgagcagcaccctcacgttgaccaaggacgagtat gaacgacataacagctatacctgtgaggccactcacaagacatcaacttcacccattgtcaagagcttcaacaggaatgagtgt (SEQ ID NO:46) describes MIN-C2 Fab Kappa chain.

EVQLEESGGGLVKPGGSLKLSCAASGFTFSGYAMSWVRQTPEKRLEWVATISS GGTYIYYPDSVKGRFTISRDNAKNTLYLQMSSLRSEDTAMYYCARLGGDNYYEYFDVWGAG TTVTVSSAKTTPPSVYPLAPGSAAQTNSMVTLGCLVKGYFPEPVTVTWNSGS LSSGVHTFPAV LQSDLYTLSSSVTVPSSTWPSETVTCNVAHPASRTA (SEQ ID NO:47) describes MIN-C2 Fab Heavy chain.

DIVITQSTASLGVSLGQRATISCRASKSVSTSGYSYMHWYQQRPGQPPKLLIYLA SNLESGVPARFSGSGSGTDFTLNIHPVEEEDAATYYC QHSRELPFTFGGGTKLEIKRADAAPTV SIFPPSSEQLTSGGASVVCFLNNFYPKDINVKWKIDGSERQNGVLNSWTDQDSKDSTYSMSST LTLTKDEYERHNSYTCEATHKTSTSPIVKSFNRNEC (SEQ ID NO:48) describes MIN-C2 Fab Kappa chain.

RADAAPTVSIFPPSSEQLTSGGASVVCFLNNFYPKDINVKWKIDGSERQNGVLN SWTDQDSKDSTYSMSSTLTLTKDEYERHNSYTCEATHKTSTSPIVKSFNRNEC (SEQ ID NO:49) describes MIN-C2 light CL region amino acid sequence.

FDVWGAGTTVTVSSAKTTPPSVYPLAPGSAAQTNSMVTLGCLVKGYFPEPVTV TWNSGSLSSGVHTFPAVLQSDLYTLSSSVTVPSSTWPSETVTCNVAHPASRTA (SEQ ID NO:50) describes MIN-C2 heavy chain CH1 region amino acid sequence.

DIVLTQSTEIMSASPGEKVTITCSASSSISYIHWFQQKPGTSPKLWIFGTSNLASG VPARFSGSGSGTSYSLTVSRMEAEDTATYYCQQRSNYPFTFGSGTKLQIKRADAAPTVS (SEQ ID NO:51) describes MIN-A2-1 light chain variable region amino acid sequence.

DIVMTQSPAIMSASPGEKVTMTCSASSSVSYMHWFQQKPGTSPKLWIYSTSNLA SGAPARFSGSGSGTSYSLTVSRMESEDAATYYCQQRSSYPSTFGGGTKLEIKRA DAAPTVS (SEQ ID NO:52) describes MIN-A2-2 light chain variable region amino acid sequence.

DIVLTQTTAIMSASPGEKVTITCSASSSVSYMYWFQQKPGTSPKLWIYSTSNLAS GVPARFSGSGSGTSYSLTISRMEAEDAATYYCQQRSSYPSTFGGGTKLEIKRADAAPTVS (SEQ ID NO:53) describes MIN-C9-1 light chain variable region amino acid sequence.

DIVITQSTAIMSASPGEKVTITCSASSSVSYTYWFQQKPGTSPKLWIYSTSNLASG VPARFSGSGSGTSYSLTISRMEAEDAATYYCQQRSSYPSTFGGGTKLEIKRADAAPTVS (SEQ ID NO:54) describes MIN-C9-2 light chain variable region amino acid sequence.

DIVITQTPAIMSASPGEKVTMTCSASSSVSYMHWFQQKPGTSPKLWIYSTSNLAS GVPARFSGSGSGTSYSLTVSRMESEDAATYYCQQRSSYPSTFGGGTKLEIKRA DAAPTVS (SEQ ID NO:55) describes MIN-D7-1 light chain variable region amino acid sequence.

DIVLTQSTAIMSASPGEKVTMTCSASSSVSYMHWFQQKPGTSPKLWIYSTSNLA SGVPARFSGSGSGTSYSLTVSRMESEDAATYYCQQRSSYPSTFGGGTKLEIKRA DAAPTVS (SEQ ID NO:56) describes MIN-D7-2 light chain variable region amino acid sequence.

DIVMTQSPEIMSASPGEKVTITCSASSSISYIHWFQQKPGTSPKLWIFGTSNLASG VPARFSGSGSGTSYSLTVSRMEAEDTATYYCQQRSNYPFTFGSGTKLQIKRADAAPTVS (SEQ ID NO:57) describes MIN-F2-1 light chain variable region amino acid sequence.

DIVITQSTEIMSASPGEKVTITCSASSSISYIHWFQQKPGTSPKLWIFGTSNLASGV PARFSGSGSGTSYSLTVSRMEAEDTATYYCQQRSNYPFTFGSGTKLQIKRADAAPTVS (SEQ ID NO:58) describes MIN-F2-2 light chain variable region amino acid sequence.

EVKLQESGPELKKPGETVEISCKASGYTFTNYGMNWVKQAPGKGLKWMGWIN TYTGEPTYAGDFKGRFAFSLETSASTAYLQINTLKNEDTATYFCARSGDGYWYYAMDYWGQ GTSVTVSSAKTTPPSVY (SEQ ID NO:59) describes MIN-A2-1 heavy chain variable region amino acid sequence.

EVQLQQSGPELKKPGETVKISCKASGYTFTNYGMNWVKQAPGKGLKWMGWI NTYTGEPTYAGDFKGRFAFSLETSASTAYLQINTLKNEDTATYFCARSGDGYWYYAMDYWG QGTSVTVSSAKTTPPSVY (SEQ ID NO:60) describes MIN-A2-2 heavy chain variable region amino acid sequence.

QVQLQESGPELKQPGETVKISCKASGYTFTNNGMNWVKQAPGKGLKWMGWI NTYTGEPTYADDFKGRFAFSLDTSASTAYLQINNLKNEDMATYFCARTGTARAFYAMDYWG QGTSVTVSSTKTTAPSVY (SEQ ID NO:61) describes MIN-C9-1 heavy chain variable region amino acid sequence.

QVQLQQSGPELKQPGETVKISCKASGYTFTNNGMNWVKQAPGKGLKWMGWI NTYTGEPTYADDFKGRFAFSLGTSASTAYLQINNLKNEDMATYFCARTGTARAFYAMDYWG QGTSVTVSSTKTTAPSVY (SEQ ID NO:62) describes MIN-C9-2 heavy chain variable region amino acid sequence.

EVQLEQSGPELKKPGETVKISCKASGYTFINYGMNWVKQAPGKGLKWMGWIN TYTGEPTYVDDFKGRFAFSLETSARTAYLQINNLKNEDMATYFCARTGTTAILNGMDYWGQG TSVTVSSAKTTPPSVY (SEQ ID NO:63) describes MIN-D7-1 heavy chain variable region amino acid sequence.

EVQLQQSGPELKKPGETVKISCKASGYTFTNYGMNWVKQAPGKGLKWMGWI NTYTGEPTYAGDFKGRFAFSLETSASTAYLQINTLKNEDTATYFCARSGDGYWYYAMDYWG

QGTSVTVSSAKTTPPSVY (SEQ ID NO:64) describes MIN-D7-2 heavy chain variable region amino acid sequence.

EVKLEESGPELKKPGETVKISCKASGYTFINYGMNWVKQAPGKGLKWMGWIN TYTGEPTYVDDFKGRFAFSLETSARTAYLQINNLKNEDMATYFCARTGTTAILNGMDYWGQG TSVTVSSAKTTPPSVY (SEQ ID NO:65) describes MIN-F2-1 heavy chain variable region amino acid sequence.

EVQLEQSGAELVRPGASVKLSCKALGYTFTDYEMHWVKQTPVHGLEWIGAIIIP GSGGTAYNQKFKGKATLTADKSSSTAYMELSSLTSEDSAVYYCTNYGSFAYWGQGTLVTVS AAKTTPPSVY (SEQ ID NO:66) describes MIN-F2-2 heavy chain variable region amino acid sequence.

RCRLQQSGPELKKPGETVKISCKASGYTFINYGMNWVKQAPGKGLKWMGWIN TYTGEPTYVDDFKGRFAF SLETSARTAYLQINNLKNEDMATYFCARTGTTAILNGMDYWGQG TSVTVSSAKTTPPSCL (SEQ ID NO:67) describes MIN-F2-3 heavy chain variable region amino acid sequence.

EVQLEQSGPELKKPGETVKISCKASGYTFINYGMNWVKQAPGKGLKWMGWIN TYTGEPTYVDDFKGRFAFSLETSARTAYLQINNLKNEDMATYFCARTGTTAILNGMDYWGQG TSVTVSSAKTTPPSVY (SEQ ID NO:68) describes MIN-F2-4 heavy chain variable region amino acid sequence.

DIQMTQSPSSLSASLGERVSLTCRASQDIGSSLNWLQQEPDGTIKRLIYATSSLDS GVPKRFSGSRSGSDYSLTISSLESEDFVDYYCLQYASSPHVRCWDQAGAETGCCTNC (SEQ ID NO:69) describes MIN-14 light chain variable region amino acid sequence.

DIVLTQSPASLAVSLGQRATISYRASKSVSTSGYSYMHWNQQKPGQPPRLLIYL VSNLESGVPARFSGSGSGTDFTLNIHPVEEEDAATYYCQH IRELTRSEGGPSW (SEQ ID NO:70) describes MIN-17-1 light chain variable region amino acid sequence.

DIQMTQSPASQSASLGESVTITCLASQTIGTWLAWYQQKPGKSPQLLIYAATSL ADGVPSRFSGSGSGTKFSFKISSLQAEDFVSYYCQQLYSTPWTFGGGTKLEIKRADAAPTV (SEQ ID NO:71) describes MIN-17-2 light chain variable region amino acid sequence.

DIVLTQSPASLAVSLGQRATISYRASKSVSTSGYSYMHWNQQKPGQPPRLLIYL VSNLESGVPARFSGSGSGTDFTLNIHPVEEEDAATYYCQH IRELTRSEGGPSW (SEQ ID NO:72) describes MIN-29 light chain variable region amino acid sequence.

DIVLTQSPASLAVSLGQRATISYRASKSVSTSGYSYMHWNQQKPGQPPRLLIYL VSNLESGVPARFSGSGSGTDFTLNIHPVEEEDAATYYCQH IRELTRSEGGPSW (SEQ ID NO:73) describes MIN-34 light chain variable region amino acid sequence.

DIVMTQSQKFMSTSVGDRVSVTCKASQNVGTNVGWYQQKPGQSPKALIYSAS YRYSGVPDRFTGSGSGTDFTLTISNVQSEDLAEYFCQQYNNYPYTFGGGTKLEIKRADAAPTV (SEQ ID NO:74) describes MIN-42 light chain variable region amino acid sequence.

DIQMTQPPASLSASVGETVTITCRASGNIHNFLAWYQQKQGKSPQLLVYNAKTL ADGVPSRFSGSGSGTQYSLKINSLQPEDFGSYYCQHFWSTPWTFGGGTKLEIKRADAAPTV (SEQ ID NO:75) describes MIN-45 light chain variable region amino acid sequence.

QVQLQQPGAELVKPGASVKLSCKASGYTFTSYWMHWVKQRPGQGLEWIGEIN PSNGRTNYNEKFKSKATLTVDKSSSTAYMQLSSLTSEDSAVYYCATYGNYWYF (SEQ ID NO:76) describes MIN-14 heavy chain variable region amino acid sequence.

QITLKESGPGIVQPSQPFRLTCTFSGFSLSTSGIGVTWIRQPSGKGLEWLATIWW DDDNRYNPSLKSRLTVSKDTSNNQAFLNIITVETADTAIYYCAQSTMVTA (SEQ ID NO:77) describes MIN-17-2 heavy chain variable region amino acid sequence.

QVQLQQPGAELVKPGASVKLSCKASGYTFTSYWMHWVKQRPGQGLEWIGEIN PSNGRTNYNEKFKSKATLTVDKSSSTAYMQLSSLTSEDSAVYYCATYGNYWYF (SEQ ID NO:78) describes MIN-17-1 heavy chain variable region amino acid sequence.

DVKLVESGGDLXKLTEGEDIWEGLTLCRDSDQSPLAPVSKPGRVVRPQRSCTVI QGCVLRLQTAHLQVQGVLGIVSGDGESALHSVWIVGATTITINGCDQLQPLLWSLANPRHVIA TESESRGCTG (SEQ ID NO:79) describes MIN-29 heavy chain variable region amino acid sequence.

QVQLKQSGPGLVQPSQSLSITCTVSGFSLTSYGVHWVRQSPGKGLEWLGVIWG GGSTDYNAAFISRLSISKDNSKSQVFFKMNSLQANDTAIYYCARNDYPAWF (SEQ ID NO:80) describes MIN-34 heavy chain variable region amino acid sequence.

EVQLVESGGDLVKPGRSLKLSCAASGFTFSSFGMSWVRQTPDKRLEWVATISS GGTYTYYPDSVKGRFTISRDNAKNTLYLQMSSLKSEDTAMYYCSRRFYYDYD (SEQ ID NO:81) describes MIN-42 heavy chain variable region amino acid sequence.

cgggctgatgctgcaccaactgtatccatcttcccaccatccagtgagcagttaacatctggaggtgcctcagtcgtgtgcttctt gaacaacttctaccccaaagacatcaatgtcaagtggaagattgatggcagtgaacgacaaaatggcgtcctgaacagttggactgatcaggacag caaagacagcacctacagcatgagcagcaccctcacgttgaccaaggacgagtatgaacgacataacagctatacctgtgaggccactcacaaga catcaacttcacccattgtcaagagcttcaacaggaatgagtgt (SEQ ID NO:82) describes MIN-C2 light chain CL nucleotide sequence.

Ttcgatgtctggggcgcagggaccacggtcaccgtctcctccgccaaaacgacacccccatctgtctatccactggcccctg gatctgctgcccaaactaactccatggtgaccctgggatgcctggtcaagggctatttccctgagccagtgacagtgacctggaactctggatccctg tccagcggtgtgcacaccttcccagctgtcctgcagtctgacctctacactctgagcagctcagtgactgtcccctccagcacctggcccagcgaga ccgtcacctgcaacgttgcccacccagccagcaggaccgcg_(SEQ ID NO:83) describes MIN-C2 Heavy chain CH1 nucleotide sequence.

EVQLQQSGPELVKPGASVKISCKASGYSFTGYFMSWVMQSHGKSLEWIGRINP YNGDTFYNQKFKGKATLTVDKSSTTAHIELRSLASEDSAVYYCARKGLYG (SEQ ID NO:84) describes MIN-45 heavy chain variable region amino acid sequence.

gacatccagatgacccagtctccatcctccttatctgcctctctgggagaaagagtcagtctcacttgtcgagcaagtcaggac attggtagtagcttaaactggcttcagcaggaaccagatggaactattaaacgcctgatctacgccacatccagtttagattctggtgtccccaaaaggt tcagtggcagtaggtetgggtcagattattetetcaccatcagcagccttgagtetgaagattttgtagactattactgtetacaatatgetagttetectca cgttcggtgctgggaccaagctggagctgaaacgggc (SEQ ID NO:85) describes MIN-14 light chain variable region nucleotide sequence.

gacattgtgctgacacagtctcctgcttccttagctgtatctctggggcagagggccaccatctcatacagggccagcaaaagt gtcagtacatctggctatagttatatgcactggaaccaacagaaaccaggacagccacccagactcctcatctatcttgtatccaacctagaatctggg gtccctgccaggttcagtggcagtgggtctgggacagacttcaccctcaacatccatcctgtggaggaggaggatgctgcaacctattactgtcagc acattagggagcttacacgttcggaggggggaccaagctggaa (SEQ ID NO:86) describes MIN-17-1 light chain variable region nucleotide sequence.

gacattcagatgacccagtctcctgcctcccagtctgcatctctgggagaaagtgtcaccatcacatgcctggcaagtcagacc attggtacatggttagcatggtatcagcagaaaccagggaaatctcctcagctcctgatttatgctgcaaccagcttggcagatggggtcccatcaag gttcagtggtagtggatctggcacaaaattttctttcaagatcagcagcctacaggctgaagattttgtaagttattactgtcaacaactttacagtactcc gtggacgttcggtggaggcaccaagctggaaatcaaacgggctgatgctgcaccaactgta (SEQ ID NO:87) describes MIN-17-2 light chain variable region nucleotide sequence.

gtgacattgtgctgacacagtctcctgcttccttagctgtatctctggggcagagggccaccatctcatacagggccagcaaaa gtgtcagtacatctggctatagttatatgcactggaaccaacagaaaccaggacagccacccagactcctcatctatcttgtatccaacctagaatctg gggtccctgccaggttcagtggcagtgggtctgggacagacttcaccctcaacatccatcctgtggaggaggaggatgctgcaacctattactgtca gcacattagggagcttacacgttcggaggggggaccaagctgg (SEQ ID NO:88) describes MIN-29 light chain variable region nucleotide sequence.

gacattgtgctgacacagtctcctgcttccttagctgtatctctggggcagagggccaccatctcatacagggccagcaaaagt gtcagtacatctggctatagttatatgcactggaaccaacagaaaccaggacagccacccagactcctcatctatcttgtatccaacctagaatctggg gtccctgccaggttcagtggcagtgggtctgggacagacttcaccctcaacatccatcctgtggaggaggaggatgctgcaacctattactgtcagc acattagggagcttacacgttcggaggggggaccaagctgg (SEQ ID NO:89) describes MIN-34 light chain variable region nucleotide sequence.

gacattgtgatgacccagtctcaaaaattcatgtccacatcagtaggagacagggtcagcgtcacctgcaaggccagtcagaa tgtgggtactaatgtaggttggtatcaacagaaaccagggcaatctcctaaagcactgatttactcggcatcctaccggtacagtggagtccctgatcg cttcacaggcagtggatctgggacagatttcactctcaccatcagcaatgtgcagtctgaagacttggcagagtatttctgtcagcaatataac aactat ccgtacacgttcggaggggggaccaagctggaaataaaacgggctgatgctgcaccaactgta (SEQ ID NO:90) describes MIN-42 light chain variable region nucleotide sequence.

gacatccagatgactcagcctccagcctccctatctgcatctgtgggagaaactgtcaccatcacatgtcgagcaagtgggaat attcacaatttttagcatggtatcagcagaaacagggaaaatctcctcagctcctggtctataatgcaaaaaccttagcagatggtgtgccatcaaggtt cagtggcagtggatcaggaacacaatattctctcaagatcaacagcctgcagcctgaagattttgggagttattactgtcaacatttttggagtactccgt ggacgttcggtggaggcaccaagctggaaatcaaacgggctgatgctgcaccaactgta (SEQ ID NO:91) describes MIN-45 light chain variable region nucleotide sequence.

caggtccaactgcagcagcctggggctgaactggtgaagcctggggcttcagtgaagctgtcctgcaaggcttctggctaca ccttcaccagctactggatgcactgggtgaagcagaggcctggacaaggccttgagtggattggagagattaatcctagcaacggtcgtactaacta caatgagaagttcaagagcaaggccacactgactgtagacaaatcctccagcacagcctacatgcaactcagcagcctgacatctgaggactctgc ggtctattactgtgcaacctatggtaactactggtacttc (SEQ ID NO:92) describes MIN-14 heavy chain variable region nucleotide sequence.

caggtccaactgcagcagcctggggctgaactggtgaagcctggggcttcagtgaagctgtcctgcaaggcttctggctaca ccttcaccagctactggatgcactgggtgaagcagaggcctggacaaggccttgagtggattggagagattaatcctagcaacggtcgtactaacta caatgagaagttcaagagcaaggccacactgactgtagacaaatcctccagcacagcctacatgcaactcagcagcctgacatctgaggactctgc ggtctattactgtgcaacctatggtaactactggtacttc (SEQ ID NO:93) describes MIN-17-1 heavy chain variable region nucleotide sequence.

cagattactctgaaagagtctggccctgggatagttcagccatcccagcccttcagacttacttgcactttctctgggttttcactg agcacttctggtataggtgtaacctggattcgtcagccctcagggaaaggtctggagtggctggcaacgatttggtgggatgatgataaccgctacaa cccatctctaaagagcaggctcacagtctccaaagacacctccaacaaccaagcattcctgaatatcatcactgtggaaactgcagatactgccatat actactgtgctcagtctactatggttacggcggga (SEQ ID NO:94) describes MIN-17-2 heavy chain variable region nucleotide sequence.

ccaggtgcagctgaagcagtcaggacctggcctagtgcagccctcacagagcctgtccatcacctgcacagtctctggtttct cattaactagctatggtgtacactgggttcgccagtctccaggaaagggtctggagtggctgggagtgatatggggtggtggaagcacagactataa tgcagetttcatatccagactgagcatcagcaaggacaattccaagagccaagttttetttaaaatgaacagtetgcaagetaatgacacagccatatat tactgtgccagaaatgactatccggcctggttt (SEQ ID NO:95) describes MIN-34 heavy chain variable region nucleotide sequence.

gtgaggtgcaactggtggagtctgggggagacttagtgaagcctggaaggtccctgaaactctcctgtgcagcctctggattc actttcagtagetttggcatgtettgggttegccagactccagacaagaggetggagtgggtcgcaaccattagtagtggtggtacttacacetactate cagacagtgtgaaggggcgattcaccatctccagagacaatgccaagaacaccctgtacctgcaaatgagcagtctgaagtctgaggacacagcc atgtattactgttcaagaaggttctactatgattacgac (SEQ ID NO:96) describes MIN-42 heavy chain variable region nucleotide sequence.

gaggttcagctgcagcagtctggacctgagctggtgaagcctggggcttcagtgaagatatcctgcaaggcttctggttactca tttactggctactttatgagctgggtgatgcagagccatggaaagagccttgagtggattggacgtattaatccttacaatggtgatactttctacaacca gaagttcaagggcaaggccacattgactgtagacaaatcctctaccacagcccacatagagctccggagcctggcatctgaggactctgcagtctat tattgtgcaagaaagggcctctatggg (SEQ ID NO:97) describes MIN-45 heavy chain variable region nucleotide sequence.

DIVITQSTASLGVSLGQRATISC (SEQ ID NO:98) describes MIN-C2 light chain variable framework region 1 (FWR1) amino acid sequence.

DIVITQTTAIMSASPGEEVTLTC (SEQ ID NO:99) describes MIN-E6 light chain variable framework region 1 (FWR1) amino acid sequence.

DIVLTQSTEIMSASPGEKVTITC (SEQ ID NO:100) describes MIN-A2-1 light chain variable framework region 1 (FWR1) amino acid sequence.

DIVMTQSPAIMSASPGEKVTMTC (SEQ ID NO:101) describes MIN-A2-2 light chain variable framework region 1 (FWR1) amino acid sequence.

DIVLTQTTAIMSASPGEKVTITC (SEQ ID NO:102) describes MIN-C9-1 light chain variable framework region 1 (FWR1) amino acid sequence.

DIVITQSTAIMSASPGEKVTITC (SEQ ID NO:103) describes MIN-C9-2 light chain variable framework region 1 (FWR1) amino acid sequence.

DIVITQTPAIMSASPGEKVTMTC (SEQ ID NO:104) describes MIN-D7-1 light chain variable framework region 1 (FWR1) amino acid sequence.

DIVLTQSTAIMSASPGEKVTMTC (SEQ ID NO:105) describes MIN-D7-2 light chain variable framework region 1 (FWR1) amino acid sequence.

DIVMTQSPEIMSASPGEKVTITC (SEQ ID NO:106) describes MIN-F2-1 light chain variable framework region 1 (FWR1) amino acid sequence.

DIVITQSTEIMSASPGEKVTITC (SEQ ID NO: 107) describes MIN-F2-2 light chain variable framework region 1 (FWR1) amino acid sequence.

RASKSVSTSGYSYMH (SEQ ID NO:108) describes MIN-C2 light chain variable complementarity determining region 1 (CDR1) amino acid sequence.

SATSSVSYIH (SEQ ID NO:109) describes MIN-E6 light chain variable complementarity determining region 1 (CDR1) amino acid sequence.

SASSSISYIH (SEQ ID NO:110) describes MIN-A2-1 light chain variable complementarity determining region 1 (CDR1) amino acid sequence.

SASSSVSYMH (SEQ ID NO:112) describes MIN-A2-2 light chain variable complementarity determining region 1 (CDR1) amino acid sequence.

SASSSVSYMY (SEQ ID NO:113) describes MIN-C9-1 light chain variable complementarity determining region 1 (CDR1) amino acid sequence.

SASSSVSYTY (SEQ ID NO:114) describes MIN-C9-2 light chain variable complementarity determining region 1 (CDR1) amino acid sequence.

SASSSVSYMH (SEQ ID NO:115) describes MIN-D7-1 light chain variable complementarity determining region 1 (CDR1) amino acid sequence.

SASSSVSYMH (SEQ ID NO:116) describes MIN-D7-2 light chain variable complementarity determining region 1 (CDR1) amino acid sequence.

SASSSISYIH (SEQ ID NO:117) describes MIN-F2-1 light chain variable complementarity determining region 1 (CDR1) amino acid sequence.

SASSSISYIH (SEQ ID NO:118) describes MIN-F2-2 light chain variable complementarity determining region 1 (CDR1) amino acid sequence.

WYQQRPGQPPKLLIY (SEQ ID NO:119) describes MIN-C2 light chain variable framework region 2 (FWR2) amino acid sequence.

WFQQRPGTSPKLWIY (SEQ ID NO:120) describes MIN-E6 light chain variable framework region 2 (FWR2) amino acid sequence.

WFQQKPGTSPKLWIF (SEQ ID NO:121) describes MIN-A2-1 light chain variable framework region 2 (FWR2) amino acid sequence.

WFQQKPGTSPKLWIY (SEQ ID NO:122) describes MIN-A2-2 light chain variable framework region 2 (FWR2) amino acid sequence.

WFQQKPGTSPKLWIY (SEQ ID NO:123) describes MIN-C9-1 light chain variable framework region 2 (FWR2) amino acid sequence.

WFQQKPGTSPKLWIY (SEQ ID NO:124) describes MIN-C9-2 light chain variable framework region 2 (FWR2) amino acid sequence.

WFQQKPGTSPKLWIY (SEQ ID NO:125) describes MIN-D7-1 light chain variable framework region 2 (FWR2) amino acid sequence.

WFQQKPGTSPKLWIY (SEQ ID NO:126) describes MIN-D7-2 light chain variable framework region 2 (FWR2) amino acid sequence.

WFQQKPGTSPKLWIF (SEQ ID NO:127) describes MIN-F2-1 light chain variable framework region 2 (FWR2) amino acid sequence.

WFQQKPGTSPKLWIF (SEQ ID NO:128) describes MIN-F2-2 light chain variable framework region 2 (FWR2) amino acid sequence.

LASNLES (SEQ ID NO:129) describes MIN-C2 light chain variable complementarity determining region 2 (CDR2) amino acid sequence.

STSNLAS (SEQ ID NO:130) describes MIN-E6 light chain variable complementarity determining region 2 (CDR2) amino acid sequence.

GTSNLAS (SEQ ID NO:131) describes MIN-A2-1 light chain variable complementarity determining region 2 (CDR2) amino acid sequence.

STSNLAS (SEQ ID NO:132) describes MIN-A2-2 light chain variable complementarity determining region 2 (CDR2) amino acid sequence.

STSNLAS (SEQ ID NO: 133) describes MIN-C9-1 light chain variable complementarity determining region 2 (CDR2) amino acid sequence.

STSNLAS (SEQ ID NO: 134) describes MIN-C9-2 light chain variable complementarity determining region 2 (CDR2) amino acid sequence.

STSNLAS (SEQ ID NO:135) describes MIN-D7-1 light chain variable complementarity determining region 2 (CDR2) amino acid sequence.

STSNLAS (SEQ ID NO:136) describes MIN-D7-2 light chain variable complementarity determining region 2 (CDR2) amino acid sequence.

GTSNLAS (SEQ ID NO:137) describes MIN-F2-1 light chain variable complementarity determining region 2 (CDR2) amino acid sequence.

GTSNLAS (SEQ ID NO:138) describes MIN-F2-2 light chain variable complementarity determining region 2 (CDR2) amino acid sequence.

GVPARFSGSGSGTDFTLNIIIPVEEEDAATYYC (SEQ ID NO:139) describes MIN-C2 light chain variable framework region 3 (FWR3) amino acid sequence.

GVPVRFSGSGYGTSYSLTISRMEAEDAATYYC (SEQ ID NO:140) describes MIN-E6 light chain variable framework region 3 (FWR3) amino acid sequence.

GVPARFSGSGSGTSYSLTVSRMEAEDTATYYC (SEQ ID NO:141) describes MIN-A2-1 light chain variable framework region 3 (FWR3) amino acid sequence.

GAPARFSGSGSGTSYSLTVSRMESEDAATYYC (SEQ ID NO:142) describes MIN-A2-2 light chain variable framework region 3 (FWR3) amino acid sequence.

GVPARFSGSGSGTSYSLTISRMEAEDAATYYC (SEQ ID NO:143) describes MIN-C9-1 light chain variable framework region 3 (FWR3) amino acid sequence.

GVPARFSGSGSGTSYSLTISRMEAEDAATYYC (SEQ ID NO:144) describes MIN-C9-2 light chain variable framework region 3 (FWR3) amino acid sequence.

GVPARFSGSGSGTSYSLTVSRMESEDAATYYC (SEQ ID NO:145) describes MIN-D7-1 light chain variable framework region 3 (FWR3) amino acid sequence.

GVPARFSGSGSGTSYSLTVSRMESEDAATYYC (SEQ ID NO:146) describes MIN-D7-2 light chain variable framework region 2 (FWR2) amino acid sequence.

GVPARFSGSGSGTSYSLTVSRMEAEDTATYYC (SEQ ID NO:147) describes MIN-F2-1 light chain variable framework region 3 (FWR3) amino acid sequence.

GVPARFSGSGSGTSYSLTVSRMEAEDTATYYC (SEQ ID NO:148) describes MIN-F2-2 light chain variable framework region 3 (FWR3) amino acid sequence.

QHSRELPFT (SEQ ID NO:149) describes MIN-C2 light chain variable complementarity determining region 3 (CDR3) amino acid sequence.

QQRSSSPFT (SEQ ID NO:150) describes MIN-E6 light chain variable complementarity determining region 3 (CDR3) amino acid sequence.

QQRSNYPFT (SEQ ID NO:151) describes MIN-A2-1 light chain variable complementarity determining region 3 (CDR3) amino acid sequence.

QQRSSYPST (SEQ ID NO:152) describes MIN-A2-2 light chain variable complementarity determining region 3 (CDR3) amino acid sequence.

QQRSSYPST (SEQ ID NO:153) describes MIN-C9-1 light chain variable complementarity determining region 3 (CDR3) amino acid sequence.

QQRSSYPST (SEQ ID NO:154) describes MIN-C9-2 light chain variable complementarity determining region 3 (CDR3) amino acid sequence.

QQRSSYPST (SEQ ID NO:155) describes MIN-D7-1 light chain variable complementarity determining region 3 (CDR3) amino acid sequence.

QQRSSYPST (SEQ ID NO:156) describes MIN-D7-2 light chain variable complementarity determining region 3 (CDR3) amino acid sequence.

QQRSNYPFT (SEQ ID NO:157) describes MIN-F2-1 light chain variable complementarity determining region 3 (CDR3) amino acid sequence.

QQRSNYPFT (SEQ ID NO:158) describes MIN-F2-2 light chain variable complementarity determining region 3 (CDR3) amino acid sequence.

EVQLEESGGGLVKPGGSLKLSCAASGFTFS (SEQ ID NO:159) describes MIN-C2 heavy chain variable framework region 1 (FWR1) amino acid sequence.

EVKLEESGGDLVKPGGSLKLSCAASGFTFS (SEQ ID NO:160) describes MIN-E6-7 heavy chain variable framework region 1 (FWR1) amino acid sequence.

EVKLEESGGDLVKPGGSLKLSCVVSGFTFS (SEQ ID NO:161) describes MIN-E6-8 heavy chain variable framework region 1 (FWR1) amino acid sequence.

EVKLQESGPELKKPGETVEISCKASGYTFT (SEQ ID NO:162) describes MIN-A2-1 heavy chain variable framework region 1 (FWR1) amino acid sequence.

EVQLQQSGPELKKPGETVKISCKASGYTFT (SEQ ID NO:163) describes MIN-A2-2 heavy chain variable framework region 1 (FWR1) amino acid sequence.

QVQLQESGPELKQPGETVKISCKASGYTFT (SEQ ID NO:164) describes MIN-C9-1 heavy chain variable framework region 1 (FWR1) amino acid sequence.

QVQLQQSGPELKQPGETVKISCKASGYTFT (SEQ ID NO:165) describes MIN-C9-2 heavy chain variable framework region 1 (FWR1) amino acid sequence.

EVQLEQSGPELKKPGETVKISCKASGYTFI (SEQ ID NO:166) describes MIN-D7-1 heavy chain variable framework region 1 (FWR1) amino acid sequence.

EVQLQQSGPELKKPGETVKISCKASGYTFT (SEQ ID NO:167) describes MIN-D7-2 heavy chain variable framework region 1 (FWR1) amino acid sequence.

EVKLEESGPELKKPGETVKISCKASGYTFI (SEQ ID NO:168) describes MIN-F2-1 heavy chain variable framework region 1 (FWR1) amino acid sequence.

EVQLEQSGAELVRPGASVKLSCKALGYTFT (SEQ ID NO:169) describes MIN-F2-2 heavy chain variable framework region 1 (FWR1) amino acid sequence.

RCRLQQSGPELKKPGETVKISCKASGYTFI (SEQ ID NO:170) describes MIN-F2-3 heavy chain variable framework region 1 (FWR1) amino acid sequence.

EVQLEQSGPELKKPGETVKISCKASGYTFI (SEQ ID NO:171) describes MIN-F2-4 heavy chain variable framework region 1 (FWR1) amino acid sequence.

GYAMS (SEQ ID NO:172) describes MIN-C2 heavy chain variable complementarity determining region 1 (CDR1) amino acid sequence.

RYGMS (SEQ ID NO:173) describes MIN-E6-7 heavy chain variable complementarity determining region 1 (CDR1) amino acid sequence.

RYGMS (SEQ ID NO:174) describes MIN-E6-8 heavy chain variable complementarity determining region 1 (CDR1) amino acid sequence.

NYGMN (SEQ ID NO:175) describes MIN-A2-1 heavy chain variable complementarity determining region 1 (CDR1) amino acid sequence.

NYGMN (SEQ ID NO:176) describes MIN-A2-2 heavy chain variable complementarity determining region 1 (CDR1) amino acid sequence.

NNGMN (SEQ ID NO:177) describes MIN-C9-1 heavy chain variable complementarity determining region 1 (CDR1) amino acid sequence.

NNGMN (SEQ ID NO:178) describes MIN-C9-2 heavy chain variable complementarity determining region 1 (CDR1) amino acid sequence.

NYGMN (SEQ ID NO:179) describes MIN-D7-1 heavy chain variable complementarity determining region 1 (CDR1) amino acid sequence.

NYGMN (SEQ ID NO:180) describes MIN-D7-2 heavy chain variable complementarity determining region 1 (CDR1) amino acid sequence.

NYGMN (SEQ ID NO:181) describes MIN-F2-1 heavy chain variable complementarity determining region 1 (CDR1) amino acid sequence.

DYEMH (SEQ ID NO:182) describes MIN-F2-2 heavy chain variable complementarity determining region 1 (CDR1) amino acid sequence.

NYGMN (SEQ ID NO:183) describes MIN-F2-3 heavy chain variable complementarity determining region 1 (CDR1) amino acid sequence.

NYGMN (SEQ ID NO:184) describes MIN-F2-4 heavy chain variable complementarity determining region 1 (CDR1) amino acid sequence.

WVRQTPEKRLEWVA (SEQ ID NO:185) describes MIN-C2 heavy chain variable framework region 2 (FWR2) amino acid sequence.

WVRQTPDKRLEWVA (SEQ ID NO:186) describes MIN-E6-7 heavy chain variable framework region 2 (FWR2) amino acid sequence.

WVRQTPGKRLEWVA (SEQ ID NO:187) describes MIN-E6-8 heavy chain variable framework region 2 (FWR2) amino acid sequence.

WVKQAPGKGLKWMG (SEQ ID NO:188) describes MIN-A2-1 heavy chain variable framework region 2 (FWR2) amino acid sequence.

WVKQAPGKGLKWMG (SEQ ID NO:189) describes MIN-A2-2 heavy chain variable framework region 2 (FWR2) amino acid sequence.

WVKQAPGKGLKWMG (SEQ ID NO:190) describes MIN-C9-1 heavy chain variable framework region 2 (FWR2) amino acid sequence.

WVKQAPGKGLKWMG (SEQ ID NO:191) describes MIN-C9-2 heavy chain variable framework region 2 (FWR2) amino acid sequence.

WVKQAPGKGLKWMG (SEQ ID NO:192) describes MIN-D7-1 heavy chain variable framework region 2 (FWR2) amino acid sequence.

WVKQAPGKGLKWMG (SEQ ID NO:193) describes MIN-D7-2 heavy chain variable framework region 2 (FWR2) amino acid sequence.

WVKQAPGKGLKWMG (SEQ ID NO:194) describes MIN-F2-1 heavy chain variable framework region 2 (FWR2) amino acid sequence.

WVKQTPVHGLEWIG (SEQ ID NO:195) describes MIN-F2-2 heavy chain variable framework region 2 (FWR2) amino acid sequence.

WVKQAPGKGLKWMG (SEQ ID NO:196) describes MIN-F2-3 heavy chain variable framework region 2 (FWR2) amino acid sequence.

WVKQAPGKGLKWMG (SEQ ID NO:197) describes MIN-F2-4 heavy chain variable framework region 2 (FWR2) amino acid sequence.

TISSGGTYIYYPDSVKG (SEQ ID NO:198) describes MIN-C2 heavy chain variable complementarity determining region 2 (CDR2) amino acid sequence.

TISSGGTYIYYPDSVKG (SEQ ID NO:199) describes MIN-E6-7 heavy chain variable complementarity determining region 2 (CDR2) amino acid sequence.

TISGGGTYIYYPDSVKG (SEQ ID NO:200) describes MIN-E6-8 heavy chain variable complementarity determining region 2 (CDR2) amino acid sequence.

WINTYTGEPTYAGDFKG (SEQ ID NO:201) describes MIN-A2-1 heavy chain variable complementarity determining region 2 (CDR2) amino acid sequence.

WINTYTGEPTYAGDFKG (SEQ ID NO:202) describes MIN-A2-2 heavy chain variable complementarity determining region 2 (CDR2) amino acid sequence.

WINTYTGEPTYADDFKG (SEQ ID NO:203) describes MIN-C9-1 heavy chain variable complementarity determining region 2 (CDR2) amino acid sequence.

WINTYTGEPTYADDFKG (SEQ ID NO:204) describes MIN-C9-2 heavy chain variable complementarity determining region 2 (CDR2) amino acid sequence.

WINTYTGEPTYVDDFKG (SEQ ID NO:205) describes MIN-D7-1 heavy chain variable complementarity determining region 2 (CDR2) amino acid sequence.

WINTYTGEPTYAGDFKG (SEQ ID NO:206) describes MIN-D7-2 heavy chain variable complementarity determining region 2 (CDR2) amino acid sequence.

WINTYTGEPTYVDDFKG (SEQ ID NO:207) describes MIN-F2-1 heavy chain variable complementarity determining region 2 (CDR2) amino acid sequence.

AIHPGSGGTAYNQKFKG (SEQ ID NO:208) describes MIN-F2-2 heavy chain variable complementarity determining region 2 (CDR2) amino acid sequence.

WINTYTGEPTYVDDFKG (SEQ ID NO:209) describes MIN-F2-3 heavy chain variable complementarity determining region 2 (CDR2) amino acid sequence.

WINTYTGEPTYVDDFKG (SEQ ID NO:210) describes MIN-F2-4 heavy chain variable complementarity determining region 2 (CDR2) amino acid sequence.

RFTISRDNAKNTLYLQMSSLRSEDTAMYYCAR (SEQ ID NO:211) describes MIN-C2 heavy chain variable framework region 3 (FWR3) amino acid sequence.

RFTISRDNAKNTLYLQMSSLKSEDTAMYYCAR (SEQ ID NO:212) describes MIN-E6-7 heavy chain variable framework region 3 (FWR3) amino acid sequence.

RFTISRDNAKNTLYLQMSSLKSEDTAMYHCTR (SEQ ID NO:213) describes MIN-E6-8 heavy chain variable framework region 3 (FWR3) amino acid sequence.

RFAFSLETSASTAYLQINTLKNEDTATYFCAR (SEQ ID NO:214) describes MIN-A2-1 heavy chain variable framework region 3 (FWR3) amino acid sequence.

RFAFSLETSASTAYLQINTLKNEDTATYFCAR (SEQ ID NO:215) describes MIN-A2-2 heavy chain variable framework region 3 (FWR3) amino acid sequence.

RFAFSLDTSASTAYLQINNLKNEDMATYFCAR (SEQ ID NO:216) describes MIN-C9-1 heavy chain variable framework region 3 (FWR3) amino acid sequence.

RFAFSLGTSASTAYLQINNLKNEDMATYFCAR (SEQ ID NO:217) describes MIN-C9-2 heavy chain variable framework region 3 (FWR3) amino acid sequence.

RFAFSLETSARTAYLQINNLKNEDMATYFCAR (SEQ ID NO:218) describes MIN-D7-1 heavy chain variable framework region 3 (FWR3) amino acid sequence.

RFAFSLETSASTAYLQINTLKNEDTATYFCAR (SEQ ID NO:219) describes MIN-D7-2 heavy chain variable framework region 3 (FWR3) amino acid sequence.

RFAFSLETSARTAYLQINNLKNEDMATYFCAR (SEQ ID NO:220) describes MIN-F2-1 heavy chain variable framework region 3 (FWR3) amino acid sequence.

KATLTADKSSSTAYMELSSLTSEDSAVYYCTN (SEQ ID NO:221) describes MIN-F2-2 heavy chain variable framework region 3 (FWR3) amino acid sequence.

RFAFSLETSARTAYLQINNLKNEDMATYFCAR (SEQ ID NO:222) describes MIN-F2-3 heavy chain variable framework region 3 (FWR3) amino acid sequence.

RFAFSLETSARTAYLQINNLKNEDMATYFCAR (SEQ ID NO:223) describes MIN-F2-4 heavy chain variable framework region 3 (FWR3) amino acid sequence.

LGGDNYYEY (SEQ ID NO:224) describes MIN-C2 heavy chain variable complementarity determining region 3 (CDR3) amino acid sequence.

DNYGSSYDYA (SEQ ID NO:225) describes MIN-E6-7 heavy chain variable complementarity determining region 3 (CDR3) amino acid sequence.

DNYGRNYDYG (SEQ ID NO:226) describes MIN-E6-8 heavy chain variable complementarity determining region 3 (CDR3) amino acid sequence.

SGDGYWYYA (SEQ ID NO:227) describes MIN-A2-1 heavy chain variable complementarity determining region 3 (CDR3) amino acid sequence.

SGDGYWYYA (SEQ ID NO:228) describes MIN-A2-2 heavy chain variable complementarity determining region 3 (CDR3) amino acid sequence.

TGTARAFYA (SEQ ID NO:229) describes MIN-C9-1 heavy chain variable complementarity determining region 3 (CDR3) amino acid sequence.

TGTARAFYA (SEQ ID NO:230) describes MIN-C9-2 heavy chain variable complementarity determining region 3 (CDR3) amino acid sequence.

TGTTAILNG (SEQ ID NO:231) describes MIN-D7-1 heavy chain variable complementarity determining region 3 (CDR3) amino acid sequence.

SGDGYWYYA (SEQ ID NO:232) describes MIN-D7-2 heavy chain variable complementarity determining region 3 (CDR3) amino acid sequence.

TGTTAILNG (SEQ ID NO:233) describes MIN-F2-1 heavy chain variable complementarity determining region 3 (CDR3) amino acid sequence.

YGSFA (SEQ ID NO:234) describes MIN-F2-2 heavy chain variable complementarity determining region 3 (CDR3) amino acid sequence.

TGTTAILNG (SEQ ID NO:235) describes MIN-F2-3 heavy chain variable complementarity determining region 3 (CDR3) amino acid sequence.

TGTTAILNG (SEQ ID NO:236) describes MIN-F2-4 heavy chain variable complementarity determining region 3 (CDR3) amino acid sequence.

DIQMTQSPSSLSASLGERVSLTC (SEQ ID NO:237) describes MIN-14 light chain variable framework region 1 (FWR1) amino acid sequence.

DIVLTQSPASLAVSLGQRATISY (SEQ ID NO:238) describes MIN-17-1 light chain variable framework region 1 (FWR1) amino acid sequence.

DIQMTQSPASQSASLGESVTITC (SEQ ID NO:239) describes MIN-17-2 light chain variable framework region 1 (FWR1) amino acid sequence.

DIVLTQSPASLAVSLGQRATISY (SEQ ID NO:240) describes MIN-29 light chain variable framework region 1 (FWR1) amino acid sequence.

DIVLTQSPASLAVSLGQRATISY (SEQ ID NO:241) describes MIN-34 light chain variable framework region 1 (FWR1) amino acid sequence.

DIVMTQSQKFMSTSVGDRVSVTC (SEQ ID NO:242) describes MIN-42 light chain variable framework region 1 (FWR1) amino acid sequence.

DIQMTQPPASLSASVGETVTITC (SEQ ID NO:243) describes MIN-45 light chain variable framework region 1 (FWR1) amino acid sequence.

RASQDIGSSLN (SEQ ID NO:244) describes MIN-14 light chain variable complementarity determining region 1 (CDR1) amino acid sequence.

RASKSVSTSGYSYMH (SEQ ID NO:245) describes MIN-17-1 light chain variable complementarity determining region 1 (CDR1) amino acid sequence.

LASQTIGTWLA (SEQ ID NO:246) describes MIN-17-2 light chain variable complementarity determining region 1 (CDR1) amino acid sequence.

RASKSVSTSGYSYMH (SEQ ID NO:247) describes MIN-29 light chain variable complementarity determining region 1 (CDR1) amino acid sequence.

RASKSVSTSGYSYMH (SEQ ID NO:248) describes MIN-34 light chain variable complementarity determining region 1 (CDR1) amino acid sequence.

KASQNVGTNVG (SEQ ID NO:249) describes MIN-42 light chain variable complementarity determining region 1 (CDR1) amino acid sequence.

RASGNIHNFLA (SEQ ID NO:250) describes MIN-45 light chain variable complementarity determining region 1 (CDR1) amino acid sequence.

WLQQEPDGTIKRLIY (SEQ ID NO:251) describes MIN-14 light chain variable framework region 2 (FWR2) amino acid sequence.

WNQQKPGQPPRLLIY (SEQ ID NO:252) describes MIN-17-1 light chain variable framework region 2 (FWR2) amino acid sequence.

WYQQKPGKSPQLLIY (SEQ ID NO:253) describes MIN-17-2 light chain variable framework region 2 (FWR2) amino acid sequence.

WNQQKPGQPPRLLIY (SEQ ID NO:254) describes MIN-29 light chain variable framework region 2 (FWR2) amino acid sequence.

WNQQKPGQPPRLLIY (SEQ ID NO:255) describes MIN-34 light chain variable framework region 2 (FWR2) amino acid sequence.

WYQQKPGQSPKALIY (SEQ ID NO:266) describes MIN-42 light chain variable framework region 2 (FWR2) amino acid sequence.

WYQQKQGKSPQLLVY (SEQ ID NO:267) describes MIN-45 light chain variable framework region 2 (FWR2) amino acid sequence.

ATSSLDS (SEQ ID NO:268) describes MIN-14 light chain variable complementarity determining region 2 (CDR2) amino acid sequence.

LVSNLES (SEQ ID NO:269) describes MIN-17-1 light chain variable complementarity determining region 2 (CDR2) amino acid sequence.

AATSLAD (SEQ ID NO:270) describes MIN-17-2 light chain variable complementarity determining region 2 (CDR2) amino acid sequence.

LVSNLES (SEQ ID NO:271) describes MIN-29 light chain variable complementarity determining region 2 (CDR2) amino acid sequence.

LVSNLES (SEQ ID NO:272) describes MIN-34 light chain variable complementarity determining region 2 (CDR2) amino acid sequence.

SASYRYS (SEQ ID NO:273) describes MIN-42 light chain variable complementarity determining region 2 (CDR2) amino acid sequence.

NAKTLAD (SEQ ID NO:274) describes MIN-45 light chain variable complementarity determining region 2 (CDR2) amino acid sequence.

GVPKRFSGSRSGSDYSLTISSLESEDFVDYYC (SEQ ID NO:275) describes MIN-14 light chain variable framework region 3 (FWR3) amino acid sequence.

GVPARFSGSGSGTDFTLNIIIPVEEEDAATYYC (SEQ ID NO:276) describes MIN-17-1 light chain variable framework region 3 (FWR3) amino acid sequence.

GVPSRFSGSGSGTKFSFKISSLQAEDFVSYYC (SEQ ID NO:277) describes MIN-17-2 light chain variable framework region 3 (FWR3) amino acid sequence.

GVPARFSGSGSGTDFTLNIIIPVEEEDAATYYC (SEQ ID NO:288) describes MIN-29 light chain variable framework region 3 (FWR3) amino acid sequence.

GVPARFSGSGSGTDFTLNIIIPVEEEDAATYYC (SEQ ID NO:289) describes MIN-34 light chain variable framework region 3 (FWR3) amino acid sequence.

GVPDRFTGSGSGTDFTLTISNVQSEDLAEYFC (SEQ ID NO:290) describes MIN-42 light chain variable framework region 3 (FWR3) amino acid sequence.

GVPSRFSGSGSGTQYSLKINSLQPEDFGSYYC (SEQ ID NO:291) describes MIN-45 light chain variable framework region 3 (FWR3) amino acid sequence.

QVQLQQPGAELVKPGASVKLSCKASGYTFT (SEQ ID NO:292) describes MIN-14 heavy chain variable framework region 1 (FWR1) amino acid sequence.

QVQLQQPGAELVKPGASVKLSCKASGYTFT (SEQ ID NO:293) describes MIN-17-1 heavy chain variable framework region 1 (FWR1) amino acid sequence.

QITLKESGPGIVQPSQPFRLTCTFSGFSLSTS (SEQ ID NO:294) describes MIN-17-2 heavy chain variable framework region 1 (FWR1) amino acid sequence.

DVKLVESGGDLXKLTEGEDIWEGLTLCRDSDQSPLAPVSKPGRVVRPQRSCTVI QGCVL (SEQ ID NO:295) describes MIN-29 heavy chain variable framework region 1 (FWR1) amino acid sequence.

QVQLKQSGPGLVQPSQSLSITCTVSGFSLT (SEQ ID NO:296) describes MIN-34 heavy chain variable framework region 1 (FWR1) amino acid sequence.

EVQLVESGGDLVKPGRSLKLSCAASGFTFS (SEQ ID NO:298) describes MIN-42 heavy chain variable framework region 1 (FWR1) amino acid sequence.

EVQLQQSGPELVKPGASVKISCKASGYSFT (SEQ ID NO:299) describes MIN-45 heavy chain variable framework region 1 (FWR1) amino acid sequence.

SYWMH (SEQ ID NO:300) describes MIN-14 heavy chain complementarity determining region 1 (CDR1) amino acid sequence.

SYWMH (SEQ ID NO:301) describes MIN-17-1 heavy chain complementarity determining region 1 (CDR1) amino acid sequence.

GIGVT (SEQ ID NO:302) describes MIN-17-2 heavy chain complementarity determining region 1 (CDR1) amino acid sequence.

SYGVH (SEQ ID NO:303) describes MIN-34 heavy chain complementarity determining region 1 (CDR1) amino acid sequence.

SFGMS (SEQ ID NO:304) describes MIN-42 heavy chain complementarity determining region 1 (CDR1) amino acid sequence.

GYFMS (SEQ ID NO:305) describes MIN-45 heavy chain complementarity determining region 1 (CDR1) amino acid sequence.

WVKQRPGQGLEWIG (SEQ ID NO:306) describes MIN-14 heavy chain variable framework region 2 (FWR2) amino acid sequence.

WVKQRPGQGLEWIG (SEQ ID NO:307) describes MIN-17-1 heavy chain variable framework region 2 (FWR2) amino acid sequence.

WIRQPSGKGLEWLA (SEQ ID NO:308) describes MIN-17-2 heavy chain variable framework region 2 (FWR2) amino acid sequence.

RLQTAHLQVQGVL (SEQ ID NO:309) describes MIN-29 heavy chain variable framework region 2 (FWR2) amino acid sequence.

WVRQSPGKGLEWLG (SEQ ID NO:310) describes MIN-34 heavy chain variable framework region 2 (FWR2) amino acid sequence.

WVRQTPDKRLEWVA (SEQ ID NO:311) describes MIN-42 heavy chain variable framework region 2 (FWR2) amino acid sequence.

WVMQSHGKSLEWIG (SEQ ID NO:312) describes MIN-45 heavy chain variable framework region 2 (FWR1) amino acid sequence.

EINPSNGRTNYNEKFKS (SEQ ID NO:313) describes MIN-14 heavy chain complementarity determining region 2 (CDR2) amino acid sequence.

EINPSNGRTNYNEKFKS (SEQ ID NO:314) describes MIN-17-1 heavy chain complementarity determining region 2 (CDR2) amino acid sequence.

TIWWDDDNRYNPSLKS (SEQ ID NO:315) describes MIN-17-2 heavy chain complementarity determining region 2 (CDR2) amino acid sequence.

GIVSGDGESALHSVWIVG (SEQ ID NO:316) describes MIN-29 heavy chain complementarity determining region 2 (CDR2) amino acid sequence.

VIWGGGSTDYNAAFIS (SEQ ID NO:317) describes MIN-34 heavy chain complementarity determining region 2 (CDR2) amino acid sequence.

TISSGGTYTYYPDSVKG (SEQ ID NO:318) describes MIN-42 heavy chain complementarity determining region 2 (CDR2) amino acid sequence.

RINPYNGDTFYNQKFKG (SEQ ID NO:319) describes MIN-45 heavy chain complementarity determining region 2 (CDR2) amino acid sequence.

KATLTVDKSSSTAYMQLSSLTSEDSAVYYCAT (SEQ ID NO:320) describes MIN-14 heavy chain variable framework region 3 (FWR3) amino acid sequence.

KATLTVDKSSSTAYMQLSSLTSEDSAVYYCAT (SEQ ID NO:321) describes MIN-17-1 heavy chain variable framework region 3 (FWR3) amino acid sequence.

RLTVSKDTSNNQAFLNIITVETADTAIYYCAQ (SEQ ID NO:322) describes MIN-17-2 heavy chain variable framework region 3 (FWR3) amino acid sequence.

ATTITINGCDQLQPLLWSLANPRHVIATES (SEQ ID NO:323) describes MIN-29 heavy chain variable framework region 3 (FWR3) amino acid sequence.

RLSISKDNSKSQVFFKMNSLQANDTAIYYCAR (SEQ ID NO:324) describes MIN-34 heavy chain variable framework region 3 (FWR3) amino acid sequence.

RFTISRDNAKNTLYLQMSSLKSEDTAMYYCSR (SEQ ID NO:325) describes MIN-42 heavy chain variable framework region 3 (FWR3) amino acid sequence.

KATLTVDKSSTTAHIELRSLASEDSAVYYCAR (SEQ ID NO:326) describes MIN-45 heavy chain variable framework region 3 (FWR3) amino acid sequence.

DIVITQSTASLGVSLGQRATISCRASKSVST-SGYSYMHWYQQRPGQPPKLLIYLA SNLESGVPARFSGSGSGTDFTLNIHPVEEEDAATYYC QHSRELPFTFGGGTKLEIKRADAAPTV SIFPPSSEQLT-SGGASVVCFLNNFYPKDINVKWKIDGSERQNGVLN-SWTDQDSKDSTYSMSST LTLTKDEYERHNSYT-CEATHKTSTSPIVKSFNRNECSGGGSGGGSEGGGSEG GGSEGGGSEGG GSGGGSGEVQLEESGG-GLVKPGGSLKLSCAASGFTFSGYAMSWVRQTPEKR-LEWVATISSGG TYIYYPDSVKGRFTISRDNAKNT-LYLQMSSLRSEDTAMYYCARLGGDNYYEYFDVWGA GTT VTVSSAKTTPPSVY-PLAPGSAAQTNSMVTLGCLVKGYF-PEPVTVTWNSGSLSSGVHTFPAVLQ SDLYTLSSSVTVPSSTWPSETVTCNVAHPASRTA (SEQ ID NO:327) describes MIN-C2 single chain Fab (light chain-linker-heavy chain; VL+CL+linker+VH+CH1) amino acid sequence.

METDTLLLWVLLLWVPGSTGD (SEQ ID NO:328) describes Ig kappa-chain leader sequence.

EQKLISEEDL (SEQ ID NO:329) describes Myc tag.

NYGMN (SEQ ID NO:330) describes VH-CS-CDR1.1: CDR1 Consensus sequence for variable heavy chain for IgG anti-MUC1* antibodies.

GYAMS (SEQ ID NO:331) describes VH-CS-CDR1.2: CDR1 Consensus sequence for variable heavy chain for IgG anti-MUC1* antibodies.

R/GYA/GMS (SEQ ID NO:332) describes VH-CS-CDR1.3: CDR1 Consensus sequence for variable heavy chain for IgG anti-MUC1* antibodies.

WINTYTGEPTYA/VG/DDFKG (SEQ ID NO:333) describes VH-CS-CDR2.1: CDR2 Consensus sequence for variable heavy chain for IgG anti-MUC1* antibodies.

TISSGGTYIYYPDSVKG (SEQ ID NO:334) describes VH-CS-CDR2.2: CDR2 Consensus sequence for variable heavy chain for IgG anti-MUC1* antibodies.

S/TGT/DT/A--Y/FYA (SEQ ID NO:335) describes VH-CS-CDR3.1: CDR3 Consensus sequence for variable heavy chain for IgG anti-MUC1* antibodies.

TGTTAILNG (SEQ ID NO:336) describes VH-CS-CDR3.2: CDR3 Consensus sequence for variable heavy chain for IgG anti-MUC1* antibodies.

SGDGYWYYA (SEQ ID NO:337) describes VH-CS-CDR3.3: CDR3 Consensus sequence for variable heavy chain for IgG anti-MUC1* antibodies.

DNYG--YDYG/A (SEQ ID NO:338) describes VH-CS-CDR3.4: CDR3 Consensus sequence for variable heavy chain for IgG anti-MUC1* antibodies.

SASSSV/ISYM/IH/Y (SEQ ID NO:339) describes VL-CS-CDR1.1: CDR1 Consensus sequence for variable light chain for IgG anti-MUC1* antibodies.

RASKSVSTSGYSYMH (SEQ ID NO:340) describes VL-CS-CDR1.2: CDR1 Consensus sequence for variable light chain for IgG anti-MUC1* antibodies.

S/GTSNLAS (SEQ ID NO:341) describes VL-CS-CDR2.1: CDR2 Consensus sequence for variable light chain for IgG anti-MUC1* antibodies.

LASNLES (SEQ ID NO:342) describes VL-CS-CDR2.2: CDR2 Consensus sequence for variable light chain for IgG anti-MUC1* antibodies.

QQRSS/NYPS/FT (SEQ ID NO:343) describes VL-CS-CDR3.1: CDR3 Consensus sequence for variable light chain for IgG anti-MUC1* antibodies.

QHSRELPFT (SEQ ID NO:344) describes VL-CS-CDR3.2: CDR3 Consensus sequence for variable light chain for IgG anti-MUC1* antibodies.

DIQMTQSPSSLSASVGDRVTITC (SEQ ID NO:345) describes Framework Region 1 Human IgG1 Light Chain Amino Acid SEQ.

5' gat atc cag atg acc cag tcc ccg agc tcc ctg tcc gcc tct gtg ggc gat agg gtc acc atc acc tgc cgt gcc 3' (SEQ ID NO:346) describes Framework Region 1 Human IgG1 Light Chain DNA SEQ.

WYQQKPGKAPKLLIY (SEQ ID NO:347) describes Framework Region 2 Human IgG1 Light Chain Amino Acid SEQ.

5' tgg tat caa cag aaa cca gga aaa get ccg aaa eta ctg att tac 3' (SEQ ID NO:348) describes Framework Region 2 Human IgG1 Light Chain DNA SEQ.

GVPSRFSGSRSGTDFTLTISSLQPEDFATYYC (SEQ ID NO:349) describes Framework Region 3 Human IgG1 Light Chain Amino Acid SEQ.

5' gga gtc cct tct cgc ttc tct gga tcc aga tct ggg acg gat ttc act ctg acc atc agc agt ctg cag ccg gaa gac ttc gca atc tat tac 3' (SEQ ID NO:350) describes Framework Region 3 Human IgG1 Light Chain DNA SEQ.

FGQGTKVEIK (SEQ ID NO:351) describes Framework Region 4 Human IgG1 Light Chain Amino Acid SEQ.

5' ttc gga cag ggt acc aag gtg gag atc aaa 3' (SEQ ID NO:352) describes Framework Region 4 Human IgG1 Light Chain DNA SEQ.

EVQLVESGGGLVQPGGSLRLSCAAS (SEQ ID NO:353) describes Framework Region 1 Human IgG1 Heavy Chain Amino Acid SEQ.

5' gag gtt cag ctg gtg gag tct ggc ggt ggc ctg gtg cag cca ggg ggc tca ctc cgt ttg tcc tgt gca gct tct 3' (SEQ ID NO:354) describes Framework Region 1 Human IgG1 Heavy Chain DNA SEQ.

WVRQAPGKGLEWVA (SEQ ID NO:355) describes Framework Region 2 Human IgG1 Heavy Chain Amino Acid SEQ.

5' tgg gtg cgt cag gcc ccg ggt aag ggc ctg gaa tgg gtt gca 3' (SEQ ID NO:356) describes Framework Region 2 Human IgG1 Heavy Chain DNA SEQ.

RFTISADTSKNTAYLQMNSLRAEDTAVYYCSR (SEQ ID NO:357) describes Framework Region 3 Human IgG1 Heavy Chain Amino Acid SEQ.

5' cgt ttc act ata agc gca gac aca tcc aaa aac aca gcc tac ctg cag atg aac agc ctg cgt gct gag gac act gcc gtc tat tat tgt tct aga 3' (SEQ ID NO:358) describes Framework Region 3 Human IgG1 Heavy Chain DNA SEQ.

WGQGTLVTVSS (SEQ ID NO:359) describes Framework Region 4 Human IgG1 Heavy Chain Amino Acid SEQ.

5' tgg ggt caa gga acc ctg gtc acc gtc tcc tcg 3' (SEQ ID NO:360) describes Framework Region 4 Human IgG1 Heavy DNA SEQ.

SGGGSGGGSEGGGSEGGGSEGGGSEGGGSGGGSG (SEQ ID NO:361) describes Linker sequence amino acid.

EVQLVESGGGLVKPGGSLRLSCA ASGFTFS (SEQ ID NO:362) describes IGHV3 (name from Igblast): FWR1: Human IgG antibody framework region sequence with 84.7% homology (249/294) to variable heavy chain region of MIN-C2.

WVRQAPGKGLEWVS (SEQ ID NO:363) describes IGHV3 (name from Igblast): FWR2: Human IgG antibody framework region sequence with 84.7% homology (249/294) to variable heavy chain region of MIN-C2.

RFTISRDNAKNSLYLQMNSLRAEDTAV (SEQ ID NO:364) describes IGHV3 (name from Igblast): FWR3: Human IgG antibody framework region sequence with 84.7% homology (249/294) to variable heavy chain region of MIN-C2.

DIVLTQSPASLAVSPGQRATITC (SEQ ID NO:365) describes IGkV7 (name from Igblast): FWR1: Human IgG antibody framework region sequence with 76.4% homology (226/296) to variable light chain region of MIN-C2.

WYQQKPGQPPKLLIY (SEQ ID NO:366) describes IGkV7 (name from Igblast): FWR2: Human IgG antibody framework region sequence with 76.4% homology (226/296) to variable light chain region of MIN-C2.

GVPARFSGSGSGTDFTLTINPVEANDTANYY (SEQ ID NO:367) describes IGkV7 (name from Igblast): FWR 3: Human IgG antibody framework region sequence with 76.4% homology (226/296) to variable light chain region of MIN-C2.

EVQLVESGGGLVKPGGSLRLSCAASGFTFS (SEQ ID NO:368) describes IGHV3 (name from Igblast): FWR1: Human IgG antibody framework region sequence with 84.1% homology (249/296) to variable heavy chain region of MIN-E6.

WVRQAPGKGLEWVS (SEQ ID NO:369) describes IGHV3 (name from Igblast): FWR2: Human IgG antibody framework region sequence with 84.1% homology (249/296) to variable heavy chain region of MIN-E6.

RFTISRDNAKNSLYLQMNSLRAEDTAVYYCAR (SEQ ID NO:370) describes IGHV3 (name from Igblast): FWR3: Human IgG antibody framework region sequence with 84.1% homology (249/296) to variable heavy chain region of MIN-E6.

EIVMTQSPATLSVSPGERATLSC (SEQ ID NO:371) describes IGkV3 (name from Igblast): FWR1: Human IgG antibody framework region sequence with 69.5% homology (187/269) to variable light chain region of MIN-E6.

WFQQRPGTSPK LLIY (SEQ ID NO:372) describes IGkV3 (name from Igblast): FWR2: Human IgG antibody framework region sequence with 69.5% homology (187/269) to variable light chain region of MIN-E6.

GIPARFSGSGSGTEFTLTISSLQSEDFAVYYC (SEQ ID NO:373) describes IGkV3 (name from Igblast): FWR3: Human IgG antibody framework region sequence with 69.5% homology (187/269) to variable light chain region of MIN-E6.

Monoclonal Antibody

Cloning monoclonal antibodies is useful for a variety of reasons. Hybridoma cells that produce a single antibody provide a method for generating large numbers of antibodies that are identical and exert identical effect. This is useful for antibody destined for therapeutic uses. Determining the sequences of monoclonal antibodies, especially of the variable regions of the light and heavy chains are particularly useful because they enable many forms of protein engineering that will allow, for example, the generation of antibody variants like single chain antibodies (e.g. scFv) or recombinant monovalent antibodies (e.g. Fabs). Determining the sequence of monoclonals, and in particular of the variable regions, importantly enables the generation of "humanized" or partially humanized (chimeric) antibodies that are sometimes preferred for human therapies because they are better able to avoid the host immune system by appearing human.

There are many methods for generating monoclonal antibodies and for generating antibody variants that are disclosed here, e.g. single chain antibodies, bispecific antibody, recombinant Fabs, humanized and particularly humanized antibodies and the like. Methods described here are meant to be exemplary and the invention is directed to monoclonal antibodies and derivations of those antibodies generated by other methods will have the same effects as those produced by the methods described herein.

Monoclonal anti-MUC1* antibodies were produced and screened as described below. Mice were immunized with synthetic peptides corresponding to the extracellular domain of MUC1* (GTINVHDVETQFNQYKTEAAS-RYNLTISDVSVSDVPFPFSAQSGA (SEQ ID NO:1)) or a peptide variant containing a single amino acid substitution (GTINVHDVETQFNQYK-TEAASPYNLTISDVSVSDVPFPFSAQSGA (SEQ ID NO:2)). Hybridomas were generated, according to standard practice in the field. Individual hybridomas that produced anti-MUC1* antibodies were identified by virtue of their ability to bind to MUC1* peptide in an ELISA assay. Supernatants from hybridomas, identified in the previous selection round, were then added to MUC1*-positive as well as MUC1-negative cells and FACS was used to identify those hybridomas that secreted antibodies capable of recognizing MUC1* on live cells. Larger quantities of the identified MUC1* cognate antibodies were then obtained by either injecting mice with the hybridomas (ascites) or produced by large scale culture according to standard methods. The resultant antibodies were assayed as previously described. In addition, antibody clones were tested for their ability to stimulate the growth of MUC1*-positive cells by binding to and dimerizing the extracellular domain of MUC1*. Antibodies that effectively stimulated the growth of MUC1*-positive cells (pluripotent stem cells, cancer cells and transfected cells) were then biochemically cleaved to generate monovalent antibodies which should block MUC1* dimerization and thus inhibit the growth of MUC1* expressing cells. In some instances, antibodies were papain digested to generate monovalent Fabs, which were assayed for their ability to inhibit the growth of MUC1*-positive cells. In some cases, the Fab was PEGylated according to published methods and it was observed that pegylation increased the stability of the antibody fragments. The sequences of the heavy and light chains of the selected antibodies were obtained by standard methods and various constructs for making bivalent and monovalent MUC1* antibodies and antibody derivatives were made.

Single chain constructs that contain the variable regions of both heavy and light chain connected by a linker are monovalent and therefore are useful for the inhibition of MUC1*-mediated cell growth. Portions of the constant regions may also be incorporated to facilitate the recruitment of complement (ADCC) and methods for engineering such constructs are known to those skilled in the art. To discourage dimerization of the constant regions, which would result in a bivalent antibody derivative, mutations such as Cyteine replacements and the like could be incorporated. Pegylation is a commonly used method for extending the half-life of monovalent antibody fragments and was used to increase the stability of the Fabs and single chain antibodies described herein.

The anti-MUC1* antibodies of the invention may be single-chain variable fragment antibodies (scFv). Recombinant approaches have led to the development of single chain variable fragment antibody (scFv). A monomeric scFv has a molecular mass of only about 30 kDa, which is expressed in a variety of systems as a single VL-VH pair linked by a Gly/Ser-rich synthetic linker (Berezov A. et al., 2001, J Med Chem 44:2565). When expressed in bacteria or eukaryotic cells, the scFv folds into a conformation similar to the corresponding region of the parental antibody. It was shown to retain comparable affinity to that of a Fab (Kortt et al., 1994, Eur J Biochem 221:151). ScFvs are amenable to various genetic modifications such as humanization and the production of fusion proteins to enhance their potential as therapeutic agents.

Phage display method may be used to produce anti-MUC1* scFv. In this method, large repertoires of antibody variable region cDNAs are collected from the B cells and combinations of VHs and VLs are expressed in the form of scFvs on the surface of filamentous bacteriophage. The phages that express scFvs are to be panned from antigen-coated plates. The affinity of the anti-MUC1* scFv may be improved by mutating the CDRs of the construct and then repeating the panning procedure.

The anti-MUC1* antibodies of the invention may be Fab, Fab2 bispecific antibodies, Fab3 trispecific antibodies, bivalent minibody, trivalent triabody, or tetravalent tetrabodies.

One of the uses of a monovalent anti-MUC1* antibody is for the treatment of cancer cells that often overexpress MUC1*. To avoid the inhibition of non-cancerous cells that also present MUC1*, bispecific antibody may be made wherein one portion of the hybrid antibody binds to and blocks MUC1* while the other binds to another tumor-specific, or similar, antigen. For example, one portion would recognize MUC1*, while the other would bind to HER2, CEA, transferrin, EGFR, TF (tissue factor), DLLs (delta-like ligand), DLL-4, jagged, notch receptor ligands, portions of the notch receptor, and the like. The increased avidity of cooperative binding over monomeric binding would preferentially retain the antibodies on the targeted tumor cells.

The anti-MUC1* antibodies of the invention may be bispecific antibodies. Bispecific antibodies are monoclonal antibodies, preferably human or humanized antibodies that have dual-targeting specificities. Bispecific antibodies are derived from the recombination of variable domains of two antibodies with different specificities; bispecific antibodies are thus capable of binding both antigens of their parental antibodies. In the case of anti-MUC1*, one of the binding specificities could be for MUC1* and the other may be for another protein, or any other cell surface protein, for example. These bispecific anti-MUC1* antibodies may function as antagonistic or agonistic antibodies.

Methods for making bispecific antibodies are well known (Traunecker et al., EMBO J, 1991, 10:3655; WO 93/08829; Suresh et al., Methods in Enzymology, 1986, 121:210; Milstein and Cuello, 1983, Nature, 305:537). Briefly, antibody variable domains with the desired binding specificities are fused to immunoglobulin constant domain. This fusion contains an immunoglobulin heavy-chain constant domain (part of the hinge, CH2 and CH3 regions) and preferably contains the first heavy chain constant region (CH1). DNAs encoding the immunoglobulin heavy chain fusions and the immunoglobulin light chain are inserted into separate expression vectors and are cotransfected.

In the case of MUC1*, a bispecific antibody would act as a cell growth inhibitor by blocking dimerization of the MUC1* ligand binding site. If one variable region recognized MUC1* and the other recognized another tumor-specific antigen, then unwanted side effects of inhibiting MUC1*-mediated growth would be avoided. The bispecific antibody would preferentially bind to tumor cells which displayed both antigens. Such an approach has been successful with a HER2-HER3 bispecific antibody that has an enhanced specificity and anti-tumor effect (Robinson, et al. 2008), as well as an EGFR-IGFR bispecific antibody that blocks signaling from both receptors (Lu, et al. 2004). Also, the second "arm" of the bispecific antibody can target, recruit and engage cells of the immune system, such as CD3 to recruit T cells (Baeuerle and Reinhardt, 2009, Bortoletto, et al 2002), or CD16, to recruit Neutrophils, Natural Killer cells, or other monocytes (Bruenke, et al. 2005, McCall, et al. 1999). Both arms of a therapeutic antibody can be cloned in tandem as a single chain in multiple formats, such as tandem scFv molecules and the similar tandem diabodies (Chames and Baty 2009, Holliger P, 1993). Fab fragments from different antibodies can also be chemically conjugated to form bispecific Fabs (Chames and Baty 2009).

Conversely, there are many instances in which it is desirable to enhance the growth of MUC1*-positive cells. For example, pluripotent stem cells and some progenitor cells express MUC1*. Bivalent MUC1*-antibodies dimerize the MUC1* receptor on the primitive cells and enhance cell growth while maintaining the cells in a pluripotent state. Bivalent anti-MUC1* antibodies may be added exogenously or genetically added to the cells. For example, the gene that encodes a bivalent anti-MUC1* antibodies is added to primitive cells, even at times before egg and sperm fusion is complete. In this way, the resultant stem cell and its progeny will produce and secrete the ligand that stimulates its unlimited proliferation. Alternatively, a plasmid encoding the antibody is transfected into primitive cells to maintain their pluripotency by activating the MUC1* receptor or rescue stem cells that have entered the differentiation process.

Similarly, pluripotency is induced in cells by the introduction of a gene encoding MUC1*, which may be introduced alone or in combination with other genes, including those that enhance signaling through MUC1* such as genes that encode MUC1 cleavage enzymes like MMP-14 and TACE, or genes that encode NM23, the natural ligand of MUC1*.

Bivalent MUC1* antibodies and antibody derivatives are administered to patients suffering from the effects of chemotherapy and other conditions in which it is desirable to enhance proliferation of hematopoietic stem cells and precursor cells. In these instances, the patient may be administered systemically or via local injection. Various forms of stem cell transplant therapy would benefit from in situ injection of MUC1*-stimulating antibodies to establish the vitality of the transplanted cell population before the onset of differentiation.

In yet another aspect of the invention, there are many instances in which it is desirable to command the anti-apoptotic properties of MUC1* expression and growth stimulating signaling. One such example is in cases is sepsis when agents that support cell survival would stave off the disastrous effects of the condition. Transient, systemic treatment with a bivalent MUC1* antibody or antibody derivative would enhance cell survival and in doing so control the life-threatening symptoms until suitable antibiotics or other curative treatments could be administered or have time to take effect. Similarly, virulent strains of bacteria ravage areas of flesh and induce massive cell death through toxic effects. Here also, administering MUC1*-stimulating antibodies would render the cells more resistant to cell death and provide caretakers with more time to control the infection. Thus the MUC1*-stimulating antibody may be administered locally or systemically.

Other situations lend themselves to MUC1*-mediated growth stimulation. For example, animals that spontaneously produce tumors or produce tumors that grow faster could be generated via methods for making transgenic animals and in these cases, the animals would be generated such that their cells would make and secrete the MUC1* stimulating antibody. The gene for the MUC1*-stimulating antibody in this case, is positioned downstream of a tissue-specific promoter. For example, to generate a mouse that spontaneously produced breast tumors the gene for the MUC1* antibody ligand would be placed downstream of a promoter for a mammary specific protein. The gene for the MUC1* antibody that is inserted downstream of a tissue specific promoter is injected into a pronucleus or similar just prior to the complete fusion of egg and sperm to generate a transgenic animal, e.g. a mouse model, that spontaneously forms tumors or enhances tumor formation. The antibody gene may be injected separately or in combination with other genes that enhance MUC1* cleavage, or signaling, including but not limited to MMP-14, TACE, NM23 and the like.

In another aspect, a plasmid encoding a MUC1* antibody is added exogenously or transfected into an antibody-producing hybridoma in order to increase antibody production by increasing cell growth rate and rendering the cells resistant to cell death through the stimulation of MUC1*. In this aspect of the invention, the growth of antibody-producing cells is enhanced without contaminating the product which is the desired antibody. Antibody-producing cells are typically grown in media that contains reduced serum because the serum component contains many antibodies itself. Reducing the amount of serum in the cell culture media minimizes the carry over contamination but also reduces cell growth and overall yield of the desired antibody. The addition of exogenous anti-MUC1* or the transfection of the plasmid that codes for the anti-MUC1* increases cell growth and survival, while the single, known antibody can be selectively purified away from the product which is the desired antibody.

Having the sequence of a monoclonal antibody also allows one to make fusion proteins wherein one part is derived from the antibody and the other part may be derived from another protein, such as a toxin, a cytokine, like IL-2 and others, or a protein, like GFP (green fluorescent protein) that can act as a label. Antibodies and antibody variants of the invention can be biochemically fused to, or genetically engineered to be fused to labels, tags, toxins, radioactive substances, targeting motifs, leader sequence peptides, toxic materials, proteins or peptides. Similarly, unnatural amino acids can be incorporated into a recombinant antibody or antibody derivative wherein the unnatural amino acid may facilitate coupling, may have a signaling capability, may render the recombinant protein protease sensitive or insensitive, and the like.

The invention also provides for humanization or partial humanization of some or all of the anti-MUC1* antibodies and antibody variants described here. Cloning monoclonal antibodies and determining their sequences, especially of the variable regions of the light and heavy chains, enables the generation of a humanized and partially humanized (chimeric) antibodies. As is known in the art, humanized and chimeric antibodies are characterized by fewer side effects and higher efficacy because humanized antibodies are better able to evade detection by the human immune system (Lonberg 2005).

As those skilled in the art are familiar, a common method for generating a humanized antibody involves exchanging non-human sequences in non-recognition areas such as the framework regions (FWRs), for human sequences as described in Muzard, et al. 2009. Similarly, the recognition regions like the complementarity determining regions (CDRs) of a non-human monoclonal antibody are exchanged for the CDRs of a human antibody (Carter P, et al. Humanization of an anti-p185.sup.HER2 antibody for human cancer therapy Proc. Natl Acad. Sci 89:4285-4289).

Human framework regions such as those listed in SEQ ID NOS:345-360 are human framework regions that could be exchanged for the mouse FWRs in the monoclonal sequences disclosed here. Searches of the data bases for human antibody sequences are also used to identify human antibodies that are homologous to a desirable monoclonal antibody from a non-human source. For example, the amino acid sequences of SEQ ID NOS:362-367 are framework regions (FWRs) from a human antibody that is highly homologous to MIN-C2. These sequences or the sequences can be used in conjunction with the CDRs of MIN-C2 (SEQ ID NOS:331, 334, 374, 340, 342, and 344).

In another example, the amino acid sequences shown as SEQ ID NOS:368-373 are framework regions (FWRs) from a human antibody that is highly homologous to MIN-E6. These sequences can be used in conjunction with the CDRs of MIN-E6 (SEQ ID NOS:332, 334, 338, 339, 341, and 343). The nucleic acids that encode these amino acid sequences may be used to genetically engineer such chimeric, partially humanized antibodies and antibody variants.

To replace the murine framework regions with the chosen human framework regions for making a chimeric antibody construct, a combination of synthetic DNA, and DNA generated by overlap PCR is used. For constructing humanized MIN-C2, human framework region nucleotide sequences that encode amino acid sequences of SEQ ID NOS:362, 363 and 364 are used to replace the murine heavy chain framework regions bearing the SEQ ID NOS:159, 185 and 211 respectively. Further, nucleotide sequences that encode amino acid sequences of SEQ ID NOS:365, 366 and 367 are used for replacing the MIN-C2 light chain framework regions bearing the SEQ ID NOS:98, 119 and 139 respectively. For constructing humanized MIN-E6, human framework region nucleotide sequences that encode amino acid sequences of SEQ ID NOS:368, 369 and 370 are used to replace the heavy chain framework regions bearing the SEQ ID NOS:160, 186 and 212 respectively. Further, nucleotide sequences that encode amino acid sequences of SEQ ID NOS:371, 372 and 373 are used for the replacing the MIN-E6 light chain framework regions bearing the SEQ ID NOS:99, 120 and 140 respectively. Constructs of many designs including but not limited to scFab, recombinant Fabs, bispecific recombinant antibodies and scFvs are generated using these methods.

The anti-MUC1* antibodies and antibody variants disclosed herein can be humanized in this way. Following the humanization process, antibody affinity can be improved by a number of methods including by using phage display methods. After humanizing antibodies and antibody variants, some will lose affinity and require processes of "affinity maturation". One method involves molecular evolution accomplished by mutagenesis followed by selection of those that show enhanced affinity for their cognate antigen (Razai, et al. 2005). Alternatively, humanized antibodies or antibody fragments can be isolated from recombinant libraries (Nahary and Benhar, 2009, Rothe C, et al.) Another method of obtaining fully humanized antibodies is to immunize transgenic mice engineered to produce human antibodies (Jakobovitz, et al. 2007, Lonberg, 2005). The present invention anticipates the use of some or all of these methods along with the sequences of the antibody regions (CDRs) that recognize MUC1* to generate antibodies that bind to the PSMGFR sequence (SEQ ID NO:1) for in vitro as well as in vivo and therapeutic uses.

Razai, et al report that after affinity maturation, also known as molecular evolution, 5 out of 60 total CDR residues were mutated, which corresponds to about an 8% rate of CDR mutagenesis. This means that that after affinity maturation about 92% of the CDR regions remain unchanged. Others have reported similar percent change after affinity maturation (Juirez-Gonzilez, et al 2005; and Finlay, et al (2009).

Production of any of the novel antibodies and antibody variants disclosed herein can be carried out in a wide variety of cells from different organisms, including but not limited to bacteria, such as *E. coli*, with bacterial vectors (Zheng, et al. 2009), yeast cells, such as *Pichia pastoris* with yeast vectors (Schoonooghe, et al. 2009), insect cells, such as S2 cells using insect vectors (Johannson, et al.), mammalian cells, such as Chinese hamster ovary cells (CHO), using mammalian vectors (Majors, et al. 2009) and the like. Vectors and cells available for antibody synthesis are numerous and well known to those skilled in the art.

In another embodiment, antibodies and antibody variants of the invention are produced by host animals. One can make transgenic animals that, for example, make a predetermined antibody and secreted it in their milk (Zhang, et al. 2009) or other bodily fluid. Other scenarios for manipulating methods of protein engineering to develop novel and useful antibodies and antibody derivatives are possible using the sequences of the monoclonal antibodies disclosed herein.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1—Generation of Anti-MUC1* Monoclonal Antibodies

Figure 2:
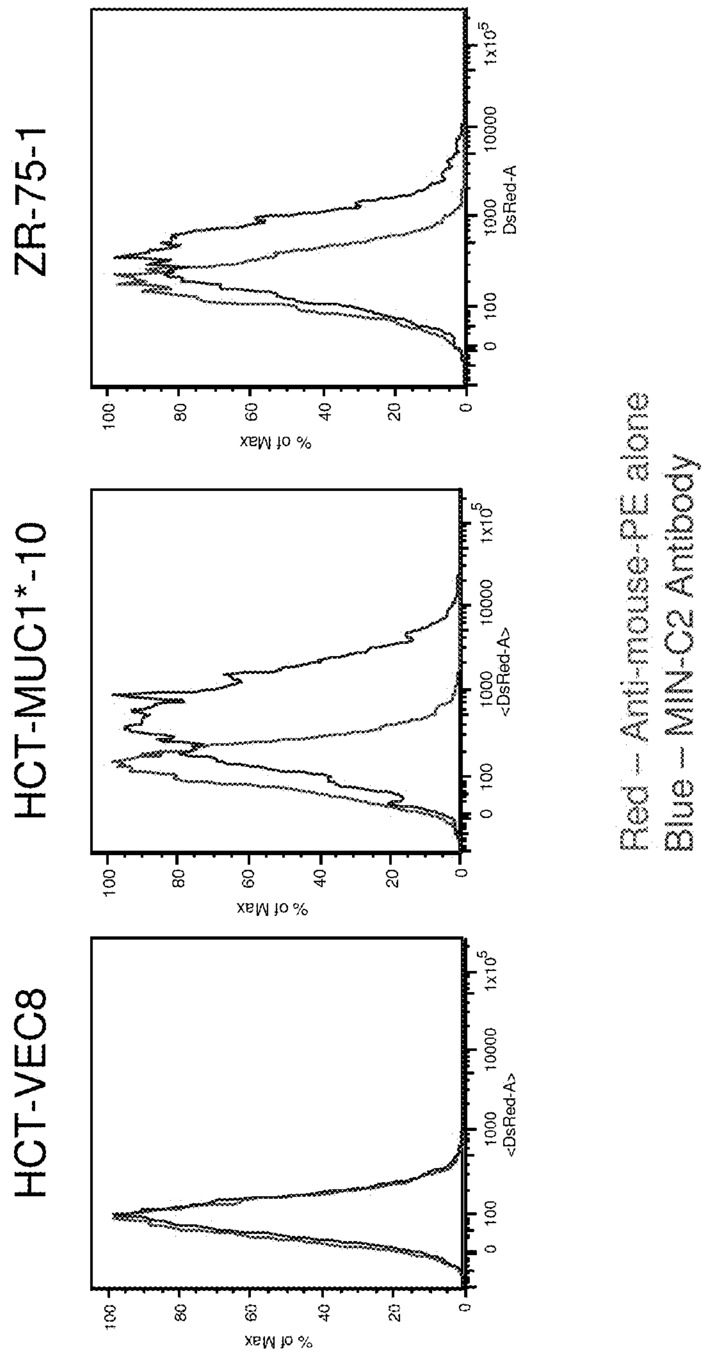
FIG. 2 shows specific binding of MIN-C2 antibody to MUC1* on cell surface: Purified antibody from the MIN-C2 hybridoma clone was diluted 1:100 then tested for binding to the surface of live cells. Fluorescence activated cell sorting (FACS) shows that MIN-C2 does not bind to MUC1-negative cells, HCT-116 cells transfected with either empty vector (HCT-VEC8), but does bind to HCT-116 cells that were transfected with MUC1* (HCT-MUC1*-10: extracellular domain consists only of GTINVHDVETQFNQYKTEAASRYNLTISDVSVSDVPFPFSAQSGA (SEQ ID NO:1). MIN-C2 similarly bound to MUC1-positive breast cancer cells ZR-75-1.
Figure 3:
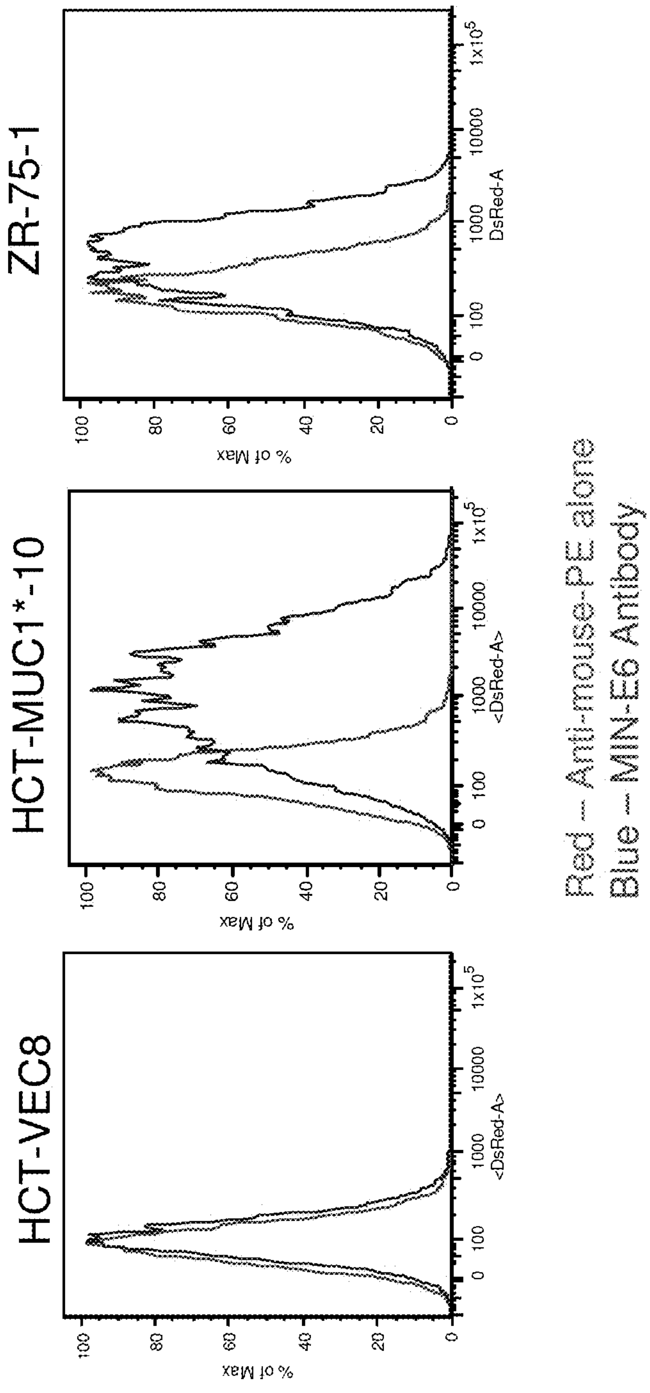
FIG. 3 shows specific binding of MIN-E6 antibody to MUC1* on cell surface: Supernatant from the MIN-E6 hybridoma clone was tested for binding to the surface of live cells. Fluorescence activated cell sorting (FACS) shows that MIN-E6 does not bind to MUC1-negative cells, HCT-116 cells transfected with either empty vector (HCT-VEC8), but does bind to HCT-116 cells that were transfected with MUC1* (HCT-MUC1*-10: extracellular domain consists only of GTINVHDVETQFNQYKTEAASRYNLTISDVSVSDVPFPFSAQSGA (SEQ ID NO:1). MIN-E6 similarly bound to MUC1-positive breast cancer cells ZR-75-1.

Monoclonal antibodies were generated to MUC1* peptide using standard hybridoma generation and subsequent screening, which is familiar to those skilled in the art. A MUC1* peptide (GTINVHDVETQFNQYKTEAASRYNLTISDVSVSDVPFPFSAQSGA, SEQ ID NO:1) or peptide variant bearing a single amino acid substitution (GTINVHDVETQFNQYKTEAASPYNLTISDVSVSDVPFPFSAQSGA, SEQ ID NO:2) was synthesized with an additional cysteine residue at the Carboxy-terminal end to allow conjugation to KLH. The conjugated peptide was used to immunize mice. Supernatants from wells containing fused cells were screened for recognition of the MUC1* peptide by ELISA. Out of these, several clones were selected based on their high titer for their ability to recognize MUC1* peptide in ELISA binding assay. Results of such binding of supernatants from six (6) hybridoma clones are shown in FIG. 1. Clones were then tested by FACS (fluorescence activated cell sorting) for their ability to bind to MUC1* on intact cells (FIGS. 2 and 3). The best of these were maintained as hybridomas and sequenced. Two clones, MIN-C2 and MIN-E6, were especially preferred on the basis of their binding to MUC1* on the cell surface of MUC1 expressing breast cancer cell line (ZR-75-1) and HCT-116 colon carcinoma cells transfected with MUC1* encoding plasmid (FIGS. 2 and 3). This process of hybridoma generation was repeated more than once, producing several monoclonal antibodies, IgG and IgM that selectively bind to the extracellular domain of MUC1*, also called the MGFR consisting essentially of the PSMGFR sequence, (GTINVHDVETQFNQYKTEAAS-RYNLTISDVSVSDVPFPFSAQSGA, SEQ ID NO:1). The sequences of variable regions of selected monoclonal anti-MUC1* antibodies are shown in FIGS. 11-14.

Example 2—Analysis of Binding of Anti-MUC1* Monoclonal Antibodies to MUC1* on the Cell Surface Recognition of MUC1* on the cell surface was analyzed by surface staining of the cells using FACS. For MIN-C2 antibody 50 μl of a 10 μg/ml solution of purified antibody was bound individually to MUC1-negative HCT116 cells transfected with empty vector (HCT116-VEC8), or transfected with MUC1* expressing vector (HCT-MUC1*-10) and MUC1 positive ZR-75-1 cells at 4 degrees Celsius for 30 minutes. Cells were washed twice, and treated with 10 μg/ml anti-mouse-PE at 4 degrees Celsius for 30 minutes. Cells were washed twice, fixed in 2% formaldehyde in PBS, and analyzed using a BD FACS Cantoll flow cytometer (FIG. 2). A similar procedure was followed for MIN-E6 antibody with the only difference that 50 1 of undiluted supernatant from MIN-E6 hybridoma was used in place of purified antibody (FIG. 3).

Figure 4:
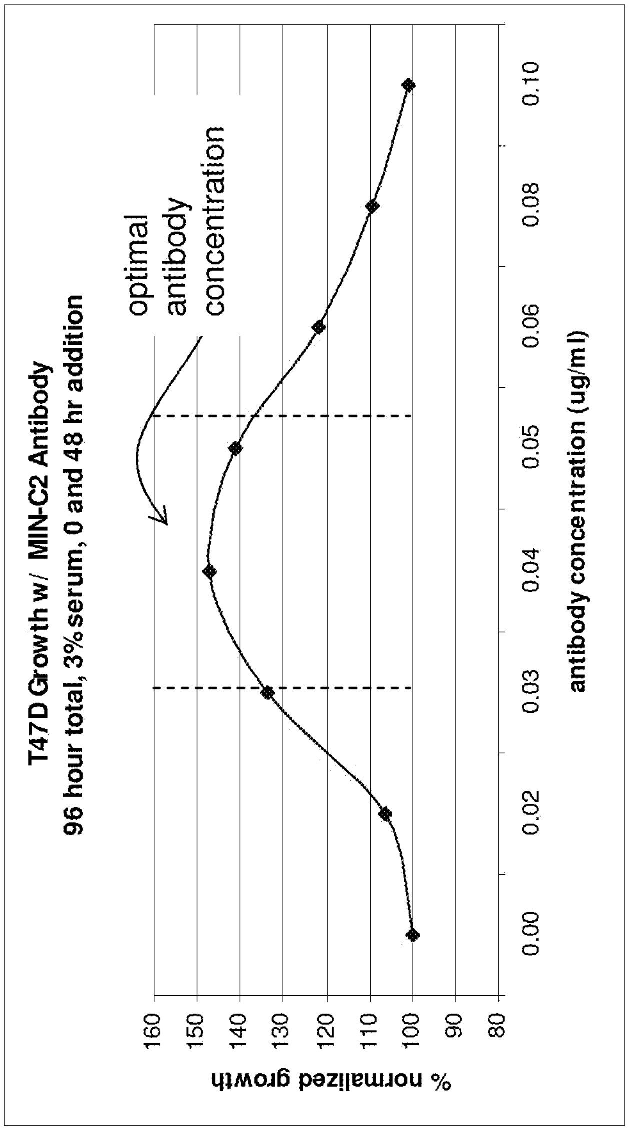
FIG. 4 shows stimulation of cell proliferation by MIN-C2 monoclonal antibody: In a cell-based assay, monoclonal antibody MIN-C2 was shown to function essentially the same as the polyclonal antibody that was generated with immunizing peptides of SEQ ID NO:1 or 2. The growth of MUC1-positive breast cancer cell line T47D was stimulated in a concentration dependent manner when purified MIN-C2 was added to cell cultures at the start of the assay, then again after 48 hours. The bell-shaped curve is characteristic of ligand-induced dimerization of the receptor; in excess, antibodies bind to each receptor rather than one antibody dimerizing each two receptors.
Figure 5:
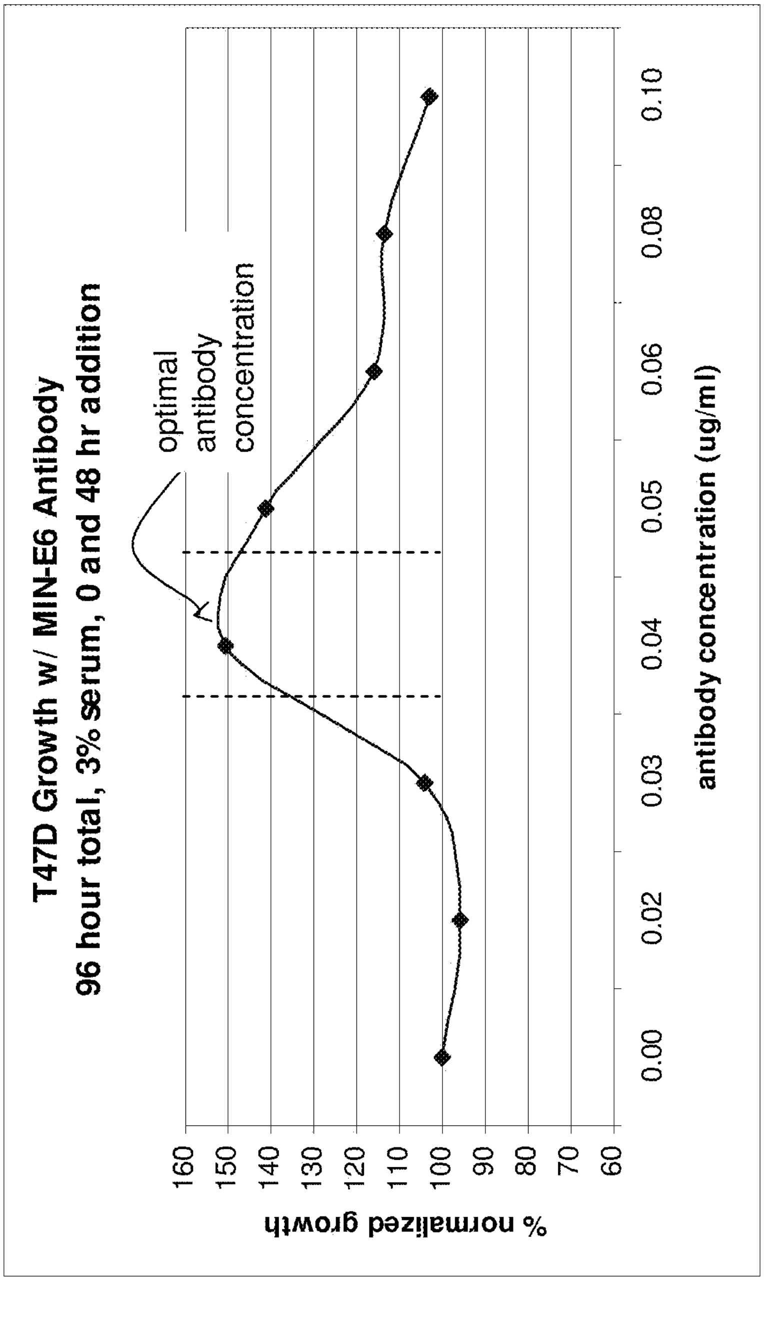
FIG. 5 shows stimulation of cell proliferation by MIN-E6 monoclonal antibody: In a cell-based assay, monoclonal anti-MUC1* antibody MIN-E6 was shown to function essentially the same as the polyclonal antibody that was generated with immunizing peptides of SEQ ID NO: 1 or 2. The growth of MUC1-positive breast cancer cell line T47D was stimulated in a concentration dependent manner when purified MIN-E6 was added to cell cultures at the start of the assay, then again after 48 hours. The bell-shaped curve is characteristic of ligand-induced dimerization of the receptor; in excess, antibodies bind to each receptor rather than one antibody dimerizing each two receptors.

Example 3—Anti-MUC1* Monoclonal Antibodies (Bivalent) MIN-C2 and MIN-E6 Induce Proliferation of MUC1 Expressing Breast Cancer Cell Line To measure the ability of anti-MUC1* monoclonal antibodies, MUC1 expressing breast cancer cell line T47D was used. 7,500 cells were plated per well of a 96 well plate in media containing 10% serum. The following day cells in three wells were trypsinized, resuspended in media and counted using a hemocytometer to obtain the zero day count. Media in the cells was changed to that containing 3% FBS and anti-MUC1* antibody was added in various concentrations. 48 hours later media was changed which was followed by a second addition of antibody. After another 48 hours the cells were counted and stimulation of cell growth estimated (FIGS. 4 and 5).

Example 4—Fab Fragment Generation and PEGylation

Figure 6:
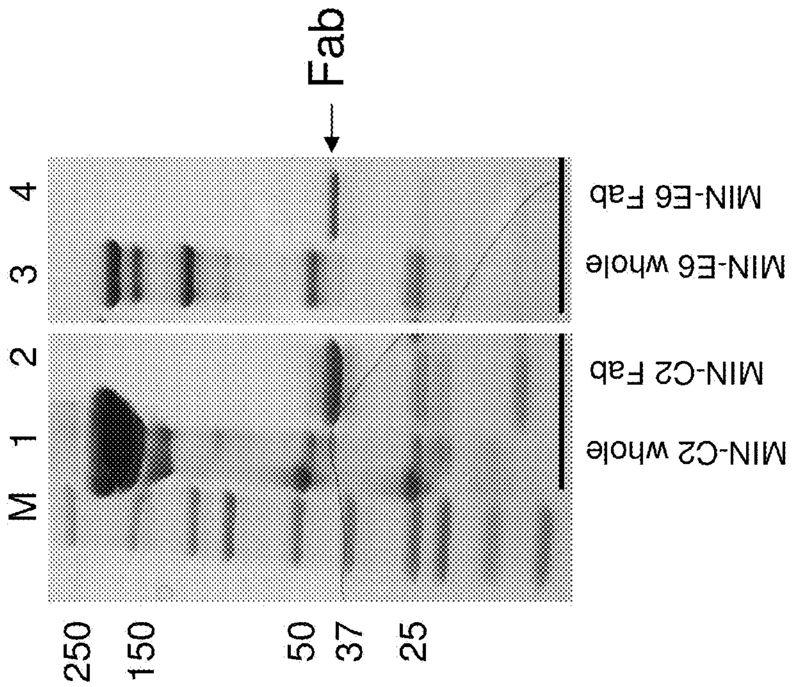
FIG. 6 shows preparation of Fab fragments from MINC-2 and MIN-E6 antibodies by Papain digestion. Digested antibody was run on 4-20% non-reducing SDS-PAGE. The digest generated the expected size (~50 kD) of Fab from both MIN-C2 and MIN-E6 (Lane 2 and 4).

To prepare a monovalent Fab fragment of MUC1* antibody, a papain digestion method was employed (Pierce). MIN-C2 and MIN-E6 antibody were effectively digested with papain and purified through Protein A-agarose affinity chromatography (FIG. 6).

Figure 7A:
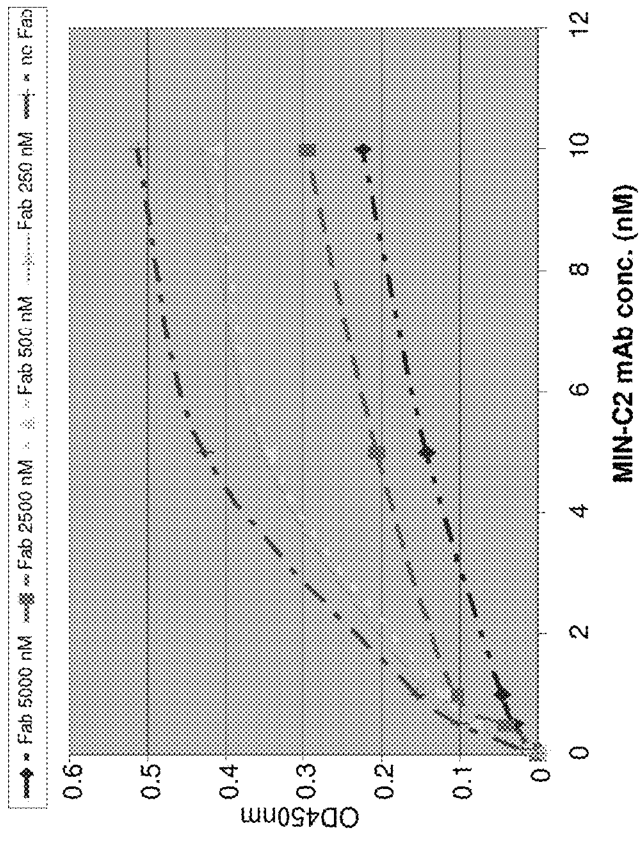
FIGS. 7A-7B show that Fab fragments of A. MIN-C2 and B. MIN-E6 monoclonal antibodies compete with the whole antibody for binding to the target peptide: In an ELISA competition assay, a synthetic peptide corresponding to the sequence of the extracellular domain of MUC1* (SEQ ID NO:1) was adsorbed onto the plate, then bound by the parent, intact monoclonal antibody. To test the ability of the Fab produced by papain digestion to compete with the parent antibody for binding to the MUC1* peptide, varying concentrations of the Fab were added. After wash steps, the ELISA was processed by standard methods. The graph shows that the Fab competes with the parent antibody for binding to the cognate peptide.
Figure 7B:
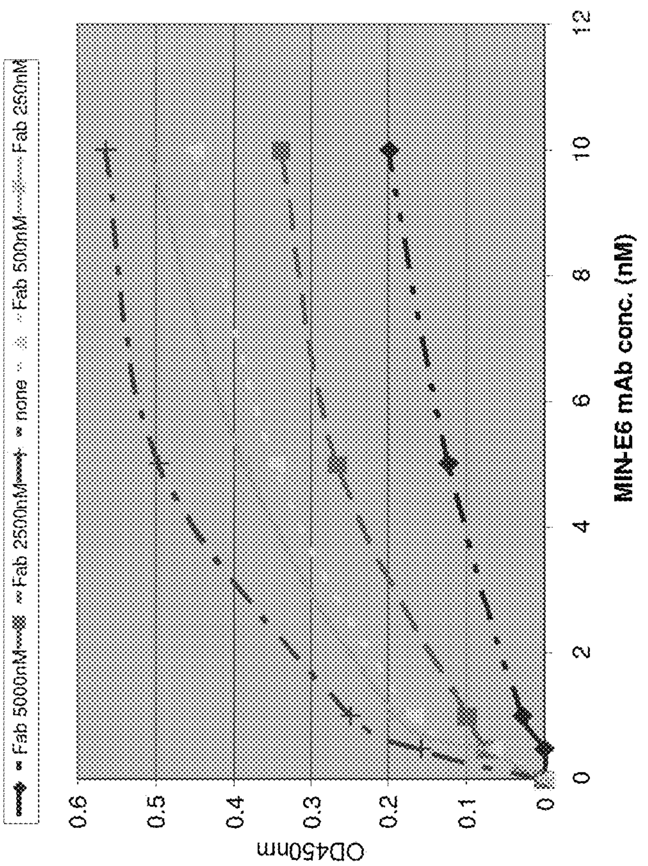

Those Fab fragments were tested along with their parental mAb in a competitive ELISA assay to confirm that the Fab fragment is capable of binding to its antigen, MUC1* peptide. As shown in FIG. 7, the Fab fragments that were generated effectively competed with their parental mAb. The Fabs were also PEGylated with TMS (PEG) reagents per the manufacturer's protocols (Pierce). Pegylated Fabs worked comparable to the un-PEGylated Fab in cell-based growth inhibition assays.

Example 5—Testing for the Effect of the Monovalent MIN-C2 and MIN-E6 Fab Fragments for Inhibition of Proliferation of Cells Overexpressing MUC1*

Figure 8:
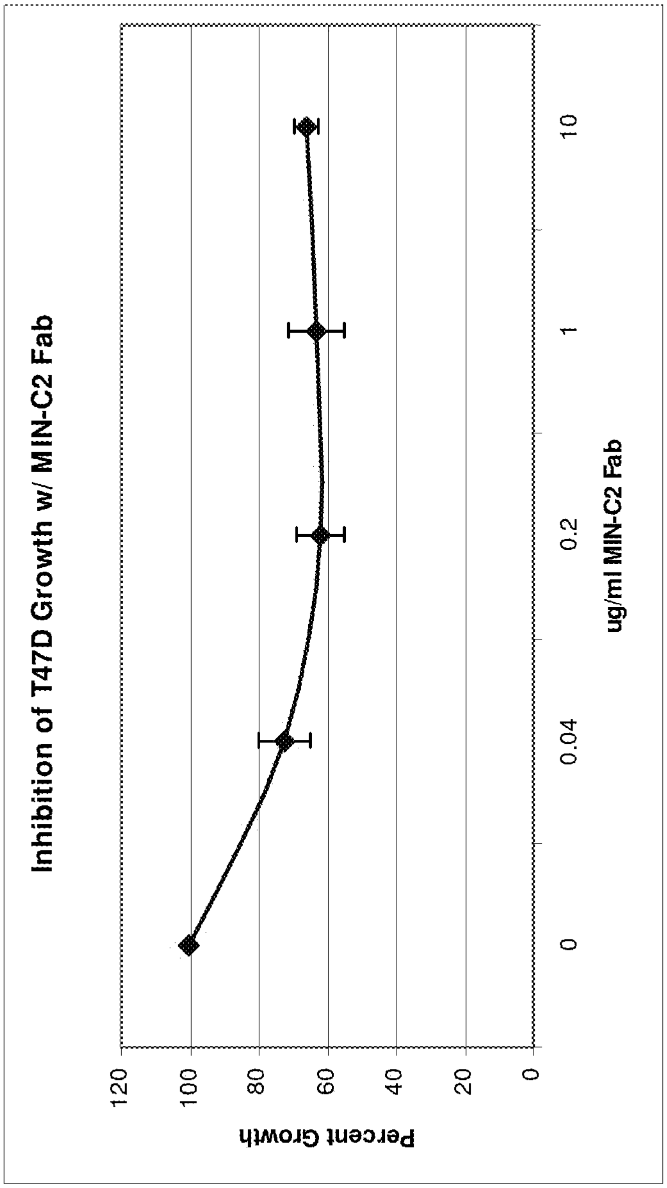
FIG. 8 shows inhibition of MUC1-positive cancer cell proliferation by MIN-C2 Fab: The ability of the monovalent form of MIN-C2, i.e. MIN-C2 Fab, to inhibit the proliferation of MUC1 positive breast cancer cell line T47D was tested. The experiment was done over a period of 96 hours with cells grown at 3% serum containing media; the Fab was added at the start of the experiment and again after 48 hours. Cells were counted on a hemocytometer.
Figure 9:
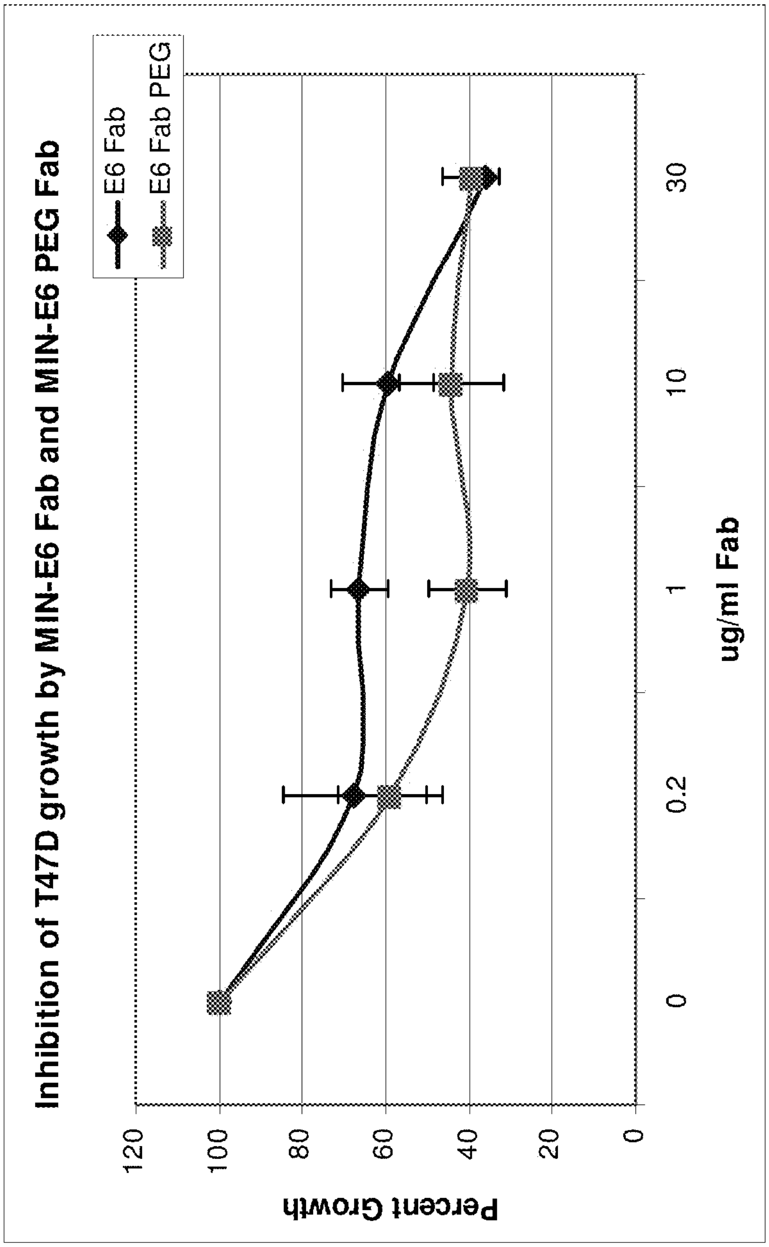
FIG. 9 shows inhibition of MUC1-positive cancer cell proliferation by MIN-E6 Fab: The ability of the monovalent form of MIN-E6, i.e. MIN-E6 Fab, to inhibit the proliferation of MUC1 positive breast cancer cell line T47D was tested. The experiment was done over a period of 96 hours with cells grown at 3% serum containing media; the Fab was added at the start of the experiment and again after 48 hours. Cells were counted on a hemocytometer. PEGylated (MIN-E6 PEG) as well as non-PEGylated forms of the Fab were tested. MIN-E6 PEG showed increase activity presumably due to increased half-life.

MUC1* expressing breast cancer cell line T47D was plated in 96 well plates (5,000 cells/well) in complete media (RPMI containing 10% FBS) and allowed to attach overnight. Next day the media was changed to that containing 3% FBS. Cells in three wells were counted following trypsinization and resuspension using hemocytometer to obtain the zero day count. Next, MIN-C2 or MIN-E6 Fab protein was added in various concentrations to individual plates. After 48 hours the media was replaced and the Fab protein was added for a second time. After a further 48 hours the cells in all the wells were counted. Inhibition of cell growth was calculated relative to the growth of cells containing no Fab protein. In the case of MIN-E6 a PEGylated form of the protein was also tested (FIG. 8, FIG. 9) and shown to function comparably to the un-PEGylated Fab.

Figure 17:
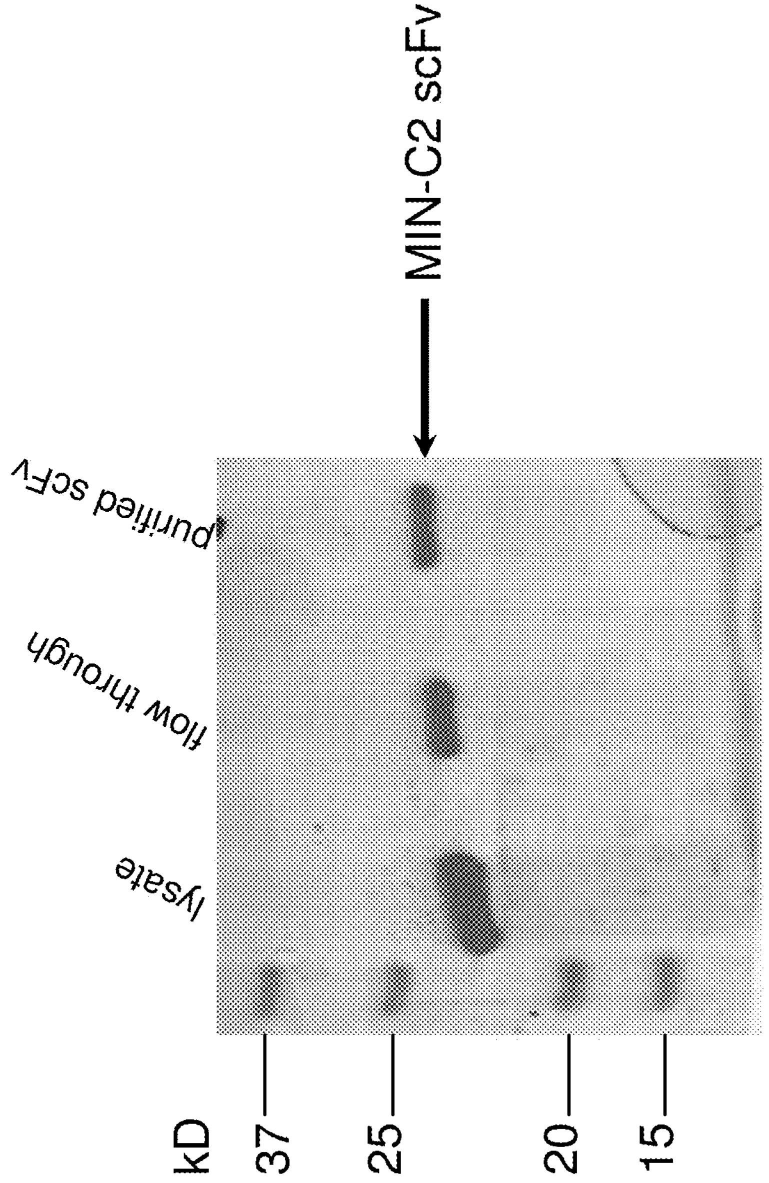
FIG. 17 shows an SDS-PAGE gel confirming purification of MIN-C2 scFv expressed in bacteria then purified by NTA-Ni++ affinity chromatography.

Example 6—Construction and Expression of MUC1* Binding Polypeptides as Single Chain Fv Fragments Using Polypeptide Linker A scFv fragment of MIN-C2 (a monoclonal antibody that recognizes a 45 amino acid membrane proximal extracellular region of MUC1 from amino acid 1110 to 1155: PSMGFR) was designed, constructed and expressed in *E. coli*. The construct was designed without any secretion signal using the vector pET21b (Novagen) that results in a protein with a carboxy-terminal tag containing six histidine residues. The design of the construct of MIN-C2 and MIN-E6 scFv are shown in FIG. 10 A and FIGS. 15 and 16. The carboxy-terminal histidine tag allows purification of the scFv protein via Ni-NTA affinity chromatography (FIG. 17).

To sequence the monoclonal antibodies, hybridoma cells producing a monoclonal antibody were grown in RPMI media containing G418 as suggested. Then, total RNA was prepared using Trizol reagent and its first strand cDNA was generated using SuperScript III first strand cDNA synthesis kit (Invitrogen, CA). To clone the variable region of heavy and light chains, degenerate primers were used according to the literature (Wang et al., 2000). For heavy chain cloning, PCR was set up using SEQ ID NOS:3-5 (reverse) with SEQ ID NO:6 or SEQ ID NO:7 (forward). For kappa chain, SEQ ID NO:8 (reverse) with SEQ ID NO:9 (forward) were used. All forward and reverse PCR primers contain EcoRI and HindIII restriction site for heavy and SacI and SalII sites for kappa chains for downstream cloning purpose. The PCR condition is as follows: 94° C. for 1 min, 45° C. for 1 min, 72° C. for 2 min with 30 cycles, and 72° C. for 10 min. Then, the PCR products were run on 1% agarose gels and a prominent PCR band ~500 bp in size for heavy and light chains were detected.

The products were purified from the agarose gel and restriction digested with corresponding enzymes and then cloned into pET21b bacterial expression vector for sequencing and simple bacterial expression to validate its full length expression.

Plasmid DNA was sequenced. DNA and amino acid sequences for the variable regions (CDRs: complementarity determining regions) for preferred monoclonal antibody MIN-C2 are given in SEQ ID NOS:10 and 11 for the variable heavy chain, VH, and SEQ ID NOS:12 and 13 for the variable light or kappa chains, VL. The DNA and amino acid sequences of the constant regions of both the heavy and light chains of MIN-C2 were also determined and are shown as SEQ ID NOS:49 and 50. Recombinant antibody fragments that have greater stability and binding affinity are generated by including these constant regions into the design. A recombinant Fab is comprised of the variable regions of the heavy (VH) and light (VL) chains plus the constant regions (CH1 and CL).

DNA and amino acid sequences for another preferred monoclonal antibody MIN-E6 were similarly determined and are given in SEQ ID NOS:19-22 for the heavy chain and SEQ ID NOS:23-24 for the light or kappa chain. The sequences of other monoclonal anti-MUC1* antibodies are shown in FIGS. 11-14. For instance, the amino acid sequences for the IgG heavy chain variable region is shown in SEQ ID NOS:59-68; and light chain variable region is shown in SEQ ID NOS:51-58. The amino acid sequences for the IgM heavy chain variable region is shown in SEQ ID NOS:76-81 and SEQ ID NO:84; and light chain variable region is shown in SEQ ID NOS:69-75.

To generate a single chain antibody fragment (scFv) comprised essentially of the variable regions of a monoclonal antibody, a linker sequence (SEQ ID NO:14) with 15 amino acids (Gly-Gly-Gly-Gly-Ser)3 was introduced in between heavy and kappa variable sequences using standard PCR. scFvs of MIN-C2 and MIN-E6 were generated. The sequence of the MIN-C2 scFv generating final heavy-linker-kappa construct is shown as (SEQ ID NOS:15 and 17). A variant of MIN-C2 scFv having a carboxyl-terminal cysteine was also generated: MIN-C2 scFv-Cys (SEQ ID NOS:16 and 18).

A single chain antibody fragment (scFv) form of monoclonal antibody MIN-E6 and an scFv-Cys variant were similarly generated. The DNA and amino acid sequences of the resultant MIN-E6 scFv and MIN-E6 scFv-Cys are shown as SEQ ID NO:25 and 27 and SEQ ID NOS:26 and 28 (Cys). The assembled DNA containing the heavy and light chain variable region sequences joined by a linker was digested with restriction enzymes, and cloned into the pET-21b bacterial expression vector and used to transform bacterial cultures.

Figure 18A:
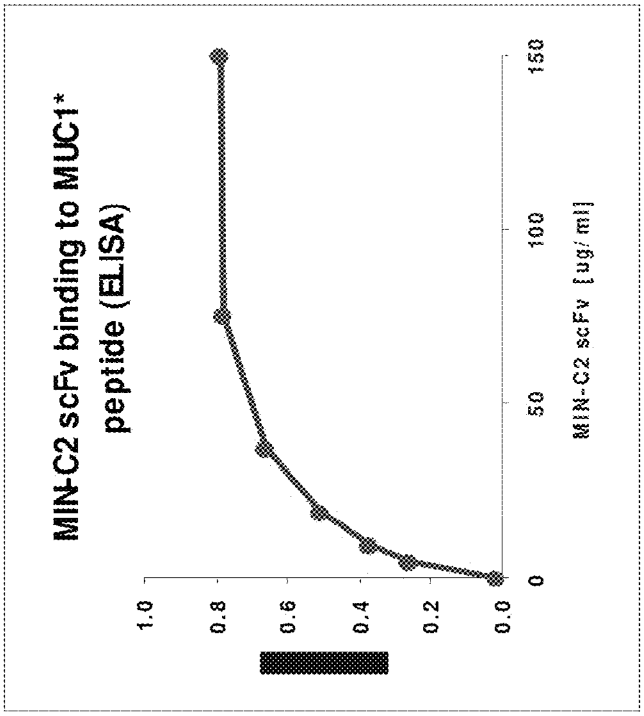
FIGS. 18A and 18B show affinity purified refolded MIN-C2 scFv improved specific binding by more than 10-fold: Refolded MIN-C2 scFv, was affinity purified by flowing, under non-denaturing conditions, over a column bearing the MUC1* extracellular domain peptide (SEQ ID NO:1). The MIN-C2 scFVs were tested by ELISA both prior to and after purification of the refolded protein by antigen affinity chromatography for the ability to bind to the peptide of SEQ ID NO:1 adsorbed onto an ELISA plate. The affinity purified protein has approximately 10-fold higher specific activity.
Figure 18B:
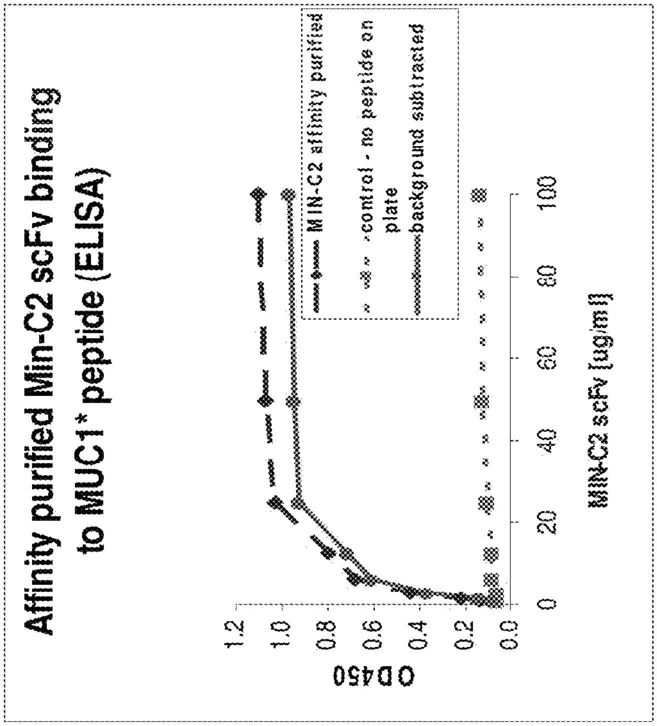

Next, bacterial cultures were induced by adding IPTG (isopropyl thio galactoside) to a concentration of 1 mM and allowing induction to proceed for 8 hours. Tests showed that all of the scFv protein was localized in the inclusion bodies. The scFv protein for MIN-C2, MIN-E6-7 was purified by solubilization of the *E. coli* inclusion body fraction with 8M urea followed by Ni-NTA column chromatography performed according to standard procedures. SDS-PAGE analysis of the eluted protein showed a single species (approximately 95% purity) with the expected size of about 28 kDa. The concentration of the eluted protein was determined by measuring absorbance at 280 nm. The protein was diluted to 150 ug/ml with binding buffer (0.02 M Tris. HCl pH 8.0, 0.5M NaCl, 8M urea, 5 mM Imidazole). To the protein was added GSH and GSSG to a final concentration of 5 mM and 0.5 mM respectively and stirred for 16 hours at 4 degrees Celsius. The eluted protein was then subjected to a refolding procedure. Refolding was done by transferring the protein into a dialysis membrane and dialyzing against 0.4 M L-arginine containing buffer (0.05 M Tris. HCl pH8.0, 0.4 M L-arginine). Final dialysis was done in 50 mM pH 8.0 and 5% glycerol. The protein was removed from dialysis membrane and spun down to remove precipitate and concentrated using centrifugal filtration with 10,000 MW cutoff membrane (Amicon Ultra, Millipore). A portion of the protein was further purified by affinity purification column. The recombinant scFv of MIN-C2 was expressed, purified (FIG. 17) and refolded. FIG. 18(A) shows that in an ELISA, MIN-C2 scFv binds specifically to the MUC1* extracellular domain peptide (PSMGFR). After refolding, some MIN-C2 scFv was target peptide affinity purified: in non-denaturing buffer, the scFv was flowed over a PSMGFR peptide column. The eluted MIN-C2 scFv showed specific activity (FIG. 18B).

Example 7—Binding of the scFv to Target MUC1* Peptide and its Ability to Compete with Parent MIN-C2 Antibody MUC1* peptide was bound to the wells of a 96 well ELISA plate by overnight incubation. This was followed by blocking with superblock (Pierce) also by overnight incubation. Next, the superblock was removed and the wells were blocked with DMEM media containing 3% FBS for 30 minutes. The scFv protein was added in various concentrations using eight serial dilutions with the highest concentration being 50 ug/ml. To determine nonspecific binding of the scFv protein, the protein was added in same dilutions to another set of wells not containing bound MUC1* peptide. The incubation was continued for 1 hour. Next, the wells were washed thrice with 0.3 ml PBST (phosphate buffered saline containing 0.02% Tween 20). This was followed by addition of rabbit anti-His antibody (AbCam) in a dilution of 1:40,000 in a media prepared by a 100 fold dilution of DMEM containing 3% FBS. This was allowed to incubate for 1 hour followed by three washes with 0.3 ml pf PBST. Next 0.1 ml of the substrate tetra methyl benzidine was added to the wells and color was allowed to develop for 15 minutes in the dark, following which 0.1 ml of 2N HCl was added. These experiments confirmed that the recombinant scFv effectively competed with the intact, parent antibody for binding to the PSMGFR (MUC1* extracellular domain) peptide.

Figure 19:
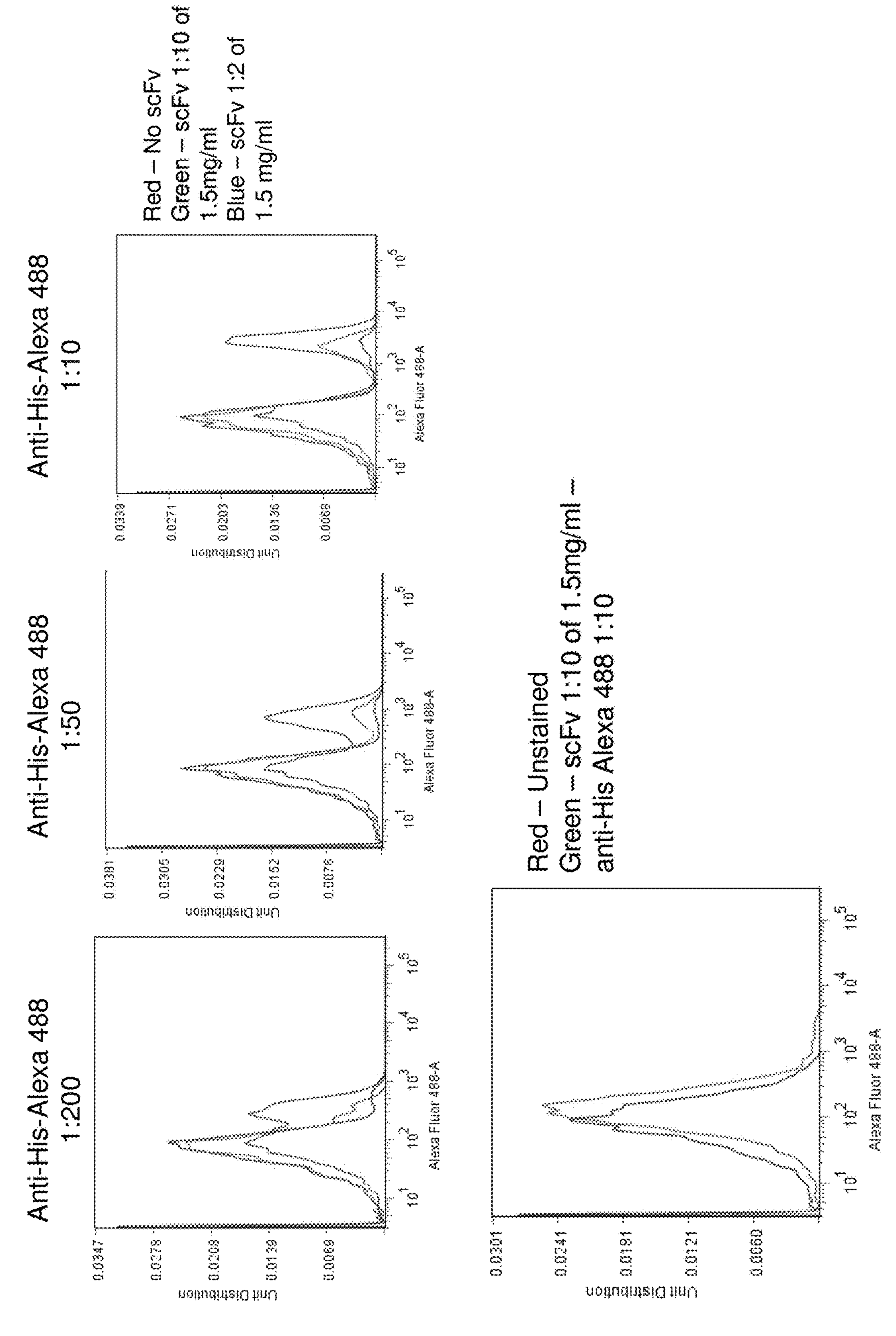
FIG. 19 shows MIN-C2 scFv recognizes MUC1* on live cells (FACS): MIN-C2 scFv, plus secondary antibody Anti-Penta-His conjugated to Alexa 488 (Qiagen), was incubated with MUC1-positive breast cancer cells (ZR-75-1/1500) cells and analyzed by FACS. The MUC1-negative control cells, HCT-116-VEC8 cells are not stained by MIN-C2 scFv.

Example 8—Cell Surface Binding of MIN-C2 scFv to MUC1 Expressing Breast Cancer Cells Breast cancer cell line ZR-75-1 was used to test the ability of the MIN-C2 scFv to recognize MUC1* on cell surface. Cells were incubated with 1:2 or 1:10 dilutions of 1.5 ug/ml scFv stock or without any scFv protein as control for 30 minutes at 4 degrees Celsius. After two washes the cells were incubated with the secondary antibody anti-penta-His conjugated to Alexa 488 (Qiagen) at dilutions of 1:200, 1:50 or 1:10 to detect the 6× Histidine tag on the scFv. Flow cytometric analysis revealed a concentration-dependent shift of a subset of cells indicating specific binding which is not seen in the absence of MIN-C2 scFv. (FIG. 19).

Example 9—Testing for the Effect of the MIN-C2 scFv Protein on Proliferation of Cancer Cells Overexpressing MUC1*

Figure 20:
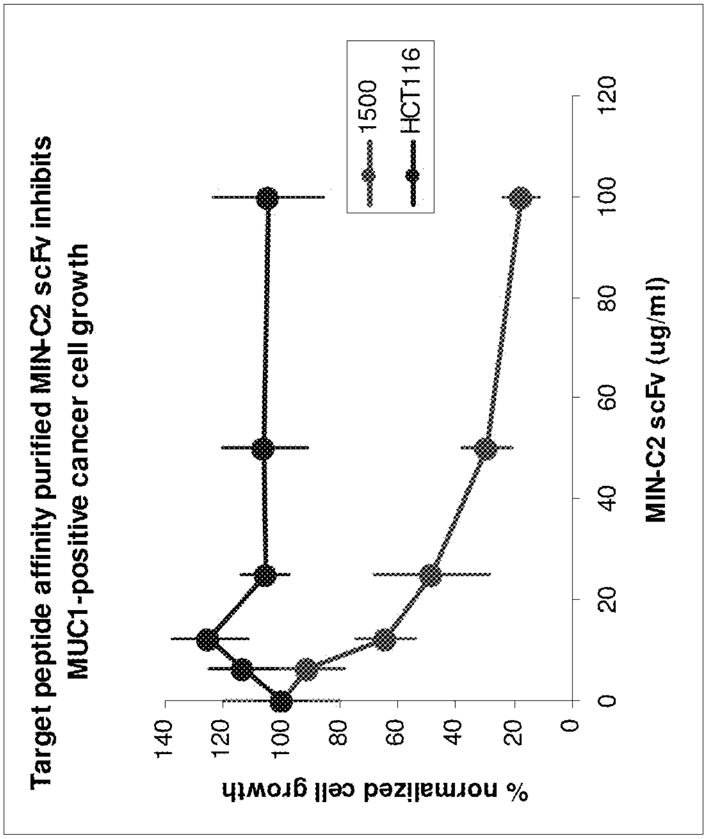
FIG. 20 shows inhibition of cancer cell growth by target peptide affinity purified MIN-C2 scFv: MUC1-positive breast cancer cell line ZR-75-1 (aka 1500) and MUC1-negative HCT-116 colon cancer cell line were treated with varying concentrations of MIN-C2 scFv that had been affinity purified over column bearing the peptide corresponding to the extracellular domain of MUC1*. The experiment was carried out over a period of 96 hours at 3% serum containing media. The scFv was added twice.

Because the MUC1* receptor stimulates cell growth when it is dimerized by its activating ligand, monomeric antibodies and antibody fragments are expected to inhibit the growth of MUC1*-positive cells. MUC1* expressing breast cancer cell line ZR-75-1 (aka 1500) was plated in 96 well plates (10,000 cells/well) in complete media (RPMI containing 10% FBS) and allowed to attach overnight. Next day the media was changed to that containing 3% FBs. As a control another cell line HCT116, colon carcinoma derived that does not express MUC1* was also plated (2,000 cells/well) in complete media (DMEM containing 10% FBS), allowed to attach overnight and media changed to that contained 3% FBS. For each cell line, cells in three wells were counted following trypsinization and resuspension using hemocytometer to obtain the zero day count. Next, The MIN-C2 scFv antibody variant was added in various concentrations. After 48 hours the media was replaced and scFv protein was added for the second time. After a further 48 hours the cells in all the wells are counted. Inhibition of cell growth was calculated relative to the growth of cells containing no scFv protein. It was observed that while the scFv protein inhibited the growth of the MUC1* expressing ZR-75-1 cells, they did not have this inhibitory effect on the control cell line HCT 116 that does not express MUC1* (FIG. 20).

Example 10—Construction and Expression of Recombinant Fab Antibody

Recombinant Fabs were also generated. In some circumstances, Fabs are preferred over scFv designs. Compared to the scFv, a recombinant Fab has a longer half-life in serum and its binding affinity is usually comparable to those of the whole parent antibody. Expression in mammalian systems provides enhanced activity via an increase in the amount of protein that is properly folded. Antibody variants produced from mammalian cells are generated on a large scale. To produce the recombinant antibody for mammalian expression, variable plus constant regions were cloned from monoclonal antibody producing hybridoma cells. Recombinant Fabs are produced using a number of antibody designs. They are essentially comprised of the VH, VL, CH and CL regions. In some cases a linker is used to join heavy chain to light chain. In other cases, heavy and light chains are carried on separate vectors and expressed in the same cell where they self-associate to form a functional Fab. Fabs of both designs were made.

Figure 21B:
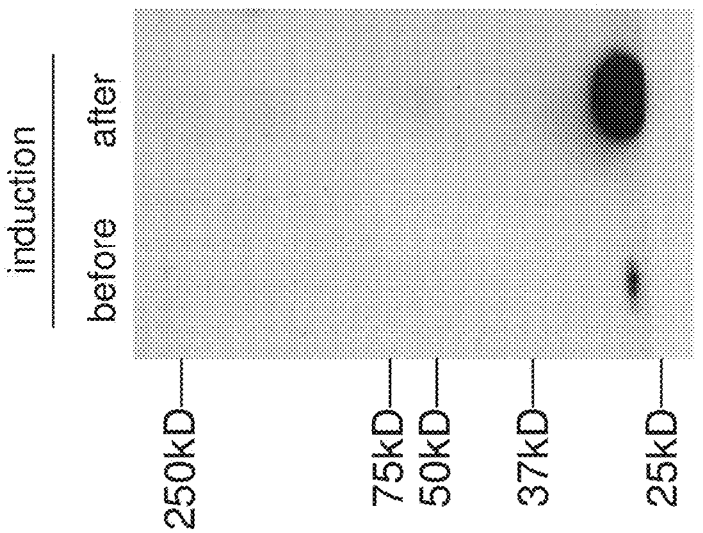
FIG. 21A-21B show 2 piece MIN-C2 Fab construct and expressed protein: MIN-C2 heavy and light chain regions were separately cloned into bacterial expression vectors. A. PCR products of MIN-C2 heavy and kappa chain from cellular RNA; and B. Bacterial protein expression of MIN-C2 Fab heavy chain.
Figure 21A:
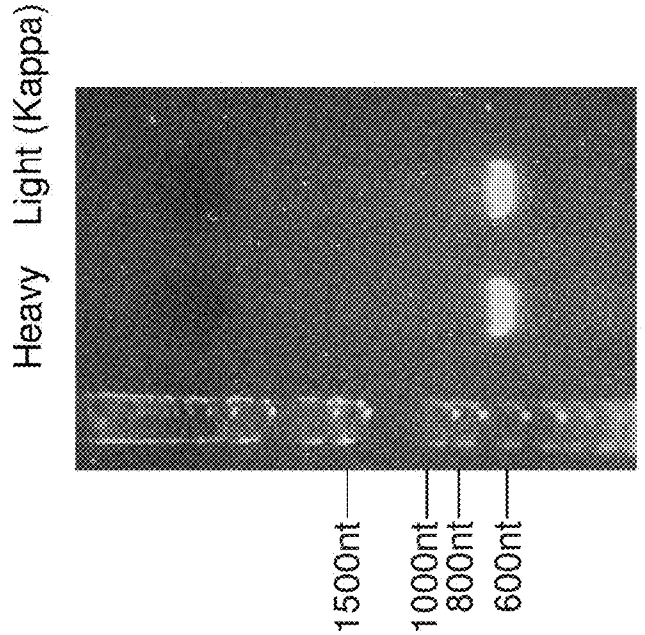

Hybridoma cells (MIN-C2 and MIN-E6 clones) producing monoclonal MUC1* antibody were grown in RPMI media containing G418 according to standard practice. Then, total RNA was prepared using Trizol reagent and first strand cDNA was generated using SuperScript III first strand cDNA synthesis kit (Invitrogen, CA). To clone heavy and light chains containing its own secretion signal sequence, degenerate PCR primers were used according to the literatures (Morrison, 2002; Kettleborough, 1993). For heavy chain cloning, PCR was set up using SEQ ID NOS:33, 34, 35, or 36 (forward) with 37 (reverse). For kappa chain, SEQ ID NOS:38, 39, 40, 41, 42 or 43 (forward) with 44 (reverse) were used. All forward and reverse PCR primers contain EcoRI and XhoI restriction site, respectively, for downstream cloning purposes. The PCR condition used was as follows: 94° C. for 60 sec, 55° C. for 60 sec, 72° C. for 60 sec with 30 cycles, and 72° C. for 10 min. Then, the PCR products were run on 1% agarose gels to determine which primers generated the desired product. FIG. 21(A) shows that the correct MIN-C2 heavy chain (prominent PCR band ~800 bp) was produced when primers of SEQ ID NOS:34 and 37 were used. Proper MIN-C2 light chain was generated using primers of SEQ ID NOS:38 and 44.

The products were purified from the agarose gel and restriction digested with corresponding enzymes and then cloned into pET21b bacterial expression vector for sequencing and simple bacterial expression to validate its full length expression. The plasmid DNA was sequenced and was found to be identical to that of the MIN-C2 scFv variant that we generated, confirming that even though different primers and different enzymatic digestion was performed, the resultant variants bear the same variable regions from the parent monoclonal antibody. The heavy (SEQ ID NOS:45 and 47) and light (SEQ ID NOS:46 and 48) chain sequences for the recombinant MIN-C2 Fab are given.

The expression of the individual Fab constructs in bacteria was tested. BL21 transformant harboring pET21b-heavy or -light chain was inoculated into 5 ml LB media containing carbenicillin (100 μg/ml) and incubated overnight at 37° C. Then, 50 ml of LB media containing carbenicillin (100 μg/ml) was inoculated with overnight bacterial culture (2.5 ml) and further incubated at 30° C. until its OD600 nm reached 0.5. The rest of the culture was spun down and frozen. IPTG was added into the 50 ml culture in final concentration of 1 mM. The culture was further incubated for 5 hours and then pelleted down. Then, bacterial pellets (before and after IPTG induction) were analyzed on SDS-PAGE and Western blotting. A prominent ~25 kDa band corresponding to the heavy or light chain insert was produced, suggesting that those heavy and light chains were properly expressed (FIG. 21 (B)).

Recombinant Fabs generated as described above function essentially the same as the Fabs that were enzymatically cleaved from the intact parent antibody.

For mammalian recombinant protein expression, those heavy and light inserts were cloned into mammalian expression vectors, pOptiVec and pcDNA3.3 using TOPO cloning kits (Invitrogen, CA).

Example 11—Generation of Recombinant Anti-MUC1* Single Chain Fab (scFab)

To further increase the efficiency of refolding and ultimately to increase the specific activity of the antibody variant, single chain Fabs (scFab) were generated. Recombinant single chain Fab constructs corresponding to anti-MUC1* antibodies MIN-C2 and MIN-E6 are generated using the design shown in FIG. 10B and FIG. 22. Beginning at the N-terminus, the scFab construct, comprises of the variable region of the light chain (VL), constant region of the light chain (CL), a 34 amino acid flexible linker, variable region of the heavy chain (VH) and the CH1 part of the constant region of the heavy chain. The heavy and light chains are connected by a flexible linker of having the following sequence: SGGGSGGGSEGGGSEGGGSEGGGSEGGGSGGGSG (SEQ ID NO:361). The light chain (VL+CL) and the heavy chain fragment (VH+CH1) are obtained by carrying out reverse transcription PCR using mRNA isolated from the specific hybridoma clone using specific primers.

Figure 23:
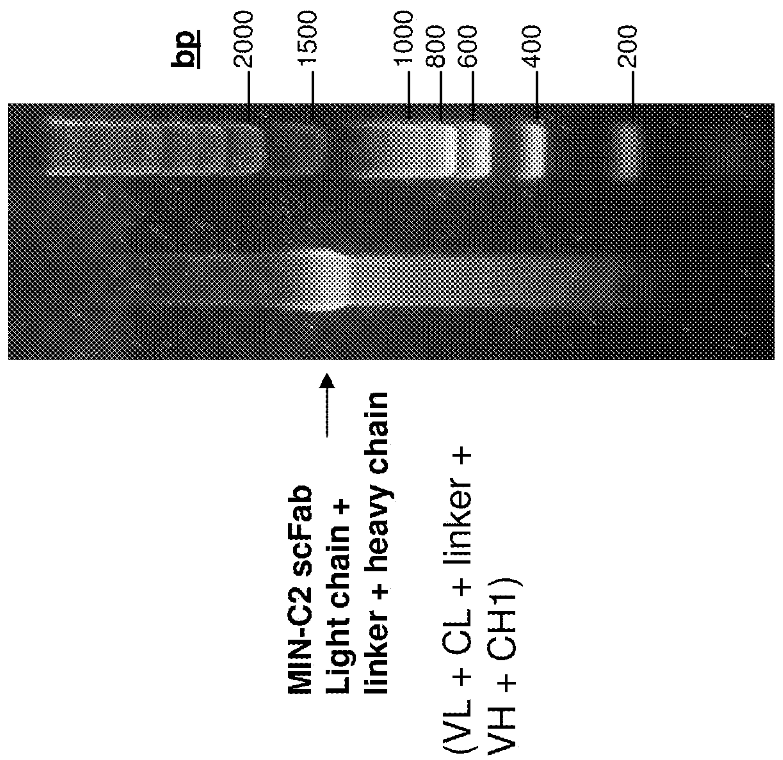
FIG. 23 shows a DNA gel with a band of molecular weight corresponding to the correct MIN-C2 scFab (single chain Fab) DNA assembly.

After correct assembly of the light chain, the heavy chain fragment and the linker, the DNA is cloned in frame into a mammalian expression vector (psecTag, Invitrogen, Carlsbad Calif.). This results in the in frame addition of a N-terminal Ig-k leader sequence and C-terminal myc and polyhistidine tag to facilitate purification. From this construct the DNA fragment which includes the Ig-k leader sequence and the purification tags is subcloned via PCR and by using appropriate restriction sites into another expression vector pCEP4 which allows high-copy replication of the plasmid DNA and uses the high expression CMV promoter. Construct thus generated is used for transient expression in mammalian cells. For this purpose human embryonic kidney cells (HEK-293) adapted to grow in suspension culture (Invitrogen, Carlsbad Calif.) is used and the secreted Fab is purified using anti-myc tag affinity chromatography. FIG. 23 shows the complete assembly of this construct using MIN-C2 sequences.

Example 12—Generation of a Humanized or Chimeric (Framework Regions are Human and CDRs are not) Anti-MUC1* Antibody The anti-MUC1* monoclonal antibodies of the invention may be humanized monoclonal antibodies or human monoclonal antibodies. An entirely antigenic murine mAb becomes human friendly when small parts of the murine antibodies are engrafted onto human immunoglobulin molecules creating either chimeric antibodies where only the Fc part of the immunoglobulin molecule is human, or humanized antibodies where only the complementarity determining regions (CDR) of the immunoglobulin are murine and 90 to 95% of the molecule is human. In one respect, fully human monoclonal antibodies may be generated in transgenic mice by employing conventional methods such as HuMAb-Mouse (GenPharm-Medarex) or XenoMouse (Abgenix, Inc.) technology. Humanized antibodies include human immunoglobulins in which residues from a CDR of the recipient are replaced by residues from a CDR of a non-human species such as mouse, rat or rabbit having the desired specificity, affinity and biological function.

Human antibodies also can be produced using techniques such as phage display libraries (Hoogenboom and Winter, J. Mol. Biol, 1991, 227:381, Marks et al., J. Mol. Biol. 1991, 222:581). Methods for humanizing non-human antibodies are well known. Humanization can be performed following the method of Winter et al. as disclosed in Jones et al., Nature, 1986, 321:522; Riechmann et al., Nature, 1988, 332:323; and Verhoeyen et al., Science, 1988, 239:1534 by substituting rodent CDR sequences or CDRs for the corresponding sequences of a human antibody. Such humanized antibodies are chimeric antibodies (U.S. Pat. No. 4,816, 567). Typically, humanized antibodies are antibodies where CDR residues are substituted by residues from analogous sites in rodent antibodies.

Therapeutic antibodies derived from non-human species may in some cases trigger immune responses when injected into humans, thereby limiting their utility. Therefore humanization or partial humanization of antibodies for therapeutic use in humans is preferred. There are many methods for generating humanized or partially humanized antibodies and antibody variants. The present invention is directed to the use of any of these processes is suitable for humanizing compositions of the invention. In one process, a mouse having human antibody loci is used to generate fully humanized antibodies (Jakobovits et al.). In another method, DNA from B cells from humans are selected for binding to a selected target, then re-inserted into the context of the full antibody.

In a common method, the framework regions of an antibody generated in a non-human host are exchanged for human framework regions, preserving the original CDR sequences. These are called chimeric antibodies. In this process only the six complementary determining regions (CDRs) three each forming the heavy and light chains of the murine antibody are retained and the sequences of the framework regions are substituted for those from a closely related human antibody (method described in Muzard et al., 2009). First, homology searches are performed to independently align the VH and VL amino acid sequences of anti-MUC1* antibody (MIN-C2 or MIN-E6) against a repertoire of human antibody sequences registered in protein Data Bank. Among the variable region sequences derived from different human antibodies that best match the anti-MUC1* VH and VL, that particular antibody sequence is chosen which has the highest combined homology to anti-MUC1* VH and VL sequences. This is necessary in order to preserve the inter domain contacts that occur in a natural antibody. Optionally, sequence identity in the range of 65-70% when calculated only over the framework region are preferred. Using a combination of chemical synthesis of DNA and PCR, humanized anti-MUC1* scFv are constructed, where the framework region sequences are swapped for those from the human antibody. The resultant DNA fragment is inserted into an expression vector and tested for expression and for binding affinity upon refolding.

Affinities are improved by testing adding the constant regions (CL and CH1) sequences from the same human antibody to the humanized VL and VH sequences of the anti-MUC1* scFv. The resulting chimeric heavy and light chains are linked through a 34 amino acid flexible linker SGGGSGGGSEGGGSEGGGSEGGGSEGGGSGGGSG (SEQ ID NO:361) to produce the single chain humanized anti-MUC1* scFab. The assembled DNA molecule is cloned into a high-copy replication and high expression mammalian expression vector pCEP4 (Invitrogen, Carlsbad Calif.) after in-frame addition of IG-k signal sequence at the N-terminus and the myc and polyhistidine tags at the C-terminus. Construct thus generated is used for expression in mammalian cells, such as human embryonic kidney cells (HEK-293) which have been adapted to grow in suspension culture (Invitrogen, Carlsbad Calif.). The secreted Fab is then purified, for example, using anti-myc tag affinity chromatography.

To further improve affinity, the in silico 3D structure of the original non-human monoclonal antibody or the chimeric antibody variant is compared to many 3D structures of human antibodies available in the protein structure data base. Further variations in the framework regions are then incorporated to make the chimeric variant more closely resemble a human antibody.

Affinity enhancement can also be achieved by using phage display methods (Finlay et al 2009) which are known to those skilled in the art.

Example 13—Comparison of Rabbit Polyclonal Antibody Generated with SEQ ID NO:1 and Monoclonal Mouse Antibody MIN-C2 for the Stimulation of Growth of Pluripotent Stem Cells Rabbit polyclonal anti-MUC1* antibody (generated by immunization with peptide of SEQ ID NO:1) was compared to monoclonal anti-MUC1* antibody MIN-C2 for their ability to enable the growth of stem cells in the absence of bFGF or feeder cell extracts, while maintaining their pluripotency; this is accomplished by dimerizing the extracellular domain of MUC1* comprising essentially the PSMGFR sequence (SEQ ID NO:1).

Human embryonic stem cells were grown on Matrigel-like substrate and cultured in minimal stem cell media: a) alone; b) with 30% fibroblast conditioned medium plus 4 ng/ml bFGF (state of the art); c) with 50 ng/ml polyclonal anti-MUC1* antibody; or d) with 50 ng/ml monoclonal anti-MUC1* MIN-C2. The pluripotency of the resultant cells was assessed based on colony morphology and on their continued expression of OCT4. Pluripotent stem cell colonies grow in discrete, flat and round colonies with even, well-defined borders while those that have entered differentiation have ragged borders and begin to grow vertically. Pluripotent stem cells express OCT4 in their nuclei. Cells that have lost OCT4 expression have entered into the differentiation process. Embryonic stem cells that were engineered to express GFP (green fluorescent protein) off of the OCT4 promoter were used, so that the pluripotent stem cells, i.e. OCT4-positive cells, would fluoresce green and therefore would be easily distinguished from those that had started to differentiate.

FIG. 24 shows that stem cells grown in minimal media alone (A), or according to the state of the art protocol, i.e. bFGF and conditioned media from feeder cells (B) have grown into colonies with ragged edges and in non-circular patterns. Additionally, the fluorescent photos (right panel) reveal that nearly half of the stem cells have differentiated and no longer express OCT4 or GFP. Panels C and D show that stem cells treated with either polyclonal anti-MUC1* or monoclonal anti-MUC1* MIN-C2 grew into well formed, flat and round colonies with well-defined borders which are the hallmark of pluripotent stem cell morphology. The corresponding fluorescent images (right panel) show that virtually every stem cell remains pluripotent as evidenced by GFP and, by extension, OCT4 expression. The efficacy of the polyclonal and monoclonal MIN-C2 are essentially the same.

REFERENCES CITED

Aboud-Pirak, et al. Inhibition of human tumor growth in nude mice by a conjugate of doxorubicin with monoclonal antibodies to epidermal growth factor receptor. Proc Natl Acad Sci USA. 1989 May; 86(10):3778-81.

Baeuerle P A and Reinhardt C *Bispecific T Cell Engaging Antibodies for Cancer Therapy* Cancer Res 2009 Jun. 15; 69(12):4941-4.

Bortoletto, et al. Optimizing anti-CD3 affinity for effective T cell targeting against tumor cells Eur J Immunol 2002 November 32(11):3102-7.

Bruenke J, et al. Br J Haematol. Effective lysis of lymphoma cells with a stabilized bispecific single-chain Fv antibody against CD19 and FcgammaRIII (CD16) 2005 July; 130 (2):218-28

Cao, et al. Construction and characterization of an enhanced GFP-tagged anti-BAFF scFv antibody. Appl Microbiol Biotechnol. 2008 June; 79(3):423-31.

Chames P and Baty D Bispecific Antibodies for Cancer Therapy. Curr Opin Drug Discov Devel. 2009 March; 12(2):276-83.

Finlay W J, Cunningham O, Lambert M A, Darmanin-Sheehan A, Liu X, Fennell B J, Mahon C M, Cummins E, Wade J M, O'Sullivan C M, Tan X Y, Piche N, Pittman D D, Paulsen J, Tchistiakova L, Kodangattil S, Gill D, Hufton S E. Affinity maturation of a humanized rat antibody for anti-RAGE therapy: comprehensive mutagenesis reveals a high level of mutational plasticity both inside and outside the complementarity-determining regions. J Mol Biol. 2009 May 8; 388(3):541-58.

Holliger P et al. Diabodies: Small bivalent and bispecific antibodies Proc Natl Acad Sci 1993 Jul. 15; 90(14):6444-8.

Hurwitz E et al. The covalent binding of daunomycin and adriamycin to antibodies, with retention of both drug and antibody activities. Cancer Res. 1975 May; 35(5):1175-81.

Jakobovits A, et al. From XenoMouse technoloby to panitumumab, the first fully human antibody product from transgenic mice. Nat Biotechnol. 2007 October; 25(10): 1134-43.

Johansson, et al. Efficient expression of recombinant human monoclonal antibodies in *Drosophila* S2 cells. J Imm Methods. 2007 318(1-2): 37-46.

Juirez-Gonzilez, et al Directed Evolution, Phage Display and Combination of Evolved Mutants: A Strategy to Recover the Neutralization Properties of the scFv Version of BCF2 a Neutralizing Monoclonal Antibody Specific to Scorpion Toxin Cn2) J Mol Biol. 2005 Mar. 11; 346(5): 1287-97.

Kettleborough C. A., Saldanha, J., Ansell, K. H. and Bendig, M. M. Optimization of primers for cloning libraries of mouse immunoglobulin genes using the polymerase chain reaction. Eur. J. Immunol. 1993. 23:206-211.

Lonberg N Human antibodies from transgenic animals. Nat Biotechnol. 2005 September; 23(9): 1117-25.

Lu D, et al. Simultaneous Blockade of Both the Epidermal Growth Factor Receptor and the Insulin-like Growth Factor Receptor Signaling Pathways in Cancer Cells with a Fully Human Recombinant Bispecific Antibody. J Biol Chem. 2004 Jan. 23; 279(4):2856-65.

Majors B S, et al. MC1-1 overexpression leads to higher viabilities and increased production of humanized monoclonal antibody in Chinese hamster ovary cells. Biotechnol Prog. 2009 July-August; 25(4):1161-8.

McCall A M, et al. Mol. Immunol. Isolation and characterization of an anti-CD16 single-chain Fv fragment and construction of an anti-HER2/neu/anti-CD16 bispecific scFv that triggers CD16-dependent tumor cytolysis Mol Immunol. 1999 May; 36(7):433-45.

McCarron, et al. Antibody Conjugates and Therapeutic Strategies Molecular Interventions 2005 5:368-380.

Morrison, S. L. Cloning, expression, and modification of antibody V regions. Current Protocols in Immunology. 2002. Unit 2.12. John Wiley & Sons, Inc., New York, N.Y.

Muzard J et al. Design and humanization of a murine scFv that blocks human platelet glycoprotein VI in vitro. FEBS J. 2009 August; 276(15):4207-22. Epub 2009 Jun. 2.

Nahary L, and Benhar I. Methods Mol Biol Design of a human synthetic combinatorial library of single-chain antibodies. 2009; 525:61-80, xiv.

Razai A, et al. J Mol Biol. Molecular evolution of antibody affinity for sensitive detection of botulinum neurotoxin type A. 2005 Aug. 5; 351(1):158-69.

Robinson M K, et al. Br J Cancer. Targeting ErbB2 and ErbB3 with a bispecific single-chain Fv enhances targeting specificity and induces a therapeutic effect in vitro 2008 Nov. 4; 99(9):1415-25.

Wang, Z., Raifu, M., Howard, M., Smith, L., Hansen, D., Goldsby, R., Ratner, D. Universal PCR amplification of mouse immunoglobulin gene variable regions: The design of degenerate primers and an assessment of the effect of DNA polymerase 3' to 5' exonuclease activity. J. Immuno. Methods. 2000. 233:167-177.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of inhibiting cell proliferation, comprising contacting cells expressing MUC1* with an isolated monoclonal antibody to MUC1*, which is monovalent for MUC1*, wherein the monoclonal antibody specifically binds to the amino acid sequence of SEQ ID NO:1 and has an amino acid sequence in the heavy chain variable region in CDR1 region comprising SEQ ID NO:331, in CDR2 region comprising SEQ ID NO:334, and in CDR3 region comprising SEQ ID NO:374, and an amino acid sequence in the light chain variable region in CDR1 region comprising SEQ ID NO:340, in CDR2 region comprising SEQ ID NO:342, and in CDR3 region comprising SEQ ID NO:344;

wherein the monoclonal antibody comprises:

in its heavy chain, a FWR1 sequence that is at least 90% identical to SEQ ID NO:362, a FWR2 sequence that is at least 90% identical to SEQ ID NO:363, or a FWR3 sequence that is at least 90% identical to SEQ ID NO:364, and in its light chain, a FWR1 sequence that is at least 90% identical to SEQ ID NO:365, a FWR2 sequence that is at least 90% identical to SEQ ID NO:366, or a FWR3 sequence that is at least 90% identical to SEQ ID NO:367.

2. The method according to claim 1, wherein the cells are cancer cells.

3. The method of claim 1, wherein the monoclonal antibody comprises:

a variable heavy chain region comprising an amino acid sequence at least 90% identical to SEQ ID NO: 11, and a variable light chain region comprising an amino acid sequence at least 90% identical to SEQ ID NO: 13.

4. The method of claim 1, wherein the monoclonal antibody is monovalent, an Fab, or a single chain variable fragment antibody (scFv).

5. The method of claim 4, wherein the Fab comprises a heavy chain region comprising an amino acid sequence at least 90% identical to SEQ ID NO: 47 and/or a kappa chain region comprising an amino acid sequence at least 90% identical to SEQ ID NO: 48.

6. The method of claim 1, wherein the monoclonal antibody is bi-valent, bi-specific, or tri-specific.

7. The method of claim 6, wherein a portion of the monoclonal antibody binds to MUC1* and another portion binds to a tumor-specific antigen on a cell surface.

8. The method of claim 1, wherein the monoclonal antibody is fused to a label, a tag, a toxin, a radioactive substance, a targeting motif a leader sequence peptide, a toxic material, a protein, or a peptide.

9. The method of claim 8, wherein the protein is a toxin, or a cytokine.

10. The method of claim 3, wherein the monoclonal antibody is monovalent, an Fab, or a single chain variable fragment antibody (scFv).

11. The method of claim 10, wherein the Fab comprises a heavy chain region comprising an amino acid sequence at least 90% identical to SEQ ID NO: 47 and/or a kappa chain region comprising an amino acid sequence at least 90% identical to SEQ ID NO: 48.

12. The method of claim 3, wherein the monoclonal antibody is bi-valent, bi-specific, or tri-specific.

13. The method of claim 12, wherein a portion of the monoclonal antibody binds to MUC1* and another portion binds to a tumor-specific antigen on a cell surface.

14. The method of claim 3, wherein the monoclonal antibody is fused to a label, a tag, a toxin, a radioactive substance, a targeting motif, a leader sequence peptide, a toxic material, a protein, or a peptide.

15. The method of claim 14, wherein the protein is a toxin, or a cytokine.

16. The method of claim 1, wherein the amino acid sequence in the heavy chain variable region in CDR1 region consists of SEQ ID NO:331, in CDR2 region consists of SEQ ID NO:334, and in CDR3 region consists of SEQ ID NO:374, and the amino acid sequence in the light chain variable region in CDR1 region consists of SEQ ID NO:340, in CDR2 region consists of SEQ ID NO:342, and in CDR3 region consists of SEQ ID NO:344.

17. The method of claim 3, wherein the amino acid sequence in the heavy chain variable region in CDR1 region consists of SEQ ID NO:331, in CDR2 region consists of SEQ ID NO:334, and in CDR3 region consists of SEQ ID NO:374, and the amino acid sequence in the light chain variable region in CDR1 region consists of SEQ ID NO:340, in CDR2 region consists of SEQ ID NO:342, and in CDR3 region consists of SEQ ID NO:344.

* * * * *

UNITED STATES PATENT AND TRADEMARK OFFICE
CERTIFICATE OF CORRECTION

PATENT NO. : 11,560,435 B2  
APPLICATION NO. : 16/539247  
DATED : January 24, 2023  
INVENTOR(S) : Bamdad et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 326 days.

Signed and Sealed this  
Thirty-first Day of December, 2024

Derrick Brent  
*Acting Director of the United States Patent and Trademark Office*